US005658908A

United States Patent [19]
Chang et al.

[11] Patent Number: 5,658,908
[45] Date of Patent: Aug. 19, 1997

[54] OPIOID DIARYLMETHYLPIPERAZINES AND PIPERDINES

[75] Inventors: Kwen-Jen Chang, Chapel Hill; Grady Evan Boswell; Dulce Garrido Bubacz, both of Cary; Mark Allan Collins, Raleigh; Ann Otstot Davis, Raleigh; Robert Walton McNutt, Jr., Durham, all of N.C.

[73] Assignee: Delta Pharmaceuticals, Inc., Chapel Hill, N.C.

[21] Appl. No.: 284,445

[22] PCT Filed: Feb. 2, 1993

[86] PCT No.: PCT/GB93/00216

§ 371 Date: Aug. 3, 1994

§ 102(e) Date: Aug. 3, 1994

[87] PCT Pub. No.: WO93/15062

PCT Pub. Date: Aug. 5, 1993

[30] Foreign Application Priority Data

Feb. 3, 1992 [GB] United Kingdom .................. 9202238

[51] Int. Cl.$^6$ ...................... A61K 31/495; C07D 241/04; C07D 403/10; C07D 409/06
[52] U.S. Cl. .......................... 514/252; 514/255; 514/317; 514/357; 544/357; 544/360; 544/364; 544/365; 544/367; 544/372; 544/379; 544/396; 546/192; 546/194; 546/333; 546/234; 435/7.1; 435/7.2; 435/7.21
[58] Field of Search .................... 544/357, 360, 544/372, 379, 396, 364, 365, 367; 514/252, 255

[56] References Cited

U.S. PATENT DOCUMENTS

| | | | |
|---|---|---|---|
| 2,630,435 | 3/1953 | Baltzly et al. | 544/396 |
| 4,518,711 | 5/1985 | Hruby et al. | 514/11 |
| 4,816,586 | 3/1989 | Portoghese | 544/340 |
| 5,574,159 | 11/1996 | Chang et al. | 544/396 |

FOREIGN PATENT DOCUMENTS

| | | |
|---|---|---|
| 0 133 323 B1 | 2/1985 | European Pat. Off. . |
| 0 287 339 A2 | 10/1988 | European Pat. Off. . |
| 0 506 468 A1 | 9/1992 | European Pat. Off. . |
| 86 4522 | 12/1986 | South Africa . |
| 90/15599 | 12/1990 | WIPO . |

OTHER PUBLICATIONS

Pakarinen, "Effects of Convulsant Agents on Learning and Memory in Squirrel Monkeys," Dissertation Abstracts International, 54(01B), 189 (Mar. 31, 1993—entered in the Louisiana State University online catalog).

Calderon et al., "Synthesis and Absolute Configuration of Optically Pure Enantiomers of(±)–BW373U86, A Nonpeptidic δ–Opioid Receptor Agonist," College on Problems of Drug Dependence, Inc., Fifty–fifth Annual Scientific Meeting, Toronto, Canada, Poster Presentation, (Jun. 12–17, 1993).

Selley, "BW373U86 A Non–peptide δ–Opioid Agonist With Novel Receptor–G–Protein–Mediated Actions," Meeting of the International Narcotics Research Conference (INRC). Skoevde, Sweden, Abstract (Jul. 11–16, 1993).

Comer, "BW373U86: Behavioral Pharmacology of a Putative Non–Peptide, Systemically–Active Delta Opioid Agonist," Dissertation Abstracts International, 53(5B). 2578 (JUl. 1, 1992—entered in the University of Michigan online catalog).

Boradbent et al., "Role of Opioid Receptor Subtypes in the Discriminative Stinulius Effects of Cocaine," Meeting of the International Narcotics Research Conference (INRC), Keystone, Colorado, Abastact, (Jun. 23–27, 1992).

Dworkin et al., "Effects of δ–Opiate Agonists and Antagonists on Cocaine and Heroin Self Administration in Rats," Meeting of the International Narcotics Research conference (INRC). Keystone, Colorado, Abstract (Jun. 23–27, 1992).

Dykstra, et al., "Effects of a Novel Delta Opioid Agonsit in Squirrel Monkeys Responding Under a Schedule of Shock Tritration," Meeting of the International Narcotics Research Conference (INRC), Keystone, Colorado, Astract (Jun. 23–27, 1992).

Lee et al., "A Non–peptide Delta–Opioid Receptor Agonsit BW373U86 Suppresses Naloxone–precipated Morphine Abstience," Meeting of the International Narcotics Research Conference (INRC), Keystone, Colorado, Abstract (Jun. 23–27, 1992).

Porreca et al., "Pharmacology of Multiple Opioid Delta Receptors," National Institute on Drug Abuse Research Monograph Series 132, Problems of Drug Dependence, 1992: Proceeding of the 54th Annual Scientific Meeting 430–436 (1993).

Iwamoto et al., "Calcium Antagonism, by KB–2796, a New Diphenylpiperazine Analogue, in Dog Vascular Smooth Muscle," J. Pharm. Pharmacol., 43, 535–539 (1991).

Goenechea et al., "Untersuchungen Zur Biotransformation von Meclozin im Menschlichen Körper," J. Clin. Chem. Clin. Biochem., 26, 105–115 (1988)—See Specification, p. 4, last paragraph and Chemical Abstracts 108: 215746g.

Iwamoto et al., "Effects of KB–2796, a New Calcium Antagonist, and Other Diphenylpiperazines on [$^3$H]Nitrendipine Binding," Japan J. Pharmacol. 48, 241–247 (1988).

Natsuka et al., "Synthesis and Structure–Activity Relationships of 1–Substituted 4–(1,2–Diphenylethyl)piperazine Derivatives having Narcotic Agonist and Antagonist Activity," J. Med. Chem., 30(10), 1779–1787 (1987).

(List continued on next page.)

*Primary Examiner*—Emily Bernhardt
*Attorney, Agent, or Firm*—Steven J. Hultquist

[57] ABSTRACT

Diarylmethylpiperazine compounds having utility as receptor-binding species, e.g., for mediating analgesia, and for combatting drug addiction, alcohol addiction, and drug overdose. The compounds may be administered orally, rectally, topically, nasally, ophthalmically, or parenterally (subcutaneously, intramuscularly, and intravenously), for veterinary and human use, and include delta receptor and mu receptor binding species.

26 Claims, No Drawings

OTHER PUBLICATIONS

Meuldermas et al., "Plasma Levels, Biotransformation and Excretion of Oxatomide (R 35 443) in Rats, Dogs and Man,"Xenobiotica, 14(6), 445–462 (9184).

Krishnamurthy, "A Highly Efficient and General N–Monomethylation of Functionalized Primary Amines Via Formylation–Borane: Methyl Sulfide Reduction," Tet. Let., 23(33), 3315–3318 (1982).

Lord et al., "Endogenous Opioid Peptides: Multiple Agonists and Receptors, " Nature, 267, 495–499 (1977).

Chang et al., "A Novel, Potent and Selective Nonpeptidic *Delta* Opioid Receptor Agonist BW 373U86", J. Pharmacol. Exp. Ther., 267, 852–857 (1993).

Childers et al., "BW373U86: A Non–peptidic δ–Opioid Agonist With Novel Receptor–g Protein–mediated Actions in Rat Brain Membranes and Neuroblastoma Cells", Molec. Pharmacol., 44,827–834 (1993).

Comer et al., "Convulsive Effects of Systemic Administration of the *Delta* Opioid Agonist BW373U86 in Mice", J. Pharmacol. Exp. Ther., 267, 888–895 (1993).

Comer et al., "Discriminative Stimulus Effects of BW373U86: A Non–peptide Ligand With Selectivity for *Delta* Opioid Receptors", J. Pharmacol. Exp. Ther., 267, 7866–874 (1993).

Dykstra et al., "A Novel *Delta* Opioid Agonist, BW373U86, in Squirrel Monkeys, Responding Under a Schedule of Shock Titration", J. Pharmacol. Exp. Ther., 267, 875–882 (1993).

Lee et al., "A Nonpeptidic Delta–opioid Receptor Agonist, BW373U86, Attenuates the Development and Expression of Morphine Abstinence Precipitated by Naloxone in Rat . . . ". J. Pharmacol. Exp. Ther., 267, 883–887 (1993).

Negus et al., "Effects of Opioid Agonists Selective for *Mu, Kappa* and *Delta* Opioid Receptors on Schedule–controlled Responding in Rhesus Monkeys: Antagonism by Quadazocine", J. Pharmacol. Exp. Ther., 267, 896–903 (1993).

Wild et al., "Binding of 373U86, A Non–peptidic δ–Opioid Receptor Agonist, is Not Regulated by Guanine Nucleotides and Sodium", Eur. J. Pharmacol.–Molec. Pharmacol., Section 246, 289–292 (1993).

Wild et al., "Antinociceptive Actions of BW373U86 in the Mouse", J. Pharmacol. Exp. Ther. 267,858–865, 1993.

Xu et al., "Differential Binding of Opioid Peptides and Other Drugs to Two Subtypes Opioid$\delta_{ncx}$ Binding Sites in Mouse Brian: Further Evidence of δ Receptor Heterogeneity", Peptides 14, 893–907 (1993).

OPIOID DIARYLMETHYLPIPERAZINES AND PIPERDINES

This application is a 371 of PCT/GB93/00216 filed Feb. 2, 1993.

TECHNICAL FIELD

This invention relates generally to diarylmethyl piperazine and diarylmethyl piperidine compounds having utility as receptor-binding species, e.g., as conjugates in agonist/ antagonist pairs for verifying/assaying receptor and neurotransmitter function. The compounds of the invention include benzhydryl piperazine compounds useful as mu and/or delta receptor opioid compounds mediating analgesia, as well as compounds having utility in combatting drug addiction, alcohol addiction, drug overdose, mental illness, urinary incontinence, cough, lung edema, diarrhea, depression, and cognitive, respiratory, and gastro-intestinal disorders.

BACKGROUND ART

In the study of opioid biochemistry, a variety of endogenous opioid compounds and non-endogenous opioid compounds has been identified. In this effort, significant research has been focused on understanding the mechanism of opioid drug action, particularly as it relates to cellular and differentiated tissue opiate receptors.

Opioid drugs typically are classified by their binding selectivity in respect of the cellular and differentiated tissue receptors to which a specific drug species binds as a ligand. These receptors include mu (μ), delta (δ), sigma (σ) and kappa (κ) receptors.

The well-known narcotic opiates, such as morphine and its analogs, are selective for the opiate mu receptor. Mu receptors mediate analgesia, respiratory depression, and inhibition of gastrointestinal transit. Kappa receptors mediate analgesia and sedation. Sigma receptors mediate various biological activities.

The existence of the opioid delta receptor is a relatively recent discovery which followed the isolation and characterization of endogenous enkephalin peptides which are ligands for the delta receptor. Research in the past decade has produced significant information about the delta receptor, but a clear picture of its function has not yet emerged. Delta receptors mediate analgesia, but do not appear to inhibit intestinal transit in the manner characteristic of mu receptors.

Opioid agents frequently are characterized as either agonists or antagonists. Agonists and antagonists are agents which recognize and bind to receptors, affecting (either initiating or blocking) biochemical/physiological sequences, a process known as transduction. Agonists inhibit or suppress neurotransmitter outputs in tissues containing receptors, e.g., inhibiting pain responses, or affecting other output-related phenomena. Antagonists also bind to receptors, but do not inhibit neurotransmitter outputs. Thus, antagonists bind to the receptor sites and block the binding of agonist species which am selective for the same receptor.

Concerning specific receptor ligands, the distinction between delta receptor agonists and antagonists heretofore has been made by their activity in the electrically stimulated mouse vas deferens assay, which typically has been considered the appropriate diagnostic tissue for the delta receptor. By contrast, mu receptor agonists are generally characterized by their activity in the electrically stimulated guinea pig ileum assay.

Only a relatively small number of essentially pure delta receptor-selective agents is known, and with the exception of the delta opioid receptor antagonists disclosed in Portoghese U.S. Pat. No. 4,816,586, all known delta receptor-selective opioid compounds are peptides, including endogenous enkephalins and other endorphins, as well as exogenous peptide analogs. The previously synthesized exogenous peptide analogs have various associated disadvantages in terms of their stability, their potentially suitable delivery routes as administered drug agents, and their in vivo tissue distribution.

Various physiological effects of the known peptide-based opioid ligands have been studied, including: analgesia; respiratory depression; gastrointestinal effects; mental, emotional, and cognitive process function; and mediation/ modulation of other physiological processes.

The aforementioned U.S. Pat. No. 4,816,586, issued Mar. 28, 1989 to P. S. Portoghese, discloses various delta-opioid receptor antagonists of specified formula. The disclosed antagonist compounds are formed by fusion of an indole, benzofuran, benzopyrazine, or quinoline ring system, to the C-ring of naltrexone. These compounds are described as possessing a unique opioid receptor antagonist profile, including compounds which are highly selective for the delta opioid receptor.

U.S. Pat. No. 4,518,711 issued May 21, 1985 to V. J. Hruby et al describes cyclic, conformationally constrained analogs of enkephalins. These compounds include both agonists and antagonists for the delta receptor, and are said to induce pharmacological and therapeutic effects, such as analgesia in the case of agonist species of such compounds. The antagonist species of the disclosed compounds are speculated to be useful in the treatment of schizophrenia, Alzheimer's disease, and respiratory and cardiovascular functions.

In addition to the above-described references relating to opioid compounds, the art relevant to the compounds of the present invention includes the polyaryl piperazine compounds described in the various references identified below.

S. Goenechea, et al, in "Investigation of the Biotransformation of Meclozine in the Human Body," *J. Clin. Chem. Clin. Biochem.*, 1988, 26(2), 105–15, describe the oral administration of a polyaryl piperazine compound in a study of meclozine metabolization in human subjects.

In "Plasma Levels, Biotransformation and Excretion of Oxatomide in Rats, Dogs, and Man," Meuldermans, W., et al, *Xenobiotica*, 1984, 15(6), 445–62, there is disclosed a metabolic study of plasma levels, biotransformation, and excretion of oxatomide.

T. Iwamoto, et al, in "Effects of KB-2796, A New Calcium Antagonist, and Diphenylpiperazines on [$^3$H]nitrendipine Binding," *Jpn. J. Pharmacol,* 1988, 48(2), 241–7, describes the effect of a polyaryl piperazine of specified formula, as a calcium antagonist.

K. Natsuka, et al, in "Synthesis and Structure-Activity Relationships of 1-Substituted 4-(1,2-Diphenylethyl) piperazine Derivatives Having Narcotic Agonist and Antagonist Activity," *J. Med. Chem.,* 1987, 30 (10), 1779–1787, disclose racemates and enantiomers of 1-substituted 4-[2-(3-hydroxyphenyl)-1-phenylethyl] piperazine derivatives.

European Patent Application No. 458,160 published Nov. 27, 1991 describes substituted diphenylmethane derivatives which are said to be useful as analgesic and antiinflammatory agents, including compounds wherein the methylene bridging group (linking the two phenyl moieties) may have as a substituent on the methylene carbon a piperidinyl or piperazinyl group.

South African Patent Application No. 8604522 published Dec. 12, 1986 discloses N-substituted arylalkyl and arylalkylene substituted amino-heterocyclic compounds, including piperidine derivatives, which are described as useful cardiovascular, antihistamine, and anti-secretory agents.

European Patent Application No. 133,323 published Feb. 20, 1985 discloses certain diphenylmethyl piperazine compounds useful as non-sedative antihistamines.

There is a continuing need in the art for improved opioid compounds, particularly compounds which are free of addictive character and other adverse side effects of conventional opiates such as morphine and pethidine.

DISCLOSURE OF INVENTION

The present invention relates to compounds of the formula:

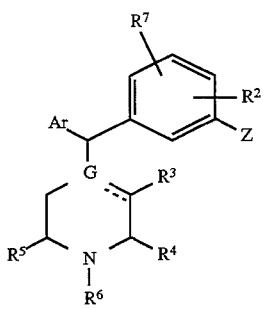

in which Ar is a 5- or 6-member carbocyclic or heterocyclic aromatic ring having on a first ring carbon atom thereof a substituent Y and on a second ring carbon atom thereof a substituent $R^1$,
wherein:

Y is selected from the group consisting of:
hydrogen;
halogen;
$C_1$–$C_6$ alkyl;
$C_1$–$C_6$ haloalkyl;
$C_3$–$C_6$ cycloalkyl;
$C_1$–$C_6$ alkoxy;
$C_3$–$C_6$ cycloalkoxy;
sulfides of the formula $SR^8$ where $R^8$ is $C_1$–$C_6$ alkyl, $C_3$–$C_6$ cycloalkyl, arylalkyl comprising a $C_5$–$C_{10}$ aryl moiety and an $C_1$–$C_6$ alkyl moiety, or $C_5$–$C_{10}$ aryl;
sulfoxides of the formula $SOR^8$ where $R^8$ is the same as above;
sulfones of the formula $SO_2R^8$ where $R^8$ is the same as above;
nitrile;
$C_1$–$C_6$ acyl; alkoxycarbonylamino (carbamoyl) of the formula $NHCO_2R^8$ where $R^8$ is the same as above;
carboxylic acid, and esters, amides, and salts thereof;
aminomethyl of the formula $CH_2NR^9R^{10}$ where $R^9$ and $R^{10}$ may be the same or different, and may be hydrogen, $C_1$–$C_6$ alkyl, $C_2$–$C_6$ hydroxyalkyl, $C_2$–$C_6$ methoxyalkyl, $C_3$–$C_6$ cycloalkyl, or $C_5$–$C_{10}$ aryl, or $R^9$ and $R^{10}$ together may form a ring of 5 or 6 atoms;
carboxamides of the formula $CONR^9R^{10}$ where $R^9$ and $R^{10}$ are the same as above, or peptide conjugates thereof;
sulfonamides of the formula $SO_2NR^9R^{10}$ where $R^9$ and $R^{10}$ are the same as above; and —$CONR^9AB$, where:
$R^9$ is the same as above;
A is a divalent ligand comprising an alkyl or polyether moiety of 6–12 atoms, e.g., a straight chain or branched alkylene group containing 2 to 8 carbon atoms and optionally 1 or 2 divalent atoms which are each an oxygen or sulfur atom, with the proviso that there are at least 2 carbon atoms between a divalent atom and the $NR^9$ group and at least 2 carbon atoms between two divalent atoms when present; and B is a dimer-forming moiety which is joined to a first valence bond of the divalent ligand A, and which is symmetric about the divalent ligand A to the compound moiety joined to the other valence bond of the divalent ligand A;

Z is selected from the group consisting of: hydroxyl, and esters thereof; hydroxymethyl, and esters thereof; and amino, and carboxamides and sulfonamides thereof;

G is carbon or nitrogen (more specifically, G is CH or N when the bond between G and the adjacent heterocyclic dng carbon beadng the $R^3$ substituent is a single bond, and G is C per se when the bond between G and the adjacent heterocyclic ring carbon bearing the $R^3$ substituent is a double bond);

$R^1$ is hydrogen, halogen, or $C_1$–$C_4$ alkyl;

$R^2$ is hydrogen, halogen, or $C_1$–$C_4$ alkyl;

$R^3$, $R^4$, and $R^5$ may be the same or different, and are independently selected from hydrogen and methyl, subject to the proviso that the total number of methyl groups does not exceed two, or any two of such $R^3$, $R^4$, and $R^5$ substituents together may form a bridge including 1 to 3 carbon atoms;

$R^6$ is selected from the group consisting of:
hydrogen;
$C_1$–$C_6$ alkyl;
$C_3$–$C_6$ cycloalkyl;
aralkyl, wherein the alkyl moiety contains from one to six carbon atoms;
alkoxyalkyl containing $C_1$–$C_4$ alkoxy and $C_1$–$C_4$ alkyl moieties;
$C_1$–$C_4$ cyanoalkyl;
$C_1$–$C_4$ hydroxyalkyl;
aminocarbonylalkyl containing a $C_1$–$C_4$ alkyl moiety; and
$R_{12}COR^{13}$, where $R^{12}$ is $C_1$–$C_4$ alkylene, and $R^{13}$ is $C_1$–$C_4$ alkyl or $C_1$–$C_4$ alkoxy; and $R^7$ is hydrogen or fluorine,
subject to the proviso that $R^1$, $R^2$ and $R^7$ may be fluorine only when Z is —OH;
and pharmaceutically acceptable esters, salts, and other physiologically functional derivatives thereof.

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substituents of substituted alkyl groups may include any sterically acceptable substituents which are compatible with such alkyl groups and which do not preclude the efficacy of the diarylmethyl piperazine or diarylmethyl piperidine compound for its intended utility (examples of substituents for substituted alkyl groups include halo, amino, amido, $C_1$–$C_4$ alkyl, $C_1$–$C_4$ alkoxy, nitro, hydroxy, etc.); (iii) saturated alkyl groups as well as unsaturated alkyl groups, the latter including groups such as alkenyl-substituted alkyl groups (e.g., allyl, methallyl, propallyl, butenylmethyl, etc.), alkynyl-substituted alkyl groups, and any other alkyl groups containing sterically acceptable unsaturation which is compatible with such alkyl groups and which does not preclude the efficacy of the diarylmethyl piperazine or diarylmethyl piperidine compound for its intended utility; and (iv) alkyl groups including linking or bridge moieties, e.g., heteroatoms such as nitrogen, oxygen, sulfur, etc.

As used herein, in reference to the present invention, the term "aryl" also is intended to be broadly construed as referring to carbocyclic as well as heterocyclic aromatic groups and encompassing unsubstituted as well as substituted aryl groups, wherein the substituents of substituted aryl groups may include any sterically acceptable substituents which are compatible with such aryl groups and which do not preclude the efficacy of the diarylmethyl piperazine or diarylmethyl piperidine compound for its intended utility (examples of substituents for substituted aryl groups include halo, amino, amido, $C_1$–$C_4$ alkyl, $C_1$–$C_4$ alkoxy, nitro, hydroxy, hydroxyalkyl containing a $C_1$–$C_4$ alkyl moiety, etc.).

The term "peptide conjugates" as used herein in reference to the present invention is intended to be broadly construed to include all suitable peptide conjugate species; preferably, such conjugates are $C_2$–$C_{30}$ peptide conjugates.

By "physiologically functional derivative" is meant a pharmaceutically accepable salt, amide, ester or salt of an ester or amide of the compound of formula (I) or any other compound which, upon administration to the recipient, is capable of providing (directly or indirectly) the said compound of formula (I) or an active metabolite or residue thereof.

In a preferred aspect of the invention, novel compounds of the above-described formula (I) are subject to further provisos that at least one of $R^3$, $R^4$, and $R^5$ is methyl, and that when G is carbon (C or CH), $R^6$ is not aralkyl. Compounds of formula (I) subject to such provisos form a preferred subclass of novel compounds of the invention, and reference hereinafter to compounds of the invention will be understood to include such subclass as a preferred selection group from among compounds of the above formula (I).

In another preferred aspect of the invention, with reference to formula (I), when $R^6$ is hydroxyalkyl, the alkyl moiety preferably contains from 2 to 4 carbon atoms.

In enantiomeric forms, compounds of the invention include individual enantiomers of the compounds of formula (I) in single species form substantially free of the corresponding enantiomer, as well as in admixture (in mixtures of enantiomeric pairs and/or in mixtures of multiple enantiomer species).

In formula (I) as described above, Ar is a 5- or 6-member carbocyclic or heterocyclic aromatic ring having on a first ring carbon atom thereof a substituent Y and on a second ring carbon atom thereof a substituent $R^1$. Ar may also comprise a carbocyclic or heterocyclic aromatic ring of such type which is further substituted with a third sterically suitable ring substitutent $Y^1$ such as an organo substituent, e.g., a hydrocarbyl group such as $C_1$–$C_8$ alkyl. The aromatic ring of Ar may be any suitable 5- or 6- member aromatic ring, including for example 5-member rings such as thiophene rings, imidazole rings, thiazole rings, furan rings, and pyrrole rings, and 6-member rings of the formula:

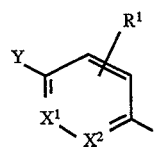

wherein:
$X^1$ and $X^2$ may be carbon or nitrogen, except that both may not simultaneously be nitrogen; and $R^1$ and Y are the same as described above.

Preferred 5-member ring species of formula (I) include thiazole ring species in which the thiazole ring is unsubstituted, and thiophene ring species in which the heterocyclic ring is either unsubstituted, monosubstituted (e.g., with a halo substituent or an aminocarbonyl substituent), or disubstituted (e.g., with both of the aforementioned mono-substituents).

A preferred class of compounds of the invention comprises diarylmethyl piperazine species thereof.

A preferred subclass of compounds of the present invention, wherein Ar is a substituted phenyl ring, which exhibits delta-opioid and/or mu-opioid agonist activity, includes compounds of the formula:

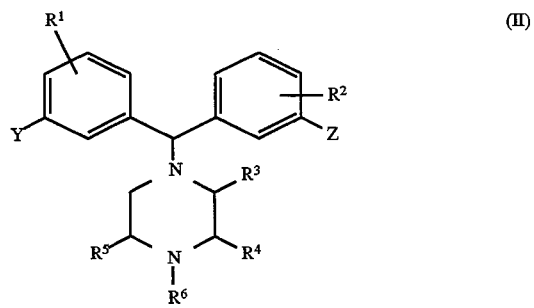

(II)

wherein:
Z=OH (including esters thereof);

$NH_2$ (including carboxamides and sulfonamides thereof); or $CH_2OH$ (including esters thereof);

Y=sulfoxides ($SOR^7$) where $R^7$ is $C_1$–$C_6$ alkyl or $C_3$–$C_6$ cycloalkyl; carboxamides ($CONR^8R^9$) where $R^8$ and $R^9$ may be the same or different, and may be hydrogen, $C_1$–$C_6$ alkyl, $C_2$–$C_6$ hydroxyalkyl, $C_2$–$C_6$ methoxyalkyl, $C_3$–$C_6$ cycloalkyl, $C_5$–$C_{10}$ aryl, or $C_2$–$C_{30}$ peptide conjugates, or $R^8$ and $R^9$ together may form a ring of 5 or 6 atoms; or sulfonamides ($SO_2N^8R^9$) where $R^8$ and $R^9$ are the same as above;

$R^1$, $R^2$=hydrogen or fluorine;

$R^3$, $R^4$, $R^5$=hydrogen or methyl, where the total number of methyl groups is one or two; and $R^6$=hydrogen, $C_1$–$C_6$ alkyl, $C_2$–$C_6$ methoxyalkyl, $C_3$–$C_6$ cycloalkyl, or $C_5$–$C_{10}$ aryl $C_1$–$C_4$ alkyl, or a pharmaceutically acceptable ester, salt, or other physiologically functional derivative thereof.

Under the sub-class of compounds of formula (II) set out above, especially preferred compounds, with respect to the various substituent groups, include compounds wherein:

Z=OH;

Y=carboxamides ($CONR^8R^9$) where $R^8$ and $R^9$ may be the same or different, and may be hydrogen, $C_1$–$C_6$ alkyl, $C_3$–$C_6$ cycloalkyl, or aryl, or $R^8$ and $R^9$ together may form a ring of 5 or 6 atoms, e.g., wherein:

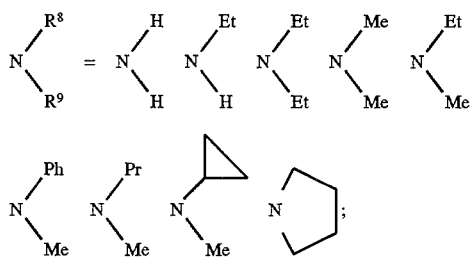

$R^1$, $R^2$=hydrogen;

$R^3$, $R^4$, $R^5$=hydrogen or methyl, where the total number of methyl groups is one or two; and $R^6$=hydrogen, $C_1$–$C_6$ alkyl, $C_2$–$C_6$ methoxyalkyl, $C_3$–$C_6$ cycloalkyl, or $C_5$–$C_{10}$ aryl $C_1$–$C_4$ alkyl.

Compounds of the above general formula (I) exhibit binding selectivity for receptor(s). Depending on the structure and stereospecificity of the particular formula (I) compounds, such compounds may exhibit binding ability to receptor(s) selected from the group consisting of delta receptors, mu receptors, kappa receptors, sigma receptors, and combinations of such receptors.

Various compounds within general formula (I) exhibit delta receptor agonist activity including mediating analgesia. Other compounds of such general formula exhibit delta receptor antagonist activity, as hereinafter more fully described. Still other compounds within the general formula exhibit mu receptor activity, and more particularly, in some instances, mixed mu receptor/delta receptor activity. For example, compounds of the preferred subclass of formula (II) within the broad scope of the general formula (I) have variously been found to exhibit mixed mu receptor/delta receptor activity.

Illustrative of compounds of the invention are the following compounds which have been synthesized and are identified below, by chemical name after an appertaining reference number, for ease of subsequent description.

1. (±)-3-((αR*)-α-((2S*,5R*)-4-Allyl-2,5-dimethyl-1-piperazinyl)-4-chlorobenzyl)phenol
2. (±)-3-((αR*)-α-((2R*,5S*)-4-Allyl-2,5-dimethyl-1-piperazinyl)-4-chlorobenzyl)phenol
3. -(α-(4-Allyl-1-piperazinyl)-4-propoxybenzyl)phenol
4. 4'-(α-(4-Allyl-1-piperazinyl)-3-hydroxybenzyl) acetophenone
5. trans-3-(α-(4-Allyl-2,3-dimethyl-1-piperazinyl)-4-chlorobenzyl)phenol
6. cis-3-(α-(4-Allyl-2,3-dimethyl-1-piperazinyl)-4-chlorobenzyl)phenoyl
7. (±)-3-((αR*)-α-((2S*,5R*)-4-Allyl-2,5-dimethyl-1-piperazinyl)-4-(methylsulfonyl) benzyl)phenol
8. trans-4-(α-(4-Allyl-2,5-dimethyl-1-piperazinyl)-3-hydroxybenzyl)benzyl alcohol
9. N-(4-((αR*)-α-((2S*,5R*)-4-Allyl-2,5-dimethyl-1-piperazinyl)-3-hydroxybenzyl)benzoyl)-L-phenylalanyl-L-leucine
10. (±)-4-((αR*)-α-((2R*,5S*)-4-Allyl-2,5-dimethyl-1-piperazinyl)-3-hydroxybenzyl)-N,N-dimethylbenzenesulfonamide
11. (±)-trans-3-(4-((Dimethylamino)sulfonyl)-α-(2,4,5,-trimethyl-1-piperazinyl) benzyl)phenol
12. (±)-trans-3-(4-(Methylsulfonyl)-α-(3,4,5-trimethyl-1-piperazinyl)benzyl)phenol
13. (±)-trans-3-(4-((Diethylamino)sulfonyl)-α-(2,4,5-trimethyl-1-piperazinyl) benzyl)phenol
14. (±)-trans-3-α-(4-(Cyclopropylmethyl)-2,5-dimethyl-1-piperazinyl)-4-((dimethylamino)sulfonyl) benzyl) phenol
15. (±)-4-((αR*)-α-((2R*,5S*)-4-Allyl-2,5-dimethyl-1-piperazinyl)-3-hydroxybenzyl)-N,N-diethylbenzenesulfonamide
16. (±)-N-(4-((αR*)-α-((2S*,5R*)-4-Allyl-2,5-dimethyl-1-piperazinyl)-3-hydroxybenzyl)benzoyl) glycylglycine
17. (±)-4-((αR*)-α-((2S*,5R*)-4-Allyl-2,5-dimethyl-1-piperazinyl)-3-hydroxybenzyl)-N,N-dimethylbenzenesulfonamide
18. (±)-trans-3-(α-(4-Allyl-2,5-dimethyl-1-piperazinyl)-4-chloro-3-methylbenzyl)phenol
19. trans-3-α-(4-Allyl-2,5-dimethyl-1-piperazinyl)-2-methylbenzyl)phenol
20. (±)-Methyl 4-α-(trans-4-allyl-2,5-dimethyl-1-piperazinyl)-3-hydroxylbenzyl)benzoate
21. (±)-4-((αR*)-α-((2R*,5S*)-4-Allyl-2,5-dimethyl-1-piperazinyl)-3-hydroxybenzyl)-N,N-diethylbenzamide
22. (±)-4-((αR*)-α-((2S*,5R*)-4-Allyl-2,5-dimethyl-1-piperazinyl)-3-hydroxybenzyl)-N,N-diethylbenzamide
23. (±)-4-α-(trans-4-Allyl-2,5-dimethyl-1-piperaziny;)-3-hydroxybenzyl)-N-isopropylbenzamide
24. (±)-3-α-(trans-4-Allyl-2,5-dimethyl-1-piperazinyl)-4-methylbenzyl)phenol
25. 3-(α-(4-Allyl-3-methyl-1-piperazinyl)-4-methylbenzyl)phenol
26. (±)-4-((αR*)-α-((2S*,5R*)-2,5-Dimethyl-4-propyl-1-piperazinyl)-3-hydroxybenzyl)-N,N-diethylbenzenesulfonamide
27. (±)-4-((αR*)-α-((2S*,5R*)-2,5-Dimethyl-1-piperazinyl)-3-hydroxybenzyl)-N,N-diethylbenzenesulfonamide
28. (±)-N,N-Diethyl-4-((αR*)-α-((2R*,5S*)-4-ethyl-2,5-dimethyl-1-piperazinyl)-3-hydroxybenzyl) benzenesulfonamide
29. (±)-4-((αR*)-α-((2R*,5S*)-2,5-Dimethyl-1-piperazinyl)-3-hydroxybenzyl)-N,N-diethylbenzenesulfonamide
30. (±)-4-((αR*)-((2S*,5R*)-2,5-Dimethyl-1-piperazinyl)-3-hydroxybenzyl)-N,N- diethylbenzenesulfonamide
31. (±)-4-((αR*)-α-((2S*,5R*)-4-Allyl-2,5-dimethyl-1-piperazinyl)-3-hydroxybenzyl)-N,N-diisopropylbenzenesulfonamide
32. 3-(α-(4-Allyl-2-methyl-1-piperazinyl)-4-methylbenzyl)phenol
33. (±)-3-((αR*)-α-((2S*,5R*)-4-Allyl-2,5-dimethyl-1-piperazinyl)-4-(methylsulfonyl) benzyl)phenol
34. (±)-4-((αR*)-α-((2R*,5S*)-4-Allyl-2,5-dimethyl-1-piperazinyl)-3-hydroxybenzyl)-N,N-diisopropylbenzenesulfonamide
35. (±)-4-((αR*)-α-((2S*,5R*)-4-Butyl-2,5-dimethyl-1-piperazinyl)-3-hydroxybenzyl)-N,N-diethylbenzenesulfonamide
36. (±)-4-((αR*)-((2S*,5R*)-4-Allyl-2,5-dimethyl-1-piperazinyl)-3-hydroxybenzyl)-N,N- dipropylbenzenesulfonamide
37. cis-4-(α-(4-((Z)-2-Butenyl)-3,5-dimethyl-1-piperazinyl)-3-hydroxybenzyl)-N,N-diethylbenzamide
38. (±)-N,N-Diethyl-4-((αR*)-α-((2S*,5R*)-4-ethyl-2,5-dimethyl-1-piperazinyl)-3-hydroxybenzyl) benzenesulfonamide
39. (±)-3-((αR*)-α-((2R*,5S*)-4-Allyl-2,5-dimethyl-1-piperazinyl)-4-bromobenzyl)phenol 40. (±)-3-((αR*)-α-((2S*,5R*)-4-Allyl-2,5-dimethyl-1-piperazinyl)-4-bromobenzyl)phenol
41. (±)-3-((αR*)-α-((2S*,5R*)-4-Allyl-2,5-dimethyl-1-piperazinyl)(5-methyl-2-pyridyl)methyl)phenol
42. 4-((αS)-α-((2S,5S)-4-Allyl-2,5-dimethyl-1-piperazinyl)-3-hydroxybenzyl)-N-ethyl-N-methylbenzamide
43. (±)-4-(α-(trans-4-(2-Chloroallyl)-2,5-dimethyl-1-piperazinyl)-3-hydroxybenzyl)-N,N-diethylbenzenesulfonamide
44. (±)-4-((αR*)-α-((2S*,5R*)-4-((E)-2-Butenyl-2,5-dimethyl-1-piperazinyl)-3-hydroxybenzyl)-N,N-diethylbenzenesulfonamide
45. (±)-N,N-Diethyl-4-((αR*)-3-hydroxy-α-((2S*,5R*)-2,4,5-trimethyl-1-piperazinyl)benzyl)benzamide
46. (±)-3-((αR*)-α-((2S*,5R*)-4-Allyl-2,5-dimethyl-1-piperazinyl)-4-((1-pyrrolidinyl)sulfonyl)benzyl)phenol
47. (±)-3-((αR*)-α-((2S*,5R*)-4-Allyl-2,5-dimethyl-1-piperazinyl)benzyl)phenol
48. (±)-4-((αR*)-α-((2S*,5R*)-4-Allyl-2,5-dimethyl-1-piperazinyl)-3-hydroxybenzyl)-N-methylbenzenesulfonanilide
49. (±)-4-((αR*)-α-((2R*,5S*)-2,5-Dimethyl-4-(2-propynyl)-1-piperazinyl)-3-hydroxybenzyl)-N,N-diethylbenzamide
50. N,N-Diethyl-4-(3-hydroxy-α-(cis-3,4,5-trimethyl-1-piperazinyl)benzyl)benzamide
51. (±)-N,N'-Dodecamethylenebis(4-((R*)-α-((2S*,5R*)-4-allyl-2,5-dimethyl-1-piperazinyl)-3-hydroxybenzyl) benzamide)
52. (±)-3-((αR*)-α-((2S*,5R*)-4-Allyl-2,5-dimethyl-1-piperazinyl)(6-methyl-3-pyridyl)methyl)phenol
53. (±)-4-((αR*)-α-((2S*,5R*)-4-Allyl-2,5-dimethyl-1-piperazinyl)-3-hydroxybenzyl)benzoic acid
54. N,N'-Hexamethylenebis(4-((R*)-α-((2R*,5S*)-4-allyl-2,5-dimethyl-1-piperazinyl)-3-hydroxybenzyl) benzamide)
55. N,N'-Octamethylenebis(4-((αR*)-α-((2 R*, 5S*)-4-allyl-2,5-dimethyl-1-piperazinyl)-3-hydroxybenzyl) benzamide)
56. N,N'-Hexamethylenebis(4-((R*)-α-((2S*,5R*)-4-allyl-2,5-dimethyl-1-piperazinyl)-3- hydroxybenzyl) benzamide)
57. (±)-4-((αR*)-α-((2S*,5R*)-4-Allyl-2,5-dimethyl-1-piperazinyl)-3-hydroxybenzyl)-N-(2-((2-amino-2-oxoethyl)amino)-2-oxoethyl)benzamide
58. N,N'-Decamethylenebis(4-((R*)-α-((2S*,5R*)-4-allyl-2,5-dimethyl-1-piperazinyl)-3-hydroxybenzyl) benzamide)
59. N,N'-Dodecamethylenebis(4-((R*)-α-((2R*,5S*)-4-allyl-2,5-dimethyl-1-piperazinyl)-3-hydroxybenzyl) benzamide)
60. N,N'-((Ethylenedioxy)diethylene)bis(4-((R*)-α-( (2S*,5R*)-4-allyl-2,5-dimethyl-1-piperazinyl)-3-hydroxybenzyl)benzamide)
61. N,N-Diethyl-4-(3-hydroxy-(α)-α-((2S,5S)-2,4,5-trimethyl-1-piperazin-yl)benzyl)benzamide
62. (±)-4-((αR*)-α-((2S*,5R*)-2,5-Dimethyl-4-propyl-1-piperazinyl)-3-hydroxybenzyl)-N,N-diethylbenzamide
63. N,N-Diethyl-4-(3-hydroxy-(αS)-α-((2R,5R)-2,4,5-tri methyl-1-piperazinyl) benzyl)benzamide
64. N,N-Diethyl-4-(3-hydroxy-(αR)-α-((2R,5R)-2,4,5-tdmethyl-1-piperazinyl) benzyl)benzamide
65. 3-((αS)-4-(Piperdinocarbonyl)-α-((2S,5S)-2,4,5-trimethyl-1-piperazinyl) benzyl)phenol
66. 3-((αR)-4-(Piperidinocarbonyl)-α-((2S,5S)-2,4,5-trimethyl-1-piperazinyl) benzyl)phenol
67. 3-((αR)-4-(1-Pyrrolidinylcarbonyl)-α-((2S,5S)-2,4,5-trimethyl-1-piperazinyl)benzyl)phenol
68. 3-((αS)-4-(1-Pyrrolidinylcarbonyl)-α-((2S,5S)-2,4,5-trimethyl-1-piperazinyl)benzyl)phenol
69. N-Ethyl-4-((αR)-3-hydroxy-α-((2S,5S)-2,4,5-trimethyl-1-piperazinyl)benzyl)-N-methylbenzamide
70. N-Ethyl-4-((αS)-3-hydroxy-α-((2S,5S)-2,4,5-trimethyl-1-piperazinyl)benzyl)-N-methylbenzamide
71. 3-((αR)-4-(Piperidinocarbonyl)-α-((2R,5R)-2,4,5-trimethyl-1-piperazinyl) benzyl)phenol
72. (±)-4-((αR*)-α-((2S*,5R*)-4-Allyl-2,5-dimethyl-1-piperazinyl)-3-hydroxybenzyl)-N-(2-hydroxyethyl)-N-methylbenzamide
73. 3-((αS)-4-(1-Pyrrolidinylcarbonyl)-α-((2R,5R)-2,4,5-trimethyl-1-piperazinyl) benzyl)phenol
74. 3-((αR)-4-(1-Pyrrolidinylcarbonyl)-α-((2R,5R)-2,4,5-trimethyl-1-piperazinyl) benzyl)phenol
75. N-Ethyl-4-((αR)-3-hydroxy-α-((2R,5R)-2,4,5-trimethyl-1-piperazinyl)benzyl)-N-methylbenzamide
76. N-Ethyl-4-((αS)-3-hydroxy-α-((2R,5R)-2,4,5-trimethyl-1-piperazinyl)benzyl)-N-methylbenzamide
77. (±)-4-(α-(trans-2,5-Dimethyl-4-(2-methylallyl)-1-piperazinyl)-3-hydroxybenzyl)-N,N-diethylbenzamide
78. (±)-1-(4-((αR*)-α-((2R*,5S*)-4-Allyl-2,5-dimethyl-1-piperazinyl)-3-hydroxybenzyl)benzoyl)pyrrolidine
79. (±)-1-(4-((αR*)-α-((2R*,5S*)-4-Allyl-2,5-dimethyl-1-piperazinyl)-3-hydroxybenzyl)benzoyl)-4-methylpiperazine
80. (±)-4-((αR*)-α-((2S*,5R*)-4-Allyl-2,5-dimethyl-1-piperazinyl)-3-aminobenzyl) N,N-dimethylbenzamide
81. (±)-4-(αR*)-α-((2 R*, 5S*)-4-Allyl-2,5-dimethyl-1-piperazinyl)-3-hydroxybenzyl)-N-ethyl-N-methylbenzamide
82. (±)-4-((αR*)-α-((2R*,5S*)-4-Allyl-2,5-dimethyl-1-piperazlnyl)-3-hydroxybenzyl)-N-methyl-N-phenylbenzamide
83. (±)-4-((αR*)-α-((2 R*, 5S*)-4-Allyl-2,5-dimethyl-1-piperazinyl)-3-hydroxybenzyl)-N-ethylbenzamide
84. (±)-4-((αR*)-α-((2S*,5R*)-4-Allyl-2,5-dimethyl-1-piperazinyl)-3-hydroxybenzyl)-N-ethylbenzamide
85. (±)-4-((αR*)-α-((2S*,5R*)-4-Allyl-2,5-dimethyl-1-piperazinyl)-3-hydroxybenzyl)-N-ethyl-N-methylbenzamide
86. (±)-4-((αR*)-α-((2S*,5R*)-4-Allyl-2,5-dimethyl-1-piperazinyl)-3hydroxybenzyl)-N-methyl-N-phenylbenzamide
87. (3S)-1-(4-((αR*)-α-((2S*,5R*)-4-Allyl-2,5-dimethyl-1-piperazinyl)-3-hydroxybenzyl)benzoyl)-4-methylpiperazine
88. (±)-1-(4-((αR*)-α-((2S*,5R*)-4-Allyl-2,5-dimethyl-1-piperazinyl)-3-hydroxybenzyl)benzoyl)pyrrolidine
89. (±)-4-((αR*)-α-((2S*,5R*)-4-Allyl-2,5-dimethyl-1-piperazinyl)-3-(hydroxymethyl)benzyl)-N,N-diethylbenzamide
90. (±)-(R*,R*)-N,N-Diethyl-4-(3-hydroxy-α-(1,2,5,6-tetrahydro-1,3,6-trimethyl-4-pyridyl)benzyl) benzamide
91. (±)-3-((αR*)-α-((2R*,5S*)-4-Allyl-2,5-dimethyl-1-piperazinyl)-4-((1-pyrrolidinyl)sulfonyl)benzyl)phenol 92. N-(4-((αR*)-α-((2R*,5S*)-4-Allyl-2,5-dimethyl-1-piperazinyl)-3-hydroxybenzyl)benzoyl)-L-phenylalanyl-L-leucine
93. (±)-4-((αR*)-α-((2S*,5R*)-4-Allyl-2,5-dimethyl-1-piperazinyl)-3-hydroxybenzyl)-N-cyclopropyl-N-methylbenzamide
94. (±)-4-((αR*)α((2S*,5R*)-4-Allyl-2,5-dimethyl-1-piperazinyl)-3-hydroxybenzyl)-N-methyl-N-propylbenzamide
95. (±)-4-((αR*)-α-((2S*, 5R*)-4-Allyl-2,5-dimethyl-1-piperazinyl)-3-hydroxybenzyl)-N-butyl-N-methylbenzamide
96. (±)-4-((αR*)-α-((2S*,5R*)-4-Allyl-2,5-dimethyl-1-piperazinyl)-3-hydroxybenzyl)-N,N-dimethylbenzamide
97. (±)-3-((αR*)-α-((2R*,5S*)-4-Allyl-2,5-dimethyl-1-piperazinyl)-4-(((benzyloxy)carbonyl)amino)benzyl)phenol
98. (±)-4-((α-R*)-3-Acetoxy-α-((2S*,5R*)-4-allyl-2,5-dimethyl-1-piperazinyl)benzyl)-N,N-diethylbenzamide
99. (±)-3-((αR*)-α-((2R*,5S*)-4-Allyl-2,5-dimethyl-1-piperazinyl)-4-(diethylcarbamoyl)benzyl)phenyl benzoate
100. (±)-3-((αR*)-α-((2R*,5S*)-4-Allyl-2,5-dimethyl-1-piperazinyl)-4-(diethylcarbamoyl) benzyl)phenyl-N,N-dimethylcarbamate
101. (±)-3-((αR*)-α((2S*,5R*)-4-Allyl-2,5-dimethyl-1-piperazinyl)-4-(diethylcarbamoyl)benzyl)phenyl benzoate
102. (±)-trans-4-(α-(4-Allyl-2,5-dimethyl-1-piperazinyl)-3-formamidobenzyl)-N,N-dimethylbenzamide
103. (±)-4-((αR*)-α-((2S*,5R*)-4-Allyl-2,5-dimethyl-1-piperazinyl)-2,4-difluoro-3-hydroxybenzyl)-N,N-diethylbenzamide
104. N,N'-Octamethylenebis(4-((R*)-α-((2S*,5R*)-4-allyl-2,5-dimethyl-1-piperazinyl)-3-hydroxybenzyl)benzamide)
105. (±)-trans-3-(α-(4-Allyl-2,5-dimethyl-1-piperazinyl)-4-chloro-2-methylbenzyl)phenol
106. trans-3-(α-(4-Allyl-2,5-dimethyl-1-piperazinyl)-3-methylbenzyl)phenol
107. 4-(α-(trans-2,5-Dimethyl-4-(2-methylallyl)-1-piperazinyl)-3-hydroxybenzyl)-N,N-diethylbenzenesulfonamide
108. (±)-3-((αR*)-α-((2S*,5R*)-4-Allyl-2,5-dimethyl-1-piperazinyl)-4-(diethylcarbamoyl)benzyl)phenyl dimethylcarbamate
109. (±)-4-((αR*)-α-((2R*,5S*)4-Allyl-2,5-dimethyl-1-piperazinyl)-2,4-difluoro-3-hydroxybenzyl)-N,N-diethylbenzamide
110. (±)-4-((αR* or αS*)-α-((2R*,5S*)-4-Allyl-2,5-dimethyl-1-piperazinyl)-3-(benzenesulfonamido)benzyl)-N,N-diethylbenzamide
111. (±)-4-α-(trans-4-Allyl-2,5-dimethyl-1-piperazinyl)-2-fluoro-5-hydroxybenzyl)-N,N-diethylbenzamide
112. (±)-3-((αR*)-α-((2R*,5S*)-4-Allyl-2,5-dimethyl-1-piperazinyl)benzyl)phenol
113. (±)-4-((αR*)-α-((2S*,5R*)-4-Allyl-2,5-dimethyl-1-piperazinyl)-3-hydroxybenzyl)benzonitrile
114. (±)-4-((αR*)-α-((2R*,5S*)-4-Allyl-2,5-dimethyl-1-piperazinyl)-3-hydroxybenzyl)benzoic acid
115. (±)-3-((αR*)-α-((2S*,5R*)-4-Allyl-2,5-dimethyl-1-piperazinyl)-3-hydroxbenzyl)benzamide
116. (±)-3-((αR*)-α-((2R*,5S*)-4-Allyl-2,5-dimethyl-1-piperazinyl)-4-diethylcarbamoyl)benzyl)phenyl pivalate
117. cis-4-(α-(3,5-Dimethyl-4-(methylallyl)-1-piperazinyl)-3-hydroxybenzyl)-N,N-diethylbenzamide
118. (αR,2R*,5R*)-4-(α-(4-Allyl-2,5-dimethyl-1-piperazinyl)-3-hydroxybenzyl)-N-ethyl-N-methylbenzamide, and (αS,2R*,5R*)-4-(α-(4-Allyl-2,5-dimethyl-1-piperazinyl)-3-hydmxybenzyl)-N-ethyl-N-methylbenzamide
119. (±)-cis-4-(α-(4-Allyl-3,5-dimethyl-1-piperazinyl)-3-hydmxybenzyl)-N,N-diethylbenzamide
120. (±)-4-((αR*)-α-((2R*,5S*)-4-Allyl-2,5-dimethyl-1-piperazinyl)-3-hydroxybenzyl)benzonitrile
121. (±)-(R*,S*)-N,N-Diethyl-4-(3-hydroxy-eF(1,2,5,6-tetrahydro-1,3,6-trimethyl-4-pyridyl)benzyl)benzamide
122. (±)-4-((αR*)-α-((2S*,5R*)-4-Allyl-2,5-dimethyl-1-piperazinyl)-3-hydroxybenzyl)-N-ethyl-N-(2-hydroxyethyl)benzamide
123. (±)-4-((αR*)-α-((2S*,5R*)-4-Allyl-2,5-dimethyl-1-piperazinyl)-3-hydroxybenzyl)-N-(5-hydroxypentyl)benzamide
124. (±)-5-((αR*)-α-((2S*,5R*)-4-Allyl-2,5-dimethyl-1-piperazinyl)-3-hydroxybenzyl)-3-bromo-N,N-diethyl-2-thiophenecarboxamide
125. (±)-5-((αR*)-α-((2S*,5R*)-4-Allyl-2,5-dimethyl-1-piperazinyl)-3-hydroxybenzyl)-N,N-diethyl-3-thiophenecarboxamide
126. (±)-5-((αR*)-α-((2S*,5R*)-4-Allyl-2,5-dimethyl-1-piperazinyl)-3-hydroxybenzyl)-N,N-diethyl-2-thiophenecarboxamide
127. (±)-3-((R*)-((2S*,5R*)-4-Allyl-2,5-dimethyl-1-piperazinyl)(2-thienyl) methyl)phenol
128. 3-((α*)-α-((2R*,5S*)-2,5-Dimethyl-4-ethyl-1-piperazinyl)benzyl)phenol
129. (±)-3-((αR*)-α-((2R*,5S*)-2,5-Dimethyl-4-propyl-1-piperazinyl)benzyl)phenol
130. (±)-N,N-Diethyl-4-((αR*)-3-hydroxy-α-((2S,5R*)-4-(2-methoxyethyl)-2,5-dimethyl-1-piperazinyl)benzyl)benzamide
131. (±)-3-((R*)-((2S*,5R*)-4-Allyl-2,5-dimethyl-1-piperazinyl)(2-thiazolyl)methyl)phenol
132. (±)-3-((αR*)-α-((2R*,5S*)-4-Allyl-2,5-dimethyl-1-piperazinyl)-4-fluorobenzyl)phenol
133. (±)-3-((αR*)-α-((2S*,5R*)-4-Allyl-2,5-dimethyl-1-piperazinyl)-4-fluorobenzyl)phenol
134. (±)-4-((αR*)-α-((2S*,5R*)-2,5-Dimethyl-4-phenethyl-1-piperazinyl)-3-hydroxybenzyl)-N,N-diethylbenzamide
135. (±)-3-((αR*)-α-((2R*,5S*)-2,5-Dimethyl-4-phenethyl-1-piperazinyl)benzyl)phenol
136. (±)-3-((αR*)-α-((2R*,5S*)-2,4,5-Trimethyl-1-piperazinyl)benzyl)phenol
137. (±)-3-((R*)-((2S*,5R*)-4-Allyl-2,5-dimethyl-1-piperazinyl)(4-bromo-2-thienyl)methyl)phenol
138. (±)-3-((R*)-((2S*,5R*)-4-Allyl-2,5-dimethyl-1-piperazinyl)(2-thienyl) methyl)phenol
139. (±)-4-((αR*)-α-((2S*,5R*)-2,5-Dimethyl-4-(2-propynyl)-1-piperazinyl)-3-hydroxybenzyl)-N,N-diethylbenzamide
140. (±)-5-((R*)-α-((2S*,5R*)-4-Allyl-2,5-dimethyl-1-piperazinyl)-3-hydroxybenzyl)-N,N-diethyl-2-thiophenecarboxamide
141. (±)-3-((R*)-((2S*,5R*)-4-Allyl-2,5-dimethyl-1-piperazinyl)(4-bromo-2-thienyl)methyl)phenol
142. (±)-3-((αS)-α-((2S,5R)-4-Allyl-2,5-dimethyl-1-piperazinyl)benzyl)phenol
143. (±)-4-((αR*)-α-((2S*,5R*)-4-(Carbamoylmethyl)-2,5-dimethyl-1-piperazinyl)-3-hydroxybenzyl)-N,N-diethylbenzamide 144. (±)-Methyl 2-((2R*,5S*)-4-((αR*)-3-hydroxybenzhydryl)-2,5-dimethyl-1-piperazinyl)acetate
145. (±)-3-((R*)-((2R*,5S*)-4-Allyl-2,5-dimethyl-1-piperazinyl)-3-pyridyl-methyl)phenol
146. (±)-3-((R*)-((2S*,5R*)-4-Allyl-2,5-dimethyl-1-piperazinyl)-3-pyridyl-methyl)phenol
147. (±)-5-((αR*)-α-((2R*,5S*)-4-Allyl-2,5-dimethyl-1-piperazinyl)-3-hydroxybenzyl)-3-bromo-N,N-diethyl-2-thiophenecarboxamide
148. (±)-3-((αR*)-α-((2S*,5R*)-4-Allyl-2,5-dimethyl-1-piperazinyl)-3-hydroxybenzyl)-N,N-diethylbenzamide
149. (±)-3-((αR*)-α-((2R*,5S*)-4-Allyl-2,5-dimethyl-1-piperazinyl)-3-hydroxybenzyl)-N,N-diethylbenzamide
150. (±)-3-((R*)-((2S*,5R*)-4-Allyl-2,5-dimethyl-1-piperazinyl)(3-thienyl)methyl)phenol
151. (±)-3-((R*)-((2R*,5S*)-4-Allyl-2,5-dimethyl-1-piperazinyl)(3-thienyl) methyl)phenol
152. (−)-3-((R)-((2S,5R)-4-Allyl-2,5-dimethyl-1-piperazinyl)(2-thienyl)methyl)phenol
153. (±)-4-((αR*)-α-((2S*,5R*)-4-(Cyanomethyl)-2,5-dimethyl-1-piperazinyl)-3-hydroxybenzyl)-N,N-diethylbenzamide
154. (+)-3-((R*)-((2S*,5R*)-4-Allyl-2,5-dimethyl-1-piperazinyl)-3-pyridinylmethyl)phenol
155. (+)-3-((αR)-α-((2S,5R)-4-Allyl-2,5-dimethyl-1-piperazinyl)-3-hydroxybenzyl)-N,N-diethylbenzamide
156. (+)-3-((R*)-((2R*,5S*)-4-Allyl-2,5-dimethyl-1-piperazinyl)-3-pyridinylmethyl)phenol
157. (±)-5-((αR*)-α-((2S*,5R*)-4-Allyl-2,5-dimethyl-1-piperazinyl)-3-hydmxybenzyl)-N,N-diethyl-3-pyridinecarboxamide
158. (−)-3-((S)-((2R,5S)-4-Allyl-2,5-dimethyl-1-piperazinyl)(3-thienyl)-methyl)phenol
159. (±)-5-((αR*)-α-((2R*,5S*)-4-Allyl-2,5-dimethyl-1-piperazinyl)-3-hydroxybenzyl)-N,N-diethyl-3-pyridinecarboxamide
160. (+)-4-((αR)-α-((2S,5R)-4-Allyl-2,5-dimethyl-1-piperazinyl)-3-hydroxybenzyl)-N,N-diethylbenzamide
161. (+)-N,N-Diethyl-4-(3-hydroxy-(αS)-α-((2S,5S)-2,4,5-trimethyl-1-piperazinyl)benzyl)benzamide
162. 3-((αS)-4-(Piperidinocarbonyl)-α-((2R,5R)-2,4,5-trimethyl-1-piperazinyl)benzyl)phenol
163. (±)-5-((αR*)-α-((2R*,5S*)-4-Allyl-2,5-dimethyl-1-piperazinyl)-3-hydroxybenzyl)-N,N-diethyl-3-thiophenecarboxamide
164. (±)-4-((αR*)-α-((2S*,5R*)-4-Allyl-2,5-dimethyl-1-piperazinyl)-3-hydroxybenzyl)-N,N-diethylbenzenesulfonamide
165. (±)-4-((αR*)-α-((2R*,5S*)-2,5-Dimethyl-4-propyl-1-piperazinyl)-3-hydroxybenzyl)-N,N-diethylbenzenesulfonamide
166. (±)-4-((αR*)-α-((2R*,5S*)-2,5-Dimethyl-1-piperazinyl)-3-hydroxybenzyl)-N,N-diethylbenzenesulfonamide
167. (±)-4-((αR*)-α-((2R*,5S*)-4-Allyl-2,5-dimethyl-1-piperazinyl)-3-hydroxybenzyl)-N,N-dipropylbenzenesulfonamide
168. (±)-4-((αR*)-α-((2R*,5S*)-4-Butyl-2,5-dimethyl-1-piperazinyl)-3-hydroxybenzyl)-N,N-diethylbenzenesulfonamide
169. (±)-3-((αR*)-G-((2R*,5S*)-4-Allyl-2,5-dimethyl-1-piperazinyl)(5-methyl-2-pyridyl)methyl)phenol
170. (±)-4-((αR*)-α-((2R*,5S*)-4-((E)-2-Butenyl)-2,5-dimohyl-1-piperazinyl)-3-hydroxybenzyl)-N,N-diethylbenzenesulfonamide
171. (±)-4-((αR*)-α-((2R*,5S*)-4-Allyl-2,5-dimethyl-1-piperazinyl)-3-hydroxybenzyl)-N-methylbenzenesulfonanilide
172. (±)-3-((αR*)-α-((2R*,5S*)-4-Allyl-2,5-dimethyl-1-piperazinyl)(6-methyl-3-pyridyl)methyl)phenol
173. (±)-4-((αR*)-α-((2R*,5S*)-4-Allyl-2,5-dimethyl-1-piperazinyl)-3-(hydroxymethyl)benzyl)-N,N-diethylbenzamide
174. (±)-4-((αR*)-G-((2R*,5S*)-4-Allyl-2,5-dimethyl-1-piperazinyl)-3-aminobenzyl)-N,N-diethylbenzamide
175. (±)-3-((R*)-((2R*,5S*)-4-Allyl-2,5-dimethyl-1-piperazinyl)(2-thiazolyl)methyl)phenol
176. (±)-3-((αR*)-α-((2S*,5R*)-4-Allyl-2,5-dimethyl-1-piperazinyl)-3-hydroxybenzyl)-N-methyl-N-propylbenzamide
177. (±)-3-((αR*)-α-((2S*,5R*)-4-Allyl-2,5-dimethyl-1-piperazinyl)-3-hydroxybenzyl)-N-ethyl-N-methylbenzamide
178. (±)-3-((αR*)-α-((2S*,5R*)-4-Allyl-2,5-dimethyl-1-piperazinyl)-3-hydroxybenzyl)-N,N-dimethylbenzamide
179. (±)-3-((αR*)-α-((2S*,5R*)-4-Allyl-2,5-dimethyl-1-piperazinyl)-3-hydroxybenzyl)-N-ethylbenzamide
180. (±)-3-((αR*)-α-((2S*,5R*)-4-Allyl-2,5-dimethyl-1-piperazinyl)-3-hydroxybenzyl)-N-cyclopropyl-N-methylbenzamide
181. (±)-3-((αR*)-4-(1-Pyrrolidinylcarbonyl)-α-((2S*,5R*)-4-allyl-2,5-dimethyl-1-piperazinyl)benzyl)phenol Compounds of the above general formula (I) and the illustrative compounds (1–181) listed thereunder have utility as exogenous receptor combinant compounds, i.e., compounds useful for binding with a receptor, such as delta receptor, mu receptor, sigma receptor, kappa receptor, or two or more of such receptors. The combinant compound may be a conjugate in an agonist/antagonist pair which may be employed for transductional assay of neurotransmitter function in appertaining cellular or differentiated tissue systems. In addition to receptor assay, differential binding, and specificity applications for cellular, histological, and corporeal monitoring and assessment purposes, the compounds of the above general formula (I) variously exhibit specific bioactivity characteristics rendering them useful as treatment agents for various physiological and pathological conditions.

The compounds of the above general formula (I) include various agonist species mediating analgesia and agonist species useful for the treatment of diarrhea, depression, urinary incontinence, mental illness, cough, lung edema, gastrointestinal disorders, spinal injury, and drug addiction.

The compounds of the above general formula (I) also include antagonist species which as mentioned are useful as agonist conjugates for neurotransmitter assay applications as well as antagonist species with utility for treatment of alcohol abuse, and drug overdose of opiate or other agonist species.

In addition, to the extent that degeneration or dysfunction of opioid receptors is present or implicated in a disease state involving tissue or discrete cellular loci, isotopically labeled versions of opioid compounds of the present invention find utility in diagnostic and imaging applications, e.g., diagnostic techniques involving positron emission tomography (PET) scans of the brain.

As mentioned hereinabove, opioid receptor sites are loci on cells which recognize and bind opiate and opioid drugs, which in turn can affect (initiate/block) biochemical/physiological sequences (transduction).

In the case of the non-peptide opioid agents contemplated by the present invention, the structure/activity pattern for the various compounds within the general formula (I) is highly diverse, and subtle differences such as changes in stereochemistry can result in different transductional effects. Thus, formula (I) comprehends agonist species as well as antagonist species.

Further, empirical determinations utilizing compounds of the present invention provide strong evidence of the existence of a delta receptor subtype in the brain that is different from the delta receptor in the mouse vas deferens.

In consequence of the existence of such delta receptor subtypes, other receptor binding assays or screening techniques, e.g., analgesia screening tests, may in some instances be employed in preference to the mouse vas deferens assay as a predictor of agonist or antagonist activity for specific compounds of the present invention.

In the case of mu receptor agonists, activity is generally distinguished and measured by activity in the electrically stimulated guinea pig ileum assay.

Particular preferred compounds from the above-listed illustrative compounds (1–181) include compounds 7, 16, 29, 37, 50, 61, 64, 67, 70, 107, 112, 115, 122, 124, 127, 142, 148, 150, 152, 153, 154, 155, 164, 175, 176, 177, 178, 179, 180, 181, and pharmaceutically acceptable esters, salts, and other physiologically functional derivatives thereof.

By way of specific examples in consideration of the compounds broadly described hereinabove, Table I below shows the chemical structure of three illustrative compounds of the present invention, denoted herein as compounds "A", "B", and "C".

TABLE I

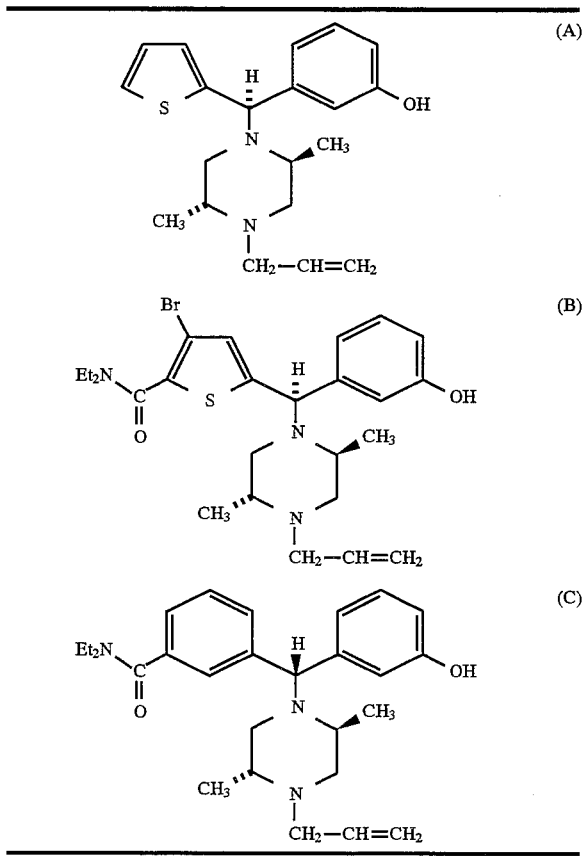

These compounds A, B, and C are highly selective opioid receptor ligand species.

Compound A, 3-((R)-((2S,5R)-4-allyl-2,5-dimethyl-1-piperazinyl)(2-thienyl)-methyl)phenol, is a predominantly mu receptor agonist and may be utilized for example in mediating surgical analgesia.

Compound B, 5-(($\alpha$R*)-$\alpha$-((2S*,5R*)-4-allyl-2,5-dimethyl-1-piperazinyl)-3-hydroxybenzyl)-3-bromo-N,N-diethyl-2-thiophenecarboxamide, is a predominantly delta receptor agonist, having utility in mediating epidural analgesia.

Compound C, 3-(($\alpha$R)-$\alpha$-((2S,5R)-4-allyl-2,5-dimethyl-1-piperazinyl)-3-hydroxybenzyl)-N,N-diethylbenzamide, is a mixed mu/delta opioid agonist with analgesic utility, especially in mediating surgical and/or post-operative analgesia.

The above compounds desirably are prepared in substantially pure enantiomer form, with an enantiopurity of at least 90% enantiomeric excess (EE), preferably at least 95% EE, more preferably at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

The mixed mu/delta receptor character of compound C and of other and related compounds within the scope of the present invention entails a substantial potential advantage over various known mu receptor compounds currently employed as analgesics.

The vast majority of currently used high potency analgesics, including morphine, fentanyl, meperidine, sufentanil, and codeine, are mu receptor binding compounds. As is well established, these compounds, while highly efficacious for mediating analgesia, have accompanying side effects, including disorientation, attenuation of mental acuity, muscle rigidity, and respiratory depression, and withdrawal side-effects including nausea, vomiting, shakes, seizures, and sweats. Such side effects are typically absent or at least much reduced in use of analgesia-mediating delta receptor binding species. Accordingly, the use of mixed mu/delta receptor species of the present invention may attenuate or even eliminate the side effects normally attendant the use of mu receptor binding compounds.

Compound A when prepared as a pure enantiomer exhibits potent mu-opioid analgesia comparable to fentanyl, a leading mu-opiate analgesic for surgical analgesia. Respiratory/analgesia studies in rats comparing Compound A to fentanyl have demonstrated similar activity profiles and duration of action. Additionally, Compound A appeared to be much safer than fentanyl at higher (equivalent) doses.

Compound B is a delta-opioid agonist. Agents of this type produce analgesia at the spinal level. Spinal analgesics such as lidocaine and morphine have side-effect liabilities due to leakage from the spinal compartment to the periphery. Compound B, by contrast, does not produce evident side effects when administered peripherally to rats and mice. The absence of such side effects implies a superior utility for Compound B and related derivatives of the present invention, in mediating spinal analgesia.

Compound C, as discussed hereinabove, is an enantiomerically pure analgesic exhibiting agonism at both mu and delta opioid receptors. In rodent test subjects, Compound C has analgesic potency comparable to mu-analgesic morphine, but produces a much reduced extent of muscle rigidity and respiratory depression. Further, rodent tests show Compound C to be free of proconvulsant activity, such as may be associated with structurally related pure delta agonists.

By way of further example, Table II below shows chemical structures of two additional illustrative compounds of the present invention, denoted hereinafter as compounds "D" and "E".

TABLE II

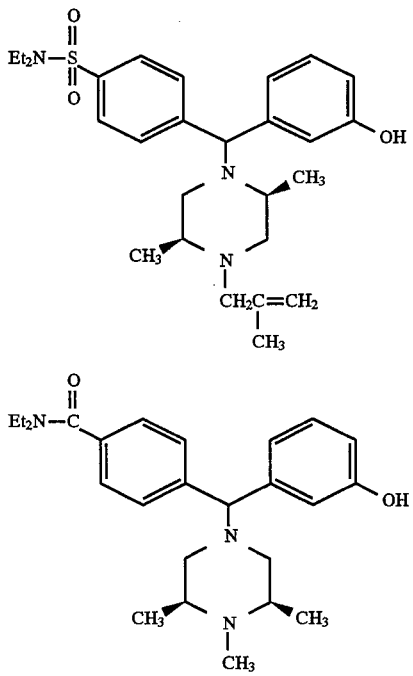

Although it might be assumed at first impression that all delta agonist compounds of the present invention would have similar in vivo profiles, with potencies parallel to mouse vas deferens activity, this is not invariably the case.

Compounds D and E provide analgesic activity in the tail flick test when injected into the brains of mice (icv). Such analgesia is reversible by injection of a non-specific opiate antagonist (naloxone) or delta-specific antagonists (ICI 174, 864 or naltrindole). Accordingly, the analgesia appears to be produced via agonist activity at a delta-opioid receptor. Nonetheless, Compound E is inactive as an agonist in the mouse vas deferens (it may be a weak antagonist), whereas Compound D is a potent agonist in the tissue.

Compounds (1)–(181), identified hereinabove as illustrative of compounds of the invention, include compounds which have significant potency in the receptor binding assay (rat brain), compounds that are predominantly active at one or the other of the delta receptor subtypes, and compounds having mu receptor activity or mixed mu receptor/delta receptor activity.

Binding assay and analgesia test results show that compounds of the present invention variously mediate analgesia in respect of a wide variety of stimuli and physiological perturbations. This in turn evidences a high level of complexity in neurotransmitter functions and stimulus-related responses associated with various opioid receptors, including mu receptors, delta receptors and delta receptor subtypes.

A number of compounds of the present invention within formula (I), or their chemical precursors (which also in many instances constitute novel compounds and thus are contemplated within the scope of the present invention), evidence biological activities in addition to opioid activity, e.g., biological activity including sigma receptor binding affinity, and multidrug resistance activity.

As is apparent from the foregoing discussion, the compounds of the present invention have broad utility in the treatment of a wide variety of physiological conditions and disorders. The invention accordingly contemplates the use of such compounds in the manufacture of a medicament for the treatment or prophylaxis of such physiological conditions and disorders. In addition to those treatment applications already mentioned, other utilities for compounds of the present invention include the treatment of bronchial disorders such as asthma, emphysema, and apnea.

Further, endogenous opioids such as enkephalins and endorphins, and their neurological systems, have been identified in connection with various CNS disorders, such as compulsive behavior, depression, psychosis, etc., and agonist or antagonist species within formula (I) of the present invention have utility in combatting such disorders.

Various agonist species as well as antagonist species of the compounds of formula (I) may also find utility in the treatment of drug (opioid/narcotic) abuse/addiction, and thus may have utility for replacement of methadone or other conventional opiate agents in drug rehabilitation programs, to the extent that conventional drug treatment agents have side effects or other disadvantages which contraindicate or limit their use.

Concerning drug addiction treatment with effective compounds within the broad scope of the present invention, it is noted that methadone is a mu-receptor opiate with actions similar to morphine, i.e., methadone is abusable and addictive. Methadone is used as a "maintenance therapy" agent for opiate addicts, so that such individuals can remain functional while satisfying their addictions in a safer and non-criminal manner. In this respect, compounds of the invention may have utility in place of, or as an adjunct to, currently used treatments for drug addiction, such as those involving naltrexone, methadone, clonidine, etc.

Certain compounds within the scope of the present invention, as mentioned, have utility in effecting local analgesia, such as spinal analgesia, and compounds of the invention may also find utility in appetite suppression applications, and the like.

Compounds of the present invention include various compounds which are delta-opioid agonists in the mouse vas deferens delta receptor subtype, as well as compounds which are antagonists at such delta receptor subtype. The compounds of the present invention also include compounds which are agonists or antagonists at the delta receptor in the brain, which appears, on the basis of empirical determinations, to be a different delta receptor subtype than the delta receptor in the mouse vas deferens. A substantial number of compounds of the aforementioned general formula (I) of the invention have either agonist or antagonist activity at both delta receptor subtypes. A number of these compounds have high activity at the mu-opioid receptor, either as pure mu receptor binding compounds or as mixed mu receptor/delta receptor binding compounds, and still other compounds within the broad scope of the present invention have significant affinity for the sigma receptor.

In in vitro tests for agonist/antagonist activity, such as receptor binding affinity tests, and inhibition of electrically stimulated muscle twitch tests, compounds of the present invention exhibit potency over a range of from nanomolar to micromolar concentrations, depending on the specific compound employed.

One preferred sub-class of delta and/or mu receptor diarylmethylpiperazine compounds within the scope of the present invention comprises compounds of the formula:

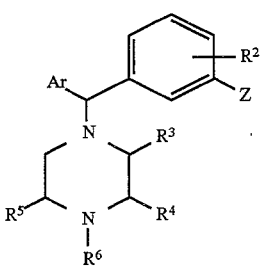

(III)

in which Ar is a 5- or 6-member carbocyclic or heterocyclic aromatic dng having on a first ring carbon atom thereof a substituent Y and on a second ring carbon thereof a substituent $R^1$,
wherein:

Z=OH (including esters thereof); $NH_2$ (including carboxamides and sulfonamides thereof) or $CH_2OH$ (including esters thereof);

Y=hydrogen;

halogen;

nitrile;

$C_1$–$C_6$ alkyl;

$C_3$–$C_6$ cycloalkyl;

$C_1$–$C_6$ alkoxy;

$C_3$–$C_6$ cycloalkoxy;

sulfones ($SO_2R_7$) where $R^7$ is $C_1$–$C_6$ alkyl or $C_3$–$C_6$ cycloalkyl or $C_5$–$C_{10}$ aryl;

alkoxycarbonylamino (carbamoyl) of the formula $NHCO_2R_7$ where $R^7$ is the same as above; aminomethyl ($CH_2NR^8R^9$) where $R^8$ and $R^9$ may be the same or different and may be hydrogen, $C_5$–$C_{10}$ aryl, $C_2$–$C_6$ hydroxyalkyl, $C_2$–$C_6$ methoxyalkyl, $C_1$ –$C_6$ alkyl or $C_3$–$C_6$ cycloalkyl, or taken together may form a ring of 5 or 6 atoms;

sulfonamides ($SO_2NR^8R^9$) where $R^8$ and $R^9$ are the same as above;

$C_1$–$C_6$ acyl;

carboxylic acid, including esters and salts thereof; or carboxamides ($CONR^{10}R^{11}$) where $R^{10}$ and $R^{11}$ may be the same or different and may be hydrogen, $C_5$–$C_{10}$ aryl, $C_1$–$C_6$ alkyl, $C_3$–$C_6$ cycloalkyl, $C_2$–$C_6$ hydroxyalkyl, or $C_2$–$C_6$ methoxyalkyl, or taken together may form a ring of 5 or 6 atoms, or where either $R^{10}$ or $R^{11}$ may be a dipeptide, or where either $R^{10}$ or $R^{11}$ may be an alkyl or polyether chain of 6–12 atoms joined to the corresponding position of another diarylmethyl piperazine moiety so as to provide a symmetrical dimeric compound;

$R^1$,$R^2$=hydrogen, halogen, or $C_1$–$C_4$ alkyl;

$R^3$,$R^4$, $R^5$=hydrogen or methyl, where the total number of methyl groups is 1 or 2, or any two taken together may form a bridge of 1 to 3 carbons; and $R^6$=hydrogen;

$C_1$–$C_6$ alkyl;

$C_3$–$C_6$ cycloalkyl;

$C_5$–$C_{10}$ aryl $C_1$–$C_6$ alkyl;

alkoxyalkyl containing $C_1$–$C_4$ alkoxy and $C_1$–$C_4$ alkyl moieties;

$C_1$–$C_4$ cyanoalkyl;

$C_2$–$C_4$ hydroxyalkyl;

aminocarbonylalkyl containing a $C_1$–$C_4$ alkyl moiety; or —$R^{12}COR^{13}$, where $R^{12}$ is $C_1$–$C_4$ alkylene, and $R^{13}$ is $C_1$–$C_4$ alkyl or $C_1$–$C_4$ alkoxy.

Another preferred sub-class of compounds of the present invention, wherein Ar is a six-member ring, which includes members exhibiting delta-opioid agonist activity in the mouse vas deferens test as well as members exhibiting mu receptor (mu agonist) activity, comprises compounds of the formula:

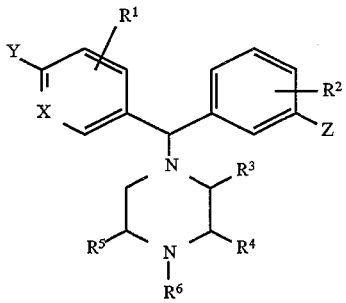

(IV)

wherein:

X=nitrogen or carbon (N or CH);

Z=OH(including esters thereof);

$NH_2$(including carboxamides and sulfonamides thereof); or $CH_2OH$ (including esters thereof);

Y=hydrogen;

halogen;

methyl;

nitrile;

sulfones ($SO_2R^7$) where $R^7$ is $C_1$–$C_6$ alkyl, $C_3$–$C_6$ cycloalkyl, $C_5$–$C_{10}$ aryl $C_1$–$C_4$ alkyl;

alkoxycarbonylamino (carbamoyl) of the formula $NHCO_2R^7$ where $R^7$ is the same as above;

carboxamides ($CONR^8R^9$) where $R^8$ and $R^9$ may be the same or different and may be hydrogen, $C_1$–$C_6$ alkyl, $C_3$–$C_6$ cycloalkyl, $C_5$–$C_{10}$ aryl, $C_2$–$C_6$ hydroxyalkyl, or $C_2$–$C_6$ methoxyalkyl, or taken together may form a 5- or 6-membered ring;

$CONR^8AB$ where $R^8$ is the same as above, A is a divalent ligand selected from the group consisting of alkylene and etheric bridging groups, and B is a dimer-forming moiety joined to a first valence bond of the divalent ligand A and symmetric about A to the compound moiety joined to the other valence bond of the divalent ligand A;

sulfonamides ($SO_2NR^8R^9$) where $R^8$ and $R^9$ are the same as above; or carboxylic acids, including esters and salts thereof;

$R^1$=hydrogen, halogen, or $C_1$–$C_4$ alkyl;

$R^2$=hydrogen or fluorine;

$R^3$, $R^4$, $R^5$=hydrogen or methyl, where the total number of methyl groups is one or two; and $R^6$=hydrogen;

$C_1$–$C_6$ alkyl;

$C_3$–$C_6$ cycloalkyl;

$C_5$–$C_{10}$ aryl $C_1$–$C_6$ alkyl;

alkoxyalkyl containing $C_1$–$C_4$ alkoxy and $C_1$–$C_4$ alkyl moieties;

$C_1$ –$C_4$ cyanoalkyl;

$C_2$–$C_4$ hydroxyalkyl;

aminocarbonylalkyl containing a $C_1$–$C_4$ alkyl moiety; or —$R^{12}COR^{13}$, where $R^{12}$ is $C_1$–$C_4$ alkylene, and $R^{13}$ is $C_1$–$C_4$ alkyl or $C_1$–$C_4$ alkoxy.

Under the sub-class of compounds of formula (IV) set out above, especially preferred compounds, with respect to the various substituent groups, include compounds wherein:

Z=OH (including esters thereof), with esters being made from acyl groups such as $CH_3CO$, $PhCO$, $Me_2NCO$, and $Me_3CCO$;

NH₂ (including carboxamides and sulfonamides thereof, e.g., formamide and benzenesulfonamide); or

CH₂OH;

Y=hydrogen;

halogen (Cl, F, I, Br);

methyl;

nitrile;

sulfones of the formula $SO_2R^7$, where $R^7$ is $C_1$–$C_6$ alkyl or $C_5$–$C_{10}$ aryl $C_1$–$C_6$ alkyl, e.g., $R^7$=Me;

alkoxycarbonylamino (carbamoyl) of the formula $NHCO_2R^7$ where $R^7$ is the same as above, e.g., $R^7$=CH₂Ph;

carboxamides (CONR⁸R⁹) where $R^8$ and $R^9$ may be same or different and may be hydrogen, $C_5$–$C_{10}$ aryl, $C_1$–$C_6$ alkyl, $C_2$–$C_4$ hydroxyalkyl, $C_2$–$C_4$ methoxyalkyl, or $C_3$–$C_6$ cycloalkyl, or taken together may form a 5- or 6-membered ring, e.g., wherein:

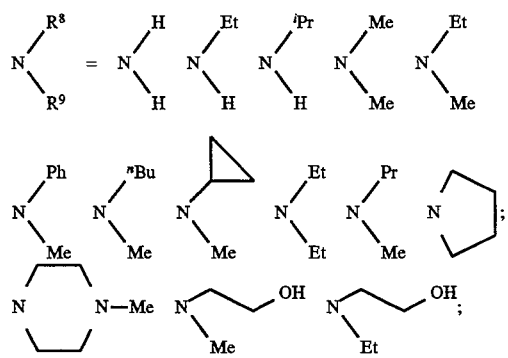

sulfonamides ($SO_2NR^8R^9$) where $R^8$ and $R^9$ are the same as above, e.g., wherein:

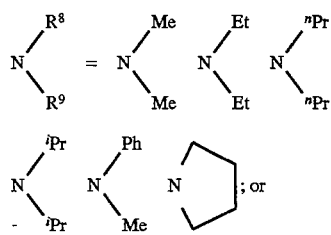

carboxylic acid, and esters and salts thereof;

$R^1$=hydrogen, methyl, or halogen;

$R^2$=hydrogen or fluorine;

$R^3$, $R^4$ and $R^5$=hydrogen or methyl, where the total number of methyl groups is 1 or 2; and $R^6$=$C_1$–$C_6$ alkyl, or $C_3$–$C_6$ cycloalkyl.

In the foregoing preferred substituent categories, $R^1$, when halogen, may suitably be any of chlorine, bromine, iodine, or fluorine, with the halogen species of chlorine, bromine, or fluorine being generally more preferred. Among the preferred $C_1$–$C_6$ alkyl and $C_3$–$C_6$ cycloalkyl species for $R^6$ are Me, Et, Pr, Bu, allyl, cyclopropylmethyl, 2-buten-1-yl,2-methyl-2-propen-1-yl, and 2-chloro-2-propen-1-yl, the last-mentioned species of 2-chloro-2-propen-1-yl being within the broad definition of alkyl as hereinearlier set forth, as comprehending alkyl groups containing further substitutents such as halo, hydroxy, amino, etc., as well as alkyl groups containing heteroatoms or other non-hydrocarbyl bridging moieties or linking groups, as well as unsaturated groups or moieties.

Other diarylmethyl piperazine compounds of the present invention exhibiting significant activity in the mouse vas deferens test include the peptide conjugates of the carboxamide series (Compound F, as shown in Table III below), and dimeric analogs of the carboxamide series (Compound G, as also shown in Table III below).

TABLE III

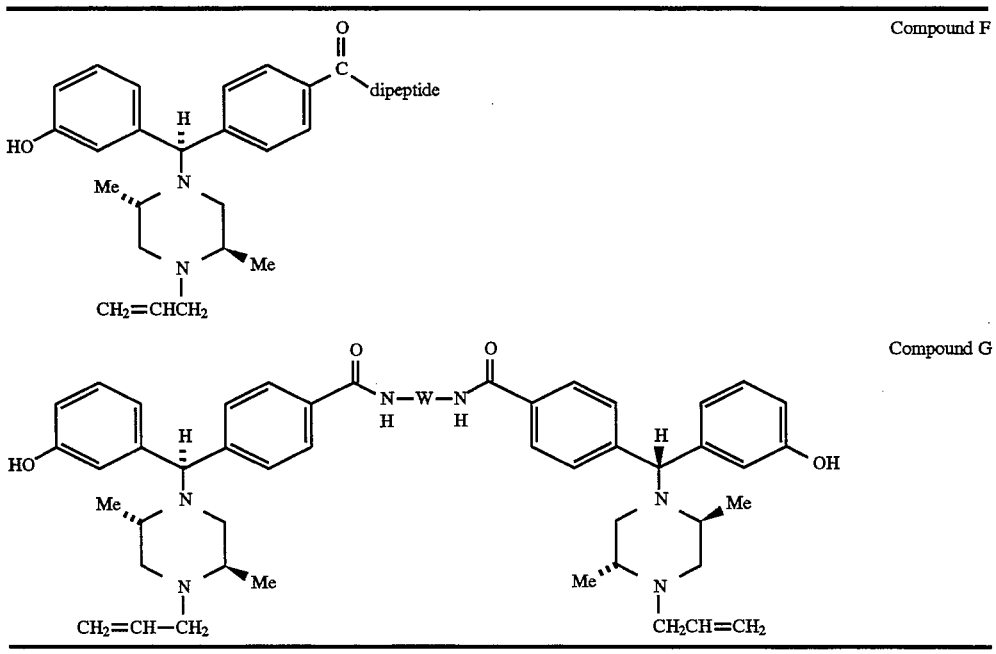

The dipeptide moiety in Compound F may be, for example, Phe-Leu, or Gly-Gly, or any other suitable dipeptide substituent. The bridge group W in Compound G of Table III may comprise an alkylene bridge group, such as for example $(CH_2)_6$ or $(CH_2)_8$, or a polyether bridge moiety, e.g., $(CH_2CH_2OCH_2)_2$.

A particularly preferred subclass of compounds of formula (III) include those wherein:

Y=hydrogen;

sulfones ($SO_2R^7$) where $R^7$ is $C_1$–$C_6$ alkyl or $C_3$–$C_6$ cycloalkyl;

carboxamides ($CONR^8R^9$) where $R^8$ and $R^9$ may be the same or different, and may be hydrogen, $C_1$–$C_6$ alkyl, $C_2$–$C_6$ hydroxyalkyl, $C_2$–$C_6$ methoxyalkyl, $C_3$–$C_6$ cycloalkyl, $C_5$–$C_{10}$ aryl, or $C_2$–$C_{30}$ peptide conjugates, or $R^8$ and $R^9$ together may form a ring of 5 or 6 atoms; or sulfonamides ($SO_2NR^8R^9$) where $R^8$ and $R^9$ are the same as above;

$R^1$, $R^2$=hydrogen or fluorine;

$R^3$, $R^4$, $R^5$=hydrogen or methyl, where the total number of methyl groups is one or two; and $R^6$=hydrogen, $C_1$–$C_6$ alkyl, $C_2$–$C_6$ methoxyalkyl, or $C_3$–$C_6$ cycloalkyl.

In the subclass compounds of the above description, the aryl moiety Ar preferably is selected from phenyl, thiazolyl, furanyl, thiophenyl, and pyrrolyl, and more preferably is phenyl or thiophenyl. In addition to the Y and $R^1$ aromatic ring substituents, the aromatic ring Ar in formula (III), as well as in other chemical formulae herein depicted and representing compounds of the invention (containing Ar as an aromatic ring moiety thereof), may be further substituted with other, sterically acceptable ring substituents, such as organo substituents, e.g., hydrocarbyl radicals including $C_1$–$C_6$ alkyl, $C_2$–$C_6$ alkenyl, $C_2$–$C_6$ alkynyl, $C_1$–$C_6$ hydroxyalkyl, etc. When Ar is phenyl, preferred species of the subclass compounds include those in which the substituent Y is carboxamide (aminocarbonyl).

A highly preferred subclass of compounds of the present invention comprises diarylmethyl piperazines of the formula:

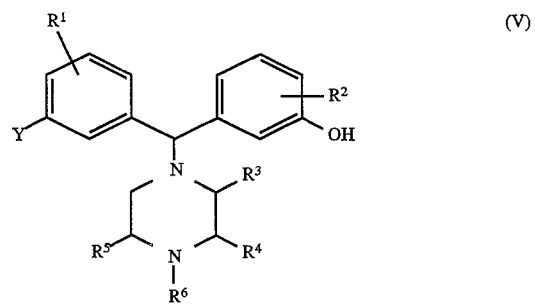
(V)

wherein the substituents $R^1$, $R^2$, $R^3$, $R^4$, R5, $R^6$, and Y are as described immediately above.

Under the sub-class of compounds of formula (V) set out above, especially preferred compounds, with respect to the various substituent groups, include compounds wherein:

Y=carboxamides ($CONR^8R^9$) where $R^8$ and $R^9$ may be the same or different, and may be hydrogen, $C_1$–$C_6$ alkyl, $C_3$–$C_6$ cycloalkyl, or $C_5$–$C_{10}$ aryl, or $R^8$ and $R^9$ together may form a ring of 5 or 6 atoms, e.g., wherein:

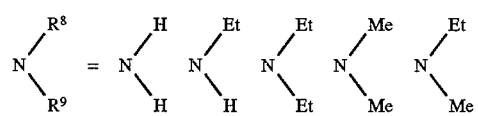

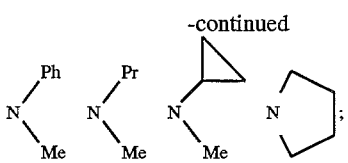

$R^1$, $R^2$=hydrogen;

$R^3$, $R^4$, $R^5$=hydrogen or methyl, where the total number of methyl groups is one or two; and $R^6$=hydrogen, $C_1$–$C_6$ alkyl, $C_2$–$C_6$ methoxyalkyl, or $C_3$–$C_6$ cycloalkyl.

Particularly preferred diarylmethyl piperazine species according to the present invention include Compounds A–G, described hereinabove, as well as Compounds H–K, whose structures are set out in Table IV below.

TABLE IV

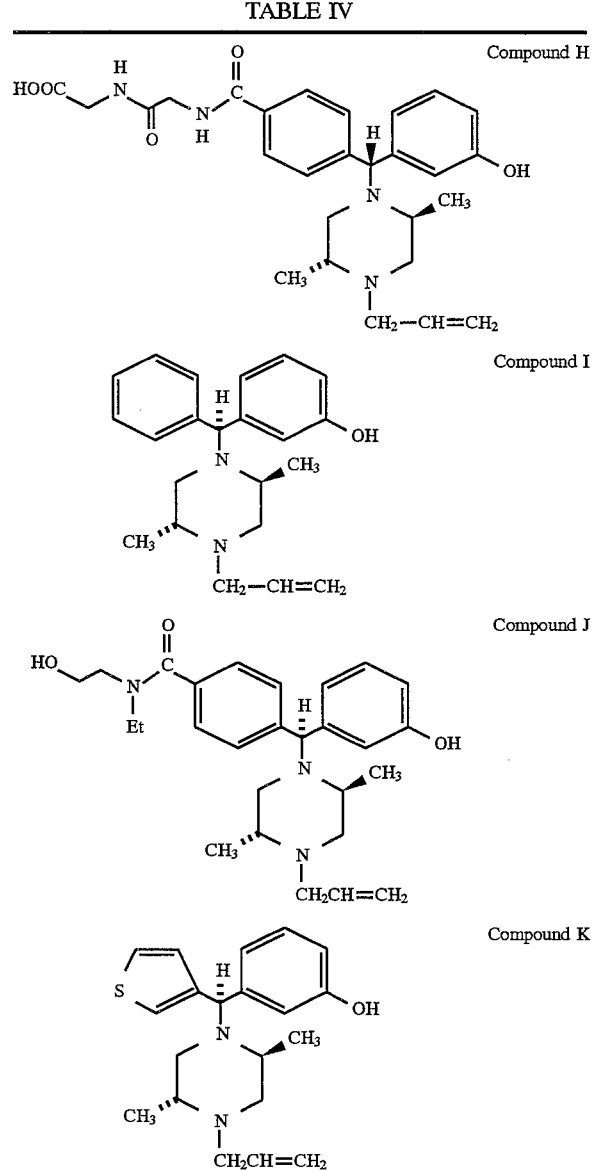

Compound H is an agonist species exhibiting delta receptor agonist activity, leading to the conclusion that this compound should mediate analgesia with the same effectiveness as delta-opiate peptide compounds.

Compounds I and K exhibit significant agonist activity at the mu-opiate (morphine-binding) receptor, in addition to delta-receptor opiate properties. Compounds I and K, in addition to their multi-receptor profile, are strong analgesics and may provide morphine-like activity with reduced respiratory depression.

Compound J exhibits potent delta receptor agonist activity.

Compounds of the present invention have pharmaceutical activity, including, inter alia, analgesic activity, and are useful in treating animals, e.g., mammals such as humans, for conditions in which analgesia is desired.

A method of producing an analgesic response in an animal subject in need of such treatment comprises administering to the animal subject an analgesia-inducing amount of a compound of formula (I).

In addition, various compounds of the present invention having appertaining therapeutic utility may be usefully employed in the treatment of conditions including: drug and alcohol addiction/overdose; mental, emotional, and cognitive disorders; cough; lung edema; and gastrointestinal disorders. Correspondingly, the present invention contemplates a method of treating an animal subject having such condition (s) and in need of such treatment, comprising administering to such animal an effective amount of a compound of the present invention which is therapeutically effective for said condition.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered compounds of formula (I) at any suitable therapeutically effective and safe dosage, as may readily be determined within the skill of the art, and without undue experimentation.

In general, suitable doses of the formula (I) compounds for achievement of therapeutic benefit, including treatment of each of the conditions described hereinabove, will be in the range of 1 microgram (µg) to 100 milligrams (mg) per kilogram body weight of the recipient per day, preferably in the range of 10 µg to 50 mg per kilogram body weight per day and most preferably in the range of 10 µg to 50 mg per kilogram body weight per day. The desired dose is preferably presented as two, three, four, five, six, or more sub-doses administered at appropriate intervals throughout the day. These sub-doses may be administered in unit dosage forms, for example, containing from 10 µg to 1000 mg, preferably from 50 µg to 500 mg, most preferably from 50 µg to 250 mg of active ingredient per unit dosage form. Alternatively, if the condition of the recipient so requires, the doses may be administered as a continuous infusion.

The mode of administration and dosage forms will of course affect the therapeutic amounts of the compounds which are desirable and efficacious for the given treatment application.

For example, orally administered dosages are typically at least twice, e.g., 2–10 times, the dosage levels used in parenteral administration methods, for the same active ingredient. In oral administration for inducing analgesia, dosage levels for mu receptor binding compounds of the invention may be on the order of 5–200 mg/70 kg body weight/day. Intrathecal administration dosage levels are generally on the order of about 10% of the levels characteristic of parenteral administration dosage levels. In tablet dosage forms, typical active agent dose levels suitable for inducing analgesia are on the order of 10–100 mg per tablet.

The compounds of formula (I) may be administered per se as well as in the form of pharmaceutically acceptable esters, salts, and other physiologically functional derivatives thereof.

Examples of pharmaceutically acceptable esters of the invention include: (a) carboxylic acid esters of hydroxy groups in compounds of formula (I) in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl- or arylalkyl-sufonyl (e.g. methanesulfonyl); amino acid esters (e.g. L-valyl or L-isoleucyl); dicarboxylic acid esters (e.g. hemisuccinate); carbonate esters (e.g. ethoxycarbonyl); and carbamate esters (e.g. dimethylaminocarbonyl, (2-aminoethyl) aminocarbonyl); and (b) alcohol esters of carboxylate groups in compounds of formula (I) in which the alcohol moiety of the ester grouping is selected from straight or branched chain alcohols (e.g. ethanol, t-butanol), phenols (e.g. 4-methoxyphenol), alkoxyalcohols (e.g. ethoxyethanol), arylalkyl alcohols (e.g. benzyl alcohol), and aminoalcohols (e.g. 2-aminoethanol).

Examples of pharmaceutically acceptable salts of the compounds of formula (I) and physiologically functional derivatives thereof include salts derived from an appropriate base, such as an alkali metal (for example, sodium, potassium), an alkaline earth metal (for example, calcium, magnesium), ammonium and $NX_4^+$ (wherein X is $C_{1-4}$ alkyl). Pharmaceutically acceptable salts of an amino group include salts of: organic carboxylic acids such as acetic, lactic, tartaric, malic, lactobionic and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxy group consist of the anion of said compound in combination with a suitable cation such as $Na^+$, $NH_4^+$, or $NX_4^+$ (wherein X is for example a $C_{1-4}$ alkyl group).

For therapeutic use, salts of compounds of formula (I) will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention.

The present invention also contemplates pharmaceutical formulations, both for veterinary and for human medical use, which comprise as the active agent one or more compound(s) of the invention, as well as the use of a compound of the invention, such as a compound within the above-discussed formulae (I)–(V), in the manufacture of a medicament for the treatment or prophylaxis of the conditions and disorders variously described herein.

In such pharmaceutical and medicament formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, nasal, ophthalmic, subcutaneous, intramuscular, intravenous, transdermal, intrathecal, intra-articular, intra-arterial, sub-arachnoid, bronchial, lymphatic, and intra-uterine administration. Formulations suitable for parenteral administration are preferred.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorised" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or muti-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thiotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The present invention also contemplates a process for the preparation of a compound of formula (I), as defined hereinabove, wherein G is nitrogen, or a pharmaceutically acceptable ester, salt, or other physiologically functional derivative thereof, which comprises the following steps:

(A) the alkylation of a piperazine of formula (VII) by an alkylating agent of formula (VI),

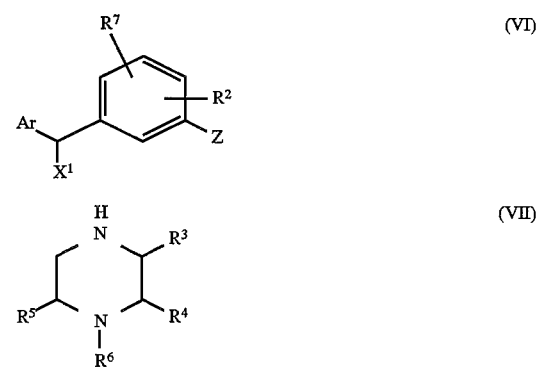

wherein Ar, $R^1$–$R^7$, Y and Z are as defined in formula (I), and Z may be protected, if necessary, with a suitable protecting group such as tert-butyldimethylsilyl, and wherein $X^1$ is a suitable leaving group such as chloride, bromide, tosylate ($CH_3(C_6H_4)SO_{3-}$), mesylate ($CH_3SO_{3-}$), or other such groups known in the art, or (B) the transformation of a compound of formula (VIII),

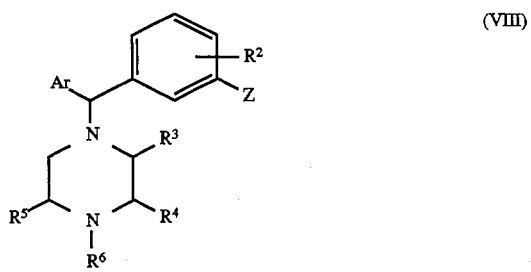

(VIII)

wherein Y, as defined in formula (I), is restricted to reactive halogen (e.g. bromine or iodine) and Ar, $R_1$–$R_6$, and Z are as defined in formula (I), and Z may be protected, if necessary, with a suitable protecting group such as tert-butyldimethyisilyl, or Y may be hydrogen when Ar is a heterocyclic ring such as thienyl or thiazolyl, into a compound of formula (I) wherein G is nitrogen and $R^7$ is hydrogen and Y may be all groups as defined in formula (I) that are compatible with the transformation, via metal mediated substitution reactions, including intermediate formation of an arylmetallic species, which provide new substituents Y at the position of the prior substituents Y (reactive halogen or hydrogen).

A compound of formula (I) wherein G is nitrogen may be prepared by reacting an alkylating agent of formula (VI) with a piperazine of formula (VII) in a solvent such as toluene or acetonitrile. The group $R^6$ of a piperazine of formula (VII) may initially be hydrogen, and after reaction to form a compound of formula (I) wherein G is nitrogen and $R^6$ is hydrogen, the compound of formula (I) may be further alkylated with an appropriate alkylating agent $R^6$–$X^1$, where $R^6$ is an organo group, to provide compounds of formula (I) with varied groups $R^6$ as defined hereinabove. Such alkylating agents are commercially available or may be prepared by published procedures. As an alternative to alkylation with an alkylating agent $R^6$–$X^1$, the method of reductive amination may be employed by treating the compound of formula (I) wherein G is nitrogen and $R^6$ is hydrogen with an appropriate commercially available aldehyde in the presence of a reducing agent such as sodium cyanoborohydride in solvents such as alcohols or ethers to furnish the desired group $R^6$.

A compound of formula (I) wherein G is nitrogen may also be prepared from a compound of formula (VIII) by treatment with a cyanating reagent, such as cuprous cyanide, in a suitable solvent such as dimethylformamide or N-methylpyrrolidone, to provide the corresponding compound of formula (I) wherein Y is nitrile, which may be further hydrolyzed to a compound of formula (I) wherein Y is carboxylic acid with alkali or aqueous mineral acid. The carboxylic acid may then be converted to a compound of formula (I) wherein Y is carboxamide ($CONR^9R^{10}$ or $CONR^9AB$ as defined in formula (I)) by various means known in the art, such as formation of the acid chloride (e.g. with thionyl chloride) or by formation of the mixed anhydride (e.g with isobutyl chloroformate) or by formation of an activated ester with conventional peptide-coupling reagents (e.g. dicyclohexylcarbodiimide or benzotriazol-1-yloxy-tris (dimethylamino)phosphonium hexafluorophosphate), any of which activated intermediates may be converted to the desired carboxamide by reaction with an appropriate amine ($HNR^9R^{10}$ or $HNR^9ANR^9H$) in a suitable solvent such as dichloromethane or dimethylformamide. Similarly, reaction of such activated intermediates with a peptide may provide compounds of formula (I) wherein Y is a peptide conjugate of a carboxamide.

Alternatively, a compound of formula (I) where Y is carboxylic acid (or sulfinic acid) may be formed directly from a compound of formula (VIII) by low-temperature (e.g. –60° C. to –78° C.) metal exchange of the reactive halogen with an organometallic reagent, such as n-butyllithium, or an activated form of a metal, such as lithium or magnesium, or, in the case where Ar is a heterocyclic ring such as thienyl or thiazolyl, by proton abstraction with a similar organometallic reagent, to provide an intermediate arylmetallic compound, followed by reaction with carbon dioxide to provide the carboxylic acid (or sulfur dioxide to afford the sulfinic acid) in an anhydrous solvent such as tetrahydrofuran, under an inert atmosphere (e.g. nitrogen). The carboxylic acid may then be converted to the carboxamide by the method described above, or the sulfinic acid may be converted to the sulfonyl chloride (for example, with N-chlorosuccinimide) which is then treated with an amine ($HNR^9R^{10}$) to afford the desired compound of formula (I) wherein Y is sulfonamide ($SO_2NR^9R^{10}$).

Alternatively, the intermediate arylmetallic compound generated from a compound of formula (VIII) may be treated with an appropriate carbamoyl chloride ($ClCONR^9R^{10}$) to produce a compound of formula (I) wherein Y is $CONR^9R^{10}$. Alternatively, a compound of formula (VIII) may be treated with a transition metal catalyst, such as tetrakis(triphenylphosphine)palladium, in the presence of excess amine and carbon monoxide in a solvent such as tetrahydrofuran or acetonitrile, to produce a compound of formula (I) wherein Y is $CONR^9R^{10}$.

Optionally, the arylmetallic species prepared hereinabove may be treated with appropriate commercial alkylating agents such as iodomethane or dimethylformamide to provide a compound of formula (I) wherein Y is alkyl or acyl, respectively. Optionally, a compound of formula (I) wherein Y is carboxylic acid may be be convened to a compound of formula (I) wherein Y is alkoxyamino-carbonyl, by the well-known method of the Curtius rearrangement, for example by preparing the acyl azide by addition of sodium azide to the acid chloride or other activated form of the carboxylic acid as hereinabove described, and heating the resulting acyl azide in the presence of an appropriate alcohol.

A compound of formula (I) wherein Y is carboxylic acid may be converted into a pharmaceutically acceptable ester by formation of an intermediate esterifying agent of the acid, such as an acid halide or mixed anhydride, followed by treatment with an appropriate alcohol.

A compound of formula (I) may be obtained as a single enantiomeric species by classical resolution with an enantiopure acid, such as mandelic acid, or by formation of readily separable diastereomers by an enantiopure derivatizing agent, or by chiral chromatography, or by enzymatic resolution of a compound of formula (I) or a suitable derivative, or by preparation of the compound of formula (I) from enantiopure precursors, which may themselves be obtained as single enantiomers by similar means.

Compounds of formula (VI) may be obtained from the appropriate alcohols of formula (IX), where Z is protected with a suitable protecting group, by methods such as halogenation with thionyl chloride or triphenylphosphine/carbon tetrabromide, or reaction with methanesulfonyl chloride or toluenesulfonyl chloride, in a solvent such as dichloromethane.

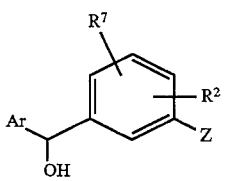 (IX)

Piperazines of formula (VII) are commercially available, or may be prepared by published procedures or variations of published procedures where $R^6$ is varied by appropriate alkylation with agents $R^6$–$X^1$.

Compounds of formula (VIII) may be prepared by alkylation of a piperazine of formula (VII) with an alkylating agent of formula (X), in similar fashion to the piperazine alkylation described above. Alklylating agents of formula (X) are likewise obtained from alcohols of formula (XI) by similar methods to those described above for compounds of formula (VI).

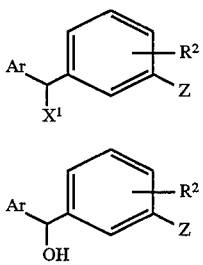

(X)

(XI)

Alcohols of formula (IX) or (XI) may be prepared by low-temperature (e.g. –60° C. to –78° C.) addition of substituted arylmetallic species, prepared from compounds of formula (XII), wherein $X^2$ is reactive halogen (e.g. iodine or bromine), or may be hydrogen in the case of heterocyclic rings such as thienyl or thiazolyl, by methods described hereinabove, to Z-protected benzaldehydes of formula (XIII), including compounds wherein $R^7$ is hydrogen which provide compounds of formula (XI).

Ar—$X^2$ (XII)

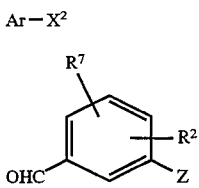 (XIII)

Conversely, compounds of formula (IX) or (XI) may also be formed by similar addition of Z-protected phenylmetallic species, derived from compounds of formula (XIV), including compounds wherein $R^7$ is hydrogen which provide compounds of formula (XI), to arylaldehydes of formula (XV).

Ar—CHO (XV)

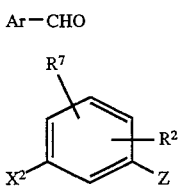 (XIV)

Compounds (XII)–(XV) and their suitably protected derivatives are commercially available or may be prepared by literature procedures.

A compound of formula (I) may be converted into a pharmaceutically acceptable ester by reaction with an appropriate esterifying agent, e.g. an acid halide or anhydride. The compound of formula (I), including esters thereof, may be converted into pharmaceutically acceptable salts thereof in conventional manner, for example, by treatment with an appropriate acid. An ester or salt of a compound of formula (I) may be converted into the parent compound, for example, by hydrolysis.

Based on the foregoing discussion as well as general synthesis considerations, it will be appreciated that various syntheses are useful for preparation of diarylmethyl piperazine and diarylmethyl piperidine compounds of the present invention, as will be readily apparent to those of ordinary skill in the art. Illustrative synthetic methods for production of compounds within the broad scope of the present invention are set out below by way of example, it being understood that compounds of the invention are amenable to manufacture by various other synthesis routes and methods within the skill of the art, and that the illustrative synthesis methods set out below are therefore not to be limitingly construed as regards the scope of the invention. It is to be further appreciated that the novel compounds of the present invention comprehend various novel intermediates, precursors, pro-drugs, analogues, and derivatives of compounds specifically identified herein with reference to the invention.

When the synthesis procedures which are employed for producing compounds of the invention yield racemic mixtures as reaction products, such racemic mixtures may be resolved by suitable means and method well-known and established in the art, as for example by formation of diastereomeric salts with enantiopure carboxylic acids, by chiral chromatographic resolution, by enzymatic resolution, or by other suitable conventional methods.

SYNTHESIS REACTION SCHEMES

Set out below is an illustrative synthetic scheme for the formation of (±)-4-((αR*)-α-((2S*,5R*)-4-allyl-2,5-dimethyl-1-piperazinyl)-3-hydroxybenzyl)-N,N-diethylbenzamide, hereafter referred to as Compound L, and resolution thereof into constituent enantiomers, as hereinafter more specifically described in Example 6 hereof. The illustrative synthesis scheme and resolution methodology of the ensuing description may likewise be employed in the synthesis and resolution of other compounds of the invention, or alternatively other synthesis and/or resolution methodologies may be usefully employed within the skill of the art.

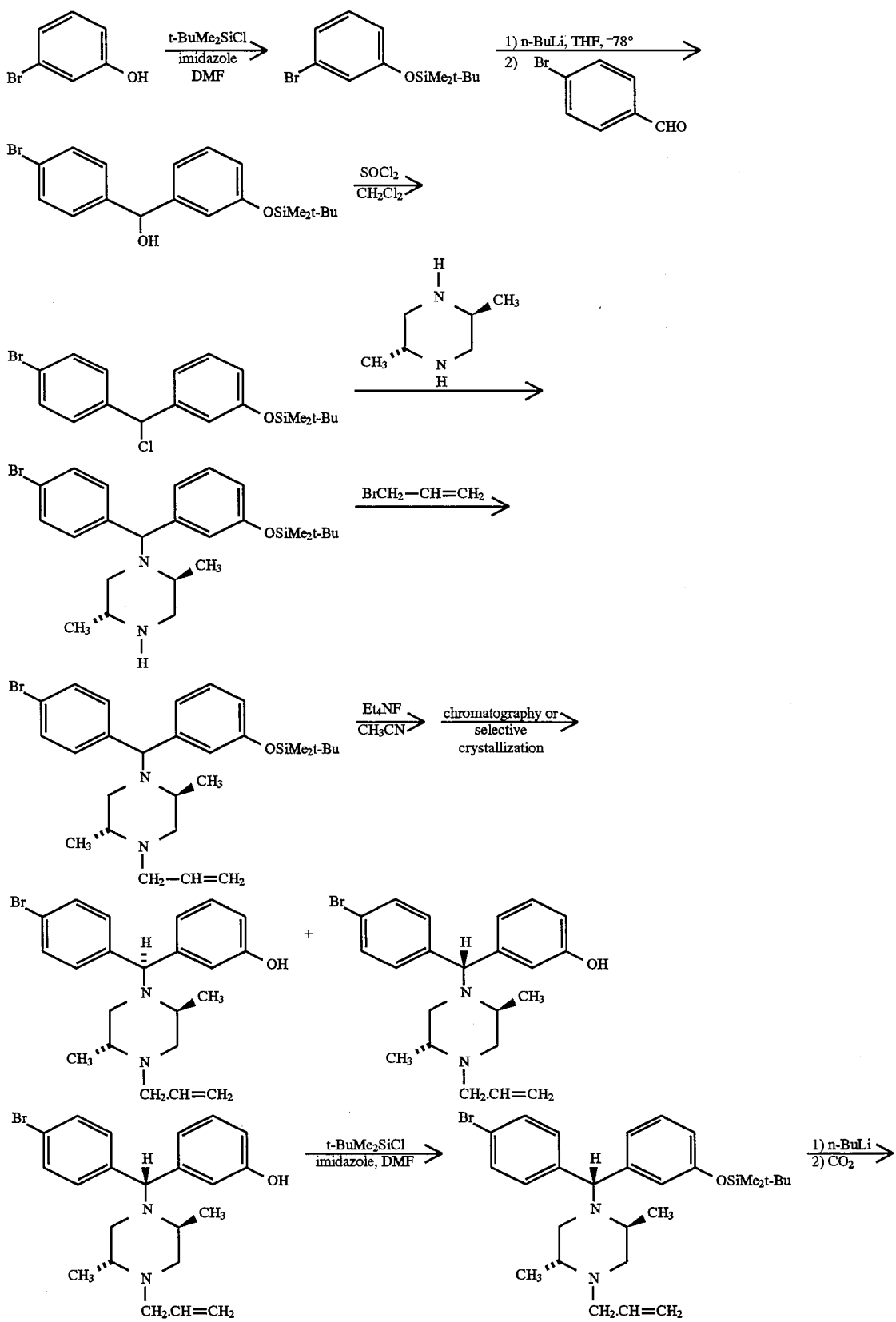

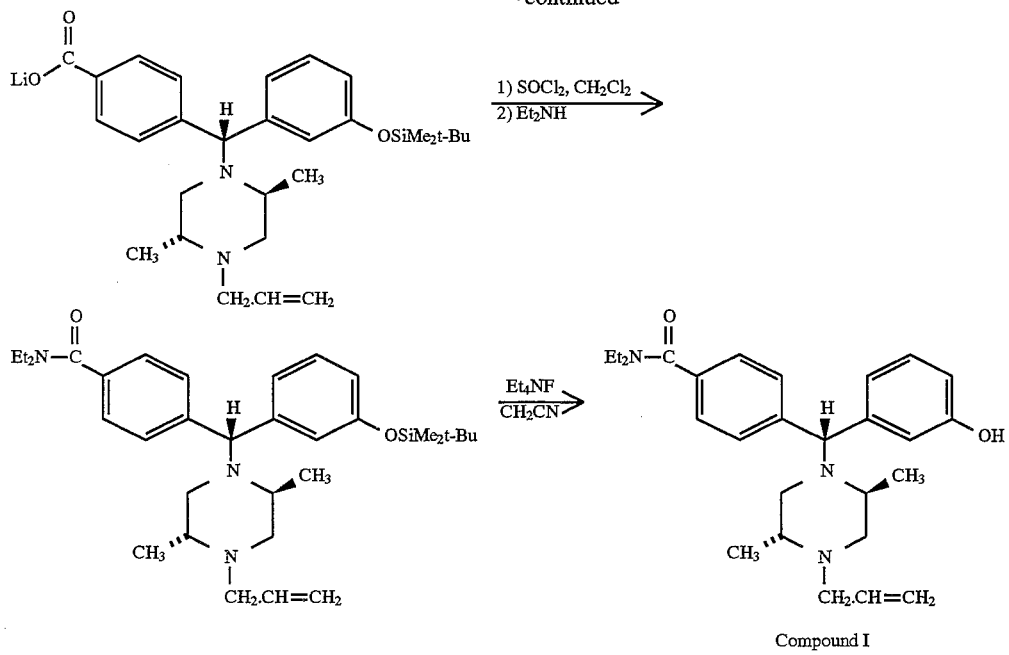

Compound I

With respect to the foregoing synthesis scheme, the initial benzhydryl alcohol could be prepared from 3-(t-butyldimethylsilyloxy)bromobenzene by the following scheme:

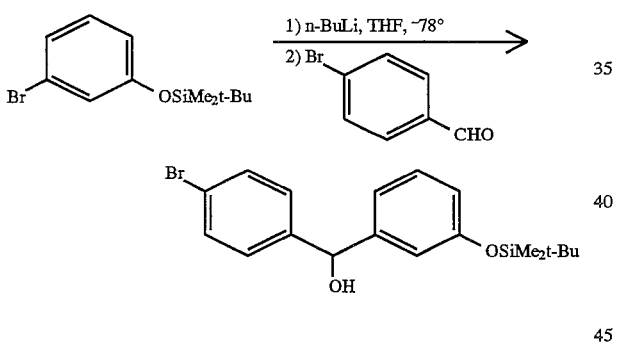

The intermediate could also be prepared via the benzophenone, which in turn could be obtained from an organometallic addition to 4-bromobenzonitrile:

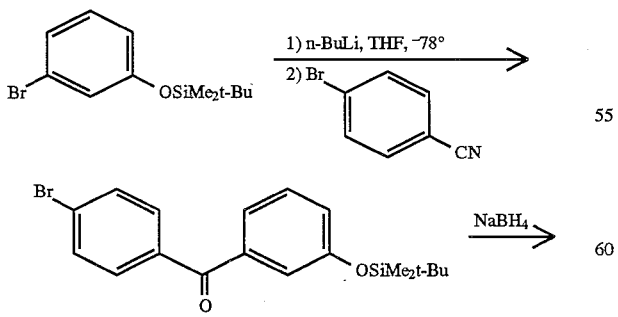

Alternatively, similar intermediates could be derived via Friedel-Crafts acylation of bromobenzene with an appropriate Lewis acid catalyst, using a suitable acid-stable protecting group R for the phenol, as shown below. (The Friedel-Crafts reaction may also produce the ortho-substituted isomeric benzhydryl alcohol).

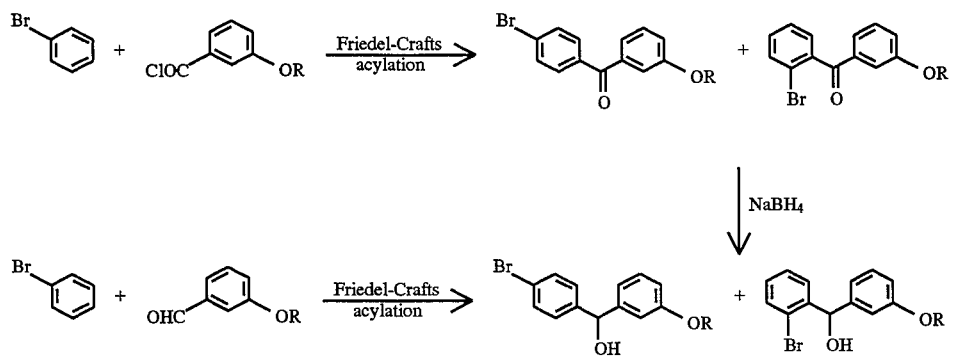

Other alternatives to intermediates involve condensation of an appropriately substituted piperazine with a carbonyl compound. Condensation with a benzaldehyde could provide an ammonium salt that could add an aryllithium to provide benzhydryl piperazine compounds wherein X=CONEt$_2$, Y=CH$_2$CH=CH$_2$, or wherein X=Br, Y=CH$_2$CH=CH$_2$, as mixtures with their diasteromers, or protected precursors to those compounds.

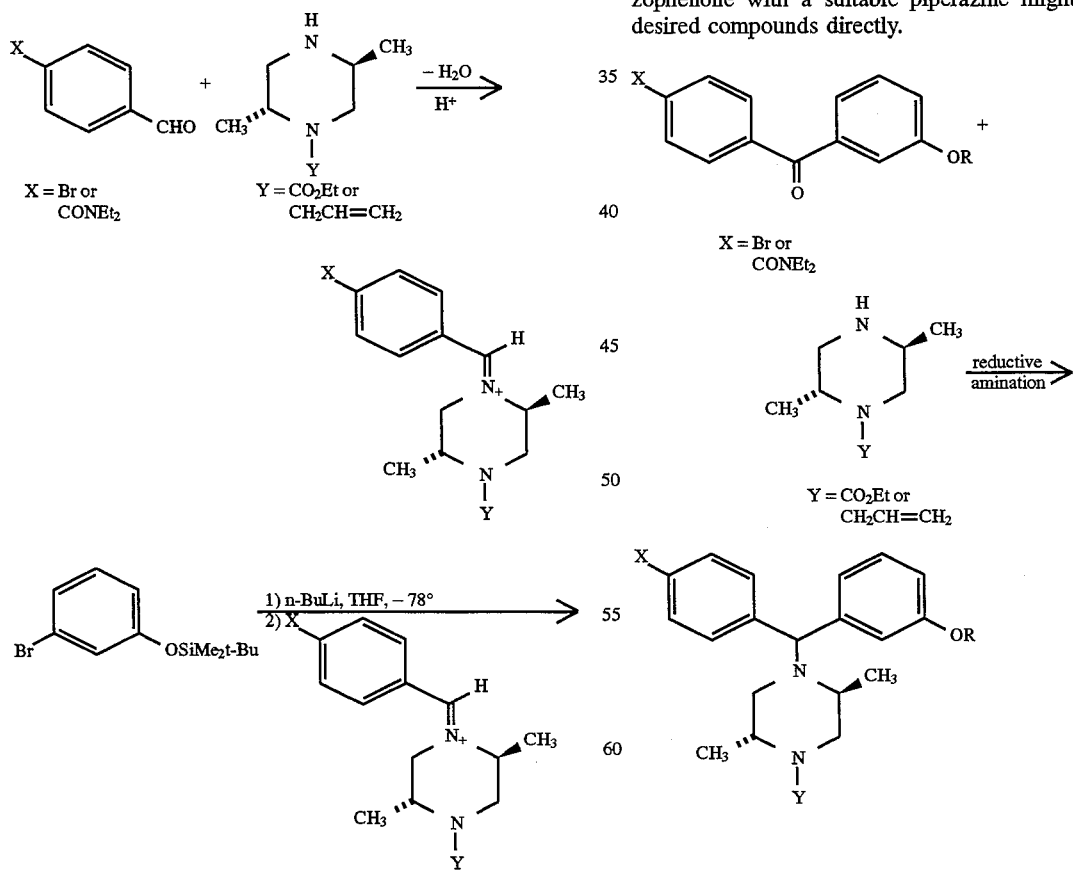

Similarly, reductive amination of the appropriate benzophenone with a suitable piperazine might provide the desired compounds directly.

Compound L can also be synthesized by the alternative synthetic route set out below.

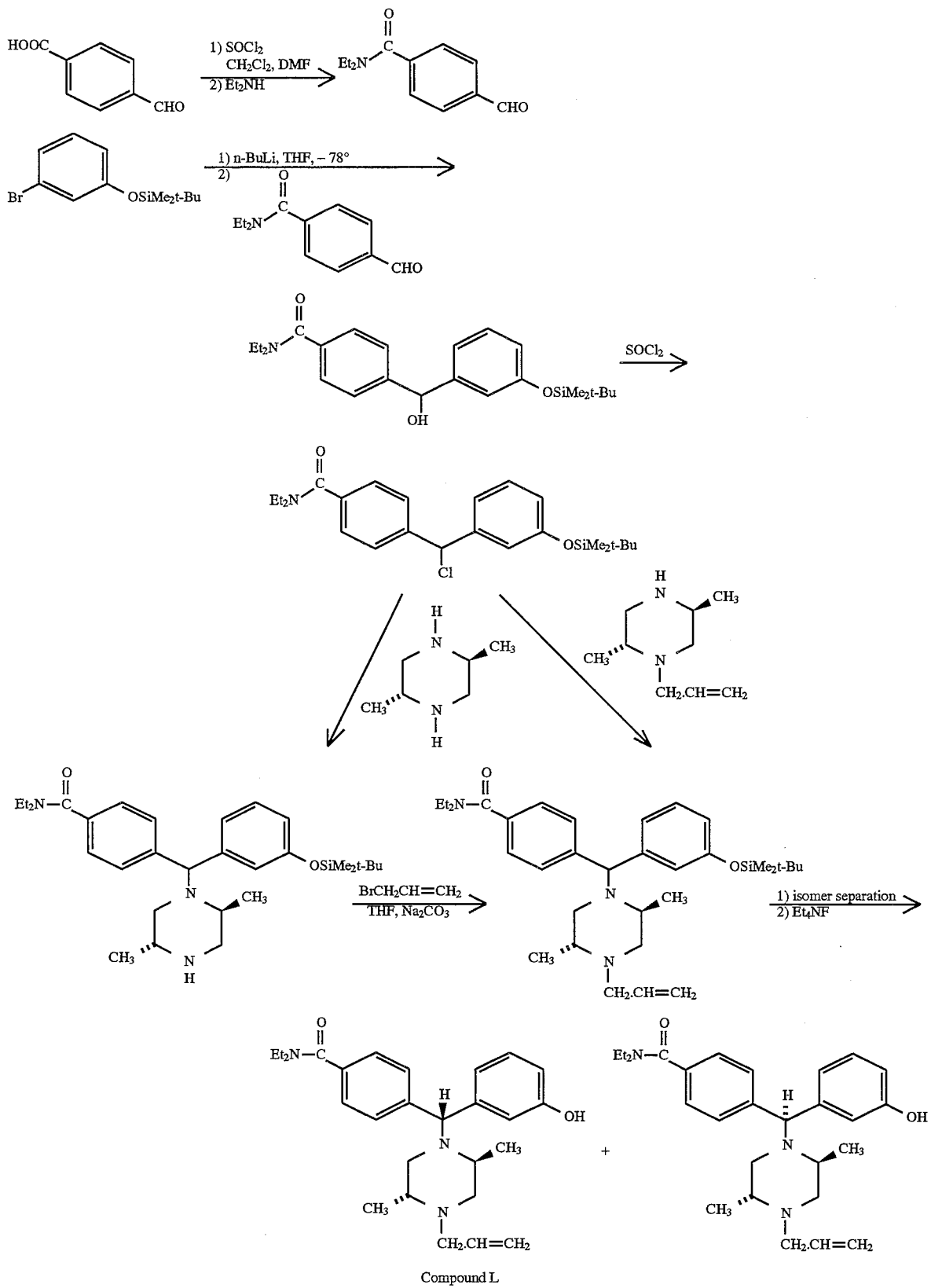
Compound L
The N-allyl-trans-2,5-dimethylpiperazine reactant utilized in the above synthesis scheme may suitably be formed by the following synthetic process.

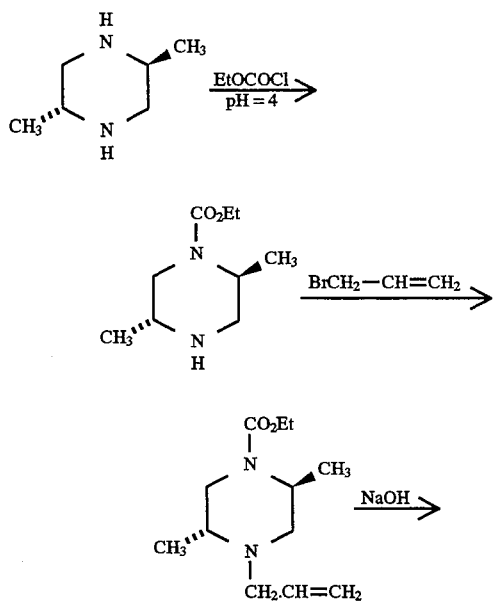

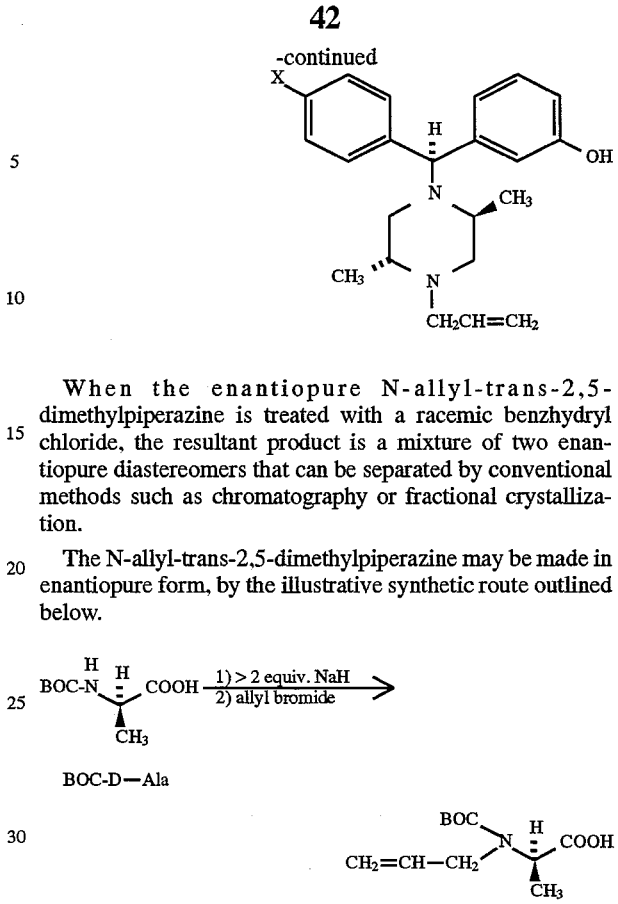

When the enantiopure N-allyl-trans-2,5-dimethylpiperazine is treated with a racemic benzhydryl chloride, the resultant product is a mixture of two enantiopure diastereomers that can be separated by conventional methods such as chromatography or fractional crystallization.

The N-allyl-trans-2,5-dimethylpiperazine may be made in enantiopure form, by the illustrative synthetic route outlined below.

A chiral synthesis method for the production of benzhydrylpiperazines is set out below.

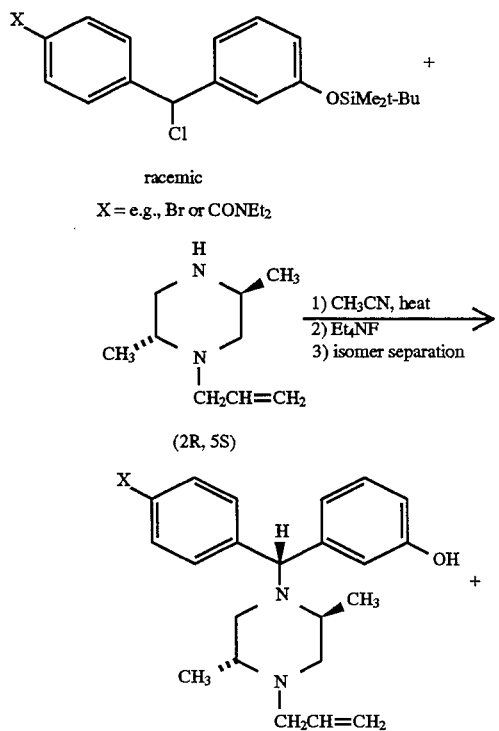

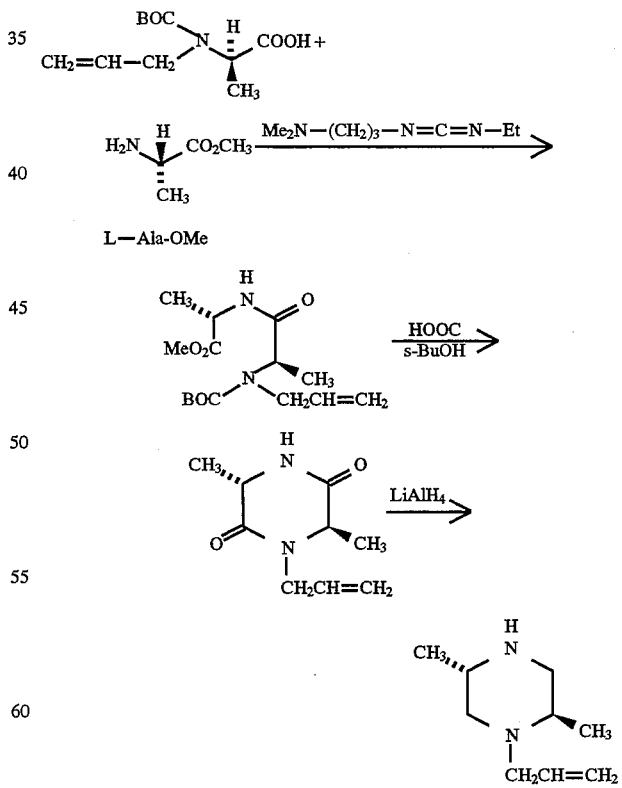

In addition to the foregoing, Compound L may be synthesized via a nitrile synthesis route, utilizing cuprous cyanide as a nitrilation agent, as shown below.

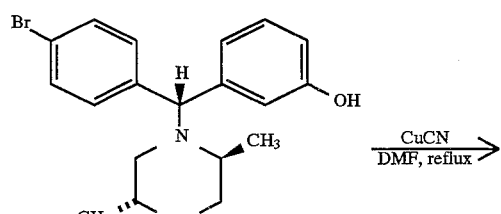
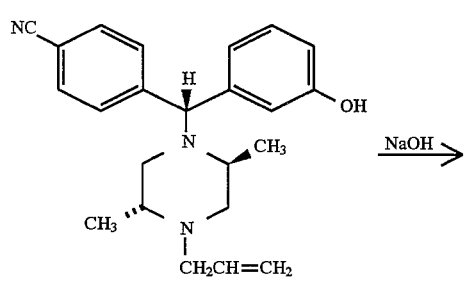
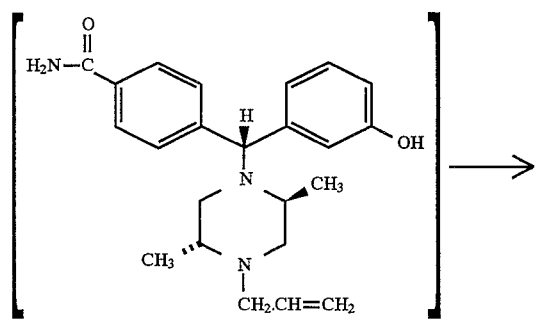
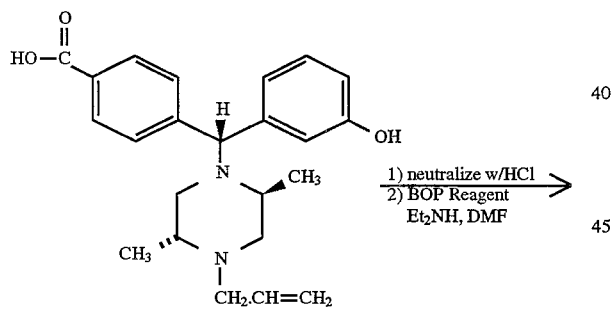
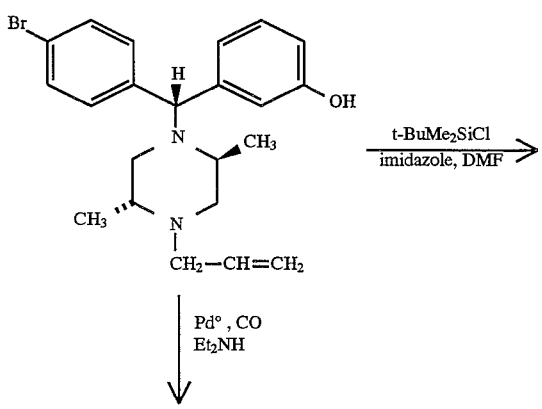
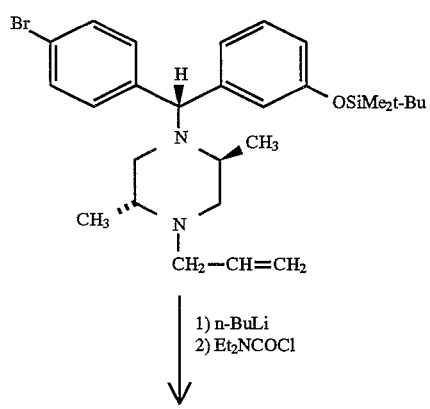
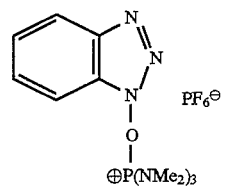
Compound L
BOP Reagent =
Alternative syntheses of Compound L from a corresponding halogenated compound are set out below.

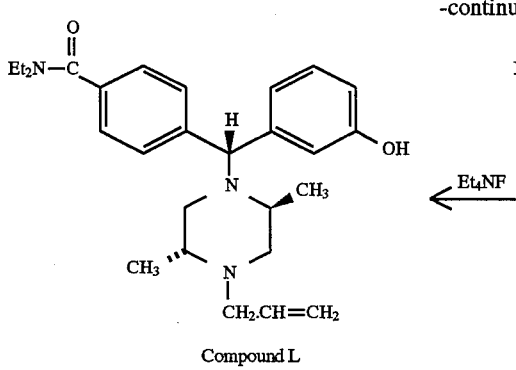

Compound L

-continued

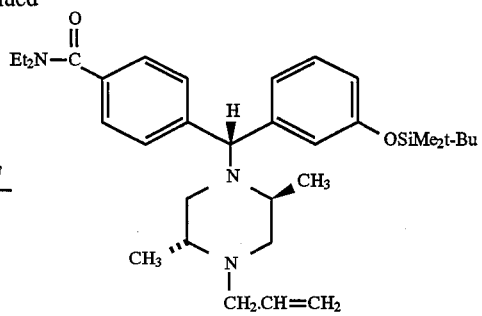

← Et₄NF

The foregoing have been illustratively set out as examples of synthetic techniques which may be usefully employed to form compounds such as Compound L, as well as other benzhydryl piperazine compounds of the present invention, via corresponding or analogous reagents. Of the foregoing synthetic methods described to form Compound L, the nitrile synthesis route is empirically preferred due to its slightly greater convenience as compared to the other described synthetic routes.

The features and advantages of the invention are more fully shown with respect to the following non-limiting examples.

Certain specifications and methods common to many of the following examples relating to chemical synthesis are described in the next paragraph.

Melting points were determined with a Thomas-Hoover apparatus and are uncorrected. All chemical reagents were purchased from Aldrich Chemical Company, Milwaukee, Wis, unless otherwise specified.

Commercial solvents were used without further purification except tetrahydrofuran, which was distilled from potassium. Nuclear magnetic resonance (NMR) spectra were obtained with Perkin-Elmer R-24 and Varian XL-200 or XL-300 spectrometers. HPLC analyses were performed with a Waters liquid chromatography system equipped with a 700 Satellite WISP, 600E System Controller and a 991 Photodiode Array detector, with a 4.6×250 mm Cyclobond I column (Advanced Separations Technologies, Whippany, N.J.), at a flow rate of 1 ml/min. Optical rotations were obtained with a Perkin-Elmer 241 polarimeter. Mass spectra were performed by Oneida Research Services, Whitesboro, N.Y. X-Ray crystallography was performed by Molecular Structure Corporation, College Station, Texas. Analytical thin layer chromatography was performed on Analtech glass plates pre-coated with silica gel GF (250 microns), and preparative thin layer chromatography on Analtech Uniplates pre-coated with silica gel GF (1000 and 2000 microns). Elemental analyses were performed by Atlantic Microlab, Norcross, Ga.

EXAMPLE I (±)-3-((αR*)-α-((2S*,5R*)-4-Allyl-2,5-dimethyl-1-piperazinyl)-4-bromo-benzyl)phenol A solution of 3-bromophenol (500 g, 2.89 mol), tert.-butylchlorodimethylsilane (436 g, 2.89 mol), and imidazole (500 g, 7.22 mol) in 500 mL of dimethylformamide was stirred overnight at room temperature. The reaction solution Was poured into 3000 mL of water and extracted with two 2000 mL portions of diethyl ether. The combined ether extracts were dried over sodium sulfate and the solvent removed to give 846 g of 3-(bromophenoxy)-tert-butyldimethylsilane as a pale yellow liquid. NMR (300 MHz, CDCl₃): δ0.2 (s,6H); 1.0 (s,9H); 6.75 (m,1H); 7.0 (br s, 1H); 7.1 (m,2H).

The crude silyl ether (146 g, 0.51 mol) was dissolved in dry tetrahydrofuran under nitrogen and cooled to −78° C. A solution of 1.6 M n-butyllithium in hexane (318 mL, 0.51 mol) was added dropwise at a rate to maintain temperature below −70° C. The reaction was stirred for 30 minutes after the addition was complete, and the cold solution was transferred to another vessel containing a cold (−78 ° C.) solution of 4-bromobenzaldehyde (94.3 g, 0.51 mol) in 1000 mL of dry tetrahydrofuran under nitrogen. The transfer rate was monitored to maintain reaction temperature below −70 ° C. The reaction volume was stirred for another 45 minutes at −78 ° C. and then quenched with 100 mL of saturated aqueous ammonium chloride. After warming to room temperature, the mixture was diluted with 2000 mL of diethyl ether and washed with 2000 mL of water followed by 500 mL of saturated sodium chloride. The ethereal solution was dried over sodium sulfate and the solvent removed to give 197.2 g of crude α-(4-bromophenyl)-3-(tert-butyldimethylsilyloxy)benzyl alcohol as a yellow oil. NMR (200 MHz, CDCl₃): δ0.2 (s, 6H); 0.9 (s,6H); 5.7 (s, 1H); 6.75 (dd,J₁=2 Hz, J₂=8 Hz,1H); 6.8 (br s, 1H); 6.9 (d,J=8 Hz,1H); 7.15 (t,J=8 Hz,1H); 7.25 and 7.45 (AB q,J=8 Hz,4H).

The crude benzhydryl alcohol (53.2 g, 135 mmol) was dissolved in 1000 mL of dichloromethane and 14.7 mL (202 mmol) of thionyl chloride was added dropwise. The solution was stirred overnight at room temperature and the solvent was removed under vacuum. The crude product was redissolved in 500 mL of toluene and the solvent again was removed under vacuum to eliminate excess thionyl chloride, providing crude α-(4-bromophenyl)-3-(tert-butyldimethylsilyoxy) benzyl chloride as a dark oil. NMR (200 MHz, CDCl₃): δ0.2 (s,6H); 1.0 (s,9H); 6.0 (s,1H); 6.78 (dd,J₁=1 Hz,J₂=8 Hz,1H); 6.9 (m,2H); 7.2 (t,J=8 Hz,2H); 7.27 and 7.47 (AB q,J=8 Hz,4H).

The crude benzhydryl chloride (approx. 135 mmol) was combined with 46.3 g (405 mmol) of trans-2,5-dimethylpiperazine (purified by recrystallization from toluene to mp=115°–119° C.) and 30 mL of toluene and heated at reflux overnight under nitrogen. The toluene was removed under vacuum, and the residue was redissolved in 2000 mL of diethyl ether and washed with 500 mL of 1.0M sodium hydroxide and 1000 mL of water. The ether solution was dried over sodium sulfate and the solvent removed to give a dark oil. The product was purified by chromatography on silica gel with 1–10% ethanol in dichloromethane to give 41.0 g (62%) of (±)-trans-1-(4-bromo-α-(3-(tert-butyldimethylsilyloxy)phenyl)benzyl)-2,5-dimethylpiperazine as a 1:1 mixture of diastereomers. NMR (300 MHz, CDCl$_3$); δ0.15 (s, 6H); 0.9 (m,12H); 1.2 (d,J=6 Hz,3H); 1.4–1.6 (m,2H); 2.2–3.0 (m,5H); 5.2 and 5.3 (s,1H); 6.6–7.5 (m,8H).

The purified benzhydrylpiperazine (41.0 g, 83.7 mmol) was dissolved in 500 mL of dry tetrahydrofuran with 7.3 mL (84 mmol) of allyl bromide and 22 g (200 mmol) of sodium carbonate and heated at reflux overnight under nitrogen. The cooled reaction solution was filtered and the solvent removed to give 44.1 g of crude (±)-trans-1-allyl-4-(4-bromo-α-(3-(tert-butyldimethyl-silyloxy)phenyl)benzyl)-2,5-dimethylpiperazine as a brown oil. NMR (200 MHz, CDCl$_3$): δ0.15 (s,6H); 0.95 (m,12H); 1.15 (2 overlapping d,J=6 Hz,3H); 1.8 (m,1H); 2.1 (m,1H); 2.35–2.65 (m,3H); 2.7–2.9 (m,2H); 3.35 (dd,J$_1$=5 Hz,J$_2$=12 Hz,1H); 5.0–5.2 (m,3H); 5.85 (m,1H); 6.6–7.5 (m,8H).

The crude brown oil product (44.1 g, 83.3 mmol) was dissolved in 200 mL of acetonitrile with 20 g (approx. 130 mmol) of tetraethylammonium fluoride hydrate and stirred for 1 hour at room temperature. After evaporation of solvent, the residue was redissolved in dichloromethane and washed with water (pH=8) to remove the bulk of ammonium salts. The dichloromethane solution was dried over sodium sulfate and the solvent removed to give 40 g of residue. The product was purified by chromatography on silica gel (Waters Prep 500) with 0.5–1% ethanol in dichloromethane containing 0.1% triethylamine. The two diastereomers of the product were separated by chromatography and were obtained initially as oils. Dichloromethane solutions of the diastereomers were shaken with water (pH=8) and the products precipitated as white crystalline solids. The less mobile isomer (R$_f$=0.45 on silica gel with dichloromethane:ethanol:ammonium hydroxide/95:5:1) gave 7.3 g (21%) of (±)-3-((αR*)-α-((2S*,5R*)-4-allyl-2,5-dimethyl-1-piperazinyl)-4-bromobenzyl)phenol, mp 162°–167° C. NMR (200 MHz, DMSO-d$_6$): δ0.94 (d,J=6 Hz,3H); 1.06 (d,J=6 Hz,3H); 1.82 (dd,J$_1$=7.5 Hz,J$_2$=11.6 Hz,1H); 2.07 (dd,J$_1$=7 Hz,J$_2$=11 Hz,1H); 2.5–2.6 (m,3H);2.71 (dd,J$_1$=3 Hz,J$_2$11 Hz,1H); 2.84 (dd,J$_1$=7 Hz,J$_2$=14 Hz,1H); 3.16 (dd,J$_1$=6 Hz,J$_2$=14 Hz,1H); 4.92 (s,1H); 5.09 (dd,J$_1$=2 Hz,J$_2$=10 Hz,1H); 5.17 (dd, J$_1$=2 Hz,J$_2$=17 Hz,1H); 5.78 (m,1H); 6.64 (s,1H); 6.66 (t,J=7.5 Hz,2H); 7.13 (t,J=7.5 Hz,1H); 7.32 and 7.49 (AB q,J=8.5 Hz,4H). A portion was converted to the dihydrochloride salt with excess ethanolic hydrogen chloride and the product was precipitated from ethanol with diethyl either to give a white hygroscopic solid. Calculated for C$_{22}$H$_{27}$BrN$_2$O HCl0.33 H$_2$O: C, 53.46; H, 6.05; N, 5.67; total halogen calculated as Cl, 21.43. Found: C, 53.65; H, 6.39; N, 5.53; total halogen calculated as Cl, 20.98. Assignment of relative stereochemistry was made by X-ray crystallographic structure determination.

The above compound could also be obtained by fractional crystallization from an isomer mixture that had been partially enriched in the desired isomer by chromatography on a short silica gel column with 1:1 dichloromethane:ethyl acetate. Thus, a mixture (115 g) of (±)-3-((αR*)-α-((2S*,5R*)-4-allyl-2,5-dimethyl-1-piperazinyl)-4-bromobenzyl) phenol (70%) and (±)-3-((αR*)-α-((2R*,5S*)-4-allyl-2,5-dimethyl-1-piperazinyl)-4-bromobenzyl)phenol (30%) was heated to 70° C. in 2150 mL acetonitrile/370 mL tetrahydrofuran and then filtered hot. The filtrate was cooled to 42° C. and seeded with crystals of (±)-3-((αR*)-α-((2S*,5R*)-4-allyl-2,5-dimethyl-1-piperazinyl)-4-bromobenzyl)phenol. The solution cooled to 34° C. and filtered to give 18.8 g of (±)-3-((αR*)-α-((2S*,5R*)-4-allyl-2,5-dimethyl-1-piperazinyl)-4-bromobenzyl)phenol in 95% isomeric purity. Additional crops gave 22.2 g of material of similar purity. The total of 40.0 g was recrystallized in the same fashion to give 32.7 g of (±)-3-((αR*)-α-((2S*,5R*)-4-allyl-2,5-dimethyl-1-piperazinyl)-4-bromobenzyl)phenol with isomeric purity >98%.

EXAMPLE 2

(±)-3-((αR*)-α-((2R*,5S*)-4-Allyl-2,5-dimethyl-1-piperazinyl)-4-bromo-benzyl)phenol The first isomer to elute from the column of Example 1 was obtained as described as 4.84 g (14%) of white crystals, mp=184°–187° C. NMR (200 MHz, DMSO-d$_6$): δ0.95 (d, J=6 Hz,3H); 1.05 (d,J=6 Hz,3H); 1.85 (dd,J$_1$=7.5 Hz,J$_2$=11 Hz,1H); 2.1 (dd,J$_1$=7 Hz,J$_2$=12 Hz,1H); 2.4–2.65 (m,3H); 2.7 (dd,J$_1$=4 Hz,J$_2$=2 Hz,1H); 2.85 (dd,J$_1$=7 Hz,J$_2$=4 Hz,1H); 3.15 Hz,J$_2$=16 Hz,1H); 5.1 (d,J=11 Hz,1H); 5.13 (s,1H); 5.18 (d,J=16 Hz,IH); 5.8 (m,1H); 6.61 (d,J=8 Hz,1H); 6.75 (d,J=8 Hz,1H); 6.83 (s,1H); 7.08 (t,J=8 Hz,1H); 7.2 and 7.5 (ABq,J=8 Hz,4H); 9.3 (s,1H). A portion was converted to the dihydrochloride salt with excess ethanolic hydrogen chloride and the product was precipitated from ethanol with diethyl either to give a white hygroscopic solid. Calc. for C$_{22}$H$_{27}$BrN$_2$O2 HCl0.5H$_2$O: C, 53.14; H, 6.08; N, 5.63;total halogen calc. as Cl, 21.39. Found: C, 53.23; H, 6.40; N, 5.50; total halogen calculated as Cl, 21.04.

The above compound could also be obtained by fractional crystallization from an isomer mixture that had been partially endched in the desired isomer by chromatography on a short silica gel column with 1:1 dichloromethane:ethyl acetate. Thus, a mixture (614 g) of (±)-3-((αR*)-α-((2S*,5R*)-4-allyl-2,5-dimethyl-1-piperazinyl)-4-bromobenzyl) phenol (40%) and (±)-3-((αR*)-α-((2R*,5S*)-4-allyl-2,5-dimethyl-1-piperazinyl)-4-bromobenzyl)phenol (60%) was dissolved in 1350 mL of isopropanol at reflux and allowed to cool to 35° C. Filtration gave 149.4 g of (±)-3-((αR*)-α-((2R*,5S*)-4-allyl-2,5-dimethyl-1-piperazinyl)-4-bromobenzyl)phenol containing 3% of the other isomer. Additional crops gave 40.8 g of similar purity which was combined to give a total of 190.2 g and recrystallized from 1200 mL of isopropanol to give 119.6 g of white crystals in >99% isomeric purity.

EXAMPLE 3

(±)-4-((αR*)-α-((2S*,5R*)-4-Allyl-2,5-dimethyl-1-piperazinyl)-3-hydroxy-benzyl)benzonitrile A solution of (±)-3-((αR*)-α-((2S*,5R*)-4-allyl-2,5-dimethyl-1-piperazinyl)-4-bromobenzyl)phenol (Example 1) (32.6 g, 0.0786 mol) and cuprous cyanide (14.1 g, 0.157 mol) in 500 mL dimethylformamide was heated at reflux for three days under nitrogen. The reaction mixture was cooled to room temperature and then poured into a mixture of 2000 mL 30% sodium cyanide:1500 mL diethyl ether. The diethyl ether was washed with 600 mL of water followed by brine. The solvent was removed to give 33.1 g of a brown oil that partially crystallized upon standing. The mixture was triturated with diethyl ether and filtered to give 14.6 g (51%) of (±)-4-((αR*)-α-((2S*,5R*)-4-allyl-2,5-dimethyl-1-piperazinyl)-3-hydroxybenzyl)benzonitrile as a light brown solid. A small amount was recrystallized from ethyl acetate to give a white solid, mp 186°–187° C. Calc. for C$_{27}$H$_{36}$N$_3$O: C, 76.42; H, 7.53; N, 11.62. Found: C, 76.31; H, 7.54; N, 11.55. NMR (200 MHz, DMSO-d$_6$): δ0.95 (d, J=6 Hz, 3H); 1.08 (d, J=6 Hz, 3H); 1.77 (dd, J=8 Hz and 11 Hz, 1H); 2.10 (dd, J=11 Hz and 10.5 Hz, 1H); 2.49–2.90 (m, 5H); 3.18 (dd, J=5.5 Hz and 14 Hz, 1H); 5.06–5.22 (s, 2d, 3H); 5.7–5.9 (m, 1H); 6.66–6.70 (s, 2d, 3H); 7.15 (t, J=8 Hz, 1H); 7.6 and 7.8 (ABq, J=8 Hz, 4H); 9.4 (s, 1H).

EXAMPLE 4

(±)-4-((αR*)-α-((2S*,5R*)-4-allyl-2,5-dimethyl-1-piperazinyl-3-hydroxy-benzyl)benzamide (±)-3-((αR*)-α-((2S*,5R*)-4-Allyl-2,5-dimethyl-1-piperazinyl)-4-bromobenzyl)phenol (0.30 g, 0.72 mmol), from Example 1, was treated with tert-butylchlorodimethylsilane to give 0.36 g of a colorless oil which was then treated with n-butyllithium (0.45 mL of 1.6M solution in hexane) and carbon dioxide as described in Example 6, Method B, to give 0.35 g of a colorless glass.

Thionyl chloride (78 µL, 1.1 mmol) was added to a cold (0° C.) solution of the product from above (0.35 g, 0.70 mmol) in dichloromethane. After two hours at 0° C., the mixture was added dropwise to cold concentrated ammonium hydroxide (1.5 mL), stirred for one hour at room temperature and diluted with water and dichloromethane. The organic layer was washed with water, dried over sodium sulfate and evaporated, and the residue was purified by preparative thin layer chromatography (silica gel, dichloromethane: ethanol: ammonium hydroxide/90:10:1) to give 0.21 g (58%) of (±)-4-((αR*)-α-((2S*, 5R*)-4-allyl-2,5-dimethyl-1-piperazinyl)-3-(tert-butyldimethylsiiyloxy)benzyl)benzamide as a yellow oil. NMR (CDCl$_3$): δ 0.15 (s, 6H); 0.9 (s, 9H); 1.0 (d, 3H); 1.2 (d, 3H); 1.9 (m, 1H); 2.2 (m, 1H); 2.4–2.7 (m, 3H); 2.85 (m, 1H); 2.95 (m, 1H); 3.4 (m, 1H); 5.2 (m, 3H); 5.7–6.1(m, 2H); 6.0 (br s, 1H); 6.6 (s, 1H); 6.8 (s, 1H); 7.15 (t, 1H); 7.5 (d, 2H); 7.75 (d, 2H).

The product from above (0.21 g, 0.43 mmol) was treated with tetraethylammonium fluoride hydrate (0.15 g, approximately 0.8 mmol) in acetonitrile solution. The solvent was removed, the residue extracted between chloroform and pH 8 buffer, and the chloroform layer was dried over sodium sulfate and evaporated. The crude product was converted to the monohydrochloride salt by titration to pH=4.5 with ethanolic hydrochloric acid, followed by precipitation with diethyl ether to give 97.4 mg (60%) of a white solid. Calculated for $C_{23}H_{29}N_3O_2$ HCl0.5 $H_2O$: C, 64.34; H, 7.65; N, 9.38; Cl, 7.91. Found: C, 64.44, H, 7.93; N, 9.30; Cl, 7.94. mass spectrum (Cl–CH$_4$) m/z 380 (M+1, 100%), 153 (9%), 226 (10%). A portion of the crude product was purified by chromatography on silica gel with dichloromethane:ethanol (2–10%) to give a pale yellow foam. NMR (CDCl$_3$): δ 1.0 (d, J=6 Hz, 3H); 1.1 (d, J=6 Hz, 3H); 3.85 (m, 2H); 3.4 (m, 1H); 5.2 (m, 3H); 5.9 (m, 1H); 6.3 (br s, 2H); 6.6 (m, 3H); 7.1 (t, J=8 Hz, 1H); 7.5 (d, J=9 Hz, 2H); 7.6 (d, J=9 Hz, 2H).

EXAMPLE 5

(±)-4-((αR*)-α-(2S*,5R*)-4-Allyl-2,5-dimethyl-1-piperazinyl)-3-hydroxy-benzyl)benzoic acid A solution of (±)-4-((αR*)-α-((2S*,5R*)-4-allyl-2,5-dimethyl-1-piperazinyl)-3-hydroxybenzyl)benzonitrile (Example 3) (20.81 g, 0.0575 mol) and sodium hydroxide pellets (16.1 g, 0.402 mol) in 200 mL 95% ethanol was heated at reflux overnight. The solution was cooled to room temperature, the pH was adjusted to 6 with concentrated hydrochloric acid and the solvent was removed in vacuo. The resulting solid was triturated with methylene chloride and filtered to give 42.0 g of (±)-4-((αR*)-α-((2S*,5R*)-4-allyl-2,5-dimethyl-1-piperazinyl)-3-hydroxybenzyl)benzoic acid mixed with sodium chloride as a pale brown solid. The crude carboxylic acid (1.5 g) was stirred overnight in 40 mL of distilled water. The acid was collected by filtration and dried under vacuum at 55° C. The acid (0.47 g) was slurried in ethanol and titrated with 0.2M ethanolic hydrochloric acid to pH 5.2. The solvent was removed and the resulting solid was again stirred overnight in distilled water. Filtration and drying gave 0.27 g of (±)-4-((αR*)-α-((2S*,5R*)-4-allyl-2,5-dimethyl-1-piperazinyl)-3-hydroxy-benzyl)benzoic acid as a tan solid. Calc. for $C_{23}H_{28}N_2O_3$ 1.5 $H_2O$: C, 67.78; H, 7.67; N, 6.87. Found: C, 67.78; H, 7.38; N, 6.90. NMR (200 MHz, $D_2O$/NaOD) δ: 0.83 (d, J=6 Hz, 3H); 0.98 (d, J=6 Hz, 3H); 1.9–2.1 (m, 2H); 2.3–2.8 (br m, 5.1 (m, 3H); 5.6–5.8 (m, 1H); 6.3 (d, J=7 Hz, 1H); 6.4–6.45 (s,d,2H); 6.95 (t,J=8 Hz, 1H); 7.3 and 7.6 (ABq, J=8 Hz, 4H).

EXAMPLE 6

(±)-4-((αR*)-α-((2S*,5R*)-4-Allyl-2,5-dimethyl-1-piperazinyl)-3-hydroxy-benzyl)-N,N-diethylbenzamide

METHOD A

A solution of crude (±)-4-((αR*)-α-((2S*,5R*)-4-allyl-2,5-dimethyl-1-piperazinyl)-3-hydroxybenzyl)benzoic acid (Example 5, from 7.1 mmol of Example 1), benzotriazol-1-yloxytris(dimethylamino)phosphonium hexafluorophosphate (3.1 g, 14 mmol), and diethylamine (3.7 mL, 35 mmol) in 100 mL dimethylformamide was stirred overnight at room temperature. The solvent was removed under vacuum. The residue was dissolved in a mixture of 200 mL 1M HCl and 200 mL diethyl ether. The pH of the aqueous layer was adjusted to 8 with 10M sodium hydroxide and then extracted with 350 mL dichloromethane. The dichloromethane layer was dried over sodium sulfate. The solvent was evaporated leaving 3.59 g of a brown oil. The oil was chromatographed on silica gel with ethyl acetate:hexane to give 1.24 g (40%) of (±)-4-((αR*)-α-((2S*,5R*)-4-allyl-2,5-dimethyl-1-piperazinyl)-3-hydroxybenzyl)-N,N-diethylbenzamide as a white solid and 0.78 g as a pink foam. The foam was crystallized from acetonitrile to give 0.55 g (total yield 58%) of the amide as white needles, mp 170°–171° C. Calc. for $C_{27}H_{27}N_3O_2$: C, 74.45; H, 8.56; N, 9.65. Found: C, 74.29; H, 8.59; N, 9.70. NMR (200 MHz, DMSO-dd$_6$) δ: 0.95 (d, J=6 Hz, 3H); 1.1 (d, br tr, 9H); 1.85 (t, J=11 Hz, 1H); 2.05–2.14 (dd, J=10 Hz and J=11 Hz); 2.5–2.9 (br m, 5H); 3.1–3.4 (br m, 5H); 5.0 (s, 1H); 5.1 (2d, 2H); 5.7–5.9 (m, 1H); 6.7 (s, 2d, (dd, J=8 Hz and J=8 Hz, 1H); 7.3 and 7.4 (Abq, J=8 Hz, 4H); 9.35 (s, 1H).

METHOD 8

(±)-3-((αR*)-α-((2S*,5R*)-4-Allyl-2,5-dimethyl-1-piperazinyl)-4-bromobenzyl)phenol (5.3 g, 12.8 mmol, Example 1) was dissolved in 25 mL of dimethylformamide with 2.72 g (18.0 mmol) of tert-butylchlorodimethylsilane and 2.05 g (30.0 mmol) of imidazole and stirred overnight at room temperature. The reaction solution was poured into 125 mL of water and extracted with 125 mL of diethyl ether. The ether extract was washed with 75 mL of 0.1M sodium hydroxide, 75 mL of water, and 25 mL of saturated sodium chloride solution. The ether solution was dried over sodium sulfate and the solvent was removed to give 7.4 g of oil which was purified by chromatography on silica gel with 1–4% ethanol in dichloromethane. Yield of (±)-(2R*,5S*)-1-allyl-4-(4-bromo-(αS*)-α-(3-(tertbutyldimethlysilyloxy)phenyl)benzyl)-2,5-dimethylpiperazine was 6.58 g of pale yellow oil. NMR (200 MHz, CDCl$_3$): δ0.15 (s,6H); 0.96 (s,9H); 0.97 (d,J=6 Hz,3H); 1.15 (d,J=6 Hz,3H); 1.87 (dd, J$_1$=9.5 Hz, J$_2$10 Hz,1H); 2.12 (dd, J$_1$=9.5 Hz, J$_2$10.5 Hz, 1H); 2.35–2.65 (m,3H); 2.75–2.95 (m,2H); 3.36 (dd, J$_1$=6 Hz, J$_2$14 Hz, 1H); 5.12 (s,1H); 5.15 (m,2H); 5.85 (m,1H); 6.59 (s,1H); 6.75 (d,J=7.7 Hz,2H); 7.17 (t,J=7.7 Hz,1H); 7.31 and 7.39 (AB q,J=8.5 Hz,4H).

The silyl ether (6.55 g, 12.4 mmol) was dissolved in 60 mL of dry tetrahydrofuran and cooled to −78° C. under nitrogen. A solution of 1.35 M n-butyllithium in hexane (9.2 mL, 12.4 mmol) was added dropwise at a rate to maintain temperature below −70° C. After the orange solution stirred an additional 30 min at low temperature, anhydrous carbon dioxide gas was introduced into the reaction solution at a rate to maintain temperature below −60° C. Carbon dioxide addition was stopped when the reaction solution became a pale yellow. The reaction was allowed to warm to room temperature with stirring and the solvent was removed under vacuum. The residue was redissolved in 50 mL of toluene and the solvent again removed under vacuum in order to eliminate residual n-bromobutane. The reaction provided 6.2 g of the lithium salt of (±)-4-((αR*)-α-((2S*,5R*)-4-allyl-2,5-dimethyl-1-piperazinyi)-3-(tert-butyldimethylsilyloxy)benzyl)benzoic acid. Mass spectrum (FAB) m/e: 495 (m+1,45%), 455 (15%), 369 (15%), 341 (100%): 297 (20%), 277 (50%).

The lithium benzoate salt (6.2 g, 12.4 mmol) was dissolved in 100 mL of dichloromethane and cooled to 0 °C. A solution of thionyl chloride (1.4 mL, 19 mmol) in 50 mL of dichloromethane was added dropwise. The reaction was stirred for 1.5 hours at 0° C. and a solution of diethylamine (8.1 mL, 78 mmol) in 80 mL of dichloromethane was added dropwise. The reaction was allowed to warm to room temperature and stir overnight. The reaction solution was washed with water and dried over sodium sulfate. After removal of solvent, the residue was purified by chromatography on silica gel with 1–3% ethanol in dichloromethane to give 2.15 g (32%) of (±)-4-((αR*)-α-((2S*,5R*)-4-allyl-2,5-dimethyl-1-piperazinyl)-3-(tert-butyldimethylsilyl-oxy)benzyl)-N,N-diethylbenzamide as a gummy residue. NMR (300 MHz, CDCl$_3$): δ0.15 (s,6H); 0.95 (s,9H); 0.97 (d,J=6 Hz,3H); 1.12 (br m,3H); 1.18 (d,J=6 Hz,3H); 1.23 (br m,3H); 1.87 (dd, J$_1$=9 Hz, J$_2$11 Hz, 1H); 2.12 (dd, J$_1$=9 Hz, J$_2$11 Hz, 1H); 2.45 (m,1H); 2.56 (dd, J$_1$=2.5 Hz, J$_2$=11 Hz, 1H); 2.58 (m,1H); 2.79 (dd, J$_1$=3 Hz, J$_2$11 Hz, 1H); 2.85 (dd, J$_1$=8 Hz, J$_2$14 Hz, 1H); 3.25 (br m,2H); 3.36 (dd, J$_1$–5.5 Hz, J$_2$14 Hz, 1H); 3.53 (br m,2H) 5.1–5.2 (m,3H); 5.85 (m,1H); 6.60 (s,1H); 6.74 (d,J=8 Hz,1H); 6.76 (d,J=8 Hz,1H); 7.17 (t,J=8 Hz,1H); 7.28 and 7.46 (AB q,J=8 Hz,4H).

The benzamide from above (2.15 g, 3.91 mmol) was dissolved in 40 mL of acetonitrile with 0.88 g (6 mmol) of tetraethylammonium fluoride hydrate and stirred for 1 hour at room temperature. After evaporation of the solvent, the residue was redissolved in dichloromethane and washed with water (pH=8), then dried over sodium sulfate and the solvent removed to give 1.67 g of gummy residue. The dihydrochloride salt was prepared by treatment with excess ethanolic hydrogen chloride followed by precipitation with diethyl ether to give 1.45 g (72%) of (±)-4-((αR*)-α-((2S*, 5R*)-4-allyl-2,5-dimethyl-1-piperazinyl)-3-hydroxybenzyl)-N,N-diethylbenzamide dihydrochloride as a hygroscopic white powder. Calc. for C$_{27}$H$_{37}$N$_3$O$_2$2HCl 0.5H$_2$O: C, 62.66; H, 7.79; N, 8.12; Cl, 13.70. Found: C, 62.47; H, 7.91; N, 8.02; Cl. 13.49. A portion was converted to the free amine by adjusting an aqueous solution to pH=8 and extracting with dichloromethane to give a spectral sample. NMR (300 MHz, CDCl$_3$): δ1.00 (d,J=6 Hz,3H); 1.12 (br m,3H); 1.16 (d,J=6 Hz,3H); 1.25 (br m,3H); 1.90 (dd, J$_1$=9 Hz, J$_2$=11 3.3 (br m,2H); 3.41 (dd, J$_1$=5 Hz, J$_2$14 Hz, 1H); 3.55 (br m,2H); 5 5.14–5.23 (m,2H); 5.88 (m, 1H); 6.58–6.64 (m,3H); 7.11 (t,J=7.8 Hz,I H); 7.28 and 7.45 (AB q,J=8 Hz,4H). Mass spectrum (Cl–CH$_4$) m/e: 436 (m+1,48%), 284 (100%), 153 (57%).

EXAMPLE 6a (±-4-((αR)-α-((2S,5R)-4-Allyl-2.5-dimethyl-1-piperazinyl-3-hydroxybenzyl-N,N-diethylbenzamide The mother liquors from crystallization of the dibenzoyl-D-tartrate salt in Example 6b were evaporated to dryness. The residue was treated with excess 1N aqueous sodium hydroxide and then titrated to pH 8 with 6N hydrochloric acid. The precipitated amine (1.05 g, 2.4 mmol) was mixed with a solution of (−)-dibenzoyl-L-tartaric acid (0.90 g, 2.4 mmol) in 30 mL of absolute ethanol and allowed to stand at room temperature for several days. The crystallized salt was treated with excess 1N aqueous sodium hydroxide and then titrated to pH 8 with 6N hydrochloric acid. The precipitated amine was purified by preparative thin layer chromatography (silica gel plates with dichloromethane:ethanol:ammonium hydroxide/90:10:1 ) to give 0.20 g (25% of theoretical for one enantiomer) of (±)-4-((αR)-α-((2S,5R)-4-allyl-2,5-dimethyl-1-piperazinyl)-3-hydroxybenzyl)-N,N-diethylbenzamide as a white solid. [α]D$_D^{20}$ =+23.7° (methanol, c=1.9). HPLC on β-cyclodextrin with methanol:0.1M aqueous ammonium acetate/35:65 gave one peak at t$_R$=8.5 min. Conversion to the monohydrochioride as in Example 6 gave 0.198 g of a white solid. Calc for C$_{27}$H$_{37}$N$_3$O$_2$ HCl 0.75 H$_2$O: C, 66.79; H, 8.20; N, 8.65; Cl, 7.30. Found: C, 66.74; H, 8.18; N, 8.63; Cl, 7.31.

EXAMPLE 6b (−)-4-((αS)-α-((2R,5S)-4-Allyl-2.5-dimethyl-1-piperazinyl)-3-hydroxybenzyl-N,N-diethylbenzamide The product of Example 6 (1.59 g as free amine, 3.6 mmol) was dissolved in 45 mL of absolute ethanol with 1.37 g (3.6 mmol) of (±)-dibenzoyl-D-tartaric acid and allowed to stand at room temperature. The resulting crystalline salt was collected by filtration and recrystaillized twice from absolute ethanol. The salt was treated with excess 1N sodium hydroxide, then titrated to pH 8 with 6N aqueous hydrochloric acid. The precipitated amine was collected by filtration and purified on a short silica gel chromatography column with dichloromethane:ethanol 95:5 to give 0.33 g (41% of theoretical for one enantiomer) of (−)-4-((αS)-α-((2R,5S)-4-allyl-2,5-dimethyl-1-piperazinyl)-3-hydroxybenzyl)-N,N-diethylbenzamide as a tan solid. [a]$_D^{20}$=−23.2° (methanol, c=2.1). Analytical HPLC on β-cyclodextrin with methanol:0.1M aqueous ammonium acetate/35:65 gave one peak at t$_R$=26.1 min.

EXAMPLE 7

(±)-4-((αR*)-α-((2R*,5S*)-4-Allyl-2-5-dimethyl-1-piperazinyl-3-hydroxy-benzyl)benzonitrile was prepared from the compound of Example 2 by the method described in Example 3 mp 148°–151 ° C. Calc. for C$_{23}$H$_{27}$N$_3$O: C, 76.42; H, 7.53; N, 11.62. Found: C, 76.35; H, 7.58; N, 11.59. NMR (200 MHz, DMSO-d$_6$) δ0.9 (d, J=6 Hz, 3H); 1.0 (d, J=6 Hz, 3H); 1.8 (dd, J$_1$=7 Hz, J$_2$=11 Hz, 1H); 2.1 (dd, J$_1$=6

Hz, J₂=11 Hz, 1H); 2.4–2.8 (m, 4H); 2.85 (dd, J₁=7 Hz, J=14 Hz, 1H); 3.1 (dd, J₁=5.5 Hz, J₂=14 Hz, 1H); 5.0 (s,1H) ; 5.05 (d, J=11 Hz, 1H); 5.15 (d, J=17 Hz, 1H); 5.75 (m, 1H); 6.55 (d, J=8 Hz, 1H); 6.7 (d, J=8 Hz, 1H); 6.8 (s, 1H), 7.05 (t, J=8 Hz, 1 H) 7.5 and 7.8 (AB q, J=8 Hz, 4H);9.3 (s, 1H).

EXAMPLE 8

(±)-4-((αR*)-α-((2R*,5S*)-4-Allyl-2.5-dimethyl-1-piperazinyl)-3-hydroxy-benzyl-benzoic acid A solution of crude lithium 4-((αR*)-α-((2R*,5S*)-2,5-dimethyl-1-piperazinyl)-3-tert-butyldimethylsiloxybenzyl) benzoate (11.5 g, from 23 mmol of Example 2 by the procedure of Example 6, Method B) in tetrahydrofuran was treated with 6M aqueous hydrochloric acid at room temperature for 18 hours. After dilution with water, the mixture was extracted with diethyl ether and the aqueous layer was adjusted to pH 8 with aqueous sodium hydroxide and extracted with dichloromethane. The aqueous layer was titrated to pH 6 with concentrated hydrochloric acid and the precipitated solid was collected by filtration, washed with water and dried under vacuum (60° C.) to give 2.65 g (30%) of (±)-4-((αR*)-α-((2R*,5S*)-4-allyl-2,5-dimethyl-1-piperazinyl)-3-hydroxybenzyl)benzoic acid as an off-white powder. NMR (DMSO-d₆) δ: 0.9 (d, J=6 Hz, 3H); 1.05 (d, J=6 Hz, 3H); 1.8 (dd, J₁=11 Hz, J₂=7 Hz, 1 (dd, J₁=11 Hz, J₂=7 Hz, 1H); 2.5 (m, 6H); 2.7 (d, J=1 Hz, 1H); 2.9 (dd, J₁=7 Hz, J₂=14 Hz); 3.1 (dd, J₁=14 Hz, J₂=5 Hz, 1H); 4.9–5.2 (m, 3H); 1H); 7.3 (m, 1H); 6.5 (dd, J₁=8 Hz, J₂=2 Hz, 1H); 6.8 (m.2H); 7.1 (t, J=8 Hz, 1H); 7.4 (d, J=8 Hz, 2H); 7.9 (d, J=8 Hz, 2H). Calc. for C₂₃H₂₈N₂ 1.25 H₂O: C, 68.55; H, 7.63; N, 6.95. Found: C, 68.61; H, 7.66; N, 7.02. Mass spectrum (C₁-CH₄): m/z 381 (M+1, 44%), 153 (100%), 227 (17%).

EXAMPLE 9

(±-3-((αR*)-α-((2R*,5S*)-4-Allyl-2.5-dimethyl-1-piperazinyl)benzyl:phenol

A solution of (±)-3-((αR*)-α-((2R*,5S*)-4-allyl-2,5-dimethyl-1-piperazinyl)-4-bromobenzyl)phenol (Example 2) (35.00 g, 0.0843 mol) in 400 mL anhydrous tetrahydrofuran was cooled to −78° C. n-Butyllithium (1.6M in hexane, 126 mL, 0.20 mol) was added dropwise. The reaction was stirred for 30 min. at −78° C. and then quenched with saturated ammonium chloride. After warming to room temperature, the reaction mixture was poured into 1000 mL ethyl acetate:1000 mL water. The ethyl acetate layer was washed with brine and dried over sodium sulfate. The solvent was removed to give 27.6 g of pink solid. The solid was recrystallized from ethyl acetate giving 19.4 g (68%) of (±)-3-((αR*)-α-((2R*,5S*)-4-allyl-2,5-dimethyl-1-piperazinyl)benzyl)phenol as a white solid, mp 172.5°–175.5° C. NMR (200 MHz, DMSO-d₆): δ0.96 (d, J=6 Hz, 3H); 1.08 (d, J=6 Hz, 3H); 1.85 (t, J=11 Hz, 1H); 2.09 (t, J=11 Hz, 1H); 2.5–2.9 (m, 5H); 3.15 (dd, J=5.4 Hz and 15, 1H); 4.9 (s, 1H); 5.1–5.2 (2d, 2H); 5.7–5.9 (m, 1H); 6.55 (d, J=8 Hz J=8 Hz, 1H); 6.85 (s, 1H); 7.07 (t, J=8 Hz, 1H); 7.2–7.4 (m, 5H); 9.3 (s.1H). The free amine was dissolved in ethanol and converted to the monohydrochloride salt by titration to pH of 3.8 with ethanolic hydrogen chloride. The salt was precipitated from ethanol with diethyl ether to give 15.82 g as a white solid. Calc. for C₂₂H₂₈N₂O HCl 0.5 H₂O: C, 69.18; H, 7.92; N, 7.33; Cl, 9.28. Found: C, 69.55; H, 8.03; N, 7.31; Cl, 9.27.

EXAMPLE 10

(±)-3-((αR*)-α-((2S*,5R*)-4-Allyl-2.5-dimethyl-piperazinyl)benzyl)phenol was prepared by the method described in Example 9, mp 167.5–168.5. NMR (200 MHz, DMSO-d₆): δ0.95 (d, J=6 Hz, 3H); 1.05 (d, J=6 Hz, 3H); 1.9 (dd, J₁=7 Hz, J₂=11 Hz, 1H); 2.1 (dd, J₁-7 Hz, J₂=11 Hz, 1H); 2.5–2.8 (m,4H)2.9 (dd, J₁=7 Hz, J₂=14 Hz, 1H); 3.15 (dd, J₁=5 Hz, J₂=14 Hz, 1H); 4.9 (s, 1H); 5.1 (d, J=6 Hz, 1H); 5.15 (d, J-17 Hz, 1H), 2H); 5.8 (m, 1H); 6.7 (m, 3H); 7.1–7.4 (m, 6H); 9.3 (s, 1H). Calc. for C₂₂H₂₈N₂O: C, 78.53; H, 8.39; N, 8.33. Found: C, 78.28; H, 8.45; N, 8.30. Monohydrochloride salt: Calc for C₂₂H₂₈N₂ O HCl 0.5 H₂O: C, 69.18; H, 7.92; N, 7.33; Cl, 9.28. Found C, 69.27; H, 7.93, N, 7.30; Cl, 9.17.

EXAMPLE 11 cis-4-(α-(4-((2-Butenyl)-3.5-dimethyl-1-piperazinyl)-3-hydroxybenzyl)-N,N-diethylbenzamide.

A mixture of 4-carboxybenzaldehyde (100 g, 0.66 mol), 1L of dimethylformamide and 2L of dichloromethane was cooled in an ice bath.

Thionyl chloride (53 mL, 0.73 mol) was added dropwise while stirring. After 18 hours at room temperature, the mixture was cooled again and diethylamine (275 mL, 2.6 mol) was added dropwise. After stirring at room temperature for one hour the solvent was evaporated, and the residue was dissolved in aqueous 0.1M sodium hydroxide and extracted with ethyl acetate. The organic layers were washed with water and brine, dried over sodium sulfate and evaporated to give a yellow oil. Chromatography on silica gel with dichloromethane: ethanol (0–2%) gave 44.2 g (32%) of 4-formyl-N,N-diethylbenzamide as a yellow oil.

3-Bromophenoxy-tert-butyldimethylsilane (61.7 g, 0.21 mol), prepared as in Example 1, was dissolved in 500 mL of dry tetrahydrofuran under nitrogen and cooled to −78° C. A solution of 1.6M n-butyllithium in hexane (132 mL, 0.21 mol) was added dropwise at a rate to maintain the temperature below −70° C. The reaction was stirred for thirty minutes after the addition was complete and the cold solution was transferred via cannula to another vessel containing a cold (−78 ° C.) solution of 4-formyl-N,N-diethylbenzamide (44.1 g, 0.21 mol), from above, in 500 mL of dry tetrahydrofuran under nitrogen. The transfer rate was monitored to maintain the temperature below −70° C. After stirring for one hour at −78° C., the reaction was quenched with saturated aqueous ammonium chloride, warmed to room temperature and diluted with diethyl ether. The ethereal layer was washed with water and brine, dried over sodium sulfate and evaporated to give a yellow oil. Chromatography on silica gel with dichloromethane: ethanol (0–1%) gave 45.4 g (52%) of 4-(3-(tert-butyl dimethylsiiyloxy)-α-hydroxybenzyl)-N,N-diethylbenzamide as a white solid.

Thionyl chloride (12 mL, 0.17 mol) was added to a solution of the benzhydryl alcohol from above (45.4 g, 0.11 mol) in 300 mL of dichloromethane. After stirring at room temperature for one hour the solvent was evaporated, the residue was redissolved in toluene and again evaporated to drive off excess thionyl chloride.

A mixture of the crude benzhydryl chloride (approximately 0.11 mol), cis-2,6-dimethylpiperazine (43.97 g, 0.39 mol) and 10 mL of toluene was heated to reflux under nitrogen for two hours. The reaction mixture was partitioned between aqueous 1N hydrochloric acid and diethyl ether. The aqueous layer was adjusted to pH=8 with aqueous 5M sodium hydroxide and extracted with dichloromethane. The extracts were washed with water, dried over sodium sulfate and evaporated to give 36.96 g of a yellow glass.

A mixture of the product (36.5 g, 72 mmol), 38.2 g (360 mmol) of anhydrous sodium carbonate, 9.8 g (74 mmol) of 1-bromo-2-butyne, prepared from 2-butyn-1-ol (L. Brandstoa, "Preparative Acetylenic Chemistry," 2nd edition, Elsevier, 198.8, p. 248), in 400 mL of dry tetrahydrofuran was heated to reflux under nitrogen for 48 hours. The solvent was evaporated and the residue was taken up in dichloromethane and filtered to remove inorganic salts. The filtrate was evaporated, the residue dissolved in acetonitrile and 21 g (approximately 0.11 mol) of tetraethylammonium fluoride hydrate was added. After stirring at room temperature for three hours, the solvent was removed and the residue was purified by chromatography on silica gel with dichloromethane:ethanol (0–4%) to give 12.5 g (31%) of cis-4-(α-(4-(2-butynyl)-3,5-dimethyl-1-piperazinyl)-3-hydroxybenzyl)-N,N-diethylbenzamide as a light yellow glass.

The butynylamine from above (12.5 g, 28 mmol) was dissolved in 400 mL of toluene with 7.9 g of Lindlar catalyst (Engelhard Industries) and reduced in an atmospheric hydrogenation apparatus with magnetic stirring. The reaction was complete in two hours as determined by thin layer chromatography (dichloromethane:ethanol:ammonium hydroxide/ 90:10:1). The catalyst was removed by filtration through Celite and the filtrate was evaporated to give a brown solid. Chromatography on silica gel (Waters Prep 500 with dichloromethane:ethanol:triethylamine/100:0.5–2:0.1) gave 5.47 g (43%) of cis-4-(α-(4-((Z)-2-butenyl)-3,5-dimethyl-1-piperazinyl)-3-hydroxybenzyl)-N,N-diethylbenzamide as a white solid. NMR (CDCl$_3$): δ0.9–1.3 (m, 12H); 1.65 (m, 3H); 1.8 (t, 2H); 2.6–2.9 (m, 7H); 3.2 (m, 4H); 3.3 (br m, 4H); 4.05 (s, 1H); 5.6 (m, 2H); 6.75 (m, 1H); 6.9 (m, 2H); 7.05 (t, 1H); 7.25 (d, 2H); 7.4 (d, 2H). The product was dissolved in absolute ethanol and titrated to pH=4.5 with ethanolic hydrochloric acid. The solution was concentrated and diethyl ether was added to precipitate 4.36 g (82%) of the monohydrochloride salt. Calculated for $C_{28}H_{38}N_3O_2$ HCl H$_2$O: C, 66.85; H, 8.21; N, 8.35; Cl, 7.05. Found: C, 66.79; H, 8.40; N, 8.36, Cl, 7.00. Mass spectrum (Cl–CH$_4$): m/z 450 (M+1, 100%), 282 (9%), 167 (29%).

EXAMPLE 12

(±)N,N-Diethyl-4-(3-hydroxy-αR)-α-((2S,5S)-2,4,5-trimethyl-1-piperazinyl)-benzyl)benzamide A mixture of 15.65 g (36 mmol) of N,N-diethyl-4-(3-(t-butyldimethylsilyloxy)-α-chlorobenzyl)benzamide, prepared as described in Example 11, 7.22 g (65 mmol) of (+)-(2S,5S)-2,5-dimethylpiperazine, prepared from L-Ala-L-Ala-diketopiperazine (Bachem Chemicals, Philadelphia, Pa.) as described by Jung and Rohloff (J. Org. Chem. 50, 4909–13 (1985)), and 3 mL of toluene was heated as in Example 1. The product was purified by chromatography on silica gel (Waters Prep 500 with dichloromethane containing 1% ethanol and 0.1% triethylamine) to give 4.06 g (22%) of N,N-diethyl-4-(3-(tert-butyldimethylsilyloxy)-α-((2S,5S)-2,5-dimethyl-1-piperazinyl)benzyl)benzamide as a beige foam.

A mixture of the benzhydrylpiperazine from above (4.06 g, 8.0 mmol), 80 mL of dry tetrahydrofuran, 4.24 g (40 mmol) of anhydrous sodium carbonate and 1.56 g (8.4 mmol) of methyl tosylate was heated to reflux for 40 hours. The solvent was evaporated. The residue was dissolved in dichloromethane and filtered to remove the inorganic salts. Evaporation of the filtrate gave 6.7 g of a brown oil. Chromatography on silica gel (Waters Prep 500 with dichloromethane containing 0.5% ethanol and 0.1% triethylamine) gave 1.17 g (28%) of N,N-diethyl-4-(3-(tert-butyldimethylsilyloxy)-(αR)-α-((2S,5S)-2,4,5-trimethyl-1-piperazinyl)benzyl)-benzamide as a yellow oil. The α-S isomer was also isolated (1.37 g, 33%).

The αR isomer from above (1.17 g, 2.2 mmol) was treated with tetraethylammonium fluoride as described in Example 1, to give 0.82 g (90%) of (+)-N,N-diethyl-4-(3-hydroxy-(αR)-α-((2S,5S)-2,4,5-trimethyl-1-piperazinyl)benzyl) benzamide as a beige solid. NMR (CDCl$_3$): δ0.95 (d, J=6 Hz, 3H); 1.05 (d, J=7 Hz, 3H); 1.2 (br m, 6H); 2.05–2.6 (m, 5H); 2.2(s, 3H); 3.05 (m, 1H); 3.25 (br m, 2H); 3.5 (br m, 2H); 4.4 (s, 1H); 6.6 (m, 1H); 6.9 (m, 2H); 7.05 (t, J=8 Hz, 1H); 7.25 (d, J=8 Hz, 2H); 7.45 (d, J=8 Hz, 2H). Titration to pH 4, in ethanol solution, with ethanolic hydrochloric acid followed by precipitation with diethyl ether gave 0.28 g (56%) of the monohydrochloride salt as a white powder. Calc for $C_{25}H_{35}N_3O_2$ HCl1.25 H$_2$O: C, 64.09; H, 8.28; N, 8.97; Cl, 7.57. Found: C, 64.12; H, 8.29; N, 8.92; Cl, 7.65. $[\alpha]_D^{20}$=22° (absolute ethanol, 7 mg/mL). Relative stereochemistry was determined by x-ray crystallography (Molecular Structure Corp., College Station, Texas).

EXAMPLE 13

(±)-N,N-Diethyl-4-(3-hydroxy-(αR)-α-((2RR)-2,4,5-trimethyl-1-piperazinyl)-benzyl)benzamide The procedure described in Example 12 was followed with 11.62 g (27 mmol) of N,N-diethyl-4-(3-(tert-butyldimethylsilyloxy)-α-chlorobenzyl) benzamide, prepared as in Example 11, and 9.42 g (82 mmol) of (−)-(2R, 5R)-2,5-dimethylpiperazine, prepared from D-Ala-D-Ala-diketopiperazine (Bachera Chemicals, Philadelphia, Pa.) as described by Jung and Rohloff (J. Org. Chem. 50, 4909–13 (1985)). The crude product was dissolved in 100 mL of acetonitrile and 8.07 g (40 mmol) of tetraethylammonium fluoride hydrate was added. The solution was stirred at room temperature overnight. The solvent was evaporated, and the residue was treated with 100 mL of aqueous 1N hydrochloric acid and extracted with 200 mL of diethyl ether. The aqueous layer was adjusted to pH 8 with aqueous 5M sodium hydroxide, and extracted with dichloromethane. The organic layers were combined, dried over sodium sulfate, and evaporated to give 8.03 g (75%) of N,N-diethylo4-(3-hydroxy-α-((2R,5R)-2,5-dimethyl-1-piperazinyl)benzyl)-benzamide as a light brown solid.

The benzhydrylpiperazine from above (4.11 g, 10.4 mmol) was combined with 1.6 mL (41.6 mmol) of 96% formic acid and 2.3 mL (31.2 mmol) of 37% aqueous formaldehyde. The mixture was kept at 80 ° C. for 18 hours, cooled to room temperature, treated with 6 mL of aqueous 6M hydrochloric acid and extracted with diethyl ether. The aqueous layer was diluted with water and adjusted to pH=8 with aqueous 10N sodium hydroxide. The resulting slurry was extracted with dichloromethane. The combined organic layers were dried over sodium sulfate and evaporated to give 3.71 g of a beige solid. Chromatography on silica gel with dichloromethane:methanol (1 to 7%) gave 3.01 g (70%) of N,N-diethyl-4-(3-hydroxy-α((2R,5R)-2,4,5-trimethyl-1-piperazinyl)benzyl)benzamide as a beige solid.

The product from above (2.44 g, 5.9 mmol) was dissolved in 20 mL of dimethylformamide with tert-butylchlorodimethylsilane (1.33 g, 8.9 mmol) and imidazole and stirred at room temperature overnight. The reaction mixture was poured into cold water and extracted with diethyl ether. The combined ethereal layers were washed with water, dried over sodium sulfate and evaporated to give 2.99 g (96%) of a yellow oil. The two diastereomers of the product were separated by chromatography on silica gel with dichloromethane:ethanol (0.5 to 1%). The less mobile isomer ($R_f$=0.61 on silica gel with dichloromethane:ethanol: ammonium hydroxide/90:10:1) was isolated to give 0.79 g (25%) of N,N-diethyl-4-(3-tert-butyldimethylsilyloxy)-(αR)-α-((2R, 5R)-2,4,5-trimethyl-1-piperazinyl)benzyl) benzamide as a beige solid. NMR (CDCl$_3$): δ0.15 (s, 6H); 0.95 (s, 9H); 0.9–1.3 (m, 12H); 2.0–2.3 (m, 2H); 2.2 (s, 3H); 2.35–2.6 (m, 3H); 3.0 (m, 1H); 3.2 (br m, 2H); 3.5 (br m, 2H); 4.45 (s, 1H); 6.65 (m, 1H); 6.9–7.05 (m, 2H); 7.1 (t, J=8 Hz, 1H); 7.3 (d, J=8 Hz, 2H); 7.45 (d, J=8, 2H).

The purified product (0.79 g, 1.51 mmol) was dissolved in 40 mL of acetonitrile with 0.45 g (2.26 mmol) of tetraethylammonium fluoride hydrate and stirred at room temperature overnight. The solvent was evaporated. The residue was dissolved in dichloromethane and washed with water adjusted to pH=8. After drying over sodium sulfate, the solvent was evaporated and the residue was dissolved in absolute ethanol. Titration of this solution to pH=4.4 with ethanolic hydrochloric acid, followed by precipitation with diethyl ether gave 0.61 g (87%) of (+)-N,N-diethyl-4-(3-hydroxy-(αR)-α-((2R,5R)-2,4,5-trimethyl-1-piperazinyl) benzyl)benzamide monohydrochloride as a beige powder. Calc for $C_{25}H_{35}N_3O_2$ HCl 0.75 $H_2O$: C, 65.34; H, 8.23; N, 9.14; Cl, 7.71. Found: C, 65.18; H, 8.33; N, 8.94; Cl, 7.52. Mass spectrum (Cl–CH$_4$) m/z 410 (M+1, 100%). $[\alpha]_D^{20}$=+ 10.9 (absolute ethanol, c=19.7 mg/mL). Stereochemistry of the benzhydryl carbon was assigned by comparison to the diastereomer of Example 12 by TLC and NMR.

EXAMPLE 14

(±)-4-((αR*)-α-((2R*,5S*)-4-Allyl-2,5-dimethyl-1-piperazinyl)-3-hydroxybenzyl)-N,N-diethylbenzamide (±)-4-((αR*)-α-((2R*,5S*)-4-Allyl-2,5-dimethyl-1-piperazinyl)-3-hydroxybenzyl)-N,N-diethylbenzamide was prepared from the compound of Example 8 by the procedures described in Example 6, Method A. NMR (200 MHz, DMSO-d$_6$): δ0.9 (d, J=6 Hz, 3H); 1.1 (d, J=6 Hz, 3H); 1.1–1.3 (br m, 6H); 1.8 (dd, J$_1$=8 Hz, J$_2$=12 Hz, 1H); 2.1 (t, J=11 Hz, 1H); 2.4–3.0 (br m, 5H); 3.15 (dd, J$_1$=5 Hz, J$_2$=14.5 Hz, 1H), 3.1–3.6 (br m, 4H); 5.0 (s, 1H); 5.1 (d, J=10 Hz, 1H); 5.15 (d, J=17 Hz, 1H); 5.8 (m, 1H); 6.6 (d, J=7.5 Hz, 1H); 6.8 (d, J=7.5 Hz, 1H); 6.85 (s, 1H); 7.1 (t, J=8 Hz, 1H); 7.3 (s, 4H); 9.3 (s, 1H). C for $C_{27}H_{37}N_3O_2$ HCl $H_2O$: C, 66.17; H, 8.23; N, 8.57; Cl, 7.23. Found: C, 66.00; H, 8.24; N, 8.57; Cl, 7.20.

EXAMPLE 15

(±)-4-((αR*)-α-((2R*,5S*)-2,5-dimethyl-1-piperazinyl)-3-hydroxybenzyl)-N,N-diethylbenzamide (±)-4-((αR*)-α-((2R*,5S*)-4-Allyl-2,5-dimethyl-1-piperazinyl)-3-hydroxybenzyl)-N-N-diethylbenzamide (Example 14) (21.75 g, 0.0499 mol) was dissolved in 330 mL methanol:90 mL water. Trifluoroacetic acid (3.9 mL, 0.0499 mol) was added, followed by 14.5 g of 5% palladium on carbon. The solution was heated at reflux for three days and filtered through Celite. The solvent was removed, and the residue was purified by chromatography on silica gel with ethanol (0–20%) in dichloromethane containing 1% tdethylamine. The solvent was removed, and the residue was redissolved in dichloromethane and washed with water at pH 8. The organic layer was dried over sodium sulfate and concentrated to dryness. The resulting solid was triturated overnight in ethyl acetate. Filtration gave 9.09 g (46%) of (±)-4-((αR*)-α-((2R*, 5S*)-2,5-dimethyl-1-piperazinyl)-3-hydroxybenzyl)-N,N diethylbenzamide as a tan solid. Calc. for $C_{24}H_{33}N_3O_2$ 0.5 $H_2O$: C, 71.26; H, 8.47; N, 10.39. Found: C, 71.12; H, 8.47; N, 10.49. NMR (300 MHz, CDCl$_3$): δ0.9 (d, J=6 Hz, 3H),1.2 (d and brtr, 9H); 1.5 (t, J=10 Hz, 1H); 2.2 (br m, 1H); 2.5 (m, 1H); 2.6 (d, J=9 Hz, 1H); 2.8 (m, 2H); 3.1–3.5 (br m, 5.3 (s, 1H); 6.6 (d, J=8 Hz, 1H) 6.7 (d, J=8 Hz, 1H); 6.8 (s, 1H); 7.1 (t, J=8 Hz, 1H); 7.2 and 7.3 (AB q, J=8 Hz, 4H), 9.0 (br s, 1H).

EXAMPLE 16

(±)-((αR*)-α-((2,5R*)-2,5-Dimethyl-1-piperazinyl)-3-hydroxybenzyl-N,N-diethylbenzamide, mp 178°–180° C., was prepared from Example 6 by the methods described in Example 15. Calc. for $C_{24}H_{33}N_3O_2$: C, 72.87; H, 8.41; N, 10.62. Found: C, 72.72; H, 8.41; N, 10.47. NMR (200 MHz, DMSO-d$_6$): δ0.85 (d, J=6 Hz, 3H); 1.1 (d, J=6 Hz, 3H); 1.0–1.3 (br m, 6H); 1.5 (t, J=10 Hz, 1H); 2.3 (br m, 1H), 2.45–2.6 (m, 2H), 2.7–2.9 (m, 2H); 3.1–3.5 (br. m, 5H), 5.25 (s, 1H); 6.6 (s, 1H); 6.6 (d, J=8 Hz, 1H); 6.7 (d, J=8 Hz, 1H); 7.2 J=8 Hz, 1H); 7.3 and 7.4 (AB q, J=8 Hz, 4H); 9.2 (br s, 1H).

EXAMPLE 17

(±)-3-((αR*)-α-((2S*,5R*)-4-allyl-2,5-dimethyl-1-piperazinyl-4-(diethylcarbamoyl) benzyl)phenyl benzoate Benzoyl chloride (0.33 2.3 mmol) was added dropwise to a solution of (±)-4-((αR*)-α-((2S*,5R*)-4-allyl-2,5-dimethyl-1-piperazinyl)-3-hydroxy-benzyl)-N,N-diethylbenzamide (0.92 g, 2.1 mmol) (Example 6) and triethylamine (0.60 mL, 4.2 mmol) in 20 mL dichloromethane. The reaction mixture was stirred for 1 hour and then was washed twice with 20 mL of water, dried over sodium sulfate, and concentrated to dryness. The residue was purified by chromatography on silica gel with dichloromethane:ethanol to give 0.92 g (74%) of (±)-3-((αR*)-α-((2S*,5R*)-4-allyl-2,5-dimethyl-1-piperazinyl)-4-(diethylcarbamoyl)benzyl)phenyl benzoate. NMR (300 MHz, CDCl$_3$): δ0.9 (d, 3H); 1.2 (d, brt, 9H); 1.9 (t, J=11 Hz, 1H); 2.1 (dd, 1H); 2.5 (br m, 1H); 2.6 (m, 2H); 2.8 (m, 2H); 3.2–3.6 (br m, 5H); 5.2 (2d, 2H); 5 1H); 5.8 (m, 1H); 7–7.2 (2d, s, 3H); 7.3 (m, 3H); 7.5 (m, 4H); 7.6 (t, 1H), 8.2 (d, 2H).

The benzoate was dissolved in ethanol and titrated with ethanolic hydrogen chloride to pH 4.3. The solution was evaporated to dryness. The monohydrochloride salt was precipitated from dichloromethane with diethyl ether and collected by filtration to give 0.79 g of the hydrated monohydrochloride salt as a white solid. Calc. for $C_{34}H_{41}N_3O_3$ HCl $H_2O$: C, 68.73; H, 7.46; N, 7.07; Cl, 5.97. Found: C, 68.92; H, 7.44; N, 7.11; Cl, 6.03.

EXAMPLE 18

(±)-3-α(αR*)-α-((2R*,5S*)-4-Allyl-2,5-dimethyl-1-piperazinyl)-4-(diethyl-carbamoyl)phenyl benzoate (±)-3-((αR*)-α-((2R*,5S*)-4-Allyl-2,5-dimethyl-1-piperazinyl)-4-(diethyl-carbamoyl)phenyl benzoate was prepared from the compound of Example 14 by the method described in Example 17. NMR (300 MHz, DMSO-d$_6$): δ0.95 (d, J=6 Hz, 3H); 1.1 (d, J=6 Hz, 3H); 1.0–1.2 (br m, 6H), 1.85 (m, 1H); 2.1 (dd, J$_1$=9 Hz, J$_2$=13 Hz, 1H); 2.5–2.7 (br m, 3H); 2.7 (d,J=11 Hz, 1H); 2.85 (dd, J$_1$=7 Hz, J$_2$=15 Hz, 1H); 3.1–3.5 (br m, 5H), 5.1 (d, J=11 Hz, 1H); 5.15 (s, 1H); 5.15 (d, J=18 Hz, 1H) 5.8 (m, 1H); 7.15 (d, J=7.5 Hz, 1H); 7.3–7.5 (m, 7H), 7.6 (t, 7 Hz, 2H); 7.75 (t, J=7.5 Hz, 1H); 8.1 (d, 7 Hz, 2H). Calc. for $C_{34}H_{41}N_{O3}$ HCl 1.2 H20: C, 68.31; H, 7.49; N, 7.03; Cl, 5.93. Found: C, 68.30; H, 7.51; N, 6.96; Cl, 5.95.

EXAMPLE 19

(±)-4-((αR*)-3-Acetoxy-α-((2S*, 5R*)-4-allyl-2,5-dimethyl-1-piprazinyl)benzyl)-N,N-diethylbenzamide A solution of (±)-4-((αR*)-α((2S*,5R*)-4-allyi-2,5-dimethyl-1-piperazinyl)-3-hydroxybenzyl)-N,N-diethylbenzamide (1.2 g, 2.8 mmol, Example 6), acetic anhydride (0.40 mL, 4.2 mmol), and triethylamine (0.80 mL, 5.6 mmol) in 30 mL of dichloromethane was stirred overnight under nitrogen. The solution was washed twice with 15 mL of 5% sodium bicarbonate, dried over sodium sulfate and the solvent removed. The product was purified by chromotography on silica gel with ethyl acetate (30–100%) in dichloromethane to give 0.94 g (71%) of (±)-4-((αR*)-3-acetoxy-α-((2S*,5R*)-4-allyl-2,5-dimethyl-1-piperazinyl)benzyl)-N,N-diethylbenzamide as a white foam. NMR (200 MHz, DMSO-$d_6$): δ0.9 (d, J=6 Hz, 3H); 1.1 (d, J=6 Hz, 3H); 1.0–1.2 (br m, 6H); 1.75 (dd, $J_1$=7.5 Hz, $J_2$=12 Hz, 1H); 2.1 (dd, $J_1$=8.5 Hz, $J_2$=12.5 Hz, 1H); 2.2 (s, 3H); 2.4–2.6 (m, 3H); 2.7 (m, 1H; 2.8 (dd, $J_1$=7.5 Hz, $J_2$=15 Hz, 1H); 3.1 (dd, $J_1$=6 Hz, $J_2$=14 Hz, 1H); 3.1 –3.4 (br m, 4H); 5.05 (d, J=15 Hz, 1H); 5.1 (s, 1H); 5.15 (d, 10 Hz, 1H); 5.8 (m, 1H) 1H); 7.0 (d, J=8 Hz, 1H); 7.15 (d, J=8 Hz, 1H); 7.25 and 7.4 (ABq, J=8 Hz, 4H); 7.4(t, J=8 Hz, 1H). The amine was dissolved in ethanol and convened to the monohydrochloride salt by titration with ethanolic hydrogen chloride. After the solvent was removed, the salt was dissolved in a minimal amount of dichloromethane and precipitated with diethyl ether. Filtration gave 0.50 g of the hygroscopic salt. Calc for $C_{29}H_{39}N_3O_3$ HCl $H_2O$: C, 65.46; H, 7.97; N, 7.90; Cl, 6.66. Found: C, 65.43; H, 7.97; N, 8.00; Cl, 6.79.

EXAMPLE 20

(±)-3-((αR*-α-((2S*,5R*)-4-Allyl-2,5-dimethyl-1-piperazinyl-4-diethylcarbamoyl) benzyl)phenyl dimethylcarbamate (±)-3-((αR*)-α-((2S*,5R*)-4-Allyl-2,5-dimethyl-1-piperazinyl)-3-hydroxybenzyl)-N,N-diethylbenzamide (Example 6) (6.96 g, 0.016 mol) was dissolved in 150 mL of anhydrous tetrahydrofuran. A 50% oil dispersion of sodium hydride (1.15 g, 0.0240 mol) was slowly added to the solution. The reaction was stirred for 15 minutes and dimethylcarbamyl liloride (1.62 mL, 0.0176 mol) was added slowly. The reaction was stirred for 1 hour, poured onto ice, and extracted with diethyl ether. The diethyl ether extract was washed with brine, dried over sodium sulfate, and concentrated to dryness. The residue (8.34 g) was chromatographed on silica gel with ethanol (0–10%) in dichloromethane to give 8.10 g of (×)-3-((αR*)-α-((2S*,5R*)-4-allyl-2,5-dimethyl-1-piperazinyl-4-(diethylcarbamoyl) benzyl)phenyl dimethylcarbamate as a yellow oil. NMR (300 MHz, $CDCl_3$): δ0.95 (d, 3H); 1.05–1.3 (d, br t, 9H); 1.8 (dd, $J_1$=9 Hz, $J_2$=11 Hz, 1H); 2.1 (dd, J1=J2=11Hz, 1H); 2.4 (br m, 1H); 2.6 (br m, 2H); 2.8 (m, 2H); 3.0 (s, 3H); 3H), 3.3 (br m, 2H); 3.35 (dd, 1H), 3.5 (br m, 2H); 5.1 (d, J=8 Hz, 1H); 5.15 (d, J=15 Hz, 1H); 5.2 (s, 1H); 5.8 (m, 1H), 6.9 (s, 1H); 7.0 (d, J=8 Hz, 1H); 7.05 (d, J=8 Hz, 1H); 7.3 (t, J=8 Hz, 1H), 7.3 and 7.45 (AB q, J=8 Hz, 4H). The amine was dissolved in ethanol and titrated to pH 3.8 with ethanolic hydrogen chloride. After evaporation of solvent, the salt was redissolved in dichloromethane and precipitated with diethyl ether to give 3.98 g of the hydrated monohydrochloride salt as a tan solid. Calc. for $C_{30}H_{42}N_4O_3$ HCl $H_2O$, C, 64.21; H, 8.08; N, 9.98; Cl, 6.32. Found: C, 64.46, H, 8.04; N, 10.10, Cl, 6.43.

EXAMPLE 21

(±)-3-((αR*)-α-((2R*, 5S*)4-Allyl-2,5-dimethyl- 1-piperazinyl)-4-(diethylcarbamoyl) benzyl) phenyldimethylcarbamate (±)-3-((αR*)-α-((2R*,5S*)-4-Allyl-2,5-dimethyl-1-piperazinyl)-4-(diethylcar-bamoyl)benzyl)phenyl dimethylcarbamate was prepared from the compound of Example 14 by the method described in Example 20. NMR (300 MHZ, DMSO-$d_6$): δ0.95 (d, J=6 Hz, 3H); 1.1 (d, J=6 Hz, 3H); 1.0–1.2 (br m, 6H); 1.8 (m, 1H); 2.1 (dd, $J_1$=7Hz, $J_2$=11 Hz, 1H); 2.4–2.6 (m, 3H), 2.7 d, J=1 Hz, 1H); 2.8 (m, 1H); 2.9 (s, 3H); 3.0 (s, 3H); 3.1–3.5 (br m, 5H); 5.1 (d, J=8.5 Hz, 1H); 5.1 (d, J=17.5 Hz, 1H); 5.2 (s, 1H); 5.8 (m, 1H); 6.9 (d, J=8 Hz, 1H); 7.1 (s, 1H); 7.25 (d, J=8 Hz, 1H); 7.3 (t, J=8 Hz, 1H); 7.3 (s, 4H). Calc. for $C_{30}H_{42}N_4O_3$ HCl 1.5 $H_2O$: C, 63.20; H, 8.13; N, 9.83; Cl, 6.22. Found: C, 63.09; H, 8.19; N, 9.78; Cl, 6.27.

EXAMPLE 22

(±)-3-((αR*-α-((2R*,5S*)-4-Allyl-2,5-dimethyl-1-piperazinyl)-4-(diethycarbamoylbenzylphenyl pivalate (±)-3-((αR*)-α-((2R*,5S*)-4-Allyl-2,5-dimethyl-1-piperazinyl)-4-(diethycarbamoyl)benzyl)phenyl pivalate was made from the compound of Example 14 and trimethylacetyl chloride by following the procedure described in Example 17. NMR (300 MHz, $CDCl_3$): δ0.95 (d, J=6 Hz, 3H), 1.15 (d, J=6 Hz, 3H); 1.1–1.3 (br m, 6H); 1.35 (s, 9H); 1.9 (m, 1H); 2.1 (dd, $J_1$=9 Hz, $J_2$=11 Hz, 1H); 2.45 (m, 1H); 2.6 (m, 2H); 2.8 (m, 2H); 3.35 $J_1$=7 Hz, $J_2$=14 Hz, 1H); 3.2–3.6 (br m, 4H), 5.1 (d, J=8 Hz, 1H); 5.15 (d, J=15.5 Hz, 1H); 5.2 (s, 1H); 6.8 (s, 1H); 6.95 (d, J=8 Hz, 1H); 7.0 (d, J=8 Hz, 1H); 7.3 (t, J=8 Hz, 1H); 7.3 and 7.45 (AB q, J=8 Hz, 4H). Calc. for $C_{32}H_{45}N_3O_3$ HCl 0.5 $H_2O$: C, 68.00; H, 8.38; N, 7.43; Cl, 6.27. Found: C, 67.88; H, 8.38; N, 7.42; Cl, 6.33.

EXAMPLE 23

N-(4-((αR*)-α-((2R*,5S*)-4-Allyl-2,5-dimethyl-1-piperazinyl-3-hydroxy-benzyl)benzoyl-L-phenylalanyl-L-leucine A solution of carbobenzyloxy-L-phenylalanine (5.00 g, 16.7 mmol), L-leucine-tert-butylester hydrochloride (3.74 g, 16.7 mmol), benzotriazol-1-yloxytris (dimethylamino) phosphonium hexafluorophosphate (7.39 g, 16.7 mmol) and triethylamine (4.66 mL, 33.4 mmol) in 250 mL acetonitrile was stirred for 1.5 hr. The reaction mixture was taken up in 750 mL ethyl acetate and washed sequentially with 500 mL of 5% citric acid, 500 mL of saturated sodium bicarbonate, and 250 mL brine. The organic layer was dried over sodium sulfate, and the solvent was removed. The crude material was purified by chromatography on silica gel with hexane-:ethyl acetate yielding 6.52 g of tert-butyl N-((benzyloxy) carbonyl)-L-phenylalanyl-L-leucinate as a white crystalline solid.

A portion of the protected dipeptide (0.50 g, 1.1 mmol) was combined with 10% palladium on carbon (0.10 g) in 100 mL methanol and reduced under hydrogen on a Parr hydrogenator for 3 hrs. The mixture was filtered and concentrated to dryness to give 0.35 g (98%) of tert-butyl-L-phenylalanyl-L-leucinate The crude lithium salt of (±)-4-((αR*)-α-((2R*,5S*)-4-allyl-2,5-dimethyl-1-piperazinyl)-3-(tert-butyldimethylsilyloxy)benzyl)benzoic acid (0.52 g, 1.0 mmol) (Example 8, infra) was converted to the free acid with ethanolic hydrogen chloride. After removal of solvent, the carboxylic acid was combined with the tert-butyl-L-phenylalanyl-L-leucinate, benzotriazol-1-yloxytris (dimethylamino)phosphonium hexafluorophosphate (0.47 g, 1.0 mmol), and triethylamine (0.16 mL, 1.0 mmol) in 20 mL acetonitrile. After 2 hrs the reaction mixture was taken up in 20 mL ethyl acetate, washed twice with 20 mL saturated sodium bicarbonate, and filtered. The organic layer was dried over sodium sulfate and concentrated to dryness. The residue was purified by chromatography on silica gel with dichloromethane:ethanol to give 0.45 g (53%) of tert-butyl N-(4-((αR*)-α-((2R*,5S*)-4-allyl-2,5-dimethyl-1-piperazinyl)-3-((tert-butyldimethylsilyl)oxy)benzyl) benzoyl)-L-phenylalanyl-L-leucinate as a white solid.

A portion of the benzhydrylpiperazine from above (0.36 g, 0.44 mmol) was stirred with tetraethylammonium fluoride hydrate (0.12 g, 0.67 mmol) in 10 mL of acetonitrile for 1 hr. The solvent was removed and the residue purified by chromatography on silica gel with dichloromethane:ethanol to give 0.180 g (58%) of tert-butyl N-(4-((αR*)-α-((2R*, 5S*)-4-allyl-2,5-dimethyl-1-piperazinyl)-3-hydroxybenzyl) benzoyl)-L-phenylalanyl-L-leucinate as a white solid.

A portion of the tert-butyl ester (0.17 g, 0.25 mmol) was stirred for 1 hr in 10 mL trifluoroacetic acid. The solvent was removed and the resulting solid was dried under high vacuum to give 0.190 g (86%) of N-(4-((αR*)-α-((2, R*,5S*)-4-allyl-2,5-dimethyl-1-piperazinyl)-3-hydroxybenzyl)benzoyl)-L-phenylalanyl-L-leucine as the trifluoroacetic acid salt. Calc. for $C_{38}H_{48}N_4O_5 2\ C_2HF_3O_2\ H_2O$: C, 56.88; N, 5.91; N, 6.32. Found: C, 57.15; H, 5.80; N, 6.23.

EXAMPLE 24

N-(4-((αR*)-α-((2S*,5R*)-4-allyl-2,5-dimethyl-1-piperazinyl-3-hydroxy-benzyl]benzoyl-L-phenylalan-L-leucine N-(4-((αR*)-α-((2S*,5R*)-4-allyl-2,5-dimethyl-1-piperazinyl)-3-hydroxybenzyl)benzoyl)-L-phenylalanyl-L-leucine was prepared from (±)-3-((αR*)-α-((2S*,5R*)-4-allyl-2,5-dimethyl-1-piperazinyl)-4-bromobenzyl)phenol (Example 1) by the methods described in Example 23. NMR(300MHz,DMSO-d$_6$): δ0.85 (d,J=6Hz,3H); 0.92 (d,J= 6Hz,3H); 1.05 (d,J=6Hz,1H); 1.17(d,J=6Hz,2H); 1.24 (d,J= 6Hz,2H); 1.39 (d,J=6Hz, 1H); 1.5–2.4(m,4H); 2.55–3.15 (m,5H); 3.2–4.0 (m,3H); 4.1–4.8 (m,3H); 5.4–6.0 (m, 4H); 6.5–8.5 (m,13H). Calc. for $C_{38}H_{48}N_4O2.7\ C_2HF_{O2}$: C,54.95; H,5.39; N,5.91. Found: C.54.70; H,5.62; N,5.76.

EXAMPLE 25

(±)-N-(4-((αR*)-α-((2S*,5R*)-4-Allyl-2,5-dimethyl-1-piperazinyl)-3-hydroxy-benzyl) benzoyl) glycylglycine N-Carbobenzyloxy-glycine (2.1 g, 10 mmol) and glycine-tert-butyl ester (1.3 g, 10 mmol) were coupled using benzotriazol-1-yloxytris(dimethylamino) phosphonium hexafluorophosphate (4.4 g, 10 mmol) and triethylamine (1.5 g, 15 mmol) in acetonitrile following the method described in Example 23 to give 2.5 g(79%) of N-carbobenzyloxy-glycylglycine-tert-butyl ester after chromatography on silica gel.

The carbobenzyloxy group was removed from the dipeptide (1.0 g, 3.1 mmol) using palladium on carbon as described in Example 23 to give the glycylglycine-tert-butyl ester (0.57 g, 3.0 mmol, 99%).

The dipeptide (0.41 g, 2.1 mmol) was coupled with the lithium salt of (±)-4-((αR*)-α-((2S*,5R*)-4-allyl-2,5-dimethyl-1-piperazinyl)-3-hydroxbenzyl)benzoic acid (1.1 g, 2.1 mmol) from Example 6, Method B, and the tert-butyl ester and silylether were removed by the methods described in Example 23 to give 0.64 g (34%) of (±)-N-(4-((αR*)-α-((2S*,5R*)-4-allyl-2,5-dimethyl-1-piperazinyl)-3-tert-butyldimethylsilyloxy)benzyl)benzoyl)-glycylglycine as the trifluoroacetate salt. Calc for $C_{27}H_{34}N_4O_5\ 3.5\ CF_3COOH$: C,45.70, H, 4.23; N, 6.27. Found: C, 45.55; H, 4.50; N, 6.08.

A small amount was converted to the free amine for NMR analysis. NMR (300 MHz, DMSO-d$_6$): δ0.95 (d, J=6Hz, 3H); 1.05 (d, J=6Hz, 3H); 1.9 (m, 1H); 2.1 (dd, J=6.5 Hz and J=10 Hz, 1H); 2.4–2.7 (m, 3H); 2.7 (d, J=10 Hz, 1H); 2.8 (dd, J=7Hz and J=10Hz, 1H); 3.15 (dd, J=4Hz and J=13.5 Hz, 1H); 3.3 (d, J=4Hz, 2H); 3.8 (d, J=5Hz, 2H); 5.0 (s, 1H); 5.1 (d, J=10 Hz, 1(d, J=17Hz, 1H), 5.8 (m, 1H); 6.8 (2d, J=8Hz, 2H); 6.8 (s, 1H); 7.1 (t, J=1H); 7.25 (br t, J=3Hz, 1H); 7.45 and 7.8 (ABq, J=8Hz, 4H); 8.8 (br t, J=5Hz, 1H).

EXAMPLE 26

(±)-4-((αR* Or S*)-α-(trans-4-Allyl-2,5-dimethyl-1-piperazinyl)-3-(hydroxy-methyl)benzyl)-N,N-diethylbenzamide A mixture of 3-bromobenzyl alcohol (15.0 g, 80 mmol), tert-butylchlorodiphenylsilane (22.9 mL, 88 mmol), imidazole (12.0 g, 176 mmol) and 75 mL of dimethylformamide was stirred at room temperature overnight. The reaction mixture was poured into cold water, extracted with diethyl ether, the extracts washed with water and brine, dried over sodium sulfate and evaporated. The resulting oil was purified by chromatography on silica gel with hexane to give 23.7 g (70%) of 3-bromobenzyl tert-butyldiphenylsilyl ether as a colorless oil.

Starting with the silyl ether from above (23.72 g, 56 mmol), the method in Example 11 was followed, using trans-2,5-dimethylpiperazine, to give (±)-4-((αR* or S*)-α-(trans-2,5-dimethyl-1-piperazinyl)-3-((tert-butyldiphenylsilyloxy)methyl)benzyl)-N,N-diethylbenzamide as a mixture of diastereomers. Chromatography on silica gel (Waters Prep 500 with dichloromethane:ethanol:triethylamine/100:1–1.5:0.1 ) gave 3.21 g (26% from benzhydryl chloride) of the more mobile isomer (R$_f$=0.39 on silica gel with dichloromethane:methanol:ammonium hydroxide/90:10:1) which was treated with allyl bromide as in Example 1 to give 3.15 g (92%) of (±)-4-((αR* or S*)-α-((2R*,5S*)-4-allyl-2,5-dimethyl-1-piperazinyl)-3-((tert-butyldiphenylsilyloxy)methyl)benzyl-N,N-diethylbenzamide as a light yellow glass.

The product from above (3.15 g, 4.6 mmol) was treated with tetraethylammonium fluoride hydrate (1.4 g, 9.2 mmol) in acetonitrile solution for 1 hr at room temperature. Chromatography of the crude product on silica gel with dichloromethane:methanol (90:10) gave 1.91 g (92%) of (±)-4-( (αR* or S*)-α-(trans-4-allyl-2,5-dimethyl-1-piperazinyl)-3-(hydroxymethyl)benzyl)-N,N-diethylbenzamide as an off-white solid. NMR (CDCl$_3$): δ1.0 (d, J=6 Hz, 3H); 1.2 (d, J=6 Hz and br m, 9H); 1.8 (br s, 2H); 2.15 (t, J=9 Hz, 1H); 2.5 (m, 1H); H); 2.8 (m, 2H); 3.2–3.7 (br m, 5H); 4.6 (s, 2H); 5.1–5.3 (m, 3H); 5.8 (m, 1H); 7.1–7.5 (m, 8H). A solution of the product (0.50 g, 1.1 mmol) in absolute ethanol was titrated to pH 4.5 with ethanolic hydrochloric acid, concentrated and treated with diethyl ether to precipitate 0.43 g (80%) of the monohydrochloride salt. Calc. for C$_{28}$H$_{39}$N$_3$O$_2$ HCl 0.5 H$_2$O: C, 67.93; H, 8.35; N, 8.49; Cl, 7.16. Found: C, 68.02; H, 8.38; N, 8.48; Cl, 7.10. Mass spectrum (Cl–CH$_4$): m/z 450 (M+1, 100%), 432 (39%).

EXAMPLE 27

(±-4-((αR*)-α-((2S*,5R*)4-Allyl-2,5-dimethyl-1-piperazinyl)-3-hydroxybenzyl)-N-(2-((2-amino-2-oxoethyl)amino/-2-oxoethyl)benzamide A solution of crude (±)-4-((αR*)-α-((2S*,5R*)-4-allyl-2,5-dimethyl-1-piperazinyl)-3-hydroxybenzyl)benzoic acid (2.5 g, 3.4 mmol, Example 5), glycine-glycine amide hydrochloride (Sigma Chemical Co.) (1.0 g, 6.0 mmol), triethylamine (3.3 mL, 26 mmol), and benzotriazol-1-yloxytris(dimethylamino)phosphonium hexafluorophosphate (5.8 g, 13 mmol) in 100 mL dimethylformamide was stirred overnight under nitrogen. The reaction was poured into 450 mL aqueous sodium bicarbonate and extracted with 500 mL ethyl acetate. The ethyl acetate extract was washed with 350 mL water followed by 50 mL brine and dried over sodium sulfate. The solvent was removed to give 0.80 g of an oil which was purified by chromatography on silica gel with ethanol (5–20%) in dichloromethane to give 0.20 g (12%) of (±)-4-((αR*)-α-((2S*, 5R*)-4-allyl-2,5-dimethyl-1-piperazinyl)-3-hydroxybenzyl)-N-(2-((2-amino-2-oxoethyl)amino)-2-oxoethyl)benzamide as a white foam. NMR (300 MHz, CDCl$_3$): δ0.9–1.2 (br m, 6H); 1.8 (br m, 1H); 2.1 (br m, 1H); 2.5–3.0 (br m, 5H); 3.2 (br m, 1 H) 3.6 (d, J=6 Hz, 2H); 3.9 (d, J=6 Hz, 2H); 4.9–5.3 (br m, 3H), 5.8 (m, 1H); 6.7 (m, 3H), 7.2 (m, 3H); 7.8 and 7.6 (ABq, J=8 Hz, 4H); 8.15 (t, J=5.8 Hz, 1H); 8.75 (t, J=5.8 Hz, 1H); 9.4 (s, 1H).

The amine was converted to the monohydrochloride salt by dissolving in ethanol and titrating to pH 3.5 with ethanolic hydrogen chloride. The salt was precipitated with diethyl ether to give 0.083 g of the hygroscopic salt as a white foam. Calc. for C$_{27}$H$_{35}$N$_{54}$ HCl 0.5 C$_2$H$_5$OH H$_2$O: C, 58.89; H, 7.24; N, 12.26; Cl, 6.21. Found: C, 58.88; H, 7.08; N, 12.02; Cl, 5.93.

EXAMPLE 28

(±)-4-((αR* or S*)-α-(trans-4-allyl-2,5-dimethyl-1-piperazinyl)-3-(hydroxymethyl)benzyl-N,N-diethylbenzamide The less mobile isomer (R$_f$=0.35 on silica gel with dichloromethane:methanol:ammonium hydroxide/90:10:1; 3.70 g, 30%) of (±)-4-((αR* or S*)-α-(trans-2,5-dimethyl-1-piperazinyl)-3-((tert-butyldiphenylsilyloxy)methyl)benzyl)-N,N-diethylbenzamide (3.70, 5.7 mmol), from Example 26, was treated with allyl bromide as in Example 1. The product (3.70 g, 5.4 mmol) was treated with tetraethylammonium fluoride hydrate as in Example 26 to give 2.20 g (90%) of (±)-4-((αR* or S*)-α-(trans-4-allyl-2,5-dimethyl-1-piperazinyl)-3-(hydroxymethyl)benzyl)-N,N-diethylbenzamide as an off-white solid. NMR (CDCl$_3$): δ1.0 (d, J=7 Hz, 3H); 1.2 (d, J=7 Hz, and br m, 9H); 1.7 (br s, 1H); 1.8 (dd, J$_1$=14, J$_2$=8 Hz 1H); 2.15 (dd, J$_1$=1H); 2.4–2.7 (m, 3H); 2.7–2.95 (m, 2H); 3.2–3.7 (br m, 5H); 4.65 (s, 2H (m, 3H); 5.8 (m, 1H); 7.15–7.4 (m, 8H). The product (0.50 g, 1.1 mmol) was converted to the monohydrochloride salt as in Example 26 to give 0.39 g (72%) of a beige solid. Calc. for C$_{28}$H$_{39}$N$_3$O$_2$ HCl 0.75 H$_2$O: C, 67.31; H, 8.37; N, 8.41; Cl, 7.10. Found: C, 67.60; H, 8.36; N, 8.46; Cl, 7.16. Mass spectrum (Cl—CH4): m/z 450 (M+1, 100%), 432 (36%).

EXAMPLE 29

(±)-4-((αR* or S*)-α-(trans-4-Allyl-2,5-dimethyl-1-piperazinyl-2,4-difluoro-3-hydroxybenzyl-N,N-diethylbenzamide 2,6-Difluorophenol (8.6 g, 66 mmol) was treated with tert-butylchlorodimethylsilane (17.4 g, 0.12 mol) and imidazole (13.1 g, 0.19 mol) by the method in Example 1 to give 13.41 g (83%) of tert-butyldimethylsilyl 2,6-difluorophenyl ether.

A solution of the silyl ether (10.23 g, 42 mmol) in 80 mL of dry tetrahydrofuran was cooled to −70 ° C. under nitrogen and sec-butyllithium (38.2 mL of 1.1M solution in cyclohexane) was added at a rate to maintain the temperature below −60° C. After two hours, the cold (−70° C.) solution was added via cannula under nitrogen to a cold (−70° C.) solution of 4-formyl-N,N-diethylbenzamide, prepared as in Example 11, in 100 mL of dry tetrahydrofuran at a rate to maintain the temperature below −70° C. After 30 minutes, the reaction mixture was warmed to room temperature, quenched with saturated aqueous ammonium chloride and diluted with diethyl ether. The organic layer was washed with water and brine, dried over sodium sulfate and evaporated to give a yellow oil. Purification by chromatography on silica gel (Waters Prep 500, dichloromethane:ethanol/100:0.75) gave 10.45 g (55%) of 4-(3-(tert-butyldimethylsilyloxy)-2,4-difluoro-α-hydroxybenzyl)-N,N-diethylbenzamide as a clear gum.

Using the methods in Example 1, the fluorinated benzhydryl alcohol (10.45 g, 23.0 mmol) was treated successively with thionyl chloride and trans-2,5-dimethylpiperazine. The silyl protecting group was cleaved in the course of the reaction sequence.

The two diastereomers of (±)-4-((αR* or S*)-α-(trans-2,5-dimethyl-1-piperazinyl)-2,4-difluoro-3-hydroxybenzyl)-N,N-diethylbenzamide were isolated by chromatography on silica gel (Waters Prep 500 with dichloromethane:ethanol:triethylamine/100:0.5–1.5:0.1). The more mobile isomer gave 2.08 g (17% from benzhydryl alcohol) of an off-white solid.

A mixture of the more mobile isomer from above (1.57 g, 3.6 mmol), 25 mL of dimethylformamide and 0.32 mL (3.7 mmol) of allyl bromide was heated to 50° C. under nitrogen for 18 hours. The solvent was removed under vacuum and the residue was purified by chromatography on silica gel with 1–4% methanol in dichloromethane to give 0.68 g (40%) of (±)-4-((αR* or S*)-α-(trans-4-allyl-2,5-dimethyl-1-piperazinyl)-2,4-difluoro-3-hydroxybenzyl)-N,N-diethylbenzamide as a beige resin. NMR (CDCl$_3$): δ1.0–1.3 (m, 12H); 2 (br t, J=10 Hz, 1H); 2.2 (brt, J=10 Hz, 1H); 2.4–2.7 (3H); 2.9–3.1 (m, 2H); 3.2–3.7 (br m, 5H); 5.2–5.3 (m, 2H); 5.7 (s 1H); 5.9–6.1 (m, 1H); 6.25 (dd, J$_1$=22 Hz, J$_2$=9 Hz, 1H); 6.75 (t, J=9 Hz, 1H); 7.3 (d, 2H); 7.4 (d, J=8 Hz, 2H). A solution of the product in absolute ethanol was titrated to pH 3.8 with ethanolic hydrochloric acid, concentrated and treated with diethyl ether to precipitate 0.56 g (77%) of the monohydrochloride salt as a beige solid. Calc. for C$_{27}$H$_{35}$F$_2$N$_3$O$_2$ HCl 1.5 H$_2$O: C, 60.61; H, 7.35; N, 7.85; Cl, 6.63. Found: C, 60.45; H, 7.33; N, 7.82; Cl, 6.69. Mass spectrum (Cl–CH$_4$) m/z 472 (M+1, 49%), 318 (19%), 153 (100%).

EXAMPLE 30

(±)-4-((αR* or S*)-α-(trans-4-Allyl-2,5-dimethy)-1-piperozyl-2,4-difluoro-3-hydroxybenzyl)-N,N-diethylbenzamide The less mobile isomer of (±)-4-((αR* or S*)-α-(trans-2,5-dimethyl-1-piperazinyl)-2,4-difluoro-3-hydroxybenzyl)- N,N-diethylbenzamide, from Example 29, (2.72 g, 5.0 mmol) was suspended in 40 mL of dimethylformamide. Allyl bromide (0.44 mL, 5.1 mmol) was added and the mixture was heated to 50° C. under nitrogen for 18 hours. The solvent was removed under vacuum and the residue purified by chromatography on silica gel with 1–10% methanol in dichloromethane to give 0.56 g of (±)-4-((αR* or S*)-α-(trans-4-allyl-2,5-dimethyl-1-piperazinyl)-3-allyloxy-2,4-difluoro-benzyl)-N,N-diethylbenzamide as a yellow oil.

A mixture of the diallylated product from above (0.40 g, 0.78 mmol), 0.16 g of 5% palladium on carbon and 15 mg (0.078 mmol) of p-toluenesulfonic acid in 20 mL of methanol was heated to reflux under nitrogen for 18 hours. After filtering through Celite, the solvent was evaporated and the residue purified by chromatography on silica gel with 1–5% methanol in dichloromethane to give 0.10 g (27%) of (±)-4-((αR* or S*)-α-(trans-4-allyl-2,5-dimethyl-1-piperazinyl)-2,4-difluoro-3-hydroxybenzyl)-N,N-diethylbenzamide as a colorless glass. NMR (CDCl$_3$): δ1–1.3 (m, 12H); 2.0 and 2.2 (dd, J$_1$=10 Hz, J$_2$=6 Hz, 2H); 2.6 (m, 2H); 2.8 (m, 2H); 2 1H); 3.2 and 3.5 (br m, 5H); 5.15 (m, 3H); 5.7 (br s, 1H); 5.85 (m, 1H); 6.8 J=9 Hz, 1H); 7.0 (quartet, J=8 Hz, 1H); 7.25 (m, 4H). A solution of the product in absolute ethanol was titrated to pH 3.5 with ethanolic hydrochloric acid, concentrated and treated with diethyl ether to precipitate 72 mg (65%) of the monohydrochloride salt as a beige solid. Calc. for C$_{27}$H$_{35}$N$_3$O$_2$ HCl 1.75 H$_2$O$_2$: C, 60.10; H, 7.05; N, 7.78; Cl, 6.57. Found: C, 60.07; H, 7.37; N, 7.76; Cl, 6.63. Mass spectrum (Cl–CH$_4$): m/z 472 (M+1, 100%), 471 (M, 9%), 318 (15%), 153 (35%).

EXAMPLE 31

(±)-4-(α-(trans-4-Allyl-2,5-dimethyl-1-piperazinyl)-2-fluoro-5-hyroxybenzyl)-N,N-diethylbenzamide tert-Butyldimethylsilyl 2-fluorophenyl ether (2.73 g, 12 mmol), prepared from 2-fluorophenol by the method in Example 1, was treated with sec-butyllithium (11 mL of 1.1M solution in cyclohexane) and 4-formyl-N,N-diethylbenzamide, (2.46 g, 12 mmol) from Example 11, by the procedure described in Example 29. Chromatography on silica gel with 1% methanol in dichloromethane gave 1.77 g (34%) of 4-(5-(tert-butyidimethylsilyloxy)-2-fluoro-α-hydroxybenzyl)-N,N-diethylbenzamide as a yellow oil that crystallized on standing.

The benzhydrol from above (1.77 g, 4.1 mmol) was treated with thionyl chloride (0.45 mL, 6.2 mmol) by the method in Example 1. The crude product (approximately 4.1 mmol) was treated with trans-2,5-dimethylpiperazine (1.64 g, 14.3 mmol) as in Example 1. Chromatography on silica gel with 1–7% methanol in dichloromethane gave 0.44 g (20% from benzhydryl chloride) of (±)-4-(α-(trans-2,5-dimethyl-1-piperazinyl)-5-(tert-butyldimethylsilyloxy)-2-fluorobenzyl)-N,N-diethylbenzamide as a yellow oil.

The benzhydrylpiperazine from above (0.44 g, 0.83 mmol) was treated with allyl bromide (0.074 mL, 0.85 mmol) and anhydrous sodium carbonate (0.44 g, 4.2 mmol) as in Example 1. The product was purified by preparative thin layer chromatography (silica gel with dichloromethane:methanol:ammonium hydroxide/90:10:1) to give 0.37 g (78%) of (±)-4-(α-(trans-4-allyl-2,5-dimethyl-1-piperazinyl)-5-(tert-butyldimethylsilyloxy)-2-fluorobenzyl)-N,N-diethylbenzamide as a yellow oil. Reaction with tetraethylammonium fluoride hydrate in acetonitrile as in Example 1, followed by chromatography on silica gel with dichloromethane:methanol/4:1 gave 0.24 g (77%) of (±)-4-(α-(trans-4-allyl-2,5-dimethyl-1-piperazinyl)-2-fluoro-5-hydroxybenzyl)-N,N-diethylbenzamide as a light amber resin. NMR (CDCl$_3$): δ1.0–1.3 (m, 12H); 2.0–2.3 (m, 2H); 2.5–3.05 (m, 5H); 3.2–3.6 (br m, 5H); 5.1–5.3 (m, 2H); 5.25 and 5.55 (s, 1H); 5.7–6.0 (m, 1H); 6.5–7.2 (m, 3H); 7.25 (d, J=8 Hz, 2H); 7.4 (d, J=8 Hz, solution of the product in absolute ethanol was titrated to pH 4 with ethanolic hydrochloric acid, concentrated and treated with diethyl ether to precipitate 0.21 g (63%) of the monohydrochloride as an off-white powder. Calc. for C$_{27}$H$_{36}$FN$_3$O$_2$ HCl 1.25 H$_2$O: C, 63.27; H, 7.77; N, 8.20; Cl, 6.92. Found: C, 63.33; H, 7.78; N, 8.24; Cl, 7.00. Mass spectrum (Cl–CH4) m/z: 454 (M+1, 100%), 453 (M, 6%), 300 (17%), 153 (95%).

EXAMPLE 32

(±)-4-((αR* or S*)-α-(trans-4-Allyl-2,5-dimethyl-1-piperazinyl-3-amino-benzyl)-N,N-diethylbenzamide A mixture of 3-bromoaniline (46.8 mL, 0.43 mol), 1,1,4,4-tetramethyl-1,4-bis-(N,N-dimethylamino)disilethylene (121 mL, 0.43 mol) and zinc iodide (0.69 g, 2.1 mmol) was heated to 140° C. for five hours under nitrogen. Vacuum distillation (108°–113 ° C., 2 mm Hg) of the crude product gave 46.65 g (46%) of 1-(3-bromophenyl)-2,2,5,5-tetramethyl-1-aza-2,5-disilacyclopentane as a light yellow oil.

The protected aniline (23.64 g, 0.101 mol) was treated with n-butyllithium (1.5M in hexane, 66 mL, 0.101 mol) and 4-formyl-N,N-diethylbenzamide (20.70 g, 0.101 mol) as in Example11. Chromatography of the crude product on silica gel (Waters Prep 500, dichloromethane:ethanol/100:1–3) gave 7.59 g (25%) of 4-(3-amino-α-hydroxybenzyl)-N,N-diethylbenzamide as a light yellow hygroscopic solid.

The product (25 mmol) was treated with 2M ethanolic hydrochloric acid (20 mL). The solvent was evaporated and the residue shaken with toluene and evaporated again to remove residual ethanol. The resulting yellow solid was suspended in dichloromethane, 2.7 mL (37.5 mmol) of thionyl chloride was added, and the mixture was stirred at room temperature for one hour. The solvent was evaporated, and the residue was taken up in toluene and evaporated again to drive off the excess thionyl chloride. The crude product (approximately 25 mmol) was then treated with trans-2,5-dimethylpiperazine (28.5 g, 0.25 mol) in toluene as described in Example1. The product was purified by chromatography on silica gel (Waters Prep 500, dichloromethane:ethanol: triethylamine/100:1.5–3:0.1), to give 3.71 g (38%) of (±)-4-α-(trans-2,5-dimethyl-1-piperazinyl)-3-aminobenzyl)-N,N-diethyl-benzamide as a yellow solid.

The benzhydrylpiperazine (3.71 g, 9.4 mmol) was treated with allyl bromide (0.83 mL, 9.6 mmol) and anhydrous sodium carbonate (5.0 g, 47 mmol) as in Example 1 to give (±)-4-(α-(trans-4-allyl-2,5-dimethyl-1-piperazinyl)-3-aminobenzyl)-N,N-diethylbenzamide. The two diastereomers in the product were separated by chromatography on silica gel (Waters Prep 500, dichloromethane:ethanol:triethylamine/100:0.5–1:0.1 ) to give 1.01 g (25%) of the more mobile isomer ($R_f$=0.48 on silica gel with dichloromethane:methanol:ammonium hydroxide/90:10:1) as an off-white solid. NMR (CDCl$_3$): δ1.0 (d, J=7 Hz, 3H); 1.15 (d, J=7 Hz, 3H); 1.2 (br m, 6H); 1.9 (t, J=9 Hz, 1H); 2.1 (t, 1H); 2.4–2.9 (m, 6H); 3.1–3.7 (m, 6H); 5.1–5.2 (m, 3H); 5.7–6.0 (m, 1H); 6.65 (d, J=8 Hz, 2H); 6.7 (S, 1H); 6.8 (d, J=8 H$_2$, 1H); 7.1 (t, J=8 Hz, 1H); 7.3 (d, J=8 Hz, 2H); 7.5 (d, J=8 Hz, 2H). A solution of the product (0.10 g, 0.23 mmol) in absolute ethanol was titrated to pH 4.5 with ethanolic hydrochloric acid, concentrated and treated with diethyl ether to precipitate 74.6 mg (67%) of the monohydrochloride salt as a beige solid. Calc. for C$_{27}$H$_{38}$N$_4$O HCl 0.75 H$_2$O: C, 66.92; H, 8.42; N, 11.56; Cl, 7.32. Found: C, 66.97; H, 8.45; N, 11.51; Cl, 7.43. Mass spectrum (C1–CH$_4$): m/z 435 (M+1, 26%), 281 (65%), 153 (100%).

EXAMPLE 33

(±)-4-((αR* or S*)-α-(trans-4-Allyl-2,5-dimethyl-1-piperazinyl-3-amino-benzyl)-N,N-diethylbenzmide The less mobile isomer ($R_f$=0.44 on silica gel with dichloromethane:methanol: ammonium hydroxide/90:10:1 ) from chromatography of (±)-4-α-(trans-4-allyl-2,5-dimethyl-1-piperazinyl)-3aminobenzyl)-N,N-diethylbenzamide from Example 32 was isolated. NMR (CDCl$_3$): 0.98 (d, J=7 Hz, 3H); 1.15 (d, J=7 Hz, 3H); 1.2 (br m, 6H); 1.9 (t J=8 Hz, 1H); 2.1 (t, J=8 Hz, 1H); 2.4–2.9 (m, 5H); 3.1–3.7 (m, 7H); 5.1–5.2 (m, 3H); 5.7–5.9 (m, 1H); 6.55 (dd, J$_1$=10, J$_2$=2 Hz, 2H); 6.7 (S, 1H); 6.8 (d, J=8) Hz, 1H); 7.15 (t, J=8 Hz, 1H); 7.2 (d, J=8 Hz, 2H); 7.3 (d, J=8, 2H). A solution of the product (0.33 g, 0.76 mmol) in absolute ethanol was titrated to pH 4.5 with ethanolic hydrochloric acid, concentrated and treated with diethyl ether to precipitate 0.20 g (55%) of the monohydrochloride salt as a pink solid. Calc. for C$_{27}$H$_{38}$N$_4$O HCl 0.75 H$_2$O: C, 66.92; H, 8.42; N, 11.56; Cl, 7.32. Found: C, 67.01; H, 8.42; N, 11.51; Cl, 7.30. Mass spectrum (Cl–CH4): m/z 435 (M+1, 4%), 281 (19%), 153 (71%).

EXAMPLE 34

(±)-4-(3-Hydroxy)-α-(cis-3,4,5-trimethyl-1-piperazinyl)benzyl-N,N-diethylbenzamide A mixture of (±)-4-(3-((tert-butyldimethylsilyl)oxy)-α-(cis-3,5-dimethyl-1-piperazinyl)benzyl)-N,N-diethylbenzamide (18.5 g, 36.5 mmol) (from Example 11), 88% formic acid (5.1 g, 110 mmol) and 37.6% formaldehyde (2.8 g, 95 mmol) was heated at 80° C. overnight. The reaction mixture was cooled to room temperature and 20 mL of 7.2M hydrochloric acid was added slowly. The mixture was washed three times with 40 mL of dichloromethane. The pH of the aqueous layer was adjusted to 8 with a saturated solution of sodium bicarbonate and then extracted with 3×40 mL of dichloromethane. The organic extracts were dried over magnesium sulfate and evaporated to dryness to give 12.6 g (84%) of (±)-4-(3-hydroxy)-α-(cis 3,4,5-trimethyl-1-piperazinyl)benzyl)-N,N-diethylbenzamide as a tan foam. NMR (300 MHz, CDCl$_3$): δ1.0–1.3 (br m, 2d, J=6 Hz and J=6 Hz, 12H); 2.3 (br dd, 2H), 2.6 (s 3H); 2.7–3.0 (br m, 4H); 3.2–3.6 (br m, 4H); 4.2 (s, 1H), 6.7 (d, J=7 Hz, 1H); 6.8 (d, J=8 Hz, 1H); 6.9 (s, 1H); 7.1 (t, J=8 Hz, 1H); 7.25 and 7.40 (AB q, J=8 Hz, 4H). A portion of the product was dissolved in dichloromethane:ethanol and converted to the dihydrochloride salt with an excess of ethereal hydrogen chloride. The solvent was removed and the residue was redissolved in a minimum amount of dichloromethane. Diethyl ether was added to give an oily precipitate which solidified with stirring. Filtration gave the hydrated dihydrochloride salt. Calc. for C$_{25}$H$_{35}$N$_3$O$_2$2 HCl 1.5 H$_2$O C, 58.93; H, 7.91; N, 8.25; Cl, 13.92. Found: C, 58.84; H, 7.89; N, 8.09; Cl, 13.69.

EXAMPLE 3

(±)-4-((αR* or S*)-α-(trans-4-Allyl-2,5-dimethyl-1-piperazinyl)-3-(benzenesulfonamido)benzyl-N,N-diethylbenzamide Benzenesulfonylchloride (150 mL, 1.8 mmol) was added slowly to a solution of (±)-4-((αR* or S*)-α-(trans-4-allyl-2,5-dimethyl-1-piperazinyl)-3-aminobenzyl)-N,N-diethylbenzamid (Example 32) in 20 mL dichloromethane at 0° C. The reaction mixture was allowed to slowly warm to room temperature while stirring overnight. The reaction was washed with water at pH 8 and concentrated to dryness to give 0.56 g of a brown oil. The oil was purified on silica gel (Waters Prep 500A) with ethanol (0–1%) in dichloromethane containing 0.1% triethylamine to give 300 mg (29%) of (±)-4-((αR* or S*)-α-(trans-4-allyl-2,5-dimethyl-1-piperazinyl)-3-(benzenesulfonamido)benzyl)-N,N- diethylbenzamide. NMR (200 MHz, CDCl$_3$): δ0.9 (d, J=6 Hz, 3H), 1.0–1.2 (br m, 6H), 1.1 (d, J=6 Hz, 3H); 1.8 (dd, J$_1$=10 Hz, J$_2$=11 Hz, 1H); 2.1 (dd, J$_1$=10 Hz, J$_2$=11 Hz, 1H); 2.2–6 (m, 3H); 2.6–2.8 (m, 2H); 3.1–3.6 (br m, 4H), 3.25 (dd, J$_1$=3 Hz, J$_2$=12.5 Hz,1H); 5.8 (m, 1H); 6.9–7.2 (m, 6H); 7.3–7.5 (m, 5H), 7.7 (half of AB q, J=8 Hz, 2The amine was dissolved in ethanol and converted to the dihydrochloride salt with an excess of ethanolic hydrogen chloride. The product was precipitated from ethanol with diethyl ether to give 230 mg of the hydrated dihydrochloride salt as a white solid. Calc for C$_{33}$H$_{42}$N$_4$O$_3$S 2 HCl 1.25 H$_2$O: C, 59.14; H, 6.99; N, 8.36, Cl, 10.58, S, 4.78. Found: C, 58.79; H, 7.06; N, 8.72; Cl, 10.72; S, 4.78.

EXAMPLE 36

(±)-trans-4-(α-(4-Allyl-2,5-dimethyl-1piperazinyl)-3-formamidobenzyl-N,N-diethylbenzamide (±)-4-(α-(trans-4-Allyl-2,5-dimethyl-1-piperazinyl)-3-aminobenzyl)-N,N-diethylbenzamide (0.42 g, 0.97 mmol) (Example 32, infra) was dissolved in 15 mL of ethyl formate and heated at reflux overnight under nitrogen. The reaction was concentrated to dryness and purified by chromatography on silica gel with ethanol (0–10%) in dichloromethane to give 0.23 g (51%) of (±)-trans-4-(α-(4-allyl-2,5-dimethyl-1-piperazinyl)-3-formamidobenzyl)-N,N-diethylbenzamide. NMR (300 MHz, CDCl$_3$): δ1.0 (m, 3H); 1.2 (d, m, 9H); 1.8–2.2 (m, 3H); 2.4–2.9 (m, 5H); 3.2–3.6 (m, 5H); 5.1–5.3 (m, 3H) 5.8 (m, 1H); 6.7–7.8 (m, 8H); 7.9–8.1 (m, 1H), 8.6–8.9 (m, 1H). The amine was dissolved in ethanol and converted to the monohydrochloride salt by titration with ethanolic hydrogen chloride. The solution was concentrated to dryness. The resulting foam was dissolved in a minimal amount of ethanol and precipitated with diethyl ether to give 0.96 g of the hydrated monohydrochloride salt as an off-white solid. Calc. for C$_{28}$H$_{38}$N$_4$O$_2$ HCl 1.5 H$_2$O: C, 63.92; H, 8.05; N, 10.65; Cl, 6.74. Found: C, 64.21; H, 7.96; N, 10.77; C! , 6.92.

EXAMPLE 7

(±)-3-((αR*)-α-((2R*,5S*)-4-Allyl-2,5-dimethyl-1-piperazinyl)-4-(((benzyloxy)-carbonylamino)benzylphenol A solution of crude lithium (±)-4-((ecR*)-α-((2R*,5S*)-4-allyl-2,5-dimethyl-1-piperazinyl)-3-(tert-butyldimethylsilyloxy)benzyl)benzoate (2.7 g, made from 5.4 mmol of Example 2 by the procedure in Example 6, Method B) in 50 mL of dichloromethane was cooled in an ice bath, and a solution of thionyl chloride (0.60 mL, 8.0 mmol) in 10 mL of dichloromethane was added dropwise. After stirring for 1 hour, the solvent was removed in vacuo below 25° C. The residue was redissolved in 100 mL of acetone and chilled to 0° C. A solution of sodium azide (1.7 g, 27 mmol) in 15 mL of water was added to the mixture. The reaction was stirred at 0° C. for 1 hour (with appropriate safety shield) and then warmed to room temperature and stirred for 2 hours. The reaction mixture was diluted with 85 mL of water and the acetone was removed in vacuo. The aqueous solution was basified with 1N sodium hydroxide and the acyl azide was extracted with 500 mL diethyl ether. The ether extract was diluted with 250 mL toluene, and the solution volume was concentrated to 75 mL. Benzyl alcohol (1.1 mL, 11 mmol) was added, and the reaction was heated to 100° C. for 2 days. The solvent was removed and the residue was purified by chromatography on silica gel with hexane followed by dichloromethane to give 2.89 g (89%) of the urethane as a yellow oil.

A portion of the protected product (1.4 g, 2.4 mmol) and tetraethylammonium fluoride hydrate were stirred in 20 mL of acetonitrile overnight. The solvent was removed, and the residue was purified by chromatography on silica gel with ethanol (0–5%) in dichloromethane to give (±)-3-(($\alpha$R*)-$\alpha$-((2R*, 5S*)-4-allyl-2,5-dimethyl-1-piperazinyl)-4-(((benzyloxy)carbonyl)amino)benzyl) phenol as a clear oil. NMR (CDCl$_3$, 200 MHz): $\delta$1.0 (d, J=6 Hz, 3H); 1.1 (d, J=6 Hz, 3H), 1.85 (dd, J$_1$=10 Hz, J$_2$=11 Hz, 1H); 2.1 (dd, J=10 Hz, J$_2$=11Hz, 1H); 2.4–2.9 (m, 5H); 3.3 (dd J$_1$=5 Hz, J$_2$=15 Hz, 1H); 5.1 (m, 3H); 5.2 (s, 2H); 5.8 (m, 1H); 6.6 1H); 6.9 (m, 2H); 7.1 (m, 3H); 7.4 (m, 6H). The amine was dissolved in ethanol and titrated to pH 1.7 with ethanolic hydrogen chloride. The solution was concentrated to a minimum volume and the salt was precipitated with diethyl ether to give 0.59 g (46%) of a white solid. Calc. for C$_{30}$H$_{35}$N$_3$O$_3$ HCl H$_2$O: C, 66.72, H, 7.09; N, 7.78; Cl, 6.56. Found: C, 66.93; H, 7.07; N, 7.81; Cl, 6.60.

EXAMPLE 38

(±-$\alpha$-3-(($\alpha$R*)-$\alpha$-((2R*,5S*)-2,5-dimethyl-1-piperazinyl)benzyl)phenol (±)-3-(($\alpha$R*)-$\alpha$-((2R*,5S*)-4-allyl-2,5-dimethyl-1-piperazinyl)benzyl)-phenol (37.15 g, 0.11 mol) from Example 9 was treated with 5% palladium on carbon (24.0 g) and trifluoroacetic acid (9.3 mL, 0.12 mol) in methanol-:water as in Example 15 to give 13.13 g (40%) of (±)-3-((aR*)-a-((2R*,5S*)-2,5-dimethyl-1-piperazinyl)benzyl) phenol as a white solid. NMR (200 MHz, DMSO-d$_6$) $\delta$0.85 (d, J=6Hz, 3H); 1.1 (d, J=6 Hz, 3H); 1.5 (t, J=1 0 Hz, 1H); 1.9 (br s, 1H); 2.2 (br m, 1H); 2.5 (m, 2H); 2.8 (m, 2H); 5.2 (s, 1H); 6.6 (d, J=8 Hz, 1H); 6.7 (d, J=8 Hz, 1H); 6.83 (s, 1H); 7.1 (t, J=8 Hz, 1H); 7.2 (d, J=7.5 Hz, 2H); 7.4 (d, J=7.5 Hz, 2H); 7.35 (m, 1H). A portion (0.319 g, 1.1 mmol) was suspended in absolute ethanol and titrated to pH 4 with ethanolic hydrogen chloride, concentrated and treated with diethyl ether to give 0.27 g (74%) of the monohydrochloride salt as a white powder. Calculated for C$_{19}$H$_{24}$N$_2$O HCl 0.75 H$_2$O: C, 65.88; H, 7.71; N, 8.09; Cl, 10.24. Found: C, 65.91; H, 7.72; N, 7.98; Cl, 10.26. Mass spectrum (Cl-CH4): m/z 297 (M+1, 100%), 183 (25%), 113 (2.4%).

EXAMPLE 39

(±)-3-(($\alpha$R*)-$\alpha$-((2R*,5S*)-2,4,5-Trimethyl-1-piperizinylbenzylphenol (±)-3-(($\alpha$R*)-$\alpha$-((2R*,5S*)-2,5-Dimethyl-1-piperazinyl) benzyl)phenol (100 g, 3.4 mmol) from Example 38 was treated with 37% aqueous formaldehyde (0.76 mL, 10.2 mmol) and 96% formic acid (0.53 mL, 13.6 mmol) as in Example 13 to give 0.70 g of a beige solid. Chromatography on silica gel with dichloromethane:ethanol (1–4%) gave 0.20 g (31%) of (±)-3-(($\alpha$R*)-$\alpha$-((2R*,5S*)-2,4,5-trimethyl-1-piperazinyl)benzyl)phenol as a white solid. NMR (200 MHz, DMSO-d$_6$): $\delta$0.85 (d, J=6 Hz, 3H); 1.1 (d, J=6 Hz, 3H); 1.7 (t, J=10 Hz, 1H); 2.0 (t, J=10 Hz, 1H); 2.1 (s, 3H); 2.15 (br m, (br m, 1H); 2.6 (m, 2H); 5.15 (s, 1H); 6.6 (d, J=8 Hz, 1H); 6.75 (d, J=8 Hz, 1H); 6.82 (s, 1H); 7.1 (t, J=8 Hz, 1H); 7.2 (d, J=7 Hz, 2H); 7.3 (d, J=7 Hz, 2H); 7.3 (m, 1H); 9.2 (s, 1H). A portion (0.190 g, 0.61 mmol) was suspended in absolute ethanol and titrated to pH 4 with ethanolic hydrogen chloride, concentrated and treated with diethyl ether to give 0.179 g (84%) of the monohydrochloride salt as a white solid. Calc. for C$_{20}$H$_{26}$N$_2$O HCl: C, 69.45; H, 7.87; N, 8.10; Cl, 10.25. Found: C, 69.17; H, 7.82; N, 8.13; Cl, 10.30. Mass spectrum (Cl-CH4): m/z 311 (M+1, 100%), 310 (M+, 38%), 183 (58%), 127 (10%).

EXAMPLE 40

(±)-3-(($\alpha$R*)-$\alpha$-((2R*,5S*)-2,5-Dimethyl-4-ethyl-1-piperazinyl)benzyl)phenol A solution of (±)-3(($\alpha$R*)-$\alpha$-((2R*,5S*)-2,5-dimethyl-1-piperazinyl)benzyl)phenol from Example 38 in 2.5 mL of 7M ethanolic hydrogen chloride was evaporated to dryness. The residue was dissolved in 20 mL of acetone:water (3:2). Sodium acetate trihydrate (2.5 g, 18.3 mmol), acetaldehyde (0.34 mL, 6.1 mmol) and sodium cyanoborohydride (0.63 g, 10.1 mmol) were added. After stirring at room temperature under nitrogen for 18 hours, the mixture was acidified with aqueous 1M hydrochloric acid to pH 2 and extracted with diethyl ether. The aqueous layer was adjusted to pH 8 with 10M aqueous sodium hydroxide. The resulting suspension was extracted with dichloromethane, and the extracts were dried over sodium sulfate and evaporated to dryness to give 2.00 g of an off-white solid. Purification by chromatography on silica gel with dichloromethane:ethanol (1–10%) gave 0.30 g (15%) of (±)-3-(($\alpha$R*)-$\alpha$-((2R*,5S*)-2,5-dimethyl-4-ethyl-1-piperazinyl)benzyl)phenol as a white solid. NMR (200 MHz, DMSO-d$_6$): $\delta$0.9 (m, 6H); 1.1 (d, J=6 Hz, 3H); 1.85 (dd, J$_1$=8 Hz, J$_2$=10 Hz, 1H); 2.1 (dd, J$_1$=8 Hz, J$_2$=10 Hz, 1H); 2.3 (m, 1H); 2.4–2.7 (m, 4H); 2.75 (b d, J=10 Hz, 1H); 4.9 (s, 1H); 6.6 (d, J=8 Hz, 1H); 6.8 (d, J=8 Hz, 1H); 6.85 (s, 1H); J=8 Hz, 1H); 7.2–7.3 (m, 5H); 9.25 (s, 1H). The product (0.30 g, 0.92 mmol) was suspended in absolute ethanol and titrated to pH 4 with ethanolic hydrogen chloride, concentrated and treated with diethyl ether to precipitate 0.26 g (78%) of the monohydrochloride salt as a white powder. Calc. for C$_{21}$H$_{20}$N$_2$O HCl 0.75 H$_2$O: C, 67.36; H, 8.21; N, 7.48; Cl, 9.47. Found: C, 67.52; H, 8.18; N, 7.49; Cl, 9.51. Mass spectrum (Cl-CH$_4$): m/z 325 (M+1, 48%), 324 (M+, 34%), 183 (100%), 141 (55%).

EXAMPLE 41

N,N'-((Ethylenedioxy)diethylene)bis(4-((R*)-$\alpha$-((2S*,5R*-4-allyl-2,5-dimethyl-1-piperazinyl)-3-hydroxybenzyl)benzamide)

A solution of the crude lithium salt of (±)-4-(($\alpha$R*)-$\alpha$-((2S*,5R*)-4-allyl-2,5-dimethyl-1-piperazinyl)-3-(tert-butyldimethylsilyloxy)benzyl)benzoic acid (6.6 g, prepared from 13 mmol of Example 1 by the procedure of Example 6, Method B) in 150 mL dichloromethane was cooled in an ice bath. A solution of thionyl chloride (1.4 mL, 20 mmol) in 10 mL dichloromethane was added dropwise and the reaction was stirred overnight. The solvent was removed under vacuum below 25° C. and the residue was evaporated again with toluene to remove residual thionyl chloride.

The acid chloride intermediate was dissolved in 200 mL of dichloromethane and chilled in an ice bath. A solution of 1,8-diamino-3,6-dioxaoctane (0.97 mL, 6.6 mmol, Dr. Theodore Schuchardt & Co., Hohenbrunn, Germany) and triethylamine (3.8 mL, 27 mmol) in 30 mL dichloromethane was added dropwise and the reaction was stirred for 3 days. The solvent was removed and the residue was redissolved in 100 mL diethyl ether and washed with 50 mL of 1N sodium hydroxide. The solvent was removed to give 4.95 g (79%) of N,N'-((ethylenedioxy)diethylene)bis-(4-((R*)-α-((2S*,5R*)-4-allyl-2,5-dimethyl-1-piperazinyl)-3-(tert-butyldimethylsilyloxy)benzyl)benzamide as a dark foam.

The product was dissolved in 150 mL acetonitrile:dichloromethane (2:1) and tetraethylammonium fluoride hydrate (2.0 g) was added. After stirring overnight, the solvent was removed and the crude product was purified by chromatography on silica gel with dimethylformamide (0-4%) in dichloromethane to give 0.88 g (22%) of N,N'-(ethylenedioxy)diethylene)bis(4-((R*)-α-((2S*,5R*)-4-allyl-2,5-dimethyl-1-piperazinyl)-3-hydroxybenzyl)benzamide). NMR (300 MHz, DMSO-$d_6$): δ0.9 (d, J=6 Hz, 6H); 1.05 (d, J=6 Hz, 6H); 1.8 (dd, $J_1$=6 Hz, $J_2$=9 Hz, 2H); 2.1 (dd, $J_1$ =6.5 Hz, $J_2$=10 Hz, 2H); 2.5–2.65 (m, 6H); 2.7 (d, J=11 Hz, 2H); 2.85 (dd, $J_1$=7 Hz, $J_2$=14 Hz, 2H); 3.1 (dd, $J_1$=3 Hz, $J_2$=12 Hz, 2H); 3.4 (m, 4H); 3.5 (m, 8H); 4.9 (s, 2H);5.05 (d, J=11 Hz, 2H); 5.15 (d, J=16 Hz, 2H); 5.8 (m, 2H); 6.6 (d, J=6 Hz, 2H), 6.7 (s, 2H); 6.7 (d, J=8 Hz, 2H); 7.1 (t, J=8 Hz, 2H); 7.4 and 7.7 (ABq, J=8 Hz, 8H), 8.4 (t, J=5.5 Hz, 2H); 9.3 (s, 2H).

The amine was dissolved in ethanol and converted to the dihydrochloride salt by titration with ethanolic hydrogen chloride. The hygroscopic salt was precipitated with diethyl ether. Filtration gave 0.583 g of the salt as a white solid. Calc. for $C_{52}H_{68}N_6O_6$ 2HCl 1.25 $H_2O$: C, 64.48; H, 7.54; N, 8..68; Cl, 7.32. Found: C, 64.56; H, 7.57; N, 8.59, Cl, 7.19.

EXAMPLE 42

(±-3-((R*)-((2S*,5R*)-4-Allyl-2,5-dimethyl1-piperazinyl)(4-bromo-2-thienyl)methyl)phenol A 12 L, 3-necked round bottom flask was charged with trans-2,5-dimethylpiperazine (767 g, 6.72 mol), which had been recrystallized from toluene to mp=115°–119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise with adjustment of rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0. The organic solvents were removed by distillation under vacuum. The remaining aqueous solution was washed with 1500 mL of ethyl acetate to remove any biscarbamate impurity. The ethyl acetate wash was extracted with two 500 mL portions of 1M hydrochloric acid to recover desired product. The acid extracts were combined with the original aqueous solution and the pH was adjusted to 11 by addition of 10M sodium hydroxide, with cooling to maintain temperature below 40° C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1M sodium hydroxide. The dichloromethane solution was dried over magnesium sulfate and the solvent was removed to give 630 g (81%) of ethyl trans-4-allyl-2,5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5–1 hour of heating. The reaction was cooled below reflux temperature and 2000 mL of toluene was carefully added. Ethanol was removed by azeotropic distillation at 105° C., while adding an additional 4000 mL of toluene to the reaction flask during the course of the distillation. After collection of 9000 mL of distillate, the reaction was cooled to 100° C. and 1000 mL of toluene was carefully added. The solution was slowly cooled to 5° C. and maintained at 5° C. for 30 minutes. The solution was filtered, washing the filter cake with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid.

3-Bromophenoxy-tert-butyldimethylsilane (30.2 g, 0.105 mol), prepared as in Example 1, was dissolved in 300 mL of dry tetrahydrofuran under nitrogen and cooled to –78° C. A solution of 1.6M n-butylithium in hexane (66 mL, 0.105 mol) was added dropwise at a rate to maintain a temperature below –65° C. The reaction was stirred for thirty minutes after the addition was complete and the cold solution was transferred to another vessel containing a room temperature solution of magnesium bromide (20.2 g, 0.11 mol) in 400 mL of dry tetrahydrofuran under nitrogen. The resulting solution was allowed to warm to 15° C. while stirring. After one hour a solution of 4-bromo-2-thiophenecarboxaldehyde (20.0 g, 0.105 mol) in 100 mL of dry tetrahydrofuran was added slowly at a rate to maintain a temperature below 25° C. The resulting solution was stirred for three hours at room temperature, then washed three times with aqueous ammonium chloride, dried over sodium sulfate and evaporated to give a yellow oil. Chromatography on silica gel with dichloromethane:hexane/50:50 gave 20.23 g (48.2%) of α-(4-bromo-2-thienyl)-3-((tert-butyldimethylsilyl)-oxy) benzyl alcohol as a viscous yellow oil.

Thionyl chloride (19.5 mL, 0.27 mol) was added to a solution of the alcohol (71.3 g, 0.18 mol) in 600 mL of dichloromethane. After stirring for 16 hours the solvent was evaporated, the residue was redissolved in toluene and evaporated again to drive off excess thionyl chloride.

A mixture of the crude diarylchloromethane (approximately 0.18 mol), N-allyl-trans-2,5- dimethylpiperazine and 1000 mL of acetonitrile was heated to reflux under nitrogen for 40 hours. The solution was cooled to room temperature, filtered, and evaporated. The residue was partitioned between diethyl ether and 0.1M aqueous sodium hydroxide. The ethereal layer was washed three more times with 0.1M aqueous sodium hydroxide, dried over potassium carbonate, and evaporated to 145 g of black oil. Chromatography on silica gel with ethyl acetate removed excess N-allyl-trans-2,5-dimethylpiperazine to leave 86 g of black oil which was purified by chromatography on silica gel with dichloromethane:ethyl acetate/95:5 to yield 63.1 g (66%) of dark oil.

A mixture of the product (63.1 g, 0.118 mol), tetraethylammonium fluoride hydrate (37 g, approximately 0.2 mol) and 100 mL of acetonitrile was stirred at room temperature under nitrogen for 1 hour. The solvent was removed by evaporation, the residue was dissolved in dichloromethane, washed three times with water (adjusted to pH 8 with 1M aqueous sodium hydroxide), dried over sodium sulfate and evaporated to a tan solid. The two diastereomers of the product were separated by chromatography on silica gel with dichloromethane:ethyl acetate/75:25. Elution of the first isomer gave 15.84 g (32%) of (±)-3-((R*)-((2S*,5R*)-4-allyl-2,5-dimethyl-1-piperazinyl)(4-bromo-2-thienyl)methyl)phenol. $^{1}$H-NMR (300 MHz, DMSO-$d_6$): δ0.93 (d, J=6.0 Hz, 3H); 1.09 (d, J=6.3 Hz, 3H); 2.00 (m, 2H); 2.40 (m, 2H); 2.65–2.90 (m, 3H); 3.30 (m, 1H); 5.14 (m, 2H); 5.44 (s, 1H); 5.80 (m, 1H); 6.65–6.81 (m, 3H); 7.05 (s, 1H); 7.12 (t, J=8.0 Hz, 1H); 7.66 (s, 1H); 9.35 (s, 1H). A 500 mg portion was dissolved in ethanol and converted to the monohydrochloride salt by titration to pH 3.6 with ethanolic hydrochloric acid. The solvent was removed by evaporation and the salt was dissolved in dichloromethane, followed by precipitation with diethyl ether to give 300 mg (55%) of a white solid, mp 128°–132° C. Calculated for $C_{20}H_{25}BrN_2OS$ HCl 0.25 $H_2O$: C, 51.96; H, 5.78; N, 6.06; Br, 17.28; Cl, 7.67, S, 6.93. Found: C, 51.94; H, 5.80; N, 6.04; total halogen calc. as chlorine, 15.33; S, 7.02.

EXAMPLE 43

(±)-3-((R*)-((2R*,5S*)-4-Allyl-2,5-dimethyl-1-piperazinyl)(4-bromo-2-thienyl)methyl)phenol Elution of the second isomer from the column of Example 42 gave 18.02 g (36%) of (±)-3-((R*)-((2R*,5S*)-4-allyl-2,5-dimethyl-1-piperazinyl)(4-bromo-2-thienyl)methyl)phenol. $^{1}$H-NMR (300 MHz, DMSO-$d_6$): δ0.90 (d, J=6.1 Hz, 3H); 1.15 (d, J=6.1 Hz, 3H); 1.70 (t, 1H); 1.97 (t, 1H); 2.40 (m, 2H); 2.60–2.80 (m, 3H); 3.30 (m, 1H); 5.12 (m, 2H); 5.30 (s, 1H); 5.80 (m, 1H); 6.60 (s, 1H); 6.72 (m, 3H); 7.12 (t, J=8.2 Hz, 1H); 7.55 (s, 1H); 9.47 (s, 1H). A 500 mg portion was dissolved in ethanol and converted to the monohydrochloride salt by titration to pH 3.7 with ethanolic hydrochloric acid. The solvent was removed by evaporation and the salt was dissolved in dichloromethane, followed by precipitation with diethyl ether to give 240 mg (44%) of a white solid, mp 138°–141° C. Calculated for $C_{20}H_{25}BrN_2OS$ HCl: C, 52.46; H, 5.72; N, 6.12; Br, 17.45; Cl, 7.74, S, 7.00. Found: C, 52.31; H, 5.75; N, 6.07; total halogen calc. as chlorine, 15.55; S, 7.09.

EXAMPLE 44

(±)-3-((R*)-((2S*,5R*)-4-allyl-2,5-dimethyl-1-piperazinyl)(2-thienyl)methyl)-phenol A mixture of (±)-3-((R*)-((2S*,5R*)-4-allyl-2,5-dimethyl-1-piperazinyl)-(4-bromo-2-thienyl)methyl)phenol (Example 42, 4.0 g, 9.5 mmol), tert-butyldimethylsilyl chloride (1.66 g, 11.0 mmol), and imidazole (1.63 g, 24.0 mmol) was dissolved in 20 mL of dry dimethylformamide under nitrogen and stirred for 72 hours at room temperature. The mixture was diluted with 200 mL of ethyl acetate, washed three times with 0.1M aqueous sodium hydroxide and once with water, dried over sodium sulfate, and evaporated to give 5.4 g (100%) of a tan oil.

A solution of the product (5.4 g, 9.5 mmol) in 150 mL of dry tetrahydrofuran under nitrogen was cooled to –70° C. A solution of 1.6M n-butyllithium in hexane (6.4 mL, 10.0 mmol) was added via syringe at a rate to maintain a temperature below –60° C. The solution was cooled to –78° C. and carbon dioxide gas was introduced below the surface of the solution via cannula for 15 min. The solution was allowed to warm to room temperature with stirring. The solvent was evaporated and the residue was redissolved in toluene and evaporated again to remove butyl bromide. The resulting viscous oil was dissolved in 500 mL of dichloromethane and cooled to 0° C. under nitrogen. Thionyl chloride (1.0 mL, 14.0 mmol) was added slowly via syringe. The resulting mixture was stirred for two hours at 0° C. before adding a solution of diethylamine (5.1 mL, 50 mmol) in 60 mL of dichloromethane dropwise. The mixture was stirred for 16 hours at room temperature, washed three times with water, dried over sodium sulfate, and evaporated to give an orange brown oil. Chromatography on silica gel with dichloromethane:ethyl acetate (gradient from 90:10 to 0:100) yielded four products in order of elution: 970 mg (21.2%) of (±)-3-((R*)-((2S*,5R*)-4-allyl-2,5-dimethyl-1-piperazinyl)(2-thienyl)methyl)phenol, tert-butyldimethylsilyl ether; 550 mg (8.7%) of (±)-5-((αR*)-α-((2S*,5R*)-4-allyl-2,5-dimethyl-1-piperazinyl)-3-hydroxybenzyl)-3-bromo-N,N-diethyl-2-thiophenecarboxamide, tert-butyldimethylsilyl ether; 1050 mg (18.9%) of (±)-5-((αR*)-α-((2S*,5R*)-4-allyl-2,5-dimethyl-1-piperazinyl)-3-hydroxybenzyl)-N,N-diethyl-2-thiophenecarboxamide, tert-butyldimethylsilyl ether; and 880 mg (15.8%) of (±)-5-((αR*)-α-((2S*,5R*)-4-allyl-2,5-dimethyl-1-piperazinyl)-3-hydroxybenzyl)-N,N-diethyl-3-thiophenecarboxamide, tert-butyldimethylsilyl ether.

The first material to elute, (±)-3-((R*)-((2S*,5R*)-4-allyl-2,5-dimethyl-1-piperazinyl)(2-thienyl)methyl)phenol, tert-butyldimethylsilyl ether (1.06 g, 2.32 mmol), was combined with tetraethylammonium fluoride hydrate (750 mg, approximately 4 mmol) and 100 mL of acetonitrile and stirred at room temperature for 16 hours under nitrogen. The solvent was removed by evaporation and the residue was dissolved in dichloromethane, washed three times with pH 8 buffer solution, dried over sodium sulfate and evaporated to a brown glass. Chromatography on silica gel with dichloromethane:acetonitrile/2:1 yielded 610 mg of (±)-3-((R*)-((2S*,5R*)-4-allyl-2,5-dimethyl-1-piperazinyl)(2-thienyl)methyl)phenol as a white solid. $^{1}$H-NMR (300 MHz, DMSO-$d_6$): δ0.92 (d, J=5.9 Hz, 3H); 1.10 (d, J=5.8 Hz, 3H); 2.02 (q, 2H); 2.40 (m, 2H); 2.74 (m, 2H); 2.85 (m, 1H); 3.30 (m, 1H); 5.14 (m, 2H); 5.48 (s, 1H); 5.80 (m, 1H); 6.60 (d, J=7.8 Hz, 1H); 6.79 (d, J=7.8 Hz, 1H); 6.85 (s, 1H); 7.0–7.2 (m, 3H); 7.52 (d, J=4.9 Hz, 1H); 9.31 (s, 1H). The amine was dissolved in ethanol and converted to the monohydrochloride salt by titration to pH 3.7 with ethanolic hydrochloric acid. The solvent was removed by evaporation and the salt was dissolved in dichloromethane, followed by precipitation with diethyl ether to give 500 mg (56%) of a white solid, mp 115°–121° C. Calculated for $C_{20}H_{26}N_2OS$ HCl 0.4 $H_2O$: C, 62.21; H, 7.26; N, 7.25; Cl, 9.18; S, 8.30. Found: C, 62.21; H, 7.21; N, 7.23; Cl, 9.19; S, 8.22.

EXAMPLE 45

(±)-5-((αR*)-α-((2S*,5R*)-4-Allyl-2,5-dimethyl-1-piperazinyl-3-hydroxy-benzyl)-3-bromo-N,N-diethyl-2-thiophenecarboxamide

Method A

The second material to elute from the column of Example 44 (620 mg, 0.98 mmol), was deprotected with tetraethylammonium fluoride hydrate as in Example 44. Chromatography over silica gel with dichloromethane:acetonitrile/1:1 yielded 280 mg of a colorless glass. $^1$H-NMR (300 MHz, DMSO-d$_6$): δ0.93 (d, J=5.8 Hz, 3H); 1.13 (m, 9H); 1.90–2.20 (m, 2H); 2.40 (m, 2H); 2.65–3.00 (m, 3H); 3.30 (m, 5H); 5.14 (m, 2H); 5.47 (s, 1H); 5.80 (m, 1H); 6.65 (d, J=7.8 Hz, 1H); 6.80 (d, J=7.8 Hz, 1H); 6.83 (s, 1H); 7.06 (s, 1H); 7.14 (t, J=7.8 Hz, 1H); 9.41 (s, 1H). The amine was dissolved in ethanol and converted to the monohydrochloride salt by titration to pH 3.6 with ethanolic hydrochloric acid. The solvent was removed by evaporation and the salt was dissolved in dichloromethane, followed by precipitation with diethyl ether to give 150 mg (27%) of a white solid, mp 114°–124° C. Calculated for $C_{25}H_{34}BrN_3O_2S$ HCl: C, 53.91; H, 6.33; N, 7.55; Br, 14.35; Cl, 6.37, S, 5.76. Found: C, 53.80; H, 6.38; N, 7.59; total halogen calc. as chlorine, 12.72; S, 5.71.

Method B

A mixture of (±)-3-((R*)-((2S*,5R*)-4-allyl-2,5-dimethyl-1-piperazinyl)-(4-bromo-2-thienyl)methyl)phenol (7.7 g, 0.0183 mol, Example 42), tert-butyldimethylsilyl chloride (3.17 g, 0.021 mol), imidazole (3.13 g, 0.046 mol), and 50 mL of dry dimethylformamide was stirred at room temperature under nitrogen for 16 hours. The solution was diluted with 500 mL of ethyl acetate, washed three times with 0.1 N NaOH, dried over sodium sulfate and evaporated to give 10.3 g (105%) of crude (±)-3-((R*)-((2S*,5R*)-4-allyl-2,5-dimethyl-1-piperazinyl)(4-bromo-2-thienyl)methyl)phenol, tert-butyldimethyl-silyl ether as a dark oil.

A solution of the product (2.2 g, 4.1 mmol) in 250 mL of dry tetrahydrofuran under nitrogen was cooled to –78° C. A solution of 1.5M lithium diisopropylamide in cyclohexane (2.8 mL, 4.1 mmol) was added via syringe at a rate to maintain a temperature below –70° C. The resulting solution was stirred for one hour at –78° C., then carbon dioxide gas was introduced below the surface of the solution via cannula for 10 min. The solution was allowed to warm to room temperature with stirring. The solvent was evaporated and the residue was redissolved in toluene and evaporated again. The resulting viscous oil was dissolved in 250 mL of dichloromethane and stirred at room temperature under nitrogen. Thionyl chloride (0.42 mL, 5.75 mmol) was added, and the resulting mixture was stirred for one hour at room temperature before adding diethylamine (2.1 mL, 20.6 mmol). The mixture was stirred for 16 hours at room temperature, washed three times with water, dried over sodium sulfate, and evaporated to give a dark oil. Chromatography on silica gel with dichloromethane:ethyl acetate/9:1 gave 1.57 g (60%) of (±)-5-((αR*)-α-((2S*,5R*)-4-allyl-2,5-dimethyl-1-piperazinyl)-3-hydroxybenzyl)-3-bromo-N,N-diethyl-2-thiophenecarboxamide, tert-butyldimethylsilyl ether.

The product was deprotected with tetraethylammonium fluoride hydrate as in Example 44. Chromatography over silica gel with dichloromethane:ethyl acetate/1:1 yielded 940 mg of (±)-5-((αR*)-α-((2S*,5R*)-4-allyl-2,5-dimethyl-1-piperazinyl)-3-hydroxybenzyl)-3-bromo-N,N-diethyl-2-thiophenecarboxamide as a light tan foam. $^1$H-NMR (300 MHz, DMSO-d$_6$): δ0.91 (d, J=6.0 Hz, 3H); 1.10 (m, 9H); 1.90–2.20 (m, 2H); 2.40 (m, 2H); 2.65–3.00 (m, 3H); 3.30 (m, 5H); 5.13 (m, 2H); 5.47 (s, 1H); 5.76 (m, 1H); 6.63 (d, J=8.1 Hz, 1H); 6.78 (d, J=7.8 Hz, 1H); 6.82 (s, 1H); 7.04 (s, 1H); 7.13 (t, J=7.8 Hz, 1H); 9.38 (s, 1H). The amine was dissolved in ethanol and converted to the monohydrochloride salt by titration to pH 3.7 with ethanolic hydrochloric acid. The solvent was removed and the salt was dissolved in dichloromethane, followed by precipitation with diethyl ether to give 780 mg (57%) of a white solid, mp 147°–150° C. Calculated for $C_{25}H_{34}BrN_3O_2S$ HCl: C, 53.91; H, 6.33; N, 7.55; Br, 14.35; Cl, 6.37, S, 5.76. Found: C, 53.82; H, 6.30; N, 7.50; total halogen calc. as chlorine, 12.72; S, 5.71.

EXAMPLE 46

(±)-5-((αR*)-α-((2S*,5R*)-4-allyl-2,5-dimethyl-1-piperazinyl)-3-hydroxy-benzyl)-N,N-diethyl-2-thiophenecarboxamide The third material to elute from the column of Example 44 (1.2 g, 2.16 mmol) was deprotected with tetraethylammonium fluoride hydrate as in Example 44. Chromatography over silica gel with acetonitrile yielded 1.03 g of a tan glass. $^1$H-NMR (300 MHz, DMSO-d$_6$): δ0.93 (d, J=5.8 Hz, 3H); 1.20 (m, 9H); 1.90–2.20 (m, 2H); 2.40 (m, 2H); 2.60–3.00 (m, 3H); 3.30 (m, 5H); 5.15 (m, 2H); 5.47 (s, 1H); 5.80 (m, 1H); 6.65 (d, J=7.8 Hz, 1H); 6.80 (d, J=7.8 Hz, 1H); 6.85 (s, 1H); 7.00 (d, J=3.5 Hz, 1H); 7.14 (t, J=8.0 Hz, 1H); 7.34 (d, J=3.5 Hz, 1H); 9.35 (s, 1H). The amine was dissolved in ethanol and converted to the monohydrochloride salt by titration to pH 3.9 with ethanolic hydrochloric acid. The solvent was removed by evaporation and the salt was dissolved in dichloromethane, followed by precipitation with diethyl ether to give 200 mg (19%) of a white solid, mp 113°–116° C. Calculated for $C_{25}H_{35}N_3O_2S$ HCl 0.5 $H_2O$: C, 61.65; H, 7.66; N, 8.63; Cl, 7.28; S, 6.58. Found: C, 61.54; H, 7.60; N, 8.66; Cl, 7.30; S, 6.61.

EXAMPLE 47

(±)-5-((αR*)-α-((2S*,5R*)-4-allyl-2,5-dimethyl-1-piperazinyl)-3-hydroxy-benzyl)-N,N-diethyl-3-thiophenecarboxamide The fourth material to elute from the column of Example 44 (950 mg, 1.71 mmol), was deprotected with tetraethylammonium fluoride hydrate as in Example 44. Chromatography over silica gel with acetonitrile:ethanol/95:5 yielded 440 mg of an off-white glass. $^1$H-NMR (300 MHz, DMSO-d$_6$): δ0.91 (d, J=6.0 Hz, 3H); 1.1 (m, 9H); 1.90–2.10 (m, 2H); 2.40 (m, 2H); 2.70–2.90 (m, 3H); 3.30 (m, 5H); 5.09 (m, 2H); 5.47 (s, 1H); 5.80 (m, 1H); 6.60 (d, J=7.8 Hz, 1H); 6.80 (d, J=7.8 Hz, 1H); 6.84 (s, 1H); 7.04 (s, 1H); 7.14 (t, J=7.8 Hz, 1H); 7.67 (s, 1H); 9.33 (s, 1H). The amine was dissolved in ethanol and converted to the monohydrochloride salt by titration to pH 3.8 with ethanolic hydrochloric acid. The solvent was removed by evaporation and the salt was dissolved in dichloromethane, followed by precipitation with diethyl ether to give 300 mg (36%) of a white solid, mp 108°–112° C. Calculated for $C_{25}H_{35}N_3O_2S$ HCl 0.5 $H_2O$: C, 61.65; H, 7.66; N, 8.63; Cl, 7.28; S, 6.58. Found: C, 61.58; H, 7.63; N, 8.58; Cl, 7.33; S, 6.50.

EXAMPLE 48

(±)-3-((R*)-((2R*,5S*)-4-Allyl-2,5-dimethyl-1-piperazinyl)(2-thienyl)methyl)-phenol The procedure described in Example 44 was followed with 4.0 g (9.5 mmol) of (±)-3-((R*)-((2R*,5S*)-4-allyl-2, 5-dimethyl-1-piperazinyl)(4-bromo-2-thienyl)methyl) phenol (Example 43). Chromatography over silica gel with dichloromethane:ethyl acetate (gradient from 95:5 to 0:100) yielded four products in order of elution: 950 mg (20.7 %) of (±)-3-((R*)-((2R*,5S*)-4-allyl-2,5-dimethyl-1-piperazinyl)(2-thienyl)methyl)phenol, tert-butyldimethylsilyl ether, 480 mg (7.6%) of (±)-5-(($\alpha$R*)-$\alpha$-((2R*,5S*)-4-Allyl-2,5-dimethyl-1-piperazinyl)-3-hydroxybenzyl)-3-bromo-N,N-diethyl-2-thiophenecarboxamide, tert-butyldimethylsilyl ether, 260 mg (4.7%) of (±)-5-(($\alpha$R*)-$\alpha$-((2R*,5S*)-4-allyl-2,5-dimethyl-1-piperazinyl)-3-hydroxybenzyl)-N,N-diethyl-2-thiophenecarboxamide, tert-butyldimethylsilyl ether, and 870 mg (16%) of (±)-5-(($\alpha$R*)-$\alpha$-((2R*,5S*)-4-allyl-2,5-dimethyl-1-piperazinyl)-3-hydroxybenzyl)-N,N-diethyl-3-thiophenecarboxamide, tert-butyldimethylsilyl ether.

The first material to elute, (±)-3-((R*)-((2R*,5S*)-4-allyl-2,5-dimethyl-1-piperazinyl)(2-thienyl)methyl)phenol, tert-butyldimethylsilyl ether (950 mg, 2.08 mmol), was deprotected with tetraethylammonium fluoride hydrate as in Example 44. Chromatography over silica gel with dichloromethane:acetonitrile/1:1 yielded 610 mg (62%) of (±)-3-((R*)-((2R*,5S*)-4-allyl-2,5-dimethyl-1-piperazinyl) (2-thienyl)methyl)phenol as a white solid. $^1$H-NMR (300 MHz, DMSO-d$_6$): $\delta$0.90 (d, J=4.0 Hz, 3H); 1.13 (d, J=4.0 Hz, 3H); 1.76 (t, J=9.4 Hz, 1H); 1.98 (t, J=9.9 Hz, 1H); 2.38 (m, 2H); 2.67 (d, J=10.9 Hz, 2H); 2.75 (m, 1H); 3.15 (m, 1H); 5.1 (m, 2H); 5.26 (s, 1H); 5.80 (m, 1H); 6.70 (m, 4H); 6.92 (dd, J$_1$=3.5 Hz, J$_2$=5.1 Hz, 1H); 7.18(t, J=7.9 Hz, 1H); 7.38 (d, J=5.0 Hz, 1H); 9.38 (s, 1H). A 440 mg portion was dissolved in ethanol and converted to the monohydrochloride salt by titration to pH 3.8 with ethanolic hydrochloric acid. The solvent was removed by evaporation and the salt was dissolved in dichloromethane, followed by precipitation with diethyl ether to give 330 mg (66%) of a white solid, mp 123°–127° C. Calculated for C$_{20}$H$_{26}$N$_2$OS HCl 0.4 H$_2$O: C, 62.21; H, 7.26; N, 7.25; Cl, 9.18; S, 8.30. Found: C, 62.07; H, 7.24; N, 7.20; Cl, 9.20; S, 8.19.

EXAMPLE 49

(±)-5-(($\alpha$R*)-$\alpha$-((2R*,5S*)-4-allyl-2,5-dimethyl-1-pieprazinyl)-3-hydroxy-benzyl)-N,N-diethyl-2-thiophenecarboxamide The third material to elute from the column in Example 48 (260 mg, 0.47 mmol) was aleprotected with tetraethylammonium fluoride hydrate as in Example 44. Chromatography over silica gel with acetonitrile yielded a tan glass. $^1$H-NMR (300 MHz, DMSO-d$_6$): $\delta$0.91 (d, J=3.0 Hz, 3H); 1.17 (m, 9H); 1.75 (m, 1H); 2.0 (m,1H); 2.40 (m, 2H); 2.60–2.85 (m, 3H); 3.30 (m, 1H); 3.45(m, 4H); 5.15 (m, 2H); 5.32 (s, 1H); 5.80 (m, 1H); 6.65 (d, J=3.1 Hz, 1H); 6.75 (m, 3H); 7.20 (m, 2H); 9.45 (s, 1H). The amine was converted to the monohydrochloride salt by titration to pH 3.1 with ethanolic hydrochloric acid. The solvent was removed by evaporation and the salt was dissolved in dichloromethane, followed by precipitation with diethyl ether to give 70 mg (31%) of a white solid, mp 173°–175° C. Calculated for C$_{25}$H$_{35}$N$_3$O$_2$S HCl 0.4 H$_2$O: C, 61.87; H, 7.64; N, 8.66; Cl, 7.31; S, 6.61. Found: C, 61.93; H, 7.62; N, 8.72; Cl, 7.32; S, 6.62.

EXAMPLE 50

(±)-5-(($\alpha$R*)-$\alpha$-((2R*,5S*)-4-allyl-2,5-dimethyl-1-piperazinyl)-3-hydroxy-benzyl)-N,N-diethyl-3-thioohenecarboxamide The fourth matedal to elute from the column of Example 48 (870 mg, 1.57 mmol) was deprotected with tetraethylammonium fluoride hydrate as in Example 44. Chromatography over silica gel with acetonitrile gave an off-white glass. $^1$H-NMR (300 MHz, DMSO-d$_6$): $\delta$0.90 (d, J=6.0 Hz, 3H); 1.07 (t, J=7.0 Hz, 6H); 1.15 (d, J=5.7 Hz, 3H) 1.74 (m, 1H); 1.97 (m,1H); 2.35 (m, 2H); 2.60–2.80 (m, 3H); 3.30 (m, 5H); 5.15 (m, 2H); 5.29 (s, 1H); 5.80 (m, 1H); 6.66 (s, 1H); 6.73 (s, 1H); 6.74 (d, J=7.5 Hz, 2H); 7.19 (t, J=7.5 Hz, 1H); 7.56 (s, 1H); 9.45 (s, 1H). The amine was dissolved in ethanol and converted to the monohydrochloride salt by titration to pH 3.8 with ethanolic hydrochloric acid. The solvent was removed by evaporation and the salt was dissolved in dichloromethane, followed by precipitation with diethyl ether to give 280 mg (37%) of a white solid, mp 109°–116° C. Calculated for C$_{25}$H$_{35}$N$_3$O$_2$S HCl 0.5 H$_2$O: C, 61.65; H, 7.66; N, 8.63; Cl, 7.28; S, 6.58. Found: C, 61.58; H, 7.65; N, 8.54; Cl, 7.36; S, 6.53.

EXAMPLE 51

(±)-(R*, R*) or (R*,S*)-N,N-Diethyl-4-(3-hydroxy-$\alpha$-(1,2,5,6-tetrahydro-1,3,6-trimethyl-4-pyridyl) benzyl)benzamide Following a literature procedure (Koncewicz, J. and Skrowaezewska, Z., Politec. Wroclaw Rocz. Chem., 1968, 42, 1873–85 (Chem. Ab., 70, 114972u (1968))) 2,5-dimethylpyridine was dissolved in 400 ml glacial acetic acid and 30% hydrogen peroxide (55 mL) was added slowly. The mixture was heated to 70° C. for 48 hours, with addition of more hydrogen peroxide (55 mL) at 5 hours and 20 hours. The reaction mixture was cooled, diluted with water, and the solvents removed to give 141 g of crude 2,5-dimethylpyridine-N oxide as a pale yellow liquid.

A solution of 98% sulfudc acid (300 mL) and 90% nitric acid (100 g) was chilled in an ice bath. The pyridine-N-oxide (0.933 mol) was added slowly to the solution over 2.5 hours (following the literature procedure above). The reaction mixture was heated overnight in an 85° C. oil bath.

After cooling to room temperature, the reaction mixture was divided into thirds and each portion was poured into a 4000 mL beaker filled with ice. The resulting slurry was slowly basified with 10M sodium hydroxide. The solution was diluted with 500 mL water and extracted with two 2000 mL portions of dichloromethane. The combined organic layers were concentrated to dryness to give 120.8 g (77%) of 2,5-dimethyl-4-nitropyridine-N-oxide as a yellow solid.

A portion of the pyridine-N-oxide (106.4 g, 0.633 mol) was added slowly to 300 g of acetyl bromide at a rate that maintained the reaction temperature at 20°–30° C. (modification of procedure described in Ochiai, J. Org. Chem, 18, 549(1953)). After the addition was complete, the reaction was heated to 55° C. and left to stir overnight. The reaction mixture was cooled to room temperature and then slowly poured over ice. The mixture was slowly basified with 10M sodium hydroxide and extracted with chloroform. The chloroform extract was dried over sodium sulfate and then concentrated to dryness to give 119.2 g (93%) of 4-bromo-2,5-dimethylpyridine-N-oxide.

A portion of the pyridine-N-oxide (90.0 g, 0.445 mol) was dissolved in dichloromethane (1500 mL) and chilled to 0° C. Phosphorus tribromide (400 g) was added slowly, and the reaction was warmed to room temperature overnight.

The mixture was poured onto ice and slowly basified with 10M sodium hydroxide. The solution was extracted with 3000 mL chloroform. The chloroform was evaporated to give 56.8 g of a dark red liquid. The liquid was distilled (58° C., 1.5 mm Hg) to give 33.9 g (41%) of 4-bromo-2,5-dimethylpyridine as a clear liquid.

Pyridinium chlorochromate (46.5 g, 0.216 mol) was added to a solution of 4-(3-(tert-butyldimethylsilyloxy)-α-hydroxybenzyl)-N,N-diethylbenzamide (44.6 g, 0.108 mol) from Example 11 in 600 mL dichloromethane at 0° C. The solution was stirred overnight at room temperature and filtered through Celite. The filtrate was concentrated to a volume of 150 mL and purified by chromatography on silica gel with ethyl acetate (5–40%) in hexane to give 29.4 g (66%) of 4-(3-((tert-butyldimethylsilyl)oxy)benzoyl)-N,N-diethylbenzamide as a white solid.

A portion of the 4-bromo-2,5-dimethylpyridine (15.4 g, 83.0 mmol) was dissolved in 500 mL of anhydrous diethyl ether and chilled to –78° C. n-Butyllithium (52 mL, 1.6M in hexanes) was added dropwise and the resulting slurry was stirred for 30 minutes. 4-(3-((tert-butyldimethylsilyl)oxy)benzoyl)-N,N-diethylbenzamide (34.2 g, 83.0 mmol) was dissolved in 250 mL of anhydrous diethyl ether and chilled to –78° C. The lithiated pyridine was slowly transferred via cannula to the diarylketone solution. The temperature was allowed to rise to –40° C. for 4.5 hours. The reaction was quenched with saturated aqueous ammonium chloride. The diethyl ether layer was separated, the solvent was removed, and the residue was redissolved in 300 mL acetonitrile. Tetraethylammonium fluoride hydrate (19.8 g) was added, and the reaction was stirred overnight. The solvent was removed, and the residue was redissolved in 500 mL 1M hydrochloric acid and washed with 500 mL of diethyl ether. The pH of the aqueous solution was adjusted to 8 and the solution was extracted with dichloromethane. The solvent was removed and the residue was crystallized from acetonitrile to give 16.4 g (48%) of (±)-4-(α-(2,5-dimethyl-4-pyridyl)-α,3-dihydroxybenzyl)-N,N-diethylbenzamide.

A portion of the product (8.0 g, 20 mmol) was dissolved in 150 mL of acetic acid with 70% perchloric acid (11.4 mL) and 5% palladium on carbon (0.80 g) and hydrogenated on a Parr apparatus at 50 psi for 7 days. The reaction was filtered through Celite and washed with ethanol:water, 4:1. The solvent was removed, the residue redissolved in water, and the pH adjusted to 8 with 10M sodium hydroxide. The solution was extracted with dichloromethane and the extracts dried over sodium sulfate. The solvent was removed to give 6.4 g (84%) of (±)-4-(α-(2,5-dimethyl-4-pyridyl)-3-hydroxybenzyl)-N,N-diethylbenzamide as a brown foam.

The portion of the product (5.4 g, 14 mmol) and methyl tosylate (2.8 g, 14 mmol) were dissolved in 150 mL of tetrahydrofuran and heated at reflux for 2 days. An additional 1.3 g of methyl tosylate was added and the reaction was continued at reflux for another 24 hours. The solvent was removed to give 4-(4'-(diethylcarbamoyl)-3-hydroxybenzhydryl)-1,2,5-trimethylpyridinium 4-toluenesulfonate as an oil.

A suspension of sodium borohydride (1.1 g, 28 mmol) in 9 mL ethanol:3.5 mL water was chilled to –20° C. The pyridinium salt from above was dissolved in 5 mL ethanol and added dropwise over 1 hour. The reaction was stirred for 3 hours at –20° C. and then poured into 60 mL of chilled (–20° C.) 6M hydrochloric acid. The ethanol was removed, the pH was adjusted to 8, and the solution was extracted with dichloromethane. The extracts were dried over sodium sulfate and the solvent removed to give 6.2 g of a brown foam. The crude product was purified by chromatography on silica gel with ethanol (0–20%) in dichloromethane. The first isomer to elute gave 0.67 g (24%) of (±)-(R*, R*) or (R*, S*)-N,N-diethyl-4-(3-hydroxy-α-(1,2,5,6-tetrahydro-1,3,6-trimethyl-4-pyridyl)benzyl)benzamide. NMR (300 MHz, CDCl$_3$): δ1.0 (d, J=6Hz, 3H); 1.1–1.25 (br m,6H); 1.66 (s, 3H); 1.8 (d, J=4Hz, 2H); 2.3 (s, 3H); 2.35 (m,1H); 2.9 and 3.2 (ABq, J=16Hz, 2H); 3.2–3.6 (br m, 4H); 5.23 (s, 1H); 6.5 (d, J=8Hz, 1H); 6.6 (d, J=8Hz, 1H); 6.78 (s, 1H); 7.05 (t, J=8 Hz, 1H); 7.1 and 7.3 (ABq, J=8Hz, 4H).

The amine was dissolved in ethanol and titrated to the monohydrochloride salt with ethanolic hydrogen chloride. The ethanol was removed, the residue was dissolved in dichloromethane, and the salt was precipitated with diethyl ether to give 0.16 g of the hygroscopic salt as a white foam. Calc. for $C_{26}H_{34}N_2O_2$ HCl 1.75 $H_2O$: C, 65.81; H, 8.18; N, 5.90; Cl, 7.47. Found: C, 65.68; H, 7.98; N, 5.96; Cl, 7.49.

EXAMPLE 52

(±)-(R*,R*) or (R*,S*)-N,N-Diethyl-4-(3-hydroxy-α-(1,2,5,6-tetrahydro-1,3,6-trimethyl-4-pyridyl)benzyl)benzamide The less mobile isomer from the chromatography in Example 51 was isolated (0.11 g, 4%). NMR (200 MHz, CDCl$_3$): δ1.0 (d, J=6Hz, 3H); 1.1–1.3 (br m, 6H); 1.6(m, 1H); 1.6 (S,3H); 2.1 (br d, J=18 Hz); 2.3 (s, 3H); 275 (br m, 1H); 3.1 (s, 2H); 3.2–3.6 (br m, 4H); 5.2 (s, 1H); 6.55 (d, J=8 Hz, 1H); 6.6 (s, 1H); 6.65 (d, J=8 Hz, 1H); 7.05 (t, J=8 Hz, 1H); 7.1 and 7.25 (ABq, J=8 Hz, 4H).

The amine was converted to the monohydrochloride salt as described in Example 51. Calc. for $C_{26}H_{34}N_2O_2$ HCl 1.75 $H_2O$: C, 65.81; H, 8.18; N, 5.90; Cl, 7.47. Found: C, 65.71; H, 7.99; N, 5.98; Cl, 7.53.

EXAMPLE 53

(±)-3-((αR*)-α-((2R*,5S*)-2,5-Dimethyl-4-propyl-1-piperazinyl)benzyl)phenol (±)-3-((αR*)-α-((2R*,5S*)-2,5-Dimethyl-4-piperazinyl)benzyl)phenol (2.00 g, 6.7 mmol, Example 38) was treated with tert-butylchloridimethylsilane (1.52 g, 10.1 mmol) and imidazole (1.14 g, 16.8 mmol) in dimethylformamide as in Example 6, Method B. The product was purified by chromatography on silica gel with dichloromethane:ethanol (1–7%) to give 1.62 g (3.9 mmol, 59%) of the tert-butyldimethylsilyl ether as a yellow oil which was alkylated with 1-iodopropane (0.39 mL, 4.1 mmol) and anhydrous sodium carbonate (2.1 g, 19.5 mmol) in tetrahydrofuran by a method similar to that in Example 1. The crude product (1.60 g) was deprotected with tetraethylammonium fluoride hydrate (0.90 g, approximately 5 mmol) in acetonitrile. Chromatography on silica gel with dichloromethane:ethanol (1–3%) gave 0.63 g (28% overall) of (±)-3-((αR*)-α-((2R*, 5S*)-2,5-dimethyl-4-propyl-1-piperazinyl)benzyl)phenol as a white solid. NMR (200 MHz, DMSO-d$_6$): δ0.8 (t, J=7Hz, 3H); 0.95 (d, J=6 Hz, 3H); 1.1 (d, J=6 Hz, 3H); 1.4 (m, 2H); 1.9 (m, 1H); 2.1 (m, 2H); 2.3–2.7 (m, 4H); 2.8 (br d, J=10 Hz, 1H); 4.9 (s, 1H); 6.6 (d, J=8 Hz, 1H); 6.8 (d, J=8 Hz, 1H); 6.85 (s, 1H); 7.1 (t, J=8 Hz, 1H); 7.2–7.4 (m, 5H); 9.25 (s, 1H). The product was converted to the monohydrochloride salt as in Example 40 to give 0.55 g (79%) of a white solid. Calc. for $C_{22}H_{30}N_2O$ HCl 0.25 $H_2O$: C, 69.64; H, 8.37; N, 7.38; Cl, 9.34. Found: C, 69.28; H, 8.37; N, 7.35; Cl, 9.33. Mass spectrum (Cl—CH$_4$): m/z 339 (M+1, 100%), 338 (M+, 33%), 183 (46%), 155 (12%).

EXAMPLE 54

(±)-3-((αR*)-α-((2S*,5R*)-4-Allyl-2,5-dimethyl-1-piperazinyl)-4-(methyl-sulfonyl)benzyl)phenol A solution of 3-hydroxybenzaldehyde (183.6 g, 1.50 mol), tert-butylchlorodimethylsilane (227.6 g, 1.50 mol), and imidazole (255.4 g, 3.75 mol) in 700 mL of dimethylformamide was stirred overnight at room temperature. The reaction solution was poured into 1700 mL of water and extracted with three 350 mL portions of diethyl ether. The combined ether extracts were washed with two 350 mL portions of 1.0M sodium hydroxide, 350 mL of water, and 350 mL of saturated aqueous sodium chloride. The ether solution was dried over sodium sulfate and the solvent removed to give 268 g (76%) of 3-(tert-butyldimethylsilyloxy)benzaldehyde as a yellow oil.

A solution of 4-bromothioanisole (10.0 g, 49.0 mmol) in 60 mL of anhydrous tetrahydrofuran was cooled to −78° C. under nitrogen and 32 mL (49 mmol) of 1.55M n-butyllithium in hexane was was added dropwise at a rate to maintain temperature below −60° C. The reaction was stirred an additional 15 minutes after addition was complete, and a solution of crude 3-(tert-butyldimethylsilyloxy) benzaldehyde (11.6 g, 49 mmol) in 50 mL of dry tetrahydrofuran was added dropwise over 20 minutes. The reaction was stirred another 30 minutes and quenched at −78° C. with saturated aqueous ammonium chloride. After warming to room temperature, the reaction was diluted with 200 mL of diethyl ether and washed with 50 mL of water and 50 mL of saturated aqueous sodium chloride. After drying over sodium sulfate, the solvent was removed to give 17.5 g (99%) of crude (4-methylthio-phenyl)(3-tert-butyldimethylsilyloxyphenyl)methanol as an orange oil.

A solution of the alcohol (16.97 g) in 100 mL of dichloromethane was stirred at room temperature during dropwise additon of a solution of m-chloroperbenzoic acid (28.74 g, 141 mmol) in 400 mL of dichloromethane. After stirring for 1 hour, the reaction mixture was filtered. The filtrate was washed with 200 mL of 1.0M sodium bisulfite and three 200 mL portions of 1.0M sodium hydroxide and dried over sodium sulfate. Evaporation of the solvent gave 8.76 g of crude (4-methylsulfonylphenyl)(3-tert-butyldimethylsilyloxyphenyl)methanol as a yellow oil.

The alcohol was subsequently treated with thionyl chloride, trans-2,5-dimethylpiperazine, and allyl bromide by the procedures described in Example 1 to give 1.68 g of crude (±)-trans-4-allyl-1-(α-(3-tert-butyldimethylsilyloxyphenyl)-4-methylsulfonylbenzyl)-2,5-dimethylpiperazine as a mixture of diastereomers. The isomers were separated by chromatography on silica gel (Waters Prep 500A) with 0–0.75% ethanol in dichloromethane containing 0.1% triethylamine. The first isomer to elute (0.68 g) was deprotected by dissolving in 10 mL of tetrahydrofuran with 2.0 mL of 1.0M tetrabutylammonium fluoride in tetrahydrofuran. The solvent was removed and the residue was purified by chromatography on silica gel with 2.5% methanol in dichloromethane to give (±)-3-((αR*)-α-((2S*,5R*)-4-allyl-2,5-dimethyl-1-piperazinyl)-4-(methylsulfonyl)benzyl)phenol. $^1$H-NMR (300 MHz, DMSO-d$_6$): δ0.95 (d, J=6 Hz, 3H); 1.05 (d, J=6 Hz, 3H); 1.8 (dd, J$_1$=5 Hz, J$_2$=9 Hz, 1H); 2.1 (dd, J$_1$=5 Hz, J$_2$=9 Hz, 1H); 2.2–2.4(m, 3H); 2.7 (dd, J$_1$=3 Hz, J$_2$=11 Hz, 1H); 2.85 (dd, J$_1$=6 Hz, J$_2$=11 Hz, 1H); 3.1 (m, 1H); 3.1 (s, 3H); 5.0–5.2 (m, 3H); 5.8 (m, 1H); 6.7 (m, 3H); 7.1 (t, J=8 Hz, 1H); 7.6 and 7.85 (ABq, J=8 Hz, 4H). The product was dissolved in ethanol and converted to its dihydrochloride salt with excess ethanolic hydrogen chloride. The salt was precipitated with diethyl ether followed by hexane to give the salt as a hygroscopic white powder. Calc. for C$_{23}$H$_{30}$N$_2$O$_3$S 2 HCl 0.5 H$_2$O: C, 55.64; H, 6.70; N, 5.64. Found: C, 55.70; H, 6.97; N, 5.50. Mass spectrum (EI): (m/e) 414 (M$^+$, 1.0%); 261 (18%); 153 (100%).

EXAMPLE 55

(±)-3-((2R*,5S*)-4-Allyl-2,5-dimethyl-1-piperazinyl)-4-(methylsulfonyl)benzyl)phenol The second isomer to elute from the chromatography of Example 54 (0.34 g, 20%) was treated with tetrabutylammonium fluoride and purified in similar fashion to give the product as a beige glass. $^1$H-NMR (300 MHz, DMSO-d$_6$): δ0.95 (d, J=6 Hz, 3H); 1.05 (d, J=6 Hz, 3H); 1.88 (dd, J$_1$=6 Hz, J$_2$=10.5 Hz, 1H); 2.11 (dd, J$_1$=6.5 Hz, J$_2$=11 Hz, 1H); 2.4–2.8 (m, 4H); 2.88 (dd, J$_1$=7 Hz, J$_2$=14 Hz, 1H); 3.14 (dd, J$_1$=6 Hz, J$_2$=14 Hz, 1H); 3.23 (s,3H); 5.0–5.2 (m, 3H); 5.8 (m, 1H); 6.6 (d, J=8 Hz, 3H); 6.8 (m, 2H); 7.1 (t, J=8 Hz, 1H);7.6 and 7.9 (AB q, J=8 Hz, 4H); 9.34 (s, 1H). The dihydrochloride salt was prepared as in Example 54 to give a hygroscopic white solid. Calc for C$_{23}$H$_{30}$N$_2$O$_3$ 2 HCl 1.25 H$_2$O: C, 54.17; H, 6.82; N, 5.49. Found: C, 54.16; H, 6.85; N, 5.49. Mass spectrum (EI): (m/e) 414 (M$^+$, 0.68%); 261 (9.3%); 153 (100%).

EXAMPLE 56

(±)-4-((αR*)-α-((2R*,5S*)-4-Allyl-2,5-dimethyl-1-piperazinyl)-3-hydroxy-benzyl)-N,N-dimethylbenzenesulfonamide A 25% aqueous solution of dimethylamine (420 mL, 2.3 mol) was diluted with 1000 mL of tetrahydrofuran and added dropwise to a solution of p-bromobenzenesulfonyl chloride (200 g, 0.78 mol) in 700 mL of tetrahydrofuran. The mixture was diluted with diethyl ether and the organic layer was washed with water and saturated aqueous sodium chloride and dried over sodium sulfate. Evaporation of the solvent gave 195.4 g (95%) of 4-bromo-N,N-dimethylbenzenesulfonamide as white crystals, mp 90°–92° C. (lit. 94° C., J. Am. Chem. Soc. 45, 2696 (1923)).

The sulfonamide (97.45 g, 0.37 mol) was subsequently treated with n-butyllithium and 3-(tert-butyldimethylsilyloxy)benzaldehyde as described in Example 54, and the product was purified by chromatography on silica gel with hexane:ethyl acetate to give 89.5 g (57%) of 4-(3-(tert-butyldimethyl-silyloxy)-α-hydroxybenzyl)-N,N-dimethylbenzenesulfonamide as a yellow oil which crystallized on standing. A portion was recrystallized from ethanol:water to give white crystals, mp 100°–103° C. NMR (CDCl$_3$, 60 MHz): δ0.1 (s, 6H); 0.9 (s, 9H); 2.6 (s, 6H); 3.5 (br s, 1H); 5.7 (s, 1H); 6.5–7.7 (m, 8H).

The alcohol (88.8 g, 0.21 mol) was treated with thionyl chloride in dichloromethane as described in Example 1 to give 93.7 g of 4-(3-(tert-butyldimethylsilyloxy)-α-chlorobenzyl)-N,N-dimethylbenzenesulfonamide as a brown oil. The crude benzhydryl chloride (93.7 g, 0.21 mol) was combined with trans-2,5-dimethylpiperazine (71.8 g, 0.63 mol) in 400 mL of dimethylformamide and heated to 140° C. for 1 hour. The mixture was cooled to room temperature, poured into ice water and extracted with diethyl ether. The ether extracts were washed with 1M sodium hydroxide, water, and saturated aqueous sodium chloride, and dried over sodium sulfate. The solvent was removed and the residue was purified by chromatography on silica gel with dichloromethane:methanol to give 28.9 g (27%) of trans-4-(α-(2,5-dimethyl-1-piperazinyl)-3-(tert-butyldimethylsilyloxy)benzyl)-N,N-dimethylbenzenesulfonamide as a brown oil.

The benzhydrylpiperazine was treated with allyl bromide as in Example 1 and purified by chromatography on silica gel (Waters Prep 500) with 0.3–0.5% ethanol in dichloromethane containing 0.1% triethylamine to give 17.34 g of a light brown glass. The product was treated with tetrabutylammonium fluoride in tetrahydrofuran as in Example 54. The two diasteromers of the product were separated by chromatography on silica gel (Waters Prep 500) with 0.3–3.0% ethanol in dichloromethane containing 0.1% triethylamine. Elution of the more mobile isomer provided 4.94 g (36%) of (±)-4-((αR*)-α-((2R*,5S*)-4-allyl-2,5-dimethyl-1-piperazinyl)-3-hydroxybenzyl)-N,N-dimethylbenzenesulfonamide as a white solid, mp 205°–207° C. $^1$H-NMR (300 MHz, CDCl$_3$): δ1.05 (d, J=6 Hz, 3H); 1.2 (d, J=6 Hz, 3H); 1.9 (br m, 1H); 2.2 (br m, 1H); 2.5–2.75 (m, 3H); 2.7 (s, 6H); 2.85 (dd, J$_1$=9 Hz, J$_2$=10 Hz, 1H); 2.95 (br m, 1H); 3.35 (br m, 1H); 5.15–5.3 (m, 3H); 5.9 (m, 1H); 6.7 (dd, J$_1$=8 Hz, J$_2$=2 Hz, 1H); 6.85 (d, J=8 Hz, 1H); 6.9 (s, 1H); 7.15 (t, J=8 Hz, 1H); 7.4 and 7.75 (AB q, J=9 Hz, 4H). Mass spectrum (Cl—CH$_4$) m/e 444 (M+1, 100%); 292 (15%); 153 (52%). The product was treated with excess ethanolic hydrogen chloride and the dihydrochloride salt was precipitated with diethyl ether and hexane to give 3.19 g (66%) of a hygroscopic white powder. Calc. for C$_{24}$H$_{33}$N$_3$O$_3$S 2 HCl 1.5 H$_2$O: C, 53.03; H, 7.05; N, 7.73; S, 5.90; Cl, 13.04. Found: C, 53.09; H, 7.07; N, 7.73; S, 5.94; Cl, 13.11.

EXAMPLE 57

(±)-4-((αR*)-α-((2S*,5R*)-4-Allyl-2,5-dimethyl-1-piperazinyl)-3-hydroxy-benzyl)-N,N-dimethylbenzenesulfonamide The less mobile isomer from the chromatography of Example 56 was obtained as a pale beige glass. $^1$H-NMR (300 MHz, CDCl$_3$): δ1.0 (d, J=6 Hz, 3H); 1.2 (d, J=6 Hz, 3H); 1.9 (dd, J$_1$=10 Hz, J$_2$=12 Hz, 1H); 2.15 (dd, J$_1$=9.5 Hz, J$_2$=11 Hz, 1H); 2.5 (m, 2H); 2.6–2.9 (m, 3H); 2.7 (s, 6H); 3.45 (dd, J$_1$=5 Hz, J$_2$=13 Hz, 1H); 5.1–5.3 (m, 3H); 5.9 (m, 1H); 6.55 (s, 1H); 6.55 (d, J=8 Hz, 1H); 6.65 (d, J=8 Hz, 1H); 7.15 (t, J=8 Hz, 1H); 7.6 and 7.65 (AB q, J=8 Hz, 4H). The dihydrochloride salt was obtained as hygroscopic white solid. Calc. for C$_{24}$H$_{33}$N$_3$O$_3$S 2 HCl H$_2$O: C, 53.93; H, 6.93; N, 7.86; S, 6.00; Cl, 13.26. Found: C, 53.68; H, 7.36; N, 7.34; S, 5.93; Cl, 13.15.

EXAMPLE 58

(±)-4-((αR*)-α-((2R*,5S*)-4-Allyl-2,5-dimethyl-1-piperazinyl)-3-hydroxy-benzyl)-N,N-diethylbenzenesulfonamide The procedure of Example 56 was followed starting with 4-bromobenzenesulfonyl chloride and diethylamine. The final diastereomeric mixture was separated by chromatography in similar fashion. Elution of the more mobile isomer gave a pale brown glass. $^1$H-NMR (300 MHz, DMSO-d$_6$): δ0.95 (d, J=6 Hz, 3H); 1.05 (d, J=6 Hz, 3H); 1.05 (t, J=7 Hz, 3H); 1.8 (m, 1H); 2.1 (m, 1H); 2.4–2.6 (m, 6H); 2.7 (m, 1H); 2.9 (m, 1H); 3.1 (q, J=7 Hz, 4H); 3.1 (m, 1H); 5.0–5.2 (m, 3H); 5.8 (m, 1H); 6.6 (d, J=8 Hz, 1H); 6.75 (d, J=8 Hz, 1H); 6.8 (s, 1H); 7.05 (t, J=8 Hz, 1H); 7.5 and 7.75 (ABq, J=8 Hz, 4H). The dihydrochloride salt was obtained as a hygroscopic beige solid. Calc. for C$_{26}$H$_{37}$N$_3$O$_3$S 2 HCl H20: C, 55.51; H, 7.35; N, 7.47; S, 5.70; Cl, 12.60. Found: C, 55.42; H, 7.41; N, 7.39; S, 5.73; Cl, 12.73. Mass spectrum (El) m/e: 471 (M$^+$, 1.03%); 318 (9.2%); 153 (100%).

EXAMPLE 59

(±)-4-(αR*)-α-((2S*,5R*)-4-Allyl-2,5-dimethyl-1-piperazinyl)-3-hydroxy-benzyl)-N,N-diethylbenzenesulfonamide Elution of the less mobile isomer from the chromatography of Example 58 gave a pale brown glass. $^1$H-NMR (300 MHz, CDCl$_3$): δ1.05 (d, J=6 Hz, 3H); 1.15 (t, J=7 Hz, 6H); 1.2 (d, J=6 Hz, 3H); 1.9 (dd, J$_1$=10 Hz, J$_2$=12 Hz, 1H); 2.35 (dd, J$_1$=10 Hz, J$_2$=12 Hz, 1H); 2.5 (m, 2H); 2.65 (m, 1H); 2.9 (dd, J$_1$=9 Hz, J$_2$=12 Hz, 2H); 3.25 (q, J=7 Hz, 4H); 3.45 (m, 1H); 5.15–5.3 (m, 3H); 5.9 (m, 1H); 6.55 (d, J=8 Hz, 1H); 6.55 (s, 1H); 6.6 (d, J=8 Hz, 1H); 7.15 (t, J=8 Hz, 1H); 7.55 and 7.7 (AB q, J=8 Hz, 4H). The dihydrochloride salt was obtained as a hygroscopic white solid. Calc. for C$_{26}$H$_{37}$N$_3$O$_3$S 2 HCl H$_2$O: C, 55.51; H, 7.35; N, 7.47; S, 5.70; Cl, 12.60. Found: C, 55.48; H, 7.45; N, 7.39; S, 5.77; Cl, 12.56. Mass spectrum (El) m/e: 471 (M$^+$, 0.2%); 318 (5%); 153 (100%).

EXAMPLE 60

(±)-4-((αR*))-α-((2S*,5R*)-4-Allyl-2,5-dimethyl-1-piperazinyl)-3-hydroxy-benzyl)-N-ethyl-N-(2-hydroxyethyl)benzamide The compound was synthesized by the method of Example 6, Method A, using N-(2-hydroxyethyl)ethylamine to prepare the amide. $^1$H-NMR (200 MHz, DMSO-d$_6$) δ0.96 (d, J=6 Hz, 3H); 1.0–1.2 (br m, 3H); 1.09 (d, J=6 Hz, 3H); 1.85 (dd, J$_1$=7.6 Hz, J$_2$=11.4 Hz, 1H); 2.10(dd, J$_1$=7.4 Hz, J$_2$=10.4 Hz, 1H); 2.52–2.6 (br m, 3H); 2.74 (d, J=11 Hz, 1H); 2.86 ((dd, J$_1$=7 Hz, J$_2$=14 Hz, 1H); 3.18 (dd, J$_1$=5 Hz, J$_2$=15 Hz, 1H); 3.1–3.7 (br m, 6H); 4.78 (t, J=5 Hz, 1H); 5.00 (s, 1H); 5.11 (d, J=10 Hz, 1H); 5.18 (d, J=17 Hz, 1H); 5.8 (m, 1H); 6.68 (d, J=8 Hz, 1H); 6.70 (s, 1H); 6.72 (d, J=8 Hz, 1H); 7.16 (t, J=8 Hz, 1H); 7.31 and 7.43 (AB q, J=8 Hz, 4H). The product was dissolved in ethanol and titrated to pH 3.8 with ethanolic hydrogen chloride to give the monohydrochloride salt. Calc for C$_{27}$H$_{37}$N$_3$O$_3$ HCl 1.25 H$_2$O: C, 63.51; H, 7.99; N, 8.23; Cl, 6.94. Found: C, 63.62; H, 8.02; N, 8.09; Cl, 7.01.

EXAMPLE 61

(±)-3-((R* or S*)-((2S*,SR*)-4-allyl-2,5-dimethyl-1-piperazinyl)(2-thiazolyl)-methyl)phenol A solution of 1.6M n-butyllithium in hexane (206 mL, 0.33 mol) was cooled to −45° C. under nitrogen. A slurry of 2-bromothiazole (50 g, 0.30 mol) in 75 mL of diethyl ether was added in portions, maintaining a temp between −35° C. and −45° C. The resulting dark brown solution was stirred an additional 15 minutes at −40° C. before adding 3-(tert-butyldimethylsilyloxy)benzaldehyde (70.9 g, 0.30 mol, Example 54, infra) dropwise via syringe at a rate to maintain temperature between −25° C. and −35° C. The resulting mixture was stirred an additional 30 minutes at −15° C., then poured into a mixture of 1 L ice/600 mL 1M HCl. The organic phase was dried over sodium sulfate, and evaporated to give a brown oil. Chromatography on silica gel with hexane:ethyl acetate (gradient from 90:10 to 80:20) gave 25.5 g (26.4%) of a-(2-thiazolyl)-3-((tert-butyldimethylsilyl)oxy)benzyl alcohol as a viscous yellow oil.

Thionyl chloride (0.33 mL, 4.58 mmol) was added to a solution of the alcohol (1.0 g, 3.27 mmol) in 50 mL of dichloromethane. After stirring for 16 hours the solvent was evaporated, the residue was redissolved in toluene and evaporated again to drive off excess thionyl chloride.

A mixture of the crude diarylchloromethane (approximately 3.27 mmol), N-allyl-trans-2,5-dimethylpiperazine (1.26 g, 8.2 mmol, Example 42) and 50 mL of acetonitrile was heated to reflux under nitrogen for 16 hours. The solution was evaporated and the residue was partitioned between ethyl acetate and 0.1M aqueous sodium hydroxide. The organic layer was washed twice more with 0.1M aqueous sodium hydroxide and once with water, dried over sodium sulfate, and evaporated to 1.1 g of red-black oil. Chromatography on silica gel with hexane:ethyl acetate (gradient from 80:20 to 50:50) yielded two products in order of elution: 300 mg (20.0%) of (±)-3-((R* or S*)-((2S*,5R*) -4-allyl-2,5-dimethyl-1-piperazinyl)(2-thiazolyl)-methyl) phenol, tert-butyldimethylsilyl ether, and 280 mg (18.7%) of (±)-3-((S* or R*)-((2S*,5R*)-4-allyl-2,5-dimethyt-1-piperazinyl)(2-thiazolyl)methyl)-phenol, tert-butyldimethylsilyl ether.

The first material to elute, (±)-3-((R* or S*)-((2S*,5R*)-4-allyl-2,5-dimethyl-1-piperazinyl)(2-thiazolyl)methyl) phenol, tert-butyldimethylsilyl ether (2.65 g, 5.79 mmol), was combined with tetraethylammonium fluoride hydrate (1.86 g, approximately 9.8 mmol) and 200 mL of acetonitrile and stirred at room temperature for 16 hours under nitrogen. The solvent was removed by evaporation and the residue was dissolved in dichloromethane, washed three times with pH 8 buffer solution, dried over sodium sulfate and evaporated to a brown glass. Chromatography on silica gel with dichloromethane:methanol/95:5 yielded 620 mg of (±)-3-((R* or S*)-((2S*,5R*)-4-allyl-2,5-dimethyl-1-piperazinyl) (2-thiazolyl)methyl)phenol as a tan solid. $^1$H-NMR (300 MHz, DMSO-d$_6$) δ0.88 (d, J=5.9 Hz, 3H); 1.17 (d, J=6.0 Hz, 3H); 1.65 (m,1 H); 2.00 (m, 1H); 2.40 (m, 1H); 2.60 (m, 2H); 2.78 (m, 2H); 3.25 (m, 1H); 5.13 (m, 2H); 5.36 (s, 1H); 5.80 (m, 1H); 6.69 (m,3H); 7.15 (t, J=7.8 Hz, 1H); 7.63 (d, J=3.2, 1H); 7.69 (d, J=3.3, 1 H) 9.34 (s, 1H). The amine was dissolved in ethanol and converted to the monohydrochloride salt by titration to pH 3.7 with ethanolic hydrochloric acid. The solvent was removed by evaporation and the salt was dissolved in dichloromethane/ethanol, followed by precipitation with diethyl ether to give 400 mg of a tan solid, mp 127°–130° C. Calc. for C$_{19}$H$_{25}$N$_3$OS HCl 0.25 H$_2$O: C, 59.36; H, 6.95; N, 10.93; Cl, 9.22; S, 8.34. Found: C, 59.23; H, 6.97; N, 10.81; Cl, 9.17; S, 8.28.

EXAMPLE 62

(±-3-((S* or R*)-((2S*,5R*)-4-allyl-2,5-dimethyl-1-piperazinyl)(2-thiazolyl)-methyl)phenol The second material to elute from the column of Example 61, (±)-3-((S* or R*)-((2S*,5R*)-4-allyl-2,5-dimethyl-1-piperazinyl)(2-thiazolyl)-methyl)phenol, tert-butyldimethylsilyl ether (1.23g, 2.70 mmol), was combined with tetraethylammonium fluoride hydrate (860 mg, approximately 4.5 mmol) and 250 mL of acetonitrile and stirred at room temperature for 16 hours under nitrogen. The solvent was removed by evaporation and the residue was dissolved in dichloromethane, washed three times with pH 8 buffer solution, dried over sodium sulfate and evaporated to a brown glass. Chromatography on silica gel with dichloromethane:methanol/94:6 yielded 480 mg of (±)-3-((S* or R*)-((2S*,5R*)-4-allyl-2,5-dimethyl-1-piperazinyl)(2-thiazolyl)methyl)phenol as a tan solid. $^1$H-NMR (300 MHz, DMSO-d$_6$): δ0.90 (d, J=5.8 Hz, 3H); 1.11 (d, J=6.1 Hz, 3H); 2.00 (m, 1H); 2.14 (m, 1H); 2.38 (m, 1H); 2.43 (m, 1H); 2.60 (m, 1H); 2.70 (m, 1H); 2.78 (m, 1H); 3.25 (m, 1H); 5.18 (m, 2H); 5.61 (s, 1H); 5.80 (m, 1H); 6.63 (dd, J=1.1, 7.8); 6.71 (d, J=7.8, 1H); 7.10 (t, J=7.9 Hz, 1H); 7.74 (d, J=3.2, 1H); 7.87 (d, J=3.3, 1H) 9.34 (s, 1H). The amine was dissolved in ethanol and converted to the monohydrochloride salt by titration to pH 3.7 with ethanolic hydrochloric acid. The solvent was removed by evaporation and the salt was dissolved in dichloromethane/ethanol, followed by precipitation with diethyl ether to give 150 mg of a tan solid, mp 124°–128° C. Calc. for C$_{19}$H$_{25}$N$_3$OS HCl 0.25 H$_2$O: C, 59.36; H, 6.95; N, 10.93; Cl, 9.22; S, 8.34. Found: C, 59.21; H, 6.98; N, 10.85; Cl, 9.18; S, 8.28.

EXAMPLE 63

(±)-3-((R*)-((2S*,5R*)-4-Allyl-2,5-dimethyl-1-piperazinyl)(3-thienyl)methyl)-phenol 3-Bromophenoxy-tert-butyldimethylsilane (57.5 g, 0.20 mol, Example 1, infra) was dissolved in 300 mL of dry tetrahydrofuran under nitrogen and cooled to −78° C. A solution of 1.6M n-butyllithium in hexane (125 mL, 0.20 mol) was added dropwise at a rate to maintain a temperature below −70° C. The reaction was stirred for thirty minutes after the addition was complete and the cold solution was transferred to another vessel containing a −40° C. solution of magnesium bromide (37.8 g, 0.205 mol) in 600 mL of dry tetrahydrofuran under nitrogen. The resulting solution was allowed to warm to −15° C. while stirring. After one hour a solution of thiophene-3-carboxaldehyde (22.4 g, 0.20 mol) in 200 mL of dry tetrahydrofuran was added slowly at a rate to maintain a temperature below 25° C. The resulting solution was stirred for 30 minutes at room temperature, then washed twice with aqueous ammonium chloride, dried over sodium sulfate and evaporated to give a brown oil. Chromatography on silica gel with hexane:dichloromethane (gradient from 3:1 to 1:1) gave 44.1 g (69%) of 3-((tert-butyldimethylsilyl)oxy)-α-(3-thienyl)benzyl alcohol as a viscous yellow oil.

Thionyl chloride (7.6 mL, 0.104 mol) was added to a solution of the alcohol (23.8 g, 0.074 mol) in 400 mL of dichloromethane. After stirring for 3 hours the solvent was evaporated, and the residue was redissolved in toluene and evaporated again to drive off excess thionyl chloride.

A mixture of the crude diarylchloromethane (approximately 0.074 mol), N-allyl-trans-2,5-dimethylpiperazine, (Example 42, infra, 28.5 g, 0.185 mol) and 400 mL of acetonitrile was heated at reflux under nitrogen for 24 hours. The solution was cooled to room temperature and evaporated. The residue was redissolved in dichloromethane and washed three times with aqueous pH 8 buffer solution, dried over sodium sulfate, and evaporated to a dark oil. The product was purified by chromatography on silica gel with dichloromethane:ethyl acetate/98:2 to give two isomers.

The first isomer to elute was (±)-3-((R*)-((2S*,5R*)-4-allyl-2,5-dimethyl-1-piperazinyl)(3-thienyl)methyl)phenol, tert-butyldimethylsilyl ether (12.27 g, 36%). A portion (3.1 g, 6.79 mmol) was deprotected with tetraethylammonium fluoride hydrate as in Example 44. Chromatography on silica gel with dichloromethane:ethyl acetate/3:1 gave 1.6 g of (±)-3-((R*)-((2S*,5R*)-4-allyl-2,5-dimethyl-1-piperazinyl)(3-thienyl)methyl)phenol as a yellow foam. $^1$H-NMR (300 MHz, DMSO-d$_6$): δ0.91 (d, J=6.2 Hz, 3H); 1.08 (d, J=6.2 Hz, 3H); 1.79 (m, 1H); 2.00 (m, 1H); 2.45 (m, 1H); 2.62 (m, 2H); 2.80 (m, 1H); 3.21 (m, 1H); 3.32 (d, J=7.0 Hz, 1H); 5.14 (m, 2H); 5.80 (m, 1H); 6.68 (m, 3H); 6.98 (d, J=5.0 Hz, 1H); 7.15 (m, 2H); 7.45 (dd, J$_1$=4.9 Hz, J$_2$=3.0 Hz, 1H); 9.31 (s, 1H). The amine was dissolved in ethanol and converted to the monohydrochloride salt by titration to pH 3.5 with ethanolic hydrochloric acid. The solvent was removed by evaporation and the salt was dissolved in dichloromethane, followed by precipitation with diethyl ether to give 1.3 g (50%) of an off-white solid, mp 140°–142° C. Calculated for C$_{20}$H$_{26}$N$_2$OS HCl 0.25 H$_2$O: C, 62.65; H, 7.23; N, 7.31; Cl, 9.25; S, 8.36. Found: C, 62.49; H, 7.27; N, 7.33; Cl, 9.25; S, 8.32.

EXAMPLE 64

(±)-3-((R*)-((2R*,5S*)-4-Allyl-2,5-dimethyl-1-piperazinyl)(3-thienyl)methyl)-phenol The second isomer to elute from the column of Example 63 was (±)-3-((R*)-((2R*,5S*)-4-allyl-2,5-dimethyl-1-piperazinyl)(3-thienyl)methyl)phenol, tert-butyldimethylsilyl ether (11.15 g, 33%). A portion (3.0 g, 6.57 mmol) was deprotected with tetraethylammonium fluoride hydrate as in Example 44. Chromatography on silica gel with dichloromethane:ethyl acetate/3:1 gave 1.6 g of a white solid. $^1$H-NMR (300 MHz, DMSO-d$_6$): δ0.89 (d, J=6.1 Hz, 3H); 1.09 (d, J=6.1 Hz, 3H); 1.79 (m, 1H); 2.01 (m, 1H); 2.34 (m, 1H); 2.50 (m, 1H); 2.70 (m, 2H); 3.25 (m, 1H); 3.31 (d, J=7.1 Hz, 1H); 5.19 (m, 2H); 5.80 (m, 1H); 6.58 (m, 1H); 6.73 (d, J=7.7 Hz, 1H); 6.80(d, J=1.0 Hz, H); 6.92 (dd, $J_1$=4.8. Hz, $J_2$=0.8 Hz, 1H); 7.07 (t, J=7.8 Hz, 1H); 7.40 (dd, $J_1$=2.8 Hz, $J_2$=1.1 Hz, 1H); 7.51 (dd, $J_1$=4.5 Hz, $J_2$=2.9 Hz, 1H); 9.22 (s, 1H). The amine was dissolved in ethanol and converted to the monohydrochloride salt by titration to pH 3.6 with ethanolic hydrogen chloride. The solvent was removed by evaporation and the salt was dissolved in dichloromethane, followed by precipitation with diethyl ether to give 1.25 g (49%) of an off-white solid, mp 138°–140° C. Calc. for $C_{20}H_{26}N_2OS$ HCl 0.40 $H_2O$: C, 62.21; H, 7.26; N, 7.25; Cl, 9.18; S, 8.30. Found: C, 62.19; H, 7.25; N, 7.15; Cl, 9.24; S, 8.29.

EXAMPLE 65

(−)-3-((S)-((2R,5S)-4-Allyl-2,5-dimethyl-1-piperazinyl)(3-thienyl)methyl)-phenol (±)-3-((R*)-((2S*,5R*)-4-Allyl-2,5-dimethyl-1-piperazinyl)(3-thienyl)methyl)phenol (2.74 g, 8.0 mmol, Example 63) was added to a solution of 6.18 g (16 mmol) of (−)-di-p-toluoyl-L-tartaric acid in 20 mL of absolute ethanol. The mixture was warmed to complete solution, cooled and allowed to crystallize at room temperature. After four recrystallizations, the salt was dissolved in 20 mL of 1N aqueous sodium hydroxide, and the solution was titrated to pH 8 with 6N hydrochloric acid. The precipitated amine was collected by filtration and recrystallized from absolute ethanol to give 0.21 g of (−)-3-((S)-((2R,5S)-4-allyl-2,5-dimethyl-1-piperazinyl)(3-thienyl)methyl)phenol as white crystals, mp 193°–194° C. $[\alpha]_D^{20}$=−3.2° (ethyl acetate, c=1.4). HPLC on β-cyclodextrin with methanoh0.1M ammonium acetate/1:1 gave one peak at $t_R$=7.8 min. Calc. for $C_{20}H_{26}N_2OS$: C, 70.14; H, 7.65: N, 8.18: S, 9.36. Found: C, 70.24; H, 7.69; N, 8.23; S, 9.42.

EXAMPLE 66

(−)-3-((R)-((2S,5R)-4-Allyl-2,5-dimethyl-1-piperazinyl)(4-bromo-2-thienyl)-methyl)phenol A solution of 6.33 g (16.4 mmol) of (+)-p-ditoluoyl-D-tartaric acid in 15 mL of absolute ethanol was added to a suspension of 3.46 g of (±)-3-((R*)-((2S*,5R*)-4-allyl-2,5-dimethyl-1-piperazinyl)(4-bromo-2-thienyl)methyl)-phenol (Example 42) in 10 mL of absolute ethanol. The mixture was heated to boiling and the resulting clear solution was allowed to crystallize at room temperature. After five recrystallizations, the salt was converted to the free amine as in Example 65 and recrystallized from absolute ethanol to give 0.50 g (15% of theoretical for one enantiomer) of (−)-3-((R)-((2S, 5R)-4-allyl-2,5-dimethyl-1-piperazinyl)(4-bromo-2-thienyl)methyl)phenol as white crystals, mp 183°–185° C. $[\alpha]_D^{20}$=−14.0° (tetrahydrofuran, c=2.1). HPLC on β-cyclodextrin with methanol:0.1M ammonium acetate/1:1 gave one peak at $t_R$=8.1 min. Calc. for $C_{20}H_{25}BrN_2OS$: C, 57.00; H, 5.98; N, 6.65; Br, 18.96; S, 17.61. Found: C, 56.90; H, 6.03; N, 6.57; Br, 18.92; S, 7.52.

EXAMPLE 67

(−)-3-((R)-((2S,5R)-4-Allyl-2,5-dimethyl-1-piperazinyl)(2-thienyl)methyl)-phenol (−)-3-((R)-((2S,5R)-4-Allyl-2,5-dimethyl-1-piperazinyl) (4-bromo-2-thienyl)methyl)phenol (0.53 g, 1.3 mmol, Example 66) was debrominated with n-butyllithium as in Example 9. The crude product was recrystallized from acetonitrile to give 0.33 g (77%) of (−)-3-((R)-((2S,5R)-4-allyl-2,5-dimethyl-1-piperazinyl)(2-thienyl)methyl)phenol as beige crystals, mp 176°–178° C., $[\alpha]_D^{20}$=−23.30° (ethyl acetate, c=1.5). HPLC on β-cyclodextrin with methanol:0.1M aqueous ammonium acetate/1:1 gave one peak at $t_R$=8.5 min. Calc. for $C_{20}H_{26}BrN_2OS$ 0.25 $H_2O$: C, 69.23; H, 7.70; N, 8.07; S, 9.24. Found: C, 68.86; H, 7.47; N, 8.27; S, 9.06. The product (0.30 g, 0.87 mmol) was treated with ethanolic hydrogen chloride as in Example 42 to give 0.201 g (61%) of the monohydrochloride salt. Calc. for $C_{20}H_{26}BrN_2OS$ HCl 0.75 $H_2O$: C, 61.21; H, 7.32: N, 7.12; S, 8.17; Cl, 9.03. Found: C, 61.35; H, 7.01; N,7.30; S, 8.16; Cl, 9.11. $[\alpha]_D^{20}$=−11.9° (ethanol, c=1.05).

EXAMPLE 68

(+)-3-((S)-((2R,5)-4-Allyl-2,5-dimethyl-1-piperazinyl)(4-bromo-2-thienyl)-methyl)phenol A solution of 4.22 g (11 mmol) of (−)-p-ditoluoyl-L-tartaric acid in 15 mL of absolute ethanol was added to a suspension of 2.3 g (5.5 mmol) of (±)-3-((R*)-((2S*,5R*)-4-allyl-2,5-dimethyl-1-piperazinyl)(4-bromo-2-thienyl)-methyl)phenol (Example 42) in 5 mL of absolute ethanol. The mixture was heated to boiling and the resulting clear solution was allowed to crystallize at room temperature. After three crystallizations, the salt was converted to the free amine as in Example 65 and recrystallized from absolute ethanol to give 0.490 g (43% of theoretical for one enantiomer) of (+)-3-((S)-((2R,5S)-4-allyl-2,5-dimethyl-1-piperazinyl)(4-bromo-2-thienyl)methyl)phenol as white crystals, mp 183°–185° C. Absolute configuration was determined by x-ray crystallography. $[\alpha]_D^{20}$=+14.5° (tetrahydrofuran, c=3.3). HPLC on β-cyclodextrin with methanol: 0.1M ammonium acetate/1:1 gave one peak at $t_R$=11 min. Calc. for $C_{20}H_{25}BrN_2OS$: C, 57.00; H, 5.98; N, 6.65; Br, 18.96; S, 7.61. Found: C, 56.93; H, 5.99; N, 6.67; Br, 19.04; S, 7.67.

EXAMPLE 69

(+)-3-((S)-((2R,5S)-4-Allyl-2,5-dimethyl-1-piperazinyl)(2-thienyl)methyl-phenol

This compound was prepared as in Example 67 starting with (+)-3-((S)-((2R,5S)-4-allyl-2,5-dimethyl-1-piperazinyl)(2-thienyl)methyl)phenol (Example 68). The product was obtained as light beige crystals, mp 179°–181° C. HPLC on β-cyclodextrin with methanol:0.1M ammonium acetate/1:1 gave one peak at $t_R$=8.9 min. $[\alpha]_D^{20}$=+21.8° (ethyl acetate, c=1.2). Calc. for $C_{20}H_{26}BrN_2OS$: C, 70.14; H, 7.65; N, 8.18; S, 9.36. Found: C, 69.89; H, 7.65; N, 8.14; S, 9.42.

EXAMPLE 70

(−)-3-((αR)-α-((2R,5S)-4-Allyl-2,5-dimethyl-1-piperazinyl)-4-bromobenzyl)-phenol The mother liquors from the di-p-toluoyl-D-tartrate crystallizations in Example 72 were combined and evaporated to dryness. The residue was dissolved in 1N aqueous sodium hydroxide and titrated to pH 8 with 6N hydrochloric acid. The resulting slurry was extracted with dichloromethane, and the extracts were dried over sodium sulfate and evaporated to give 5.1 g of a white solid. A solution of (−)-di-p-toluoyl-L-tartaric acid (10.0 g, 24.7 mmol) in 150 mL of absolute ethanol was added. The solution was evaporated to dryness and the residue was recrystallized three times from 90% aqueous ethanol. The crystalline ditoluoyl-L-tartrate salt was converted to the free amine as in Example 72. Recrystallization from absolute ethanol gave 0.100 g of (−)-3-((αR)-α-((2R,5S)-4-allyl-2,5-dimethyl-1-piperazinyl)-4-bromobenzyl)phenol as white crystals, mp 211°–213° C., $[\alpha]_D^{20}$=−7.8° (tetrahydrofuran, c=2.4). HPLC on β-cyclodextrin with methanol:0.1M ammonium acetate/1:1 gave one peak at $t_R$=9.1 min. Calc. for $C_{22}H_{27}BrN_2O$: C, 63.61; H, 6.55; N, 6.74; Br, 19.24. Found: C, 63.54; H, 6.54; N, 6.69; Br, 19.29.

EXAMPLE 71

(−)-3-((αR)-α-((2R,5S)-4-Allyl-2,5-dimethyl-1-piperazinyl)benzyl)phenol

A solution of (−)-3-((αR)-α-((2R,5S)-4-allyl-2,5-dimethyl-1-piperazinyl)-4-bromobenzyl)phenol (3.00 g, 7.2 mmol), from Example 70, in 80 mL of dry tetrahydrofuran was cooled to −78° C. n-Butyllithium (9.9 mL of a 1.6M solution in hexanes) was added at a rate to keep the temperature below −70° C. After stirring at −78° C. for 30 minutes, the reaction was quenched with 15 mL of saturated aqueous ammonium chloride, warmed to room temperature, diluted with water and extracted with ethyl acetate. The ethyl acetate extracts were combined, dried over sodium sulfate, and the solvent removed under vacuum to give a white solid which was recrystallized from acetonitrile to give 2.11 g (88%) of (−)-3-((αR)-α-((2R,5S)-4-allyl-2,5-dimethyl-1-piperazinyl)benzyl)phenol as white crystals, mp 195°–197° C., $[\alpha]_D^{20}$=−2.8° (tetrahydrofuran, c=1.6). HPLC on β-cyclodextrin with methanol:0.1M ammonium acetate/1:1 gave one peak at $t_R$=8.4 min. NMR (DMSO-$d_6$, 200 MHz): δ0.95 (d, J=6 Hz, 3H); 1.1 (d, J=6 Hz, 3H); 1.8 (dd, $J_1$=7 Hz, $J_2$=11 Hz, 1H); 2.1 (dd, $J_1$=7 Hz, $J_2$=9 Hz, 1H); 2.4–2.8 (m, 4H); 2.9 (dd, $J_1$7 Hz, $J_2$=14 Hz, 1H); 3.15 (dd, $J_1$=5 Hz, $J_2$=14 Hz, 1H); 4.95 (s, 1H); 5.1 (d, J=10 Hz, 1H); 5.2 (d, J=18 Hz, 1H); 5.8 (m, 1H); 6.6 (d, J=8 Hz, 1H); 6.8 (d, J=8 Hz, 1H); 6.95 (s, 1H); 7.1 (t, J=8 Hz, 1H); 7.3 (m, 5H); 9.3 (s, 1H). Mass spectrum (Cl—$CH_4$) m/z: 337 (M+1, 69%); 336 ($M^+$, 15%); 183 (100%); 153 (92%). Calc. for $C_{22}H_{28}N_2O$: C, 78.53; H, 8.39; N, 8.33. Found: C, 78.37; H, 8.47; N, 8.38.

The product was suspended in absolute ethanol, titrated to pH 4 with ethanolic hydrogen chloride, and the resulting solution concentrated and treated with diethyl ether to precipitate the monohydrochloride salt as a white solid (0.172 g, 78%). Calc. for $C_{22}H_{28}N_2O$ HCl 0.5 $H_2O$: C, 69.18; H, 7.92; N, 7.33; Cl, 9.28. Found: C, 69.10; H, 7.92; N, 7.33; Cl, 9.33.

EXAMPLE 72

(+)-3-(αS)-α-((2S,5R)-4-Allyl-2,5-dimethyl-1-piperazinyl)-4-bromobenzyl)-phenol

A solution of (+)-di-p-toluoyl-D-tartaric acid (12.72 g, 31.4 mmol) in 100 mL of absolute ethanol was added to a suspension of (±)-3-((αR*)-α-((2R*,5S*)-4-allyl-2,5-dimethyl-1-piperazinyl)-4-bromobenzyl)phenol (6.43 g, 15.5 mmol, Example 2) in 150 mL of absolute ethanol. Water (30 mL) was added to the resulting clear solution and the mixture was concentrated to a total volume of 150 mL. After several days at room temperature, crystals were collected and recrystallized from 90% aqueous ethanol. The crystalline di-p-toluoyl-D-tartrate salt was dissolved in 1N aqueous sodium hydroxide and titrated to pH 8 with 6N hydrochloric acid. The resulting slurry was extracted with dichloromethane, the extracts dried over sodium sulfate and evaporated to give 0.92 g (28% of theoretical for one enatiomer) of the free amine as a white solid, mp 209°–212° C., $[\alpha]_D^{20}$=+7.8° (tetrahydrofuran, c=5). A portion (0.106 g) was recrystallized from absolute ethanol to give 25.8 mg of (+)-3-((αS)-α-((2S,5R)-4-allyl-2,5-dimethyl-1-piperazinyl)-4-bromo-benzyl)phenol, mp 211°–214° C. Calc. for $C_{22}H_{27}BrN_2O$: C, 63.61; H, 6.55; N, 6.74. Found: C, 63.53; H, 6.53; N, 6.70. HPLC on β-cyclodextrin with methanol: 0.1M ammonium acetate/1:1 gave one peak at $t_R$=8.9 min.

EXAMPLE 73

(+)-3-((αS-α-((2S,5R)-4-Allyl-2,5-dimethyl-1-piperazinyl)benzyl)phenol

The compound was prepared following the method in Example 9 starting with (+)-3-((αS)-α-((2S,5R)-4-allyl-2,5-dimethyl-1-piperazinyl)-4-bromobenzyl)phenol (Example 72). The product was recrystallized from acetonitrile to give 0.26 g (48%) of (+)-3-((αS)-α-((2S,5R)-4-allyl-2,5-dimethyl-1-piperazinyl)benzyl)phenol as beige crystals, mp 192°–195° C., $[\alpha]_D^{20}$=+3.7° (tetrahydrofuran, c=3.5). HPLC on β-cyclodextrin with methanol:0.1M ammonium acetate/1:1 gave one peak at $t_R$=7.8 min. Calc. for $C_{22}H_{28}N_2O$ 0.1 $CH_3CN$: C, 78.29; H, 8.37: N, 8.64. Found: C, 77.98: H, 8.31; N, 8.53.

EXAMPLE 74

(±)-Methyl 2-((2R*,5S*)-4-((αR*)-3-hydroxybenzhydryl)-2,5-dimethyl-1-piperazinyl) acetate A mixture of (±)-3-((αR*)-α-((2R*,5S*)-2,5-dimethyl-1-piperazinyl)benzyl)phenol (1.98 g, 6.7 mmol), from Example 38, tert-butylchlorodimethylsilane (1.51 g, 10.1 mmol), and imidazole (1.14 g, 16.8 mmol) in 30 mL of N,N-dimethylformamide was stirred at room temperature under nitrogen overnight. The reaction mixture was poured into cold water and extracted wtih diethyl ether. The ether extracts were dried over sodium sulfate and the solvent removed under vacuum to give a yellow oil. Chromatography on silica gel with dichloromethane:ethanol (1–7%) gave 1.68 g (61%) of (±)-(3-((αR*)-α-((2R*,5S*)-2,5-dimethyl-1-piperazinyl)-benzyl)phenyl) (tert-butyldimethylsilyl) ether as a yellow oil. NMR ($CDCl_3$, 200 MHz): δ0.1 (s, 6H); 0.9 (s, 9H); 1.05 (d, J=6 Hz, 3H); 1.2 (d, J=6 Hz, 3H); 1.7 (t, J=10 Hz, 1H); 2.45 (br m, 1H); 2.7 (m, 2H); 3.0 (m, 2H); 3.4 (br s, 1H); 5.25 (s, 1H); 6.7 (d,J=8 Hz, 1H); 6.9 (d, J=8 Hz, 1 H);7.05 (s, 1H); 7.1 (m, 3H); 7.3 (m, 3H).

Ethyl bromoacetate (0.47 mL, 4.22 mmol) and anhydrous sodium carbonate (2.2 g, 20.5 mmol) were added to a solution of the product from above in 30 mL of dry tetrahydrofuran. The mixture was heated at reflux under nitrogen overnight. After removing the solvent under vacuum, the residue was stirred with dichloromethane, the insoluble salts were filtered off, and the filtrate was evaporated under vacuum to give 2.09 g of crude (±)-ethyl 2-((2R*,5S*)-4-((αR*)-3-(t-butyldimethylsilyloxy)benzhydryl)-2,5-dimethyl-1-piperazin-yl)acetate as a yellow oil. NMR ($CDCl_3$, 200 MHz): δ0.1 (s, 6H); 0.9 (s, 9H); 0.95 (d, J=6 Hz, 3H); 1.2 (d, J=6 Hz, 3H); 1.25 (t, J=7 Hz, 3H); 1.9 (m, 1H); 2.45 (m, 1H); 2.6–2.9 (m, 4H); 3.3 (q, J=17 Hz, 2H); 4.2 (q, J=7 Hz, 2H); 5.2 (s, 1H); 6.7 (d, J=8 Hz, 1H); 6.95 (d, J=8 Hz, 1H); 7.05 (s, 1H); 7.1–7.4 (m, 6H).

The crude product was dissolved in 40 mL of methanol, sodium hydride (0.20 g of 50% oil dispersion, 4.1 mmol) was added in small portions, and the mixture was stirred at room temperature under nitrogen for 1.5 hours. The solvent was removed under vacuum and the residue was extracted between dichloromethane and water adjusted to pH 8. The dichloromethane extract was dried over sodium sulfate, the solvent was evaporated, and the residue was dissolved in acetonitrile and treated with tetraethylammonium fluoride as in Example 1. Chromatography on silica gel with dichloromethane:ethanol (0–1%) gave 0.96 g (63.5%) of (±)-methyl 2-((2R*,5S*)-4-((αR*)-3-hydroxybenzhydryl)-2,5-dimethyl-1-piperazinyl)acetate as a white solid. NMR (DMSO-$d_6$, 200 MHz): δ0.9 (d, J=6 Hz, 3H); 1.1 (d, J=6 Hz, 3H); 1.8 (m, 1H); 2.3–2.8 (m, 5H); 3.3 (m, 2H); 3.6 (s, 3H); 5.1 (s, 1H); 6.6 (d, J=8 Hz, 1H); 6.75 (d, J=8 Hz, 1H); 7.85 (s, 1H); 7.1 (5, J=8 Hz, 1H); 7.3 (m, 5Hi; 9.3 (s, 1 H). The product was converted to the monohydrochloride salt in methanol solution by titration to pH 4.5 with ethanolic hydrogen chloride. The solution was concentrated and treated with diethyl ether to precipitate 0.57 g (54%) of the salt as a white solid. Calc. for $C_{22}H_{28}N_2O_3$ HCl 0.5 $H_2O$: C, 63.84; H, 7.30; N, 6.77; Cl, 8.56. Found: C, 63.98; H, 7.34;

N, 6.74; Cl, 8.47. Mass spectrum (Cl—CH$_4$) m/z: 369 (M+1, 134%), 368 (M$^+$, 5%), 309 (5%), 185 (18%), 183 (100%).

EXAMPLE 75

(±)-5-((αR*)-α-((2R*,5S*)-4-Allyl-2,5-dimethyl-1-piperazinyl)-3-hydroxy-benzyl)-N,N-diethyt-3-pyridinecarboxamide A solution of 50.0 g (0.21 mol) of 3,5-dibromopyridine in 600 mL of anhydrous diethyl ether was cooled to −78° C. n-Butyllithium (131 mL of a 1.6M solution in hexanes) was added at a rate to keep the temperature below −75° C. After stirring for one hour at −78° C., a solution of 3-(tert-butyldimethylsilyioxy)benzaldehyde (49.64 g, 0.21 mol), prepared from 3-bromobenzaidehyde by the procedure in Example 54, in 600 mL of anhydrous diethyl ether was added at a rate to keep the temperature below −75° C. After stirring for one hour at −78° C., the reaction was quenched with 200 mL of saturated aqueous ammonium chloride and allowed to warm to room temperature. The aqueous layer was discarded and the ethereal layer was washed with water and brine, dried over anhydrous sodium sulfate and the solvent evaporated to give 104.3 g of a brown oil. Chromatography on silica gel with hexane:ethyl acetate gave 51.2 g (62%) of α-(5-bromo-3-pyridyl)-3-(tert-butyldimethylsilyioxy)benzyl alcohol as a yellow oil. NMR (CDCl$_3$, 200 MHz): δ0.1 (s, 6H); 0.9 (s, 9H); 2.8 (br s, 1H); 5.8 (s, 1H); 6.8 (m, 2H); 6.9 (d, J=8 Hz, 1H); 7.2 (t, J=8 Hz, 1H); 7.85 (t, J=8 Hz, 1H); 8.5 (dd, J$_1$=2 Hz, J$_2$=8 Hz, 2H).

The pyridylphenylmethanol (10.00 g, 25.4 mmol) was treated with thionyl chloride as in Example 42. The resulting alkyl chloride was heated with trans-N-allyl-2,5-dimethylpiperazine (9.8 g, 63.5 mmol, Example 42, infra) in toluene as in Example 42. The crude mixture of diastereomers was purified by chromatography on silica gel (Waters Prep 500, dichloromethane with 0.1% triethylamine) to give 2.72 g (27%) of the less mobile isomer (R$_F$=0.62 on silica gel with dichloromethane:ethanol:ammonium hydroxide/ 90:10:1, see next Example) and 3.91 g (39%) of the more mobile isomer (R$_F$=0.67) as light brown solids.

The more mobile isomer was treated with tetraethylammonium fluoride in acetonitrile as in Example 1 to give 2.6 g (85%) of 3-((R*)-((2R*,5S*)-4-allyl-2,5-dimethyl-1-piperazinyl)(5-bromo-3-pyridyl)methyl)phenol as a beige solid. NMR (DMSO-d$_6$, 200 MHz): δ0.95 (d, J=6 Hz, 3H); 1.1 (d, J=6 Hz, 3H); 1.8 (m, 1H); 2.1 (m, 1H); 2.4–2.9 (m, 5H); 3.2 (m, 1H); 5.1 (m, 3H); 5.8 (m, 1H); 6.7 (m, 3H); 7.2 (m, 1H); 7.9 (s, 1H); 8.6 (s, 2H); 9.45 (s, 1H).

Starting with the deprotected phenol, following the procedures in Examples 3, 5, and 6 (Method A), 0.18 g (7%) of (±)-5-((αR*)-α-((2R*,5S*)-4-allyl-2,5-dimethyl-1-piperazinyl)-3-hydroxybenzyl)-N,N-diethyl-3-pyridinecarboxamide was obtained as a beige solid. NMR (DMSO-d$_6$, 200 MHz): δ0.95 (d, J=6 Hz, 3H); 1.1 (d, J=6 Hz, 3H); 1.1 (m, 6 H); 1.8 (m, 1H) 2.1 (m, 1H); 2.5–2.9 (m, 6H); 3.1–3.6 (br m, 4H); 5.0–5.2 (m, 2H); 5.1 (s, 1H); 5.8 (m, 1H); 6.7 (m, 3H); 7.1 (m, 1H); 7.65 (s, 1H); 8.4 (s, 1H); 8.6 (s, lH); 9.4 (s, 1H). The product was dissolved in absolute ethanol, titrated to pH 4 with ethanolic hydrogen chloride, and the monohydrochloride salt was precipitated with diethyl ether as a white solid (96 mg). Calc. for C$_{26}$H$_{36}$N$_4$O$_2$ HCl H$_2$O: C, 63.59; H, 8.00; N, 11.41; Cl, 7.22; Found: C, 63.41; H, 7.81; N, 11.43; Cl, 7.31. Mass spectrum (Cl—CH4) m/z 437(M+1, 95%), 436 (M$^+$, 18%), 283 (15%), 153 (100%).

EXAMPLE 76

(±)-5-((αR*)-α-((2S*,5R*)-4-Allyl-2,5-dimethyl-1-piperazinyl)-3-hydroxy-benzyl)-N,N-diethyl-3-pyridinecarboxamide Starting with the less mobile isomer from the chromatography in Example 75, and following the same procedures, (±)-5-((αR*)-α-((2S*,5R*)-4-allyl-2,5-dimethyl-1-piperazinyl)-3-hydroxybenzyl)-N,N-diethyl-3-pyridinecarboxamide was obtained and converted to its monohydrochloride salt. NMR (DMSO-d$_6$, 200 MHz): δ0.95 (d, J=6 Hz, 3H); 1.1 (d, J=6 Hz, 3H); 1.1 (br m, 6H); 1.8 (m, 1H); 2.1(m, 1H); 2.4–3.0 (m, 5H); 3.1–3.5 (m, 5H); 5.1 (m, 3H); 5.8(m, 1H); 6.6 (d, J=8 Hz, 1H); 6.75 (d, J=8 Hz, 1H); 6.85 (s, 1H); 7.1 (t, J=8 Hz, 1H); 7.6 (s, 1H); 8.5 (s, 1H); 8.6 (s, 1H); 9.3 (s, 1H). Mass spectrum (Cl—CH$_4$) m/z: 437 (M+1, 80%), 436 (M$^+$, 18%), 238 (13%), 153 (100%). Calc. for C$_{26}$H$_{36}$N$_4$O$_2$ HCl 1.9 H$_2$O 0.05 C$_6$H$_{18}$N$_3$P: C, 61.19; H, 8.14; N, 11.26; Cl, 6.87. Found: C, 60.84; H, 7.79; N, 11.59; Cl, 7.25.

EXAMPLE 77

(−)-(2R,5S)-1-Allyl-2,5-dimethylpiperazine

Method A—Synthesis

Freshly distilled allyl bromide (7.03 g, 58.1 mmol) was added to a solution of N-BOC-D-alanine (5.00 g, 26.4 mmol) in 100 mL of dry tetrahydrofuran and the mixture was cooled to 0° C. Sodium hydride (2.0 g, 83.3 mmol, obtained after washing a 50% oil dispersion of sodium hydride with hexane to remove the oil) was added in small portions. The mixture was stirred at 0° C. under nitrogen for one hour, allowed to warm to room temperature, and stirring was continued overnight. The reaction was quenched with tetrahydrofuran:water (1:1) and evaporated to dryness. The residue was taken up in water and washed with hexane. The aqueous layer was adjusted to pH 2 with solid citric acid and extracted with ethyl acetate. The combined organic layers were dried over magnesium sulfate and the solvent was removed under vacuum to give 5.70 g of a yellow oil (94%). NMR (200 MHz, DMSO-d$_6$): δ1.3 (d, J=7 Hz, 3H); 1.4 (s, 9H); 3.6–4.1 (m, 2.5 H); 4.4 (br m, 0.5H); 5.1 (d, J=10 Hz, 1H); 5.2(d, J=14 Hz, 1H); 5.8 (m, 1H); 12.5 (br s, 1H).

L-Alanine methyl ester hydrochloride (3.43 g, 24.6 mmol), triethylamine (2.48 g, 24.6 mmol) and 1-(3-dimethylaminopropyl)-3-ethylcarbodiimide hydrochloride (4.71 g, 24.6 mmol) were added to a solution of the product from above (5.63 g, 24.6 mmol) in 80 mL of dichloromethane at 0° C. The mixture was kept in the freezer overnight, then washed with water, 1M aqueous citric acid, 5% aqueous sodium bicarbonate and water. After drying over sodium sulfate, the solvent was removed under vacuum to give 5.85 g (76%) of methyl N-allyl-N-((tert-butoxy) carbonyl)-L-alanyl-D-alaninate as a yellow oil. NMR(200 MHz, DMSO-d$_6$): δ1.25 (m, 6H); 1.4 (s, 9H); 3.6 (s, 3H); 3.7–4.0 (m, 2H); 4.3 (m, 2H); 5.1 (m, 2H); 5.8 (m, 1H); 8.1 (brs, 1H).

The product (5.73 g, 18.2 mmol) was dissolved in 80 mL of formic acid and kept at room temperature for 2 hours. The excess formic acid was removed under vacuum, the residue was dissolved in a mixture of 160 mL of 2-butanol and 40 mL of toluene and the mixture was heated at reflux for 8 hours. The solvents were removed under vacuum to give a yellow oil. Chromatography on silica gel with chloroform-:methanol (99:1) gave 2.49 g (75%) of (2R,5S)-1-allyl-2,5-dimethylpiperazine-3,6-dione as a colorless oil. NMR(200 MHz, DMSO-d$_6$): δ1.3 (d, J=7 Hz, 3H); 1.37 (d, J=7 Hz, 3H); 3.6 (dd, J$_1$=6 Hz, J$_2$=15 Hz, 1H); 3.8 (q, J=7 Hz, 1H); 4.1 (q, J=7 Hz, 1H); 4.3 (dd, J$_1$=5 Hz, J$_2$=15 Hz, 1H); 5.15 (d, J=12 Hz, 1H); 5.2 (d, J=15 Hz, 1H); 5.8 (m, 1H); 8.25 (br s, 1H), [α]$_D^{20}$=−48.5° (ethanol, c=0.9).

The diketopiperazine (2.0 g, 11.0 mmol) was dissolved in 100 mL of dry tetrahydrofuran and cooled to 0° C. under nitrogen. Lithium aluminum hydride (33 mL of a 1M solution in tetrahydrofuran) was added dropwise. The mixture was allowed to warm to room temperature, then heated at reflux overnight. After cooling to room temperature, sodium fluoride (6.0 g, 143 mmol) was added, the mixture was stirred for 30 minutes, cooled to 0° C., and 20 mL of water was added, keeping the temperature below 5° C. Stirring was continued at room temperature for another 30 minutes and the insoluble fluoride was filtered. The filtrate was evaporated under vacuum, the residue was taken up in dichloromethane, dried over magnesium sulfate, and the solvent removed under vacuum to give 1.41 g (83%) of (−)-(2R,5S)-1-allyl-2,5-dimethylpiperazine as a yellow oil, $[\alpha]_D^{20}$=−47.9° (ethanol, c=1.2). NMR (DMSO-d$_6$, 200 MHz): δ0.9 (d, J=6 Hz, 3H); 0.95 (d, J=6 Hz, 3H); 1.67 (t, J=11 Hz, 1H); 2.1 (m, 1H), 2.3 (t, J=11 Hz, 1H); 2.7 (m, 4H); 3.4 (dd, J$_1$=5 Hz, J$_2$=14 Hz, 1H); 5.1 (m, 2H); 5.8 (m, 1H). Mass spectrum (Cl—CH$_4$) m/z: 155 (M+1, 100%), 154 (M$^+$, 24%). The oil was dissolved in diethyl ether (100 mL) and treated dropwise with a solution of 1M hydrogen chloride in diethyl ether (10 mL). The beige dihydrochloride salt was collected by filtration, washed with diethyl ether and dried, $[\alpha]_D^{20}$=−14.5° (ethanol, c=1.2).

Method B—Enantiomeric Resolution

A mixture of racemic 1-allyl-2,5-dimethylpiperazine (3.82 g, 24.8 mmol, Example 42, infra) and (+)-di-p-toluoyl-D-tartaric acid (9.55 g, 24.8 mmol) in absolute ethanol (40 mL) was heated to reflux and allowed to cool gradually to room temperature. After standing for one day the salt was collected by filtration, washed with ethanol and dried to give 11.0 g. This was recrystallized four times from absolute ethanol to give the salt (4.5 g, 68% of theoretical for one enantiomer) as a white solid. The salt (3.3 g, 6.1 mmol) was partitioned between 2N sodium hydroxide solution and dichloromethane. The dichloromethane phase was separated, the alkali washed twice with dichloromethane, and the combined dichloromethane phases were dried with magnesium sulfate and evaporated to give (−)-(2R,5S)-1-allyl-2,5-dimethylpiperazine, (0.92 g, 98% recovery from the salt), $[\alpha]_D^{20}$=−55.7° (ethanol, c=1.8).

EXAMPLE 77

(+)-(2S,5R)-1-Allyl-2,5-dimethylpiperazine

Allyl bromide (4.6 mL, 53.8 mmol) was added to a solution of BOC-L-alanine (5.00 g, 26.4 mmol) in 100 mL of dry tetrahydrofuran and the mixture was cooled to 0° C. Sodium hydride (2.53 g of 50% oil dispersion, 52.8 mmol) was added in small portions. The mixture was stirred at 0° C. under nitrogen for one hour, warmed to room temperature, and stirring was continued overnight. The reaction was quenched with tetrahydrofuran:water (1:1) and evaporated to dryness. The residue was taken up in water and extracted with hexane. The aqueous layer was adjusted to pH 2 with solid citric acid and extracted with ethyl acetate. The combined organic layers were dried over magnesium sulfate and the solvent was removed under vacuum to give 4.68 g of a yellow oil. Chromatography on silica gel with chloroform:methanol (99:1) gave 3.78 g (62%) of N-allyl-N-BOC-L-alanine as a yellow oil. NMR (200 MHz, DMSO-d$_6$): δ1.3 (d, J=7 Hz, 3H); 1.4 (s, 9H); 3.6—4.1 (m, 2.5H); 4.4 (br m, 0.5H); 5.1 (d, J=10 Hz, 1H); 5.2(d, J=14 Hz, 1H); 5.8 (m, 1H); 12.5 (brs, 1H).

D-Alanine methyl ester hydrochloride (2.30 g 16.5 mmol), triethylamine (2.3 ml, 16.5 mmol) and 1-(3-dimethylaminopropyl)-3-ethylcarbodiimide hydrochloride (3.16 g, 16.5 mmol) were added to a solution of the product from above (3.78 g, 16.5 mmol) in 80 mL of dichloromethane at 0° C. The mixture was kept in the freezer overnight, then washed with water, 1M aqueous citric acid, 5% aqueous sodium bicarbonate and water. After drying over sodium sulfate, the solvent was removed under vacuum to give 3.31 g (64%) of methyl N-allyl-N-((tert-butoxy)carbonyl)-D-alanyl-L-alaninate as a yellow oil. NMR(200 MHz, DMSO-d$_6$): δ1.25 (m, 6H); 1.4 (s, 9H); 3.6 (s, 3H); 3.7—4.0 (m, 2H); 4.3 (m, 2H); 5.1 (m, 2H); 5.8 (m, 1H); 8.1 (br s, 1H).

The product (2.3 g, 7.3 mmol) was dissolved in 100 mL of formic acid and kept at room temperature for 2 hours. The excess formic acid was removed under vacuum, the residue was dissolved in 80 mL of 2-butanol and 15 mL of toluene and the mixture was heated to reflux for 4 hours. The solvents were removed under vacuum to give 1.50 g of a yellow oil. Chromatography on silica gel with chloroform:methanol (99:1) gave 0.74 g (56%) of (2S,5R)-1-allyl-2,5-dimethylpiperazine-3,6-dione as a colorless oil. NMR(200 MHz, DMSO-d$^6$): δ1.3 (d, J=7 Hz, 3H); 1.37 (d, J=7 Hz, 3H); 3.6 (dd, J$_1$=6 Hz, J$_2$=15 Hz, 1H); 3.8 (q, J=7 Hz, 1H); 4.1 (q, J=7 Hz, 1H); 4.3 (dd, J$_1$=5 Hz, J$_2$=15 Hz, 1H); 5.15 (d, J=12 Hz, 1H); 5.2 (d, J=15 Hz, 1H); 5.8 (m, 1H); 8.25 (br s, 1H).

The diketopiperazine from above was dissolved in 25 mL of dry tetrahydrofuran and cooled to 0° C. under nitrogen. Lithium aluminum hydride (12.3 mL of a 1M solution in tetrahydrofuran) was added dropwise. The mixture was warmed to room temperature, then heated to reflux overnight. After cooling to room temperature, sodium fluoride (2.0 g, 48 mmol) was added, the mixture was stirred for 30 minutes, cooled to 0° C., and 8 mL of water was added keeping the temperature below 5° C. Stirring was continued at room temperature for another 30 minutes and the insoluble fluoride was filtered off. The filtrate was evaporated under vacuum, the residue was taken up in dichloromethane, dried over sodium sulfate overnight, and the solvent removed under vacuum to give 0.54 g a yellow oil. This material was treated with an excess of ethanolic hydrogen chloride, evaporated to dryness and the residue was triturated with ether to give 0.457 g (50%) of the dihydrochloride as a beige solid. Calc. for C$_9$H$_{18}$N$_2$2HCl 0.25 H$_2$O: C, 46.66; H, 8.92; N, 12.09; Cl, 30.61. Found: C, 46.61; H, 8.88; N, 12.00; Cl, 30.44. $[\alpha]_D^{20}$=+14.7° (ethanol, c=2.2).

The salt (0.430 g) was dissolved in water, basified with 10N aqueous sodium hydroxide, extracted with dichloromethane, dried over sodium sulfate and the solvent evaporated to give 0.25 g (40% from piperazinedione) of (+)-(2S,5R)-1-allyl-2,5-dimethylpiperazine as a yellow oil. NMR (DMSO-d$_6$, 200 MHz) δ0.9 (d, J=6 Hz, 3H); 0.95 (d, J=6 Hz, 3H); 1.67 (5, J=11 Hz, 1H); 2.1 (m, 1H), 2.3 (t, J=11 Hz, 1H); 2.7 (m, 4H); 3.4 (dd, J$_1$=5 Hz, J$_2$ 14 Hz, 1H); 5.1(m, 2H); 5.8 (m, 1H). Mass spectrum (Cl—CH$_4$) m/z 155 (M+1, 100%), 154 (M$^+$, 24%).

EXAMPLE 78

(±)-5-((αR*)α-((2R*,5S*)-4-Allyl-2,5-dimethyl-1-piperazinyl)-3-hydroxy-benzyl)-3-bromo-N,N-diethyl-2-thiophenecarboxamide A mixture of (±)-3-((R*)-((2R*,5S*)-4-allyl-2,5-dimethyl-1-piperazinyl)(4-bromo-2-thienyl)methyl)phenol (Example 43, 7.25 g, 0.0172 mol), tert-butyldimethylsilyl chloride (3.00 g, 0.020 mol), imidazole (2.93 g, 0.043 mol), and 50 mL of dry dimethylformamide was stirred at room temperature under nitrogen for 16 hours. The solution was diluted with 500 mL of ethyl acetate, washed three times with 0.1N NaOH, dried over sodium sulfate and evaporated to 9.2 g (100%) of crude (±)-3-((R*)-((2R*,5S*)-4-allyl-2,5-dimethyl-1-piperazinyl)(4-bromo-2-thienyl)methyl) phenol, tert-butyl-dimethylsilyl ether as a dark oil.

A solution of the product (2.3 g, 4.29 mmol) in 250 mL of dry tetrahydrofuran under nitrogen was cooled to −78° C.

A solution of 1.5M lithium diisopropylamide in cyclohexane (2.9 mL, 4.29 mmol) was added via syringe at a rate to maintain a temperature below −70° C. The resulting solution was stirred for one hour at −78° C., then carbon dioxide gas was introduced below the surface of the solution via cannula for 10 min. The solution was allowed to warm to room temperature with stirring. The solvent was evaporated and the residue was redissolved in toluene and evaporated again. The resulting viscous oil was dissolved in 250 mL of dichloromethane and strirred at room temperature under nitrogen. Thionyl chloride (0.44 mL, 6.0 mmol) was added, and the resulting mixture was stirred for one hour at room temperature before adding diethylamine (2.2 mL, 21.5 mmol). The mixture was stirred for 16 hours at room temperature, washed three times with water, dried over sodium sulfate, and evaporated to give a dark oil. Chromatography on silica gel with dichloromethane:ethyl acetate/ 9:1 gave 1.14 g (42%) of (±)-5-((αR*)-α-((2R*,5S*)-4-allyl-2,5-dimethyl-1-piperazinyl)-3-hydroxybenzyl)-3-bromo-N,N-diethyl-2-thiophenecarboxamide, tert-butyldimethylsilyl ether.

The product was deprotected with tetraethylammonium fluoride hydrate as in Example 44. Chromatography on silica gel with dichloromethane:ethyl acetate/1:1 gave 720 mg of (±)-5-((αR*)-α-((2R*,5S*)-4-allyl-2,5-dimethyl-1-piperazinyl)-3-hydroxybenzyl)-3-bromo-N,N-diethyl-2-thiophenecarboxamide as a light brown foam. $^1$H-NMR (300 MHz, DMSO-$d_6$): δ0.89 (d, J=6.0 Hz, 3H); 1.11 (m, 9H); 1.65 (m, 1H); 1.95 (m, 1H); 2.40 (m, 2H); 2.60–2.80 (m, 3H); 3.30 (m, 5H); 5.14 (m, 2H); 5.47 (s, 1H); 5.80 (m, 1H); 6.56 (s,1H); 6.75 (m, 3H); 7.22 (t, J=8 Hz, 1H); 9.48 (s, 1H). The amine was dissolved in ethanol and converted to the monohydrochloride salt by titration to pH 3.8 with ethanolic hydrogen chloride. The solvent was removed by evaporation and the salt was dissolved in dichloromethane, followed by precipitation with diethyl ether to give 580 mg (58%) of an off-white solid, mp 147°–150° C. Calc. for $C_{25}H_{34}BrN_3O_2S$ HCl: C, 53.91; H, 6.33; N, 7.55; Br, 14.35; Cl, 6.37; S, 5.76. Found: C, 53.69; H, 6.40; N, 7.50; total halogen calc. as chlorine, 12.69; S, 5.73.

EXAMPLE 79

(±)-3-((R*)-((2R*,5S*)-4-Allyl-2,5-dimethyl-1-piperazinyl)-3-pyridylmethyl)-phenol 3-Bromopyridine (50.0 g, 0.316 mol) and 3-(tert-butyldimethylsilyloxy)benzaldehyde (74.8 g, 0.316 mol, Example 54, infra) were each dissolved in 500 mL anhydrous diethyl ether under nitrogen and chilled to −78° C. in dry ice/acetone baths. n-Butyllithium (198 mL, 0.316 mol, 1.6M in hexanes) was added dropwise to the chilled pyridine solution at a rate that maintained the temperature below −70° C. After the addition was complete, the reaction was stirred for 10 minutes. The aldehyde solution was then added to the reaction mixture via cannula, while maintaining the temperature below −70° C. The reaction was stirred at −78° C. for 45 minutes and quenched with aqueous saturated ammonium chloride. The reaction mixture was allowed to warm to room temperature and was washed with water and brine. The ether extracts were dried over sodium sulfate and the solvent removed to give 98.2 g of crude (3-(tert-butyldimethylsilyloxy)phenyl)(3-pyridyl)methanol. The crude alcohol was dissolved in 300 mL of dichloromethane and chilled in an ice bath. Thionyl chloride (34 mL, 0.47 mol) was dissolved in 30 mL of dichloromethane and added dropwise to the chilled alcohol solution. After stirring for 3 hours, the solvent was removed to give the hydrochloride salt of (tert-butyldimethylsilyl) (3-(α-chloro-3-pyridylmethyl)phenyl) ether as a brown solid. The crude alkylchloride (approx. 0.311 mol) was combined with 120 g (0.78 mol) of N-allyl-trans-2,5-dimethylpiperazine (Example 42, infra) in 100 mL of acetonitrile and heated at reflux overnight. After the reaction was cooled to room temperature, 62 g (approx. 0.43 mol) of tetraethylammonium fluoride hydrate was added, and the reaction was stirred for 1 hour. The solvent was removed and the product was purified by chromatography on silica gel with 0–20% ethanol in dichloromethane. The first isomer to elute was obtained as 14.7 g of a dark oil which crystallized from 100 mL of acetonitrile upon standing at room temperature to give 3.0 g of (±)-3-((R*)-((2R*,5S*)-4-allyl-2,5-dimethyl-1-piperazinyl)-3-pyridylmethyl)phenol, mp 115°–118° C. Calc for $C_{21}H_{28}N_3O$: C, 74.52; H, 8.34; N, 12.41. Found: C, 74.78; H, 8.11; N, 12.47. NMR (200 MHz, DMSO-$d_6$): δ0.95 (d, J=6 Hz, 3H); 1.09 (d, J=6Hz, 3H); 1.84 (dd, $J_1$=7.6 Hz, $J_2$=11.7 Hz, 1H); 2.10 (dd, $J_1$=6.8 Hz, $J_2$=10.8 Hz, 1H); 2.5–2.8 (m, 4H); 2.86 (dd, $J_1$=7.2 Hz, $J_2$=14.0 Hz, 1H); 3.18 (dd, $J_1$=5.3 Hz, $J_2$=14 Hz, 1H); 5.05 (s, 1H); 5.8 (m, 1H); 6.7 (m, 3H); 7.16 (t, J=7.6 Hz, 1H); 7.34 (dd, $J_1$=4.9 Hz, $J_2$=8.0 Hz, 1H); 7.75 (d, J=7.9 Hz, 1H); 8.43 (d, J=4.6 Hz, 1H); 8.57 (s, 1H); 9.41 (s, 1H).

EXAMPLE 80

(±)-3-((R*)-((2S*,5R*)-4-Allyl-2,5-dimethyl-1-piperazinyl)-3-pyridylmethyl)-phenol The second isomer to elute from the column of Example 79 was obtained as 6.9 g of an oil. The product was crystallized from ethyl acetate to give 2.4 g of tan solid, mp 158°–160° C. NMR (200 MHz, DMSO-$d_6$): δ0.96 (d, J=6 Hz, 3H); 1.10 (d, J=6 Hz, 3H); 1.79 (dd, $J_1$=7.2 Hz, $J_2$=10.6 Hz, 1H); 2.08 (dd, $J_1$=7.2 Hz, $J_2$=11.2 Hz, 1H); 2.3–2.75 (m, 4H); 2.85 (dd, $J_1$=7.0 Hz, $J_2$=13.9 Hz, 1H); 3.18 (dd, $J_1$=5.2 Hz, $J_2$=13.9 Hz, 1H); 5.08 (s, 1H); 5.10 (d, J=9.9 Hz, 1H); 5.17 (d, J=16.2 Hz, 1H); 5.7–5.9 (m, 1H); 7.10 (t, J=7.8 Hz, 1H); 7.40 (dd, $J_1$=4.9 Hz, $J_2$=7.8 Hz, 1H); 7.66 (d, J=8 Hz, 1H); 8.50 (d, J=6 Hz, 1H); 8.52 (s, 1H); 9.32 (s, 1H). The free amine was dissolved in ethanol and converted to the monohydrochloride salt by titrating to a pH of 3.4 with ethanolic hydrogen chloride. The solvent was removed, and the residue was redissolved in dichloromethane. The salt was precipitated with ether:hexane and collected by filtration to give a white powder. Calc for $C_{21}H_{27}N_3O$ HCl 0.75 $H_2O$: C, 65.10; H, 7.67; N, 10.85; Cl, 9.15. Found: C, 65.12; H, 7.68; N, 10.87; Cl, 9.20.

EXAMPLE 81

(±)-4-((αR*)-α-((2S*,5R*)-4-(Carbamoylmethyl)-2,5-dimethyl-1-piperazinyl)-3-hydroxybenzyl)-N,N-diethylbenzamide (±)-4-((αR*)-α-((2S*,5R*)-2,5-Dimethyl-1-piperazinyl)-3-hydroxybenzyl)-N,N-diethylbenzamide (1.0 g, 2.6 mmol, Example 16) was combined with t-butyldimethylsilyl chloride (0.60 g, 3.9 mmol) and imidazole (0.50 g, 6.5 mmol) in 30 mL dimethylformamide and stirred overnight. The solvent was removed in vacuo, and the residue was redissolved in dichloromethane (150 mL) and washed with 80 mL of aqueous 1N sodium hydroxide. The organic layer was dried with sodium sulfate and the solvent removed to give 0.70 g of the silyl ether.

A portion of the silyl ether (0.51 g, 1.0 mmol) was combined with 2-chloroacetamide (0.10g, 1.1 mmol) and sodium carbonate (0.16g, 1.5 mmol) in 4 mL of anhydrous tetrahydrofuran. The reaction was stirred for 4 hours at room temperature and then chilled in an ice bath. Sodium iodide (0.16 g, 1.1 mmol) was added; the reaction was warmed to room temperature and stirred overnight. The solvent was removed, and the residue was redissolved in 70 mL of dichloromethane. The solution was washed with 20 mL of water, and the solvent was again removed. The residue was redissolved in 20 mL of acetonitrile and stirred with tetraethylammonium fluoride hydrate (0.27 g) at room temperature overnight. The solvent was removed, and the residue was purified by chromatography on silica gel with ethyl acetate (0–3%) in dichloromethane to give (±)-4-((αR*)-α-((2S*,5R*)-4-(carbamoylmethyl)-2,5-dimethyl-1-piperazinyl)-3-hydroxybenzyl)-N,N-diethylbenzamide. NMR (300 MHz, DMSO-d$_6$): δ0.94 (d, J=5.6 Hz, 3H); 1.1 (d, J=5.9 Hz, 3H); 1.0–1.2 (br m, 6H); 1.9 (t, J=10.4 Hz, 1H); 2.2 (dd, J$_1$=8 Hz, J$_2$=13 Hz, 1H); 2.5–2.8 (m, 4H); 2.7 & 2.9 (ABq, J=15.8 Hz, 2H); 5.0 (s, 1H); 6.6–6.7 (m, 3H); 7.05 (br s, 1H); 7.14 (t, J=8 Hz, 1H); 7.27 & 7.42 (ABq, J=8 Hz, 4H); 9.35 (s, 1H).

The free amine was dissolved in ethanol and converted to the monohydrochloride salt by titrating to a pH of 3.3 with ethanolic hydrogen chloride. The ethanol was evaporated and the residue redissolved in dichloromethane. The salt was precipitated with hexane:ethyl acetate to give 0.16 g (31%) of a white solid. Calc for $C_{26}H_{36}N_4O_3$ HCl H$_2$O: C, 61.59; H, 7.75; N, 11.05; Cl, 6.99. Found: C, 61.87; H, 7.72; N, 11.13; Cl, 7.09.

EXAMPLE 82

(±)-N,N-Diethyl-4-((αR*)-3-hydroxy-α-((2S*,5R*)-4-(2-methoxyethyl)-2,5-dimethyl-1-piperazinyl)benzyl)benzamide (±)-4-((αR*)-α-((2S*,5R*)-2,5-Dimethyl-1-piperazinyl)-3-hydroxybenzyl)-N,N-diethylbenzamide, t-butyldimethylsilyl ether (0.51 g, 1.0 mmol, Example 81, infra) was combined with 2-bromoethyl methyl ether (0.16 g, 1.2 mmol), sodium carbonate (0.16 g, 1.8 mmol), and sodium iodide (0.15 g, 1.0 mmol) in 6 mL of anhydrous tetrahydrofuran. The reaction mixture was heated at reflux for 24 hours and then cooled to room temperature. The reaction was diluted with diethyl ether, filtered to remove salts, and then evaporated to dryness. The residue was purified by chromatography on silica gel with ethanol (0–3%) in dichloromethane to give 0.42 g of product which was dissolved in acetonitrile and stirred with 200 mg of tetraethylammonium fluoride hydrate for 30 minutes. The reaction mixture was concentrated to dryness, redissolved in dichloromethane, and washed with water adjusted to pH 8. The organic layer was dried over sodium sulfate and the solvent removed. The residue was purified by chromatography on silica gel with ethanol (0–5%) in dichloromethane. The crude product was dissolved in aqueous 1N hydrochloric acid and washed with diethyl ether. The aqueous layer was adjusted to pH 8 with aqueous 1N sodium hydroxide and extracted with dichloromethane. The organic extracts were dried over sodium sulfate, filtered, and the solvent removed to give (±)-N,N-diethyl-4-((αR*)-3-hydroxy-α-((2S*,5R*)-4-(2-methoxyethyl)-2,5-dimethyl-1-piperazinyl)benzyl)-benzamide. NMR (300 MHz, DMSO-d$_6$): δ0.93 (d, J=5.7 Hz, 3H); 1.08 (d, J=5.7 Hz, 3H); 1.0–1.2 (br m, 6H); 1.80 (brt, J=10 Hz, 1H); 2.15 (br t, J=11 Hz, 1H); 2.3–2.75 (m, 5H); 2.8 (d, J=9 Hz, 1H); 3.1–3.45 (br m, 4H); 3.21 (s, 3H); 3.36 (t, J=9 Hz, 2 H); 4.99 (s, 1H); 6.6–6.7 (m, 3H); 7.14 (t, J=7.5 Hz); 7.27 & 7.42 (ABq, J=8 Hz, 4H); 9.35 (s, 1H). The free amine was dissolved in ethanol and converted to the monohydrochloride salt by titrating to a pH of 3.4 with ethanolic hydrogen chloride. The solvent was removed, and the residue was redissolved in dichloromethane. The salt was precipitated with ether:hexane and collected by filtration to give 0.19 g (38%) of the monohydrochloride salt as a white powder. Calc for $C_{27}H_{39}N_3O_3$ HCl 0.75 H$_2$O: C, 64.40; H, 8.31; N, 8.34, Cl, 7.04. Found: C, 64.57; H, 8.43; N, 8.14; Cl, 7.05.

EXAMPLE 83

(±)-4-((αR*)-α-((2S*,5R*)-4-(Cyanomethyl)-2,5-dimethyl-1-piperazinyl)-3-hydroxybenzyl)-N,N-diethylbenzamide (±)-4-((αR*)-α-((2S*,5R*)-2,5-Dimethyl-1-piperazinyl)-3-hydroxybenzyl)-N,N-diethylbenzamide, tert-butyldimethylsilyl ether (0.51 g, 1.0 mmol, Example 81, infra) was combined with 2-chloroacetonitrile (0.07 mL, 1.1 mmol, Eastman Kodak, Rochester, N.Y.) and sodium carbonate in anhydrous tetrahydrofuran. The reaction mixture was chilled in an ice bath and sodium iodide (0.16 g, 1.1 mmol) was added. The reaction was allowed to warm to room temperature and stirred overnight. The solvent was removed and the residue was redissolved in dichloromethane and washed with water. The solvent was evaporated and the residue was purified by chromatography on silica gel with ethanol (0–3%) in dichloromethane. The product was dissolved in 20 mL of acetonitrile and stirred for 3 hours with tetraethylammonium fluoride hydrate (0.18 g). The solvent was evaporated and the residue was purified by chromatography on silica gel with ethanol (0–3%) in dichloromethane. Crystallization of the product from acetonitrile gave 37 mg of solid, mp 190°–192° C. Calc for $C_{26}H_{34}N_4O_4$: C, 71.86; H, 7.88; N, 12.89. Found: C, 71.83; H, 7.94; N, 12.95. NMR (200 MHz, CDCl$_3$): δ0.93 (d, J=6 Hz, 3H); 1.15 (d, J=4.7 Hz, 3H); 1.0–1.2 (br m, 6H); 1.79 (t, J=11 Hz, 1H); 2.2–2.4 (m, 5H); 3.2–3.6 (br m, 4H); 3.36 & 3.76 (ABq, J=17.4 Hz, 2H); 5.15 (s, 1H); 6.55 (s, 1H); 6.57 (d, J=8.6 Hz, 1H); 6.73 (d, J=8 Hz, 1H); 7.13 (t, J=7.6 Hz, 1H); 7.28 & 7.42 (ABq, J=8.2 Hz, 4H).

EXAMPLE 84

(±)-3-((αR*)-α-((2S*,5R*)-4-Allyl-2,5-dimethyl-1-piperazinyl)-3-hydroxy-benzyl)-N,N-diethylbenzamide A mixture of 300.0 g (1.7 mol) of 3-bromophenol, 392.1 g (2.6 mol) of tert-butylchlorodimethylsilane and 295.1 g (4.3 mol) of imidazole in 1 L of N,N-dimethylformamide was stirred at room temperature under nitrogen for 18 hours. The reaction mixture was poured into cold water and extracted with diethyl ether. The ether extracts were washed with water and brine, dried over sodium sulfate, and the solvent was evaporated under vacuum to give 650 g of crude 3-bromophenyl tert-butyldimethylsilyl ether as an orange oil. NMR (CDCl$_3$, 200 MHz) δ0.2 (s, 6H); 0.95 (s, 9H); 6.8 (m, 1H); 7.0–7.1 (m, 3H).

The silyl ether (155.2 g, 0.54 mol) was dissolved in 600 mL of dry tetrahydrofuran, dried further over molecular sieves, then transferred to a reaction flask and diluted to 1200 mL with dry tetrahydrofuran and cooled to –78° C. n-Butyllithium (310 mL of a 1.6M solution in hexane) was added, while stirring under nitrogen, at a rate to keep the temperature below –70° C. Stirring was continued at –78° C. for 45 minutes. A solution of 3-bromobenzaldehyde (100.0 g, 0.54 mol) in 900 mL of dry tetrahydrofuran was added at a rate to keep the reaction temperature below –70° C. After stirring for 30 minutes at –78° C., the reaction was quenched with 500 mL of saturated aqueous ammonium chloride and allowed to warm to room temperature. The mixture was diluted with water and diethyl ether and the ethereal layer was washed with brine, dried over sodium sulfate and evaporated to give 21 6.2 g of a yellow oil. Chromatography on silica gel with hexane:ethyl acetate (4–25%) gave 98.86 g (51%) of α-(3-bromophenyl)-(3-(tert-butyldimethylsilyloxy)benzyl alcohol as a yellow oil. NMR (CDCl$_3$, 200 MHz) δ: 0.2 (s, 6H); 0.95 (s, 9H); 2.3 (br s, 1H); 5.7 (s, 1H); 6.75 (d, J=8 Hz, 1H); 6.8 (s, 1H); 6.9 (d, J=8 Hz, 1H); 7.2 (m, 2H); 7.3 (d, J=8 Hz, 1H); 7.4 (d, J=8 Hz, 1H); 7.5 (s, 1H).

Thionyl chloride (27.5 mL, 0.38 mol) was added dropwise to a solution of the benzhydryl alcohol from above (98.9 g, 0.25 mol) in 500 mL of dichloromethane and the mixture was stirred overnight at room temperature. The solvent was removed under vacuum, the residue was redissolved in toluene, and the solvent was again removed under vacuum to eliminate excess thionyl chloride to give 154 g of crude α-(3-bromophenyl)-3-(tert-butyldimethylsilyloxy) benzyl chloride as a brown oil. NMR (CDCl$_3$, 200 MHz) δ: 0.2 (s, 6H); 0.95 (s, 9H); 6.0 (s, 1H); 6.8–7.0 (m, 3H); 7.2–7.6 (m, 5H).

A mixture of the benzhydryl chloride from above (103.5 g, 0.25 mol) and N-allyl-2,5-dimethylpiperazine (96.9 g, 0.63 mol, Example 42, infra) in 50 mL of toluene was heated at reflux overnight. Acetonitrile (350 mL) and tetraethylammonium fluoride hydrate (75 g, 0.38 mol) was added to the cooled reaction mixture. After stirring at room temperature for 30 minutes, the solvent was removed under vacuum to give 344 g of a crude mixture of diastereomers as a dark brown oil. Chromatography on silica gel with dichloromethane:ethanol (99:1) gave 31.15 g of a brown solid containing 95% of the less mobile diastereomer (R$_f$=0.42 on silica gel with dichloromethane:ethanol:ammonium hydroxide/95:5:1). Crystallization from isopropanol gave 28.6 g (55% of theoretical for one diastereomer) of (±)-3-( (αR*)-α-((2R*,5S*)-4-allyl-2,5-dimethyl-1-piperazinyl)-3-bromobenzyl)-phenol as a white solid, mp 186°–189° C. NMR (DMSO-d$_6$, 200 MHz) δ: 0.95 (d, J=6 Hz, 3H); 1.03 (d, J=6 Hz, 3H); 1.8 (dd, J$_1$=6 Hz, J$_2$=10 Hz, 1H); 2.1 (dd, J$_1$=6 Hz, J$_2$=10 Hz, 1H); 2.4–2.6 (m, 3H); 2.7 (d, J=11 Hz, 1H); 2.8 (dd, J$_1$=7 Hz, J$_2$=14 Hz, 1H); 3.2 (dd, J$_1$=6 Hz, J$_2$=13 Hz, 1H); 4.9 (s, 1H); 5.1 (d, J=10 Hz, 1H); 5.2 (d, J=18 Hz, 1H); 5.7–5.9 (m, 1H); 6.6–6.8 (m, 3H); 7.0–7.4 (m, 4H); 7.55 (s, 1H); 9.35 (s, 1H).

The bromobenzene (3.22 g, 7.75 mmol) was dissolved in 25 mL of dimethylformamide with cuprous cyanide (1.39 g, 15.5 mmol), and the reaction was heated at reflux for 3 days. The reaction was cooled to room temperature and poured into 300 mL aqueous 30% sodium cyanide. The mixture was extracted with 250 mL of ethyl acetate. The solvent was removed and the residue was purified by chromatography on silica gel with ethanol (0–20%) in dichloromethane to give 1.3 g (46%) of (±)-3-((αR*)-α-((2S*,5R*)-4-allyl-2,5-dimethyl-1-piperazinyl)-3-hydroxybenzyl)benzonitrile, mp 169°–171° C. Calc for C$_{23}$H$_{27}$N$_3$O: C, 76.42; H, 7.53; N, 11.62. Found: C, 76.35; H, 7.54; N, 11.62.

A portion of the benzonitrile (0.72 g, 1.99 mmol) was combined with 0.56 g of sodium hydroxide pellets in 8 mL of 95% ethanol and heated at reflux overnight. After cooling to room temperature, the reaction solution was adjusted to pH 5 with concentrated hydrochloric acid. The solvent was removed in vacuo, and the residue was slurried with 25 mL of dichloromethane for 3 days. Filtration gave 1.44 g of the carboxylic acid as a mixture with sodium chloride. The carboxylic acid was combined with 1.8 g (4.0 mmol) of benzotriazol-1-yloxy-tris(dimethylamino)phosphonium hexafluorophosphate and 1.0 mL (9.7 mmol) of diethylamine in 25 mL of acetonitrile and stirred overnight. The solvent was removed in vacuo, and the residue was redissolved in 150 mL 1N aqueous hydrochloric acid and 150 mL of ethyl acetate. The aqueous layer was adjusted to pH 8 with aqueous 10N sodium hydroxide and extracted with diethyl ether. The ether extracts were washed with brine, dried over sodium sulfate, and concentrated in vacuo to give 0.4 g of a brown oil. The crude product was purified by preparative thin layer chromatography (silica gel, dichloromethane:ethanol:ammonium hydroxide/95:5:1) to give 0.090 g (10% from the benzonitrile) of (±)-3-((αR*)-α-((2S*,5R*)-4-allyl-2,5-dimethyl-1-piperazinyl)-3-hydroxybenzyl)-N,N-diethylbenzamide as a white foam.

The free amine was converted to the monohydrochloride salt by dissolving in ethanol and titrating with 0.2M ethanolic hydrogen chloride to a pH of 3.45. The solvent was removed, the residue was redissolved in 10 mL of dichloromethane, and the salt was precipitated with diethyl ether. Filtration gave 0.070 g of the monohydrochloride salt as a white solid. Calc for C$_{27}$H$_{37}$N$_3$O$_2$ HCl H20: C, 66.17; H, 8.23; N, 8.57; Cl, 7.23. Found: C, 66.06; H,7.97; N, 8.55; Cl, 7.31.

EXAMPLE 85

(+)-3-((αR)-α-((2S,5R)-4-Allyl-2,5-dimethyl-1-piperazinyl)-3-hydroxybenzyl)-N,N-diethylbenzamide (R)-(−)-Mandelic acid (11.50g, 75.6 mmol) was added to a suspension of 28.55 g (68.7 mmol) of (±)-3-((αR*)-α-((2R*,5S*)-4-allyl-2,5-dimethyl-1-piperazinyl)-3-bromobenzyl)phenol (Example 84, infra) in 450 mL of absolute ethanol. The mixture was heated to complete solution and then allowed to crystallize at room temperature. Crystals were collected and recrystallized from absolute ethanol. The crystalline mandelate salt was treated with excess 1N aqueous sodium hydroxide and then titrated to pH 8 with 6N hydrochloric acid. The precipitated free amine was recrystallized from absolute ethanol to give 6.25 g (44% of theoretical for one enantiomer) of (+)-3-((αS)-α-((2S,5R)-4-allyl-2,5-dimethyl-1-piperazinyl)-3-bromobenzyl)-phenol as a white solid, mp 205°–206° C. [α]$_D^{20}$=+20° (methanol, c=2). Calc. for C$_{22}$H$_{27}$BrN$_2$O: C, 63.62; H, 6.55; N, 6.74; Br, 19.24. Found: C, 63.63; H, 6.57; N, 6.68; Br, 19.16.

A mixture of the product from above (6.09 g, 14.7 mmol) and cuprous cyanide (2.63 g, 29.4 mmol) in 55 mL of N,N-dimethylformamide was heated at reflux for 2 days. The reaction mixture was poured into 500 mL of 30% aqueous sodium cyanide, stirred for 20 minutes, then extracted with ethyl acetate. The ethyl acetate extracts were combined, washed with brine and dried over sodium sulfate, and the solvent was removed under vacuum. The resulting brown solid was purified by chromatography on silica gel with dichloromethane:ethanol (95:5) to give 3.54 g (67%) of 3-((αR)-α-((2S,5R)-4-allyl-2,5-dimethyl-1-piperazinyl)-3-hydroxybenzyl)benzonitrile as a beige solid. NMR (DMSO-d$_6$, 200 MHz): δ0.96 (d, J=6 Hz, 3H); 1.08 (d, J=6 Hz, 3H); 1.8 (dd, J$_1$=6.8 Hz, J$_2$=11 Hz, 1H); 2.1 (dd, J$_1$=6.6 Hz, J$_2$=10.7 Hz, 1H); 2.4–2.7 (m, 3H); 2.75 (dd, J$_1$=2.7 Hz, J$_2$=10.9 Hz, 1H); 2.86 (dd, J$_1$=7.0 Hz, J$_2$=14 Hz, 1H); 3.2 (dd, J$_1$=5 Hz, J$_2$=14 Hz, 1H); 5.0 (s, 1H); 5.1 (d, J=11 Hz, 1H); 5.2 (d, J=17 Hz, 1H); 5.7–5.9 (m, 1H); 6.68 (s, 1H); 6.7 (d, J=8 Hz, 2H); 7.16 (t, J=8 Hz, 1H); 7.5 (t, J=8 Hz, 1H); 7.7 (d, J=8 Hz, 2H); 7.8 (s, 1H); 9.4 (s, 1H).

The benzonitrile (3.54 g, 9.8 mmol) was dissolved in 40 mL of 95% ethanol with 2.74 g (68.6 mmol) of sodium hydroxide pellets and the mixture was heated at reflux overnight. Concentrated hydrochloric acid was added to adjust the pH to 5 and the solvent was removed under vacuum. The residue was combined with 8.67 g (19.6 mmol) of benzotriazol-1-yloxytris(dimethylamino)phosphonium hexafluorophosphate and 5.1 mL (49.0 mmol) of diethylamine in 60 mL of acetonitrile. After stirring at room temperature under nitrogen overnight, the solvent was removed under vacuum, and the residue was dissolved in 100 mL of 6N hydrochloric acid and extracted with ethyl acetate. The aqueous layer was adjusted to pH 8 with 10N aqueous sodium hydroxide and extracted with ethyl acetate. The ethyl acetate extracts were combined, washed with water adjusted to pH 8, dried over sodium sulfate, and the solvent evaporated to give 2.6 g of a beige solid. Chromatography on silica gel with dichloromethane:ethanol (1–4%) gave 1.76 g (41%) of (+)-3-((αR)-α-((2S,5R)-4-allyl-2,5-dimethyl-1-piperazinyl)-3-hydroxybenzyl)-N,N-diethylbenzamide as a beige solid. $[α]_D^{20}$=+15.0° (methanol, c=1.9). NMR (DMSO-$d_6$, 200 MHz) δ0.95 (d, J=6 Hz, 3H); 1.1 (d, J=6 Hz, 3H); 1.0–1.2 (br m, 6H); 1.9 (dd, $J_1$=8 Hz, $J_2$=12 Hz, 1H); 2.1 (dd, $J_1$=7 Hz, $J_2$=11Hz, 1H); 2.4–2.7 (m, 3H); 2.7 (dd, $J_1$=3 Hz, $J_2$=11 Hz, 1H); 2.9 (dd, $J_1$=7 Hz, $J_2$=14 Hz, 1H); 3.2 (dd, $J_1$=5 Hz, $J_2$=14 Hz, 1H); 3.1–3.5 (m, 4H); 5.0 (s, 1H); 5.1 (d, J=10 Hz, 1H); 5.2 (d, J=17 Hz, 1H); 5.7–5.9 (m, 1H); 6.7 (d, J=8 Hz, 1H); 6.69 (s, 1H); 6.7 (d, J=8 Hz, 1H); 7.1–7.2 (m, 2H); 7.3–7.4 (m, 3H); 9.4 (s, 1H). Mass spectrum (Cl—$CH_4$) m/z: 435 ($M^+$, 13%), 436 (M+1, 37%), 282 (47%), 153 (100%). The product was dissolved in absolute ethanol and titrated to pH 4 with ethanolic hydrogen chloride. The solution was concentrated and diethyl ether was added to precipitate the monohydrochloride salt (1.07 g, 56%) as a white solid. Calc. for $C_{27}H_{37}N_3O_2$ HCl 1.25 $H_2O$: C, 65.57; H, 8.25; N, 8.50; Cl, 7.17. Found: C, 65.26; H, 8.14; N, 8.82; Cl, 7.41.

EXAMPLES 86–91 were prepared in similar fashion to Example 84.

EXAMPLE 86

(±)-3-((αR*)-α-((2S*,5R*)-4-Allyl-2,5-dimethyl-1-piperazinyl)-3-hydroxybenzyl)-N-methyl-N-propylbenzamide NMR (DMSO-$d_6$, 200 MHz): δ0.8–1.0 (br m, 3H); 0.95 (d, J=6 Hz, 3H); 1.1 (d, J=6 Hz, 3H); 1.5 (br m, 2H); 1.85 (br m, 1H); 2.1 (br m, 1H); 2.4–3.0 (m, 8H); 3.0–3.2 (br m, 3H); 5.0 (br s, 1H); 5.13 (d, J=9 Hz, 1H); 5.2 (d, J=17 Hz, 1H); 5.8 (m, 1H); 6.7 (m,3H); 7.05–7.25 (m,2H); 7.3–7.5 (m, 3H); 9.36 (s, 1H).

EXAMPLE 87

(±)-3-(αR*)-α-((2S*,5R*)-4-Allyl-2,5-dimethyl-1-piperazinyl)-3-hydroxybenzyl)-N-ethyl-N-methylbenzamide NMR (DMSO-$d_6$, 200 MHz): δ0.95 (d, J=6 Hz, 3H); 1.1 (d, J=6 Hz, 3H); 1.0–1.2 (br m, 3H); 1.85 (brt, J=9 Hz, 1H); 2.1 (brt, J=8 Hz, 1H); 2.53 & 2.56 (2s,3H); 2.6–3.0 (m, 5H); 3.1–3.5 (m, 3H); 5.0 (br s, 1H); 5.1 (d, J=10 Hz, 1H); 5.17 (d, d=17 Hz, 1H); 5.8 (m, 1H); 6.7 (s, 1H); 6.6–6.75 (m, 2H); (m, 2H); 7.3–7.5 (m, 3H); 9.4 (s, 1H).

EXAMPLE 88

(±)-3-((αR*)-α-((2S*,5R*)-4-Allyl-2,5-dimethyl-1-piperazinyl)-3-hydroxybenzyl)N,N-dimethylbenzamide NMR (DMSO-$d_6$, 300 MHz): δ0.95(d, J=6 Hz, 3H); 1.05 (d, J=6 Hz, 3H); 1.85 (m, 1H); 2.1 (m, 1H); 2.8 & 2.85 (2s, 3H); 2.4–3.0 (m, 5H); 3.1 (m, 1H); 4:95 (s, 1H); 5.05 (d, J=10 Hz, 1H); 5.1 (d, J=17 Hz, 1H); 5.8 (m, 1H); 6.7 (m, 3H); 7.1 (t, J=8 Hz, 1H); 7.2 (d, J=8 Hz, 1H); 7.3–7.45 (m, 5H); 9.35 (s, 1H).

EXAMPLE 89

(±)-3-((αR*)-α-((2S*,5R*)-4-Allyl-2,5-dimethyl-1-piperazinyl)-3-hydroxybenzyl)-N-ethylbenzamide NMR (DMSO-$d_6$, 200 MHz): δ0.95(d, J=6 Hz, 3H); 1.05 (d, J=6 Hz, 3H); 1.05 (m,3H); 1.85 (m, 1H); 2.1 (m, 1H); 2.4–3.0 (m, 4H); 3.1–3.5 (m, 4H); 4:95 (s, 1H); 5.1 (d, J=10 Hz, 1H); 5.2 (d, J=17 Hz, 1H); 5.8 (m, 1H); 6.7 (m, 3H); 7.1 (t, J=8 Hz, 1H); 7.4 (t, J=8 Hz, 1H); 7.55 (d, J=8 Hz, 1H); 7.65 (d, J=8 Hz, 1H); 7.85 (s, 1H); 9.35 (s, 1H).

EXAMPLE 90

(±)-3-((αR*)-α-((2S*,5R*)-4-Allyl-2,5-dimethyl-1-piperazinyl)-3-hydroxybenzyl)-N-cyclopropyl-N-methylbenzamide NMR (DMSO-$d_6$, 500 MHz): δ0.4 (m, 4H); 0.95 (br s, 3H); 1.05 (br s, 3H); 1.85 (m, 1H); 2.1 (m, 1H); 2.4–3.0 (m, 5H); 2.9 (s, 3H); 3.1 (m, 1H); 4.95 (br s, 1H); 5.0–5.2 (br m, 2H); 5.8 (br m, 1H); 6.65 (br m, 3H); 7.1 (br m, 1H); 7.2–7.5 (m, 5H); 9.35 (s, 1H).

EXAMPLE 91

(±)-3-((αR*)-4-(1-Pyrrolidinylcarbonyl)-α-((2S*, 5R*)-4-allyl-2,5-dimethyl-1-piperazinyl)benzyl) phenol NMR (DMSO-$d_6$, 200 MHz): δ0.95(d, J=6 Hz, 3H); 1.05 (d, J=6 Hz, 3H); 1.8 (m, 5H); 2.1 (m, 1H); 2.2–3.0 (m, 7H); 3.1 (m, 1H); 3.4 (m, 2H); 4.95 (s, 1H); 5.05 (d, J=10 Hz, 1H); 5.1 (d, J=17 Hz, 1H); 5.8 (m, 1H); 6.65 (m, 3H); 7.3–7.5 (m, 4H); 9.35 (s, 1H).

EXAMPLE 92

Selected compounds of the present invention, identified below with reference to the appertaining synthesis Examples hereof, were evaluated for in vitro opioid receptor activity in various receptor systems, including brain tissue (Delta Receptor IC50; Mu Receptor IC50), mouse vas deferens (Mouse Vas Deferens ED50), and guinea pig ileum (Guinea Pig lieurn ED50).

The assay procedures used for such determinations of receptor activity are set out below.

In vitro bioassays: Vasa deferentia were removed from mice and suspended between platinum electrodes with 0.5 g of tension in organ bath chambers containing a modified Krebs' buffer of the following composition (millimolar): NaCl, 118; KCl, 4.75; $CaCl_2$, 2.6; $KH_2PO_4$, 1.20; $NaHCO_3$, 24.5; and glucose, 11. The buffer was saturated with 95% $O_2$/5% $CO_2$ and kept at 37° C. Tissues were stimulated at supramaximal voltage with 10 Hz pulse trains for 400 msec.; train interval 10 seconds; and 0.5 msec pulse duration. Intact ileums (about 3 cm length) were removed from guinea pig and suspended with 1 g of tension in a bath chamber as described for the vasa deferentia. The modified Krebs' buffer also contained $MgSO_4$ (1.20 mM). The ileums were stimulated with electrical square-wave pulses of 0.1 Hz, 0.5 msec pulse duration at supramaximal voltage. The percentage inhibition of the electrically induced muscle contractions was determined for the compounds at varying cumulative concentrations. The $ED_{50}$ values were extrapolated from curves showing the dose concentration plotted against the response (J. A. H. Lord, A. A. Waterfield, J. Hughes, H. W. Kosterlitz, Nature 267, 495, (1977)).

Inhibition of receptor binding. Rat (Sprague-Dawley) brain membranes were prepared and binding assays were performed at 24° C. for 60 min. as described by Chang, et. al (J. Biol. Chem. 254, 2610 (1979) and Mol. Pharmacol. 16, 91 (1979)) with a filtration method (GF/C filter). Delta receptor binding assays were performed with $^{125}$I-labeled [D-Ala$^2$, D-Leu$^5$] enkephalin (0.24 nM) in the presence of the highly selective mu-agonist [N-MePhe$^3$, D-Pro$^4$] morphiceptin to suppress mu-receptor cross-reactivity. Mu receptor binding assays were performed with $^{125}$I-labeled

[D-Ala$^2$, N-MePhe$^4$, Met(O)ol$^5$] enkephalin (0.1 nM). Non-specific binding was determined in the presence of 1 µM of the respective unlabeled ligand. The potency of compounds in inhibiting the binding of $^{125}$I-labeled enkephalin analogs was determined as the concentration which reduced the binding of the labeled compounds by 50 percent (IC$_{50}$).

Results are shown in Table A below.

TABLE A

In Vitro Opioid Receptor Activity of Representative Examples[a]

| Example | Delta Receptor IC50 (nM) | Mouse Vas Deferens ED50 (nM) | Mu Receptor IC50 (nM) | Guinea Pig Ileum ED50 (nM) |
|---|---|---|---|---|
| 6   | 1.8(7)  | 0.20 (8)      | 15 (6)  | 143 (12) |
| 6a  | 1.2     | 0.17 (4)      | 5.0     | 84 (4)   |
| 9   | 16      | 40 (8)        | 1.1     | 4.0(12)  |
| 11  | 1.5     | >10000 (4)    | 600     | 3600 (4) |
| 12  | 1.2     | 2.0 (4)       | 150     | >10000 (4) |
| 13  | 2.8     | (pA$_2$ = 7.0)[b] | 2400 | >10000 (4) |
| 15  | 0.7     | 4400 (4)      | 120     | 2700 (4) |
| 24  | 7.0     | 1.6 (4)       | 47      | 1200 (4) |
| 25  | 0.4     | 2.0 (4)       | 70      | 300 (4)  |
| 34  | 4.0     | >10000 (4)    | >10000  | 3700 (4) |
| 36  | 9.1     | 2.0 (4)       | 260     | 1300 (4) |
| 41  | 10      | 13 (4)        | 4.0     | 6.5 (4)  |
| 44  | 11      | 37 (4)        | 0.8     | 8.0 (4)  |
| 51  | 2.5     | 52 (4)        | 130     | 3000 (4) |
| 54  | 1.3     | 42 (4)        | 40      | 5600 (4) |
| 59  | 20      | 2.6 (4)       | 100     | 1800 (4) |
| 60  | 6.5     | 0.30(12)      | 20      | 86 (4)   |
| 67  | 27      | 20 (8)        | 0.3     | 2.1 (8)  |
| 84  | 1.6     | 8.6 (8)       | 3.0     | 10 (8)   |
| 85  | 1.9(2)  | 7.3 (16)      | 3.2(2)  | 18 (16)  |

[a]Values are the mean of (n) number of experiments or represent one determination where no number (n) is indicated.
[b]Antagonist potency (pA$_2$ value) as determined by Schild analysis (Arunlakshana, O; Schild, H. O., Brit. J. Pharmacol.1959, 14, 48–58) of data for blockade of inhibitory effect of (D-Ala2, D-Leu$^5$)-enkephalin on electrically stimulated muscle contraction in the muse vas deferens.

Pharmaceutical Formulations

In the following formulation Examples, the "Active Ingredient" may be any compound of the invention, such as a compound of formulae (I)–(V).

EXAMPLE 93

Tablet Formulations

The following formulations A, B and C are prepared by wet granulation of the ingredients with a solution of povidone, followed by addition of the magnesium stearate and compression.

Formulation A

|   |   | mg/tablet | mg/tablet |
|---|---|---|---|
| (a) | Active Ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
|   |   | 500 | 300 |

Formulation B

|   |   | mg/tablet | mg/tablet |
|---|---|---|---|
| (a) | Active Ingredient | 250 | 250 |
| (b) | Lactose | 150 | — |
| (c) | Avicel PH 101 | 60 | 26 |
| (d) | Povidone B.P. | 15 | 9 |
| (e) | Sodium Starch Glycollate | 20 | 12 |
| (f) | Magnesium Stearate | 5 | 3 |
|   |   | 500 | 300 |

Formulation C

|   | mg/tablet |
|---|---|
| Active Ingredient | 100 |
| Lactose | 200 |
| Starch | 50 |
| Povidone | 5 |
| Magnesium stearate | 4 |
|   | 359 |

The following formulations, D and E, are prepared by direct compression of the admixed ingredients.

| Formulation D | |
|---|---|
| | mg/tablet |
| Active ingredient | 250 |
| Pregelatinised Starch NF15 | 150 |
| | 400 |

| Formulation E | |
|---|---|
| | mg/tablet |
| Active ingredient | 250 |
| Lactose | 150 |
| Avicel | 100 |
| | 500 |

Formulation F (Controlled Release Formulation)
The formulation is prepared by wet granulation of the following ingredients with a solution of povidone followed by addition of the magnesium stearate and compression.

| | | mg/tablet |
|---|---|---|
| (a) | Active Ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 500 |

Drug release takes place over a period of about 6–8 hours and is complete after 12 hours.

EXAMPLE 94

Capsule Formulations

Formulation A

A capsule formulation is prepared by admixing the ingredients of Formulation D in Example 62 above and filling into two-part hard gelatin capsules.

| Formulation B | | |
|---|---|---|
| | | mg/capsule |
| (a) | Active Ingredient | 250 |
| (b) | Lactose B.P. | 143 |
| (c) | Sodium Starch Glycollate | 25 |
| (d) | Magnesium Stearate | 2 |
| | | 420 |

Capsules are prepared by admixing the above ingredients and filling into two-part hard gelatin capsules.

| Formulation C | | |
|---|---|---|
| | | mg/capsule |
| (a) | Active Ingredient | 250 |
| (b) | Macrogel 4000 BP | 350 |
| | | 600 |

Capsules are prepared by melting the Macrogel 4000 BP, dispersing the active ingredient in the melt and filling the melt into two-part hard gelatin capsules.

| Formulation D | |
|---|---|
| | mg/capsule |
| Active Ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with the release-controlling membrane (d) and filled into two-piece, hard gelatin capsules.

| | | mg/capsule |
|---|---|---|
| (a) | Active Ingredient | 250 |
| (b) | Microcrystalline Cellulose | 125 |
| (c) | Lactose BP | 125 |
| (d) | Ethyl Cellulose | 13 |
| | | 513 |

EXAMPLE 95

Injectable Formulation

| Formulation A | |
|---|---|
| Active Ingredient | 0.01 g |
| Hydrochloric acid solution, 0.1M | q.s. to pH 4.0 to 7.0 |
| Sodium hydroxide solution, 0.1M | q.s. to pH 4.0 to 7.0 |
| Sterile Water | q.s. to 10 ml |

The active ingredient is dissolved in most of the water (35°–40° C.) and the pH adjusted to between 4.0 and 7.0 using the hydrochloric acid or the sodium hydroxide as appropriate. The batch is then made up to volume with the water and filtered through a sterile micropore filter into a sterile amber glass vial 10 ml and sealed with sterile closures and overseals.

| Formulation B | |
|---|---|
| Active Ingredient | 0.125 g |
| Sterile, pyrogen-free, pH 7 phosphate buffer | q.s. to 25 ml |

EXAMPLE 96

| Intramuscular injection | |
|---|---|
| Active Ingredient | 0.02 g |
| Benzyl Alcohol | 0.10 g |
| Glycofural 75 | 1.45 g |
| Water for Injection q.s. to | 3.00 ml |

The active ingredient is dissolved in the glycofural. The benzyl alcohol is then added and dissolved, and water added to 3 ml. The resulting mixture is filtered through a sterile micropore filter and sealed in sterile amber glass vials (3 ml).

EXAMPLE 97

| Syrup | |
|---|---|
| Active Ingredient | 0.25 g |
| Sorbitol Solution | 0.10 g |
| Glycerol | 2.00 g |
| Sodium Benzoate | 0.005 g |
| Flavour, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 98

| Suppository | |
|---|---|
| | mg/suppository |
| Active Ingredient | 250 |
| Hard Fat, BP (Witepsol H15 - Dynamit Nobel) | 1770 |
| | 2020 |

One-fifth of the Witepsol H15 is melted in a steam-jacketed pan at 45° C. maxiumum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogeneous mix. The entire suspension is passed through a 250 μm stainless steel screen and, with continuous stirring, is allowed to cool to 40° C. At a temperature of 38° C. to 40° C., 2.0 g of the mixture is filled into suitable, 2 ml plastic molds. The suppositories are allowed to cool to room temperature.

EXAMPLE 99

Set out below is an illustrative formulation for pessaries comprising at least one of the diarylmethyl piperazine or diarylmethylpiperidine compounds of the present invention.

| Pessaries | |
|---|---|
| | mg/pessary |
| Active Ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE 100

Set out below are additional illustrative formulations in which the compounds of the invention may be usefully employed, including formulations in the dosage forms of oral suspensions, injectable suspensions, nebulization suspensions, aerosol formulations, powder inhalation formulations, and nasal drops.

| Tablet | |
|---|---|
| Compound of formula (I) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10 mg |
| Sodium Starch Glycollate BP ("Explotab") | 3 mg |
| Povidone BP ("K30") | 3.0 mg |
| Magnesium Stearate BP | 0.5 mg |
| | 100.0 mg |

| Oral suspension | |
|---|---|
| Compound of formula (I) | 50 mg |
| Avicel RC 591 | 75 mg |
| Sucrose syrup | 3.5 ml |
| Methylhydroxybenzoate | 5 mg |
| Color | 0.01% w/v |
| Cherry flavor | 0.1% v/v |
| Tween 80 | 0.2% v/v |
| Water | to 5 ml |

| Injectable suspension | |
|---|---|
| Compound of formula (I) | 100 mg |
| Polyvinyl pyrrolidone (PVP) | 170 mg |
| Tween 80 | 0.2% v/v |
| Methylhydroxybenzoate | 0.1% w/v |
| Water for injection | to 3 ml |

| Capsule formulation | |
|---|---|
| Compound of formula (I) | 100 mg |
| Starch 1500 | 150 mg |
| Magnesium stearate | 2.5 mg |

Fill the above-described formulation into a hard gelatin capsule.

| Suspension for Nebulization | |
|---|---|
| Compound of formula (I), sterile | 1.0 mg |
| Water for injection | to 10.0 ml |

Disperse the compound of formula (I) in the water for injection, as previously sterilized in a sterile container. Fill into sterile glass ampoules, 10 ml/ampoule under sterile conditions, and seal each ampoule by fusion of the glass.

| Aerosol Formulation | |
|---|---|
| Compound of formula (I), micronized | 1.0 mg |
| Aerosol propellant | to 5.0 ml |

Suspend the micronized compound of formula (I) in the aerosol propellant. Fill this suspension into preformed aerosol cannisters, 5 ml/cannister under pressure, through the valve orifice.

| Powder Inhalation | |
|---|---|
| Compound of formula (I), micronized | 1.0 mg |
| Lactose | 29.0 mg |

Triturate and blend the micronized compound of formula (I) with the lactose. Fill the resulting powder blend into hard gelatin capsule shells, 30 mg per capsule.

| Nasal Drops | |
|---|---|
| Compound of formula (I) | 100.0 mg |
| Methylhydroxybenzoate | 10.0 mg |
| Water for Injection | to 10.0 ml |

Disperse the compound of formula (I) and the methylhydroxybenzoate in the water for injection. Fill this suspension into suitable dropper bottles, 10 ml/bottle, and close by securing the dropper bottle and bottle cap.

EXAMPLE 101

The following formulation may be used for microinfusion applications of formulations containing at least one compound of the invention as an active ingredient component.

| Microinfusable formulation | |
|---|---|
| Active ingredient | 0.2 g |
| Sodium Chloride | 16 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 20 ml |

The active ingredient and sodium chloride are dissolved in most of the water (35°–40° C.) and the pH is adjusted to between 4.0 and 7.0 using the hydrochloric acid or the sodium hydroxide as appropriate. The bath then is made up to volume with the water and filtered through a sterile micropore filter into a sterile amber glass vial 20 ml and sealed with sterile closure and overseals.

EXAMPLE 102

Transdermal Administration

Compositions comprising compounds of formula (I) as an active ingredient may be utilized in transdermal administration devices such as transdermal patches.

The patches bearing or otherwise containing the transdermal formulation are positioned on the body of a wearer in such manner as to remain in contact with the epidermis of the recipient for a prolonged period of time.

Such patches suitably comprise the active compound (1) in an optionally buffered, aqueous solution, (2) dissolved and/or dispersed in an adhesive, or (3) dispersed in a polymer.

A suitable concentration of the active compound is about 1% to about 35%, and preferably from about 3% to about 15%.

By way of example, the active compound may be delivered from the patch by electrotransport or iontophoresis, as generally described in Pharmaceutical Research, 3(6), 31 8 (1986).

EXAMPLE 103

A specific example of a transdermal formulation comprising a compound of the invention as the active ingredient is set out below.

| Transdermal formulation | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with surface area of 10 $cm^2$.

Modes for Carrying Out the Invention

An advantageous mode of carrying out the invention involves the synthesis and use of preferred compounds of the invention (made by any suitable synthesis method, as for example the nitrile synthesis route hereinabove described), e.g., a compound selected from the group including compounds numbered 7, 16, 29, 37, 50, 61, 64, 67, 70, 107, 112, 115, 122, 124, 127, 142, 148, 150, 152, 153, 154, 155, 164, 175, 176, 177, 178, 179, 180, 181, and pharmaceutically acceptable esters, salts, and other physiologically functional derivatives thereof, in the treatment of conditions or disorders selected from those of the group consisting of: physiological pain, diarrhea, urinary incontinence, mental illness, drug and alcohol addiction/overdose, lung edema, depression, asthma, emphysema, and apnea, cognitive disorders, and gastrointestinal disorders.

Within the foregoing, an exemplary mode of carrying out the invention with respect to the use of compounds of the invention, is the administration of same in a pharmaceutically safe and effective dose, and in a suitable dosage form, to an animal subject, e.g., a human subject, for the purpose of inducing analgesia in such animal subject.

A highly preferred compound species of the present invention is Compound (C), 3-((αR)-α-((2S,5R)-4-allyl-2,5-dimethyl-1-piperazinyl)-3-hydroxybenzyl)-N,N-diethylbenzamide.

Industrial Applicability

Compounds of the present invention are highly selective opioid receptor binding compounds having utility as receptor-binding species, e.g., as conjugates in agonist/antagonist pairs for verifying/assaying receptor and neurotransmitter function.

The compounds of the invention include benzhydryl piperazine/piperidine compounds useful for mediating analgesia, as well as compounds having utility in treating conditions such as drug addiction, alcohol addiction, drug overdose, mental illness, gastrointestinal disorders, urinary incontinence, diarrhea, lung edema, cough, and respiratory disorders.

A highly preferred compound within the scope of the present invention, 3-(($\alpha$R)-$\alpha$-((2S,5R)-4-allyl-2,5-dimethyl-1-piperazinyl)-3-hydroxybenzyl)-N,N-diethylbenzamide, is a mixed mu/delta opioid agonist with substantial advantage over various known mu receptor compounds currently employed as analgesics.

What we claim is:

1. A compound of the formula:

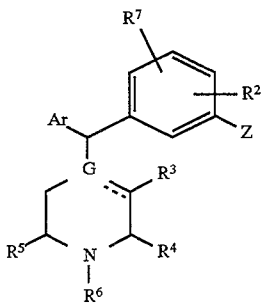

wherein:

Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R^1$, wherein Ar is joined to the compound at a ring carbon atom of the Ar ring;

Y is selected from the group consisting of:
hydrogen;
halogen;
$C_1$–$C_6$ alkyl;
$C_1$–$C_6$ haloalkyl;
$C_3$–$C_6$ cycloalkyl;
$C_1$–$C_6$ alkoxy;
$C_3$–$C_6$ cycloalkoxy;
sulfides of the formula $SR^8$ where $R^8$ is $C_1$–$C_6$ alkyl, $C_3$–$C_6$ cycloalkyl, or phenyl;
sulfoxides of the formula $SOR^8$ where $R^8$ is the same as above;
sulfones of the formula $SO_2R^8$ where $R^8$ is the same as above;
nitrile;
$C_1$–$C_6$ acyl;
alkoxycarbonylamino (carbamoyl) of the formula $NHCO_2R^8$ where $R^8$ is the same as above;
carboxylic acid, or an alkyl ester;
aminomethyl of the formula $CH_2NR^9R^{10}$ where $R^9$ and $R^{10}$ may be the same or different, and may be hydrogen, $C_1$–$C_6$ alkyl, $C_2$–$C_6$ hydroxyalkyl, $C_2$–$C_6$ methoxyalkyl, $C_3$–$C_6$ cycloalkyl, or phenyl, or $R^9$ and $R^{10}$ together may form a ring selected from the group consisting of pyrrolidinyl, piperidinyl, and 4-methylpiperazinyl;
carboxamides of the formula $CONR^9R^{10}$ where $R^9$ and $R^{10}$ are the same as above;

sulfonamides of the formula $SO_2NR^9R^{10}$ where $R^9$ and $R^{10}$ are the same as above; and
$CONR^9AB$, where:
$R^9$ is the same as above;
A is a divalent ligand having an alkyl or polyether moiety of 6–12 atoms, with the proviso that there are at least two carbon atoms between an oxygen atom and the $NR^9$ group and at least two carbon atoms between two oxygen atoms when present; and
B is a dimer-forming moiety which is joined to a first valence bond of the divalent ligand A, and which is symmetric about the divalent ligand A to the compound moiety joined to the other valence bond of the divalent ligand A;

Z is selected from the group consisting of:
hydroxyl, and acyl esters thereof whose acyl moiety is selected from the group consisting of $CH_3CO$, $C_6H_5CO$, $(CH_3)_2NCO$, and $Me_3CCO$;
hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;

G is nitrogen;

$R^1$ is hydrogen, halogen, or $C_1$–$C_4$;

$R^2$ is hydrogen, halogen, or $C_1$–$C_4$;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^6$ is selected from the group consisting of:
hydrogen;
$C_1$–$C_6$ alkyl;
$C_3$–$C_6$ cycloalkyl;
allyl;
2-buten-1-yl;
2-methyl-2-propen-1-yl;
2-chloro-2-propen-1-yl;
alkoxyalkyl having $C_1$–$C_4$ alkoxy and $C_1$–$C_4$ alkyl moieties;
$C_2$–$C_4$ cyanoalkyl;
$C_2$–$C_4$ hydroxyalkyl;
aminocarbonylalkyl having a $C_1$–$C_4$ alkyl moiety; and
$R^{12}COR^{13}$, where $R^{12}$ is $C_1$–$C_4$ alkylene, and $R^{13}$ is $C_1$–$C_4$ alkyl or $C_1$–$C_4$ alkoxy; and $R^7$ is hydrogen or fluorine, subject to the proviso that:
$R^1$, $R^2$ and $R^7$ may be fluorine only when Z is —OH, or a pharmaceutically acceptable salt thereof.

2. A compound according to claim 1, wherein $R^6$ is selected from the group consisting of allyl, 2-buten-1-yl, 2-methyl-2-propen-1-yl, and 2-chloro-2-propen-yl.

3. A compound according to claim 1, wherein $R^6$ is allyl.

4. A compound according to claim 1, wherein Ar is a monovalent radical of a 5-member ring having on a first ring carbon a substituent Y and on a second ring carbon atom a substituent $R^1$, the ring being selected from the group consisting of thiophene rings, thiazole rings, furan rings, and pyrrole rings.

5. A compound according to claim 1, wherein Ar is thiophene.

6. A compound according to claim 1, wherein Ar is phenyl having on a first ring carbon atom a substituent Y and on a second ring carbon atom a substituent $R^1$.

7. A compound according to claim 6, wherein $R^1$ is hydrogen, and Y is N,N-dialkyl carboxamide wherein each of the dialkyl substituents is independently selected from $C_1$–$C_6$ alkyl.

8. A compound according to claim 1, wherein Ar is a 6-member ring of the formula:

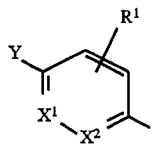

wherein:

X$^1$ and X$^2$ may be carbon or nitrogen, except that both may not simultaneously be nitrogen.

9. A compound of the formula:

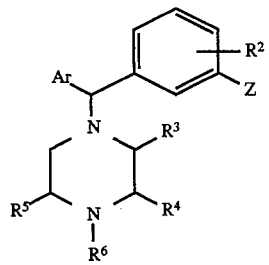

in which Ar is a 5-member heterocyclic aromatic ring selected from the group consisting of thiophenyl, thiazolyl, furanyl, and pyrrolyl, or a 6-member carbocyclic aromatic ring, said 5- or 6-member ring having on a first ring carbon atom thereof a substituent Y and on a second ring carbon atom thereof a substiment R$^1$, wherein Ar is joined to the compound at a ring carbon atom of the Ar ring; wherein:

Z=OH, and acyl esters thereof whose acyl moiety is selected from the group consisting of CH$_3$CO, C$_6$H$_5$CO, (CH$_3$)$_2$NCO, and Me$_3$CCO;

NH$_2$, formamidyl, or benzenesulfonamidyl; or

CH$_2$OH, and acyl esters thereof whose acyl moiety is selected from the group consisting of CH$_3$CO, C$_6$H$_5$CO, (CH$_3$)$_2$NCO, and Me$_3$CCO;

Y=hydrogen;

halogen;

nitrile;

C$_1$–C$_6$ alkyl;

C$_3$–C$_6$ cycloalkyl;

C$_1$–C$_6$ alkoxy;

C$_3$–C$_6$ cycloalkoxy;

sulfones (SO$_2$R$^7$) where R$^7$ is C$_1$–C$_6$ alkyl, C$_3$–C$_6$ cycloalkyl, or phenyl;

alkoxycarbonylamino (carbamoyl) of the formula NHCO$_2$R$^7$ where R$^7$ is the same as above;

aminomethyl (CH$_2$NR$^8$R$^9$) where R$^8$ and R$^9$ may be the same or different, and may be hydrogen, phenyl, C$_2$–C$_6$ hydroxyalkyl, C$_2$–C$_6$ methoxyalkyl, C$_1$–C$_6$ alkyl, or C$_3$–C$_6$ cycloalkyl, or taken together may form a ring selected from the group consisting of pyrrolidinyl, piperidinyl, and 4-methyl-piperazinyl;

sulfonamides (SO$_2$NR$^8$R$^9$) where R$^8$ and R$^9$ are the same as above;

C$_1$–C$_6$ acyl;

carboxylic acid, or an alkyl ester thereof; or carboxamides (CONR$^{10}$R$^{11}$) where R$^{10}$ and R$^{11}$ may be the same or different and may be hydrogen, phenyl, C$_1$–C$_6$ alkyl, C$_3$–C$_6$ cycloalkyl, C$_2$–C$_6$ hydroxyalkyl, or C$_2$–C$_6$ methoxyalkyl, or taken together form a ring selected from the group consisting of pyrrolidinyl, piperidinyl, and 4-methyl-piperazinyl;

R$^1$, R$^2$=hydrogen, halogen, or C$_1$–C$_4$ alkyl;

R$^3$, R$^4$ and R$^5$ may be the same or different, and are independently selected from hydrogen and methyl, and wherein at least one of R$^3$, R$^4$ or R$^5$ is not hydrogen, subject to the proviso that the total number of methyl groups does not exceed two; and R$^6$=hydrogen;

C$_1$–C$_6$ alkyl;

C$_3$–C$_6$ cycloalkyl;

allyl;

2-buten-1-yl;

2-methyl-2-propen-1-yl;

2-chloro-2-propen-1-yl;

alkoxyalkyl having C$_1$–C$_4$ alkoxy and C$_1$–C$_4$ alkyl moieties;

C$_2$–C$_4$ cyanoalkyl;

C$_2$–C$_4$ hydroxyalkyl;

aminocarbonylalkyl having a C$_1$–C$_4$ alkyl moiety; or

—R$^{12}$COR$^{13}$, where R$^{12}$ is C$_1$–C$_4$ alkylene, and R$^{13}$ is C$_1$–C$_4$ alkyl or C$_1$C$_4$ alkoxy;

or a pharmaceutically acceptable salt thereof.

10. A compound of the formula:

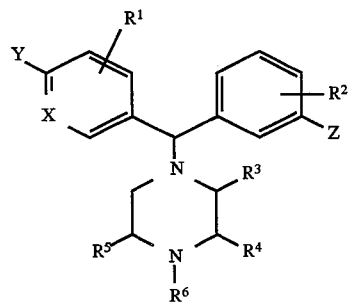

wherein:

X=nitrogen or carbon;

Z=OH, or acyl esters thereof whose acyl moiety is selected from the group consisting of CH$_3$CO, C$_6$H$_5$CO, (CH$_3$)$_2$NCO, and Me$_3$CCO;

NH$_2$, formamidyl, or benzenesulfonamidyl; or

CH$_2$OH, or acyl esters thereof whose acyl moiety is selected from the group consisting of CH$_3$CO, C$_6$H$_5$CO, (CH$_3$)$_2$NCO, and Me$_3$CCO;

Y=hydrogen;

halogen;

methyl;

nitrile;

sulfones (SO$_2$R$^7$) where R$^7$ is C$_1$–C$_6$ alkyl, or phenyl;

alkoxycarbonylamino (carbamoyl) of the formula NHCO$_2$R$^7$ where R$^7$ is the same as above;

carboxamides (CONR$^8$R$^9$) where R$^8$ and R$^9$ may be the same or different and may be hydrogen, phenyl, C$_1$–C$_6$ alkyl, C$_3$–C$_6$ cycloalkyl, C$_2$–C$_6$ hydroxyalkyl or C$_2$–C$_6$ methoxyalkyl, or taken together may form a ring selected from the group consisting of pyrrolidinyl, piperidinyl, and 4-methyl-piperazinyl;

CONR$^8$AB, where:

$R^8$ is the same as above, A is a divalent ligand having an alkyl or polyether moiety of 6–12 atoms with the proviso that there are at least two carbon atoms between an oxygen atom and the $NR^8$ group and at least two carbon atoms between two oxygen atoms when present, and B is a dimer-forming moiety joined to a first valence bond of the divalent ligand A and symmetric about A to the compound moiety joined to the other valence bond of the divalent ligand A; sulfonamides ($SO_2NR^8R^9$) where $R^8$ and $R^9$ are the same as above; or carboxylic acid, or an alkyl ester thereof;

$R^1$=hydrogen, halogen, or $C_1$–$C_4$ alkyl;

$R^2$=hydrogen or fluorine;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two; and $R^6$=hydrogen; $C_1$–$C_6$ alkyl; allyl; 2-buten-1-yl; 2-methyl-2-propen-1-yl; 2-chloro-2-propen-1-yl; cyclopropylmethyl; or $C_3$–$C_6$ cycloalkyl;

or a pharmaceutically acceptable salt thereof.

11. A compound according to claim 10, wherein:

X=nitrogen or carbon;

Z=OH or an acyl ester thereof whose acyl moiety is selected from the group consisting of $CH_3CO$, $C_6H_5CO$, $(CH_3)_2NCO$, and $Me_3CCO$;

$NH_2$, formamidyl, or benzenesulfonamidyl; or $CH_2OH$ or an acyl ester thereof whose acyl moiety is selected from the group consisting of $CH_3CO$, $C_6H_5CO$, $(CH_3)_2NCO$, and $Me_3CCO$; and Y=hydrogen; halogen; methyl; nitrile; sulfones of the formula $SO_2R^7$, where $R^7$ is $C_1$–$C_6$ alkyl, or phenyl; alkoxycarbonylamino (carbamoyl) of the formula $NHCO_2R^7$ where $R^7$ is the same as above; carboxamides ($CONR^8R^9$) where $R^8$ and $R^9$ may be the same or different and may be hydrogen, phenyl, $C_1$–$C_6$ alkyl, $C_3$–$C_6$ cycloalkyl, $C_2$–$C_4$ hydroxyalkyl or $C_2$–$C_4$ methoxyalkyl, or taken together may form a ring selected from the group consisting of pyrrolidinyl, piperidinyl, and 4-methyl-piperazinyl; sulfonamides ($SO_2NR^8R^9$) where $R^8$ and $R^9$ are the same as above; or carboxylic acid, or an alkyl ester thereof;

$R^1$=hydrogen, methyl, or halogen;

$R^2$=hydrogen or fluorine; and $R^6$=$C_1$–$C_6$ alkyl; allyl; 2-buten-1-yl; 2-methyl-2-propen-1-yl; 2-chloro-2-propen-1-yl; cyclopropylmethyl; or $C_3$–$C_6$ cycloalkyl;

or a pharmaceutically acceptable salt thereof.

12. A compound according to claim 11, wherein $R^6$ is selected from the group consisting of methyl, ethyl, propyl, butyl, allyl, cyclopropylmethyl, 2-buten-1-yl, 2-methyl-2-propen-1-yl, and 2-chloro-2-propen-1-yl.

13. A compound according to claim 11, wherein $NR^8R^9$ is selected from the group consisting of:

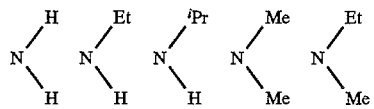

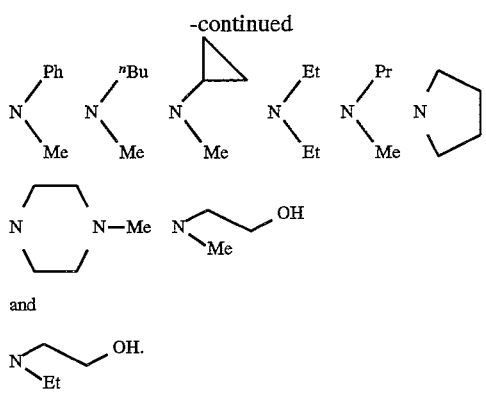

and

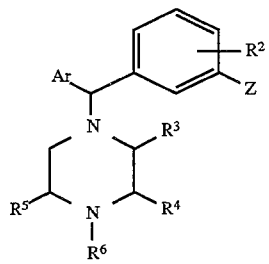

14. A compound of the formula:

![structure]

wherein:

Ar is a 5-member heterocyclic aromatic ring selected from the group consisting of thiophenyl, thiazolyl, furanyl, and pyrrolyl, or a 6-member carbocyclic aromatic ring, said 5- or 6-member ring having on a first carbon atom thereof a substituent Y and on a second ring carbon thereof a substituent $R^1$, wherein Ar is joined to the compound at a ring carbon atom of the Ar ring;

Z=OH or an acyl ester thereof whose acyl moiety is selected from the group consisting of $CH_3CO$, $C_6H_5CO$, $(CH_3)_2NCO$, and $Me_3CCO$;

$NH_2$, formamidyl, or benzenesulfonamidyl; or $CH_2OH$ or acyl esters thereof whose acyl moiety is selected from the group consisting of $CH_3CO$, $C_6H_5CO$, $(CH_3)_2NCO$, and $Me_3CCO$; and Y=halogen;

sulfoxides ($SOR^7$) where $R^7$ is $C_1$–$C_6$ alkyl, or $C_3$–$C_6$ cycloalkyl;

carboxamides ($CONR^8R^9$) where $R^8$ and $R^9$ may be the same or different, and may be hydrogen, $C_1$–$C_6$ alkyl, $C_2$–$C_6$ hydroxyalkyl or $C_2$–$C_6$ methoxyalkyl, $C_3$–$C_6$ cycloalkyl, or phenyl, or $R^8$ and $R^9$ together may form a ring selected from the group consisting of pyrrolidinyl, piperidinyl, and 4-methyl-piperazinyl; or sulfonamides ($SO_2NR^8R^9$) where $R^8$ and $R^9$ are the same as above;

$R^1$, $R^2$=hydrogen or fluorine;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two; and $R^6$=hydrogen, $C_1$–$C_6$ alkyl; allyl;2-buten-1-yl; 2-methyl-2-propen-1-yl; 2-chloro-2-propen-1-yl; $C_2$–$C_4$ methoxyalkyl, or $C_3$–$C_6$ cycloalkyl;

or a pharmaceutically acceptable salt thereof.

15. A compound according to claim 14, wherein Y is carboxamide.

16. A compound of the formula:

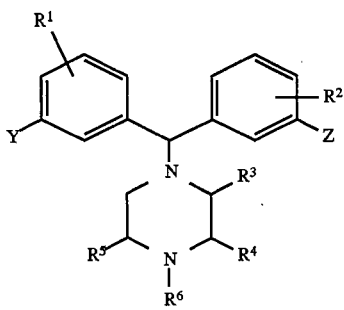

wherein:

Z=OH or acyl esters thereof whose acyl moiety is selected from the group consisting of $CH_3CO$, $C_6H_5CO$, $(CH_3)_2NCO$, and $Me_3CCO$;

$NH_2$, formamidyl, or benzenesulfonamidyl; or $CH_2OH$ or acyl esters thereof whose acyl moiety is selected from the group consisting of $CH_3CO$, $C_6H_5CO$, $(CH_3)NCO$, and $Me_3CCO$;

Y=hydrogen;

sulfoxides ($SOR^7$) where $R^7$ is $C_1$-$C_6$ alkyl, or $C_3$-$C_6$ cycloalkyl;

carboxamides ($CONR^8R^9$) where $R^8$ and $R^9$ may be the same or different, and may be hydrogen, $C_1$-$C_6$ alkyl, $C_2$-$C_6$ hydroxyalkyl or $C_2$-$C_6$ methoxyalkyl, $C_3$-$C_6$ cycloalkyl, or phenyl, or $R^8$ and $R^9$ together may form a ring selected from the group consisting of pyrrolidinyl, piperidinyl, and 4-methyl-piperazinyl; or sulfonamides ($SO_2NR^8R^9$) where $R^8$ and $R^9$ are the same as above;

$R^1$, $R^2$=hydrogen or fluorine;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two; and $R^6$=hydrogen, $C_1$-$C_6$ alkyl, allyl; 2-buten-1-yl; 2-methyl-2-propen-1-yl; 2-chloro-2-propen-1-yl; $C_2$-$C_6$ methoxyalkyl, or $C_3$-$C_6$ cycloalkyl;

or a pharmaceutically acceptable salt thereof.

17. A compound according to claim 16, wherein:

Z=OH;

Y=carboxamides ($CONR^8R^9$) where $R^8$ and $R^9$ may be the same or different, and may be hydrogen, $C_1$-$C_6$ alkyl, $C_3$-$C_6$ cycloalkyl, or phenyl, or $R^8$ and $R^9$ together may form a ring selected from the group consisting of pyrrolidinyl, piperidinyl, and 4-methyl-piperazinyl;

$R^1$, $R^2$=hydrogen or fluorine;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two; and $R^6$=hydrogen, $C_1$-$C_6$ alkyl, $C_2$-$C_6$ methoxyalkyl, or $C_3$-$C_6$ cycloalkyl;

or a pharmaceutically acceptable salt thereof.

18. A compound according to claim 17, wherein Y is carboxamide and $NR^8R^9$ is selected from the group consisting of:

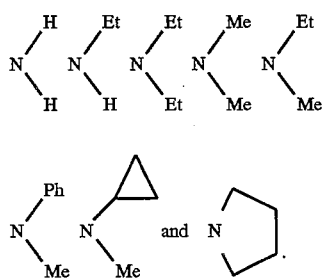

19. A compound selected from the group consisting of:

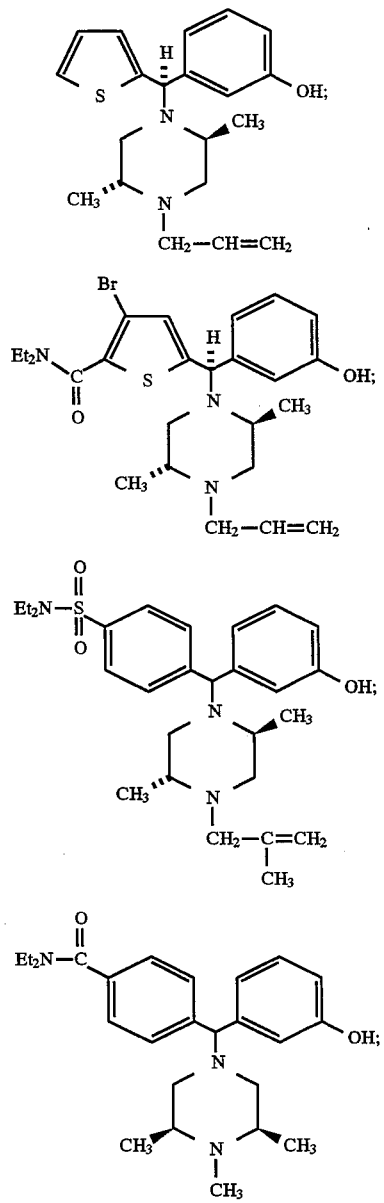

119

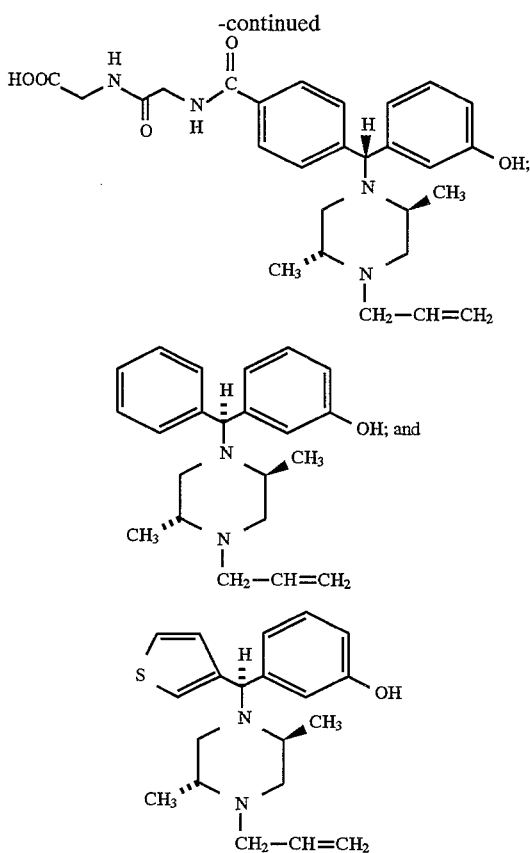

or a pharmaceutically acceptable ester, or salt thereof.

20. A compound selected from those of the group consisting of:

(±)-3-((αR*)-α-((2S*,5R*)-4-Allyl-2,5-dimethyl-1-piperazinyl)-4)-(methylsulfonyl)benzyl)phenol;

(±)-4-((αR*)-α((2R*,5S*)-2,5-Dimethyl-1-piperazinyl)-3-hydroxybenzyl)-N,N-diethylbenzamide;

cis-4-(α-(4-((Z)-2-Butenyl)-3,5-dimethyl-1-piperazinyl)-3-hydroxybenzyl)-N,N-diethylbenzamide;

N,N-Diethyl-4-(3-hydroxy-α-(cis-3,4,5-trimethyl-1-piperazinyl)benzyl)benzamide;

N,N-Diethyl-4-(3-hydroxy-(αR)-α-((2S,5S)-2,4,5-trimethyl-1-piperazinyl)benzyl)-benzamide;

N,N-Diethyl-4-(3-hydroxy-(αR)-α-((2R,5R)-2,4,5-trimethyl-1-piperazinyl)benzyl)benzamide;

3-((αR)-4-(1-Pyrrolidinylcarbonyl)-α-((2S,5S)-2,4,4-trimethyl-1-piperazinyl)benzyl)phenol;

N-Ethyl-4-((αS)-3-hydroxy-α-((2S,5S)-2,4,5-trimethyl-1-piperazinyl)benzyl)-N-methylbenzamide;

4-(α-(trans-2,5-Dimethyl-4-(2-methylallyl)-1-piperazinyl)-3-hydroxybenzyl)-N,N-diethylbenzenesulfonamide;

(±)-3-((αR*)-α-((2R*,5S*)-4-Allyl-2,5-dimethyl-1-piperazinyl)benzyl)phenol;

(±)-4-((αR*)-α-((2S*,5R*)-4-Allyl-2,5-dimethyl-1-piperazinyl)-3-hydroxybenzyl)benzamide;

(±)-4-((αR*)-α-((2S*,5R*)-4-Allyl-2,5-dimethyl-1-piperazinyl)-3-hydroxybenzyl)-N-ethyl-N-(2-hydroxyethyl)benzamide;

(±)-5-((αR*)-α-((2S*,5R*)-4-Allyl-2,5-dimethyl-1-piperazinyl)-3-hydroxybenzyl)-3-bromo-N,N-diethyl-2-thiophenecarboxamide;

120

(±)-3-((R*)-((2S*,5R*)-4-Allyl-2,5-dimethyl-1-piperazinyl)(2-thienyl)methyl)phenol;

(+)-3-((αS)-α-((2S,5R)-4-Allyl-2,5-dimethyl-1-piperazinyl)benzyl)phenol;

3-((R)-((2S,5R)-4-Allyl-2,5-dimethyl-1-piperazinyl)(2-thienyl)methyl)phenol;

(±)-4-((αR*)-α-((2S*,5R*)-4-Allyl-2,5-dimethyl-1-piperazinyl)-3-hydroxybenzyl)-N,N-diethylbenzenesulfonamide;

(±)-3-((R*)-((2R*,5S*)-4-Allyl-2,5-dimethyl-1-piperazinyl)(2-thiazolyl)methyl)phenol; and (±)-3-((αR*)-4-(1-Pyrrolidinylcarbonyl)-α-((2S*,5R*)-4-allyl-2,5-dimethyl-1-piperazinyl)benzyl)phenol;

or a pharmaceutically acceptable salt thereof.

21. (±)-4-((αR*)-α-((2S*,5R*)-4-Allyl-2,5-dimethyl-1-piperazinyl)-3-hydroxybenzyl)-N,N-diethylbenzamide, or a pharmaceutically acceptable salt thereof.

22. (±)-4-((αR)-α-((2S,5R)-4-Allyl-2,5-dimethyl-1-piperazinyl)-3-hydroxybenzyl)-N,N-diethylbenzamide, or a pharmaceutically acceptable salt thereof.

23. A pharmaceutical composition, comprising a compound of the formula:

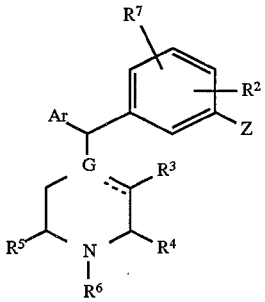

wherein:

Ar is a 5-member heterocyclic aromatic ring selected from the group consisting of thiophenyl, thiazolyl, furanyl, and pyrrolyl, or a 6-member carbocyclic aromatic ring, said 5- or 6-member ring having on a first carbon atom thereof a substituent Y and on a second ring carbon thereof a substiment $R^1$, wherein Ar is joined to the compound at a ring carbon atom of the Ar ring;

Y is selected from the group consisting of:

hydrogen;

halogen;

$C_1$–$C_6$ alkyl;

$C_1$–$C_6$ haloalkyl;

$C_3$–$C_6$ cycloalkyl;

$C_1$–$C_6$ alkoxy;

$C_3$–$C_6$ cycloalkoxy;

sulfides of the formula $SR^8$ where $R^8$ is $C_1$–$C_6$ alkyl, $C_3$–$C_6$ cycloalkyl, or phenyl;

sulfoxides of the formula $SOR^8$ where $R^8$ is the same as above;

sulfones of the formula $SO_2R^8$ where $R^8$ is the same as above;

nitrile;

$C_1$–$C_6$ acyl;

alkoxycarbonylamino (carbamoyl) of the formula $NHCO_2R^8$ where $R^8$ is the same as above;

carboxylic acid, or an alkyl ester thereof;

aminomethyl of the formula $CH_2NR^9R^{10}$ may be the same or different, and may be hydrogen, $C_1$–$C_6$ alkyl, $C_2$–$C_6$ hydroxyalkyl, $C_2$–$C_6$ methoxyalkyl, $C_3$–$C_6$ cycloalkyl, or phenyl, or $R^9$ and $R^{10}$ together may form a ring selected from the group consisting of pyrrolidinyl, piperidinyl, and 4-methyl-piperazinyl;

carboxamides of the formula $CONR^9R^{10}$ where $R^9$ and $R^{10}$ are the same as above;

sulfonamides of the formula $SO_2NR^9R^{10}$ where $R^9$ and $R^{10}$ are the same as above; and —$CONR^9AB$, where:

$R^9$ is the same as above;

A is a divalent ligand having an alkyl, or polyether moiety of 6–12 atoms, with the proviso that there are at least two carbon atoms between an oxygen atom and the $NR^9$ group and at least two carbon atoms between two oxygen atoms when present; and B is a dimer-forming moiety which is joined to a first valence bond of the divalent ligand A, and which is symmetric about the divalent ligand A to the compound moiety joined to the other valence bond of the divalent ligand A;

Z is selected from the group consisting of:

hydroxyl, and acyl esters thereof whose acyl moiety is selected from the group consisting of $CH_3CO$, $C_6H_5CO$, $(CH_3)_2NCO$, and $Me_3CCO$;

hydroxymethyl, and acyl esters thereof whose acyl moiety is selected from the group consisting of $CH_3CO$, $C_6H_5CO$, $(CH_3)_2NCO$, and $Me_3CCO$;

amino, formamidyl, and benzenesulfonamidyl; or

G is nitrogen;

$R^1$ is hydrogen, halogen, or $C_1$–$C_4$ alkyl;

$R^2$ is hydrogen, halogen, or $C_1$–$C_4$ alkyl;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^6$ is selected from the group consisting of:

hydrogen;
$C_1$–$C_6$ alkyl;
$C_3$–$C_6$ cycloalkyl;
allyl;
2-buten-1-yl;
2-methyl-2-propen-1-yl;
2-chloro-2-propen-1-yl;
alkoxyalkyl having $C_1$–$C_4$ alkoxy and $C_1$–$C_4$ alkyl moieties;
$C_2$–$C_4$ cyanoalkyl;
$C_2$–$C_4$ hydroxyalkyl;
aminocarbonylalkyl having a $C_1$–$C_4$ alkyl moiety; and
$R^{12}COR^{13}$, where $R^{12}$ is $C_1$–$C_4$ alkylene, and $R^{13}$ is $C_1$–$C_4$ alkyl or $C_1$–$C_4$ alkoxy; and $R^7$ is hydrogen or fluorine, subject to the proviso that $R^1$, $R^2$ and $R^7$ may be fluorine only when Z is —OH, or a pharmaceutically acceptable salt thereof, and a pharmaceutically acceptable carrier therefor.

24. A pharmaceutical composition according to claim 23 in a form suitable for injectable administration.

25. A pharmaceutical composition according to claim 23 in a form suitable for intrathecal administration.

26. A method of treating pain in an animal subject, comprising administering to said animal an effective amount of a compound selected from those of the formula:

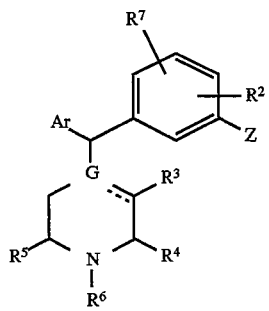

wherein:

Ar is a 5- or 6-member aromatic ring selected from the group consisting of thiophenyl, thiazolyl, furanyl, pyrrolyl, phenyl, and pyridyl, having on a first ring carbon atom thereof a substituent Y and on a second ring carbon atom thereof a substituent $R^1$, wherein Ar is joined to the compound at a ring carbon atom of the Ar ring;

Y is selected from the group consisting of:

hydrogen;
halogen;
$C_1$–$C_6$ alkyl;
$C_1$–$C_6$ haloalkyl;
$C_3$–$C_6$ cycloalkyl;
$C_1$–$C_6$ alkoxy;
$C_1$–$C_6$ cycloalkoxy;

sulfides of the formula $SR^8$ where $R^8$ is $C_1$–$C_6$ alkyl, $C_3$–$C_6$ cycloalkyl, phenyl;

sulfoxides of the formula $SOR^8$ where $R^8$ is the same as above;

sulfones of the formula $SO_2R^8$ where $R^8$ is the same as above;

nitrile;

$C_1$–$C_6$ acyl;

alkoxycarbonylamino (carbamoyl) of the formula $NHCO_2R^8$ where $R^8$ is the same as above;

carboxylic acid, or an alkyl ester thereof;

aminomethyl of the formula $CH_2NR^9R^{10}$ where $R^9$ and $R^{10}$ may be the same or different, and may be hydrogen, $C_1$–$C_6$ alkyl, $C_2$–$C_6$ hydroxyalkyl, $C_2$–$C_6$ methoxyalkyl, $C_3$–$C_6$ cycloalkyl, or phenyl, or $R^9$ and $R^{10}$ together may form a ring selected from the group consisting of pyrrolidinyl, piperidinyl, and 4-methylpiperazinyl; carboxamides of the formula $CONR^9R^{10}$ where $R^9$ and $R^{10}$ are the same as above;

sulfonamides of the formula $SO_2NR^9R^{10}$ where $R^9$ and $R^{10m}$ are the same as above; and $CONR^9AB$, where:

$R^9$ is the same as above;

A is a divalent ligand having an alkyl or polyether moiety of 6–12 atoms, with the proviso that there are at least two carbon atoms between an oxygen atom and the $NR^9$ group and at least two carbon atoms between two oxygen atoms when present; and B is a dimer-forming moiety which is joined to a first valence bond of the divalent ligand A, and which is symmetric about the divalent ligand A to the compound moiety joined to the other valence bond of the divalent ligand A;

Z is selected from the group consisting of: hydroxyl, and acyl esters thereof whose acyl moiety is selected from the group consisting of $CH_3CO$, $C_6H_5CO$, $(CH_3)_2NCO$, and $Me_3CCO$; hydroxymethyl, and acyl esters thereof whose acyl moiety is selected from the group consisting of $CH_3CO$, $C_6H_5CO$, $(CH_3)_2NCO$, and $Me_3CCO$; and amino, formamidyl and benzenesulfonamidyl;

G is nitrogen;

$R^1$ is hydrogen, halogen, or $C_1$–$C_4$ alkyl;

$R^2$ is hydrogen, halogen, or $C_1$–$C_4$ alkyl;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two;

$R^6$ is selected from the group consisting of:
hydrogen;
$C_1$–$C_6$ alkyl;
$C_3$–$C_6$ cycloalkyl;
allyl;
2-buten-1-yl;
2-methyl-2-propen-1-yl;
2-chloro-2-propen-1-yl;
alkoxyalkyl having $C_1$–$C_4$ alkoxy and $C_1$–$C_4$ alkyl moieties;
$C_2$–$C_4$ cyanoalkyl;
$C_2$–$C_4$ hydroxyalkyl;
aminocarbonylalkyl having a $C_1$–$C_4$ alkyl moiety; and
$R^{12} COR^{13}$, where $R^{12}$ is $C_1$–$C_4$ alkylene, and $R^{13}$ is $C_1$–$C_4$ alkyl or $C_1$–$C_4$ alkoxy; and $R^7$ is hydrogen or fluorine, subject to the proviso that $R^1$, $R^2$ and $R^7$ may be fluorine only when Z is —OH, or a pharmaceutically acceptable salt thereof.

* * * * *